United States Patent
Hendricks et al.

(10) Patent No.: US 9,365,839 B2
(45) Date of Patent: Jun. 14, 2016

(54) POLYMERASE COMPOSITIONS AND METHODS

(71) Applicant: LIFE TECHNOLOGIES CORPORATION, Carlsbad, CA (US)

(72) Inventors: Stephen P. Hendricks, Los Gatos, CA (US); Michael Phelan, Millbrae, CA (US); Marian Peris, San Mateo, CA (US); Cheng-Yao Chen, San Diego, CA (US); Daniel Mazur, San Diego, CA (US); Xinzhan Peng, Carlsbad, CA (US); Amy Castillo, Houston, TX (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/710,160

(22) Filed: May 12, 2015

(65) Prior Publication Data
US 2015/0247136 A1    Sep. 3, 2015

Related U.S. Application Data

(63) Continuation of application No. 13/540,935, filed on Jul. 3, 2012, now abandoned, which is a continuation of application No. 12/748,359, filed on Mar. 26, 2010, now abandoned.

(60) Provisional application No. 61/164,324, filed on Mar. 27, 2009, provisional application No. 61/184,770, filed on Jun. 5, 2009, provisional application No. 61/242,771, filed on Sep. 15, 2009, provisional application No. 61/245,457, filed on Sep. 24, 2009, provisional application No. 61/263,974, filed on Nov. 24, 2009, provisional application No. 61/289,388, filed on Dec. 22, 2009, provisional application No. 61/293,618, filed on Jan. 8, 2010, provisional application No. 61/293,616, filed on Jan. 8, 2010, provisional application No. 61/299,919, filed on Jan. 29, 2010, provisional application No. 61/299,917, filed on Jan. 29, 2010, provisional application No. 61/307,356, filed on Feb. 23, 2010.

(51) Int. Cl.
*C12N 9/12*    (2006.01)
*C07H 19/20*    (2006.01)
*C12Q 1/68*    (2006.01)

(52) U.S. Cl.
CPC .............. *C12N 9/1241* (2013.01); *C07H 19/20* (2013.01); *C12N 9/1252* (2013.01); *C12Q 1/6869* (2013.01)

(58) Field of Classification Search
None
See application file for complete search history.

(56) References Cited

U.S. PATENT DOCUMENTS

| | | |
|---|---|---|
| 4,658,649 A | 4/1987 | Brook |
| 5,001,050 A | 3/1991 | Blanco et al. |
| 5,151,507 A | 9/1992 | Hobbs et al. |
| 5,188,934 A | 2/1993 | Menchen et al. |
| 5,198,543 A | 3/1993 | Blanco et al. |
| 5,322,785 A | 6/1994 | Comb et al. |
| 5,473,060 A | 12/1995 | Gryaznov et al. |
| 5,510,270 A | 4/1996 | Fodor et al. |
| 5,558,991 A | 9/1996 | Trainor |
| 5,576,204 A | 11/1996 | Blanco et al. |
| 5,599,695 A | 2/1997 | Pease et al. |
| 5,707,804 A | 1/1998 | Mathies et al. |
| 5,723,584 A | 3/1998 | Schatz |
| 5,831,070 A | 11/1998 | Pease et al. |
| 5,874,239 A | 2/1999 | Schatz |
| 5,932,433 A | 8/1999 | Schatz |
| 6,087,095 A | 7/2000 | Rosenthal et al. |
| 6,207,229 B1 | 3/2001 | Bawendi et al. |
| 6,221,592 B1 | 4/2001 | Schwartz et al. |
| 6,255,083 B1 | 7/2001 | Williams |
| 6,294,136 B1 | 9/2001 | Schwartz |
| 6,322,901 B1 | 11/2001 | Bawendi et al. |
| 6,399,304 B1 | 6/2002 | Kilger et al. |
| 6,399,335 B1 | 6/2002 | Kao et al. |
| 6,423,551 B1 | 7/2002 | Weiss et al. |
| 6,524,829 B1 | 2/2003 | Seeger |
| 6,627,424 B1 | 9/2003 | Wang |
| 6,635,163 B1 | 10/2003 | Han et al. |
| 6,664,079 B2 | 12/2003 | Ju et al. |
| 6,815,064 B2 | 11/2004 | Treadway et al. |
| 6,818,395 B1 | 11/2004 | Quake et al. |

(Continued)

FOREIGN PATENT DOCUMENTS

| EP | 0272007 B1 | 3/1992 |
|---|---|---|
| EP | 1681356 | 7/2006 |

(Continued)

OTHER PUBLICATIONS

Motre, Aurelie et al., "Enhancing helicase-dependent amplification by fusing the helicase with the DNA polymerase", *Gene*, 420:, 2008, 17-22.

(Continued)

*Primary Examiner* — Richard Hutson

(57) ABSTRACT

Disclosed herein are modified polymerase compositions exhibiting altered polymerase activity, which can be useful in a variety of biological applications. Also disclosed herein are methods of making and using such compositions. In some embodiments, the compositions exhibit altered properties that can enhance their utility in a variety of biological applications. Such altered properties, can include, for example, altered nucleotide binding affinities, altered nucleotide incorporation kinetics, altered photostability and/or altered nanoparticle tolerance, as well as a range of other properties as disclosed herein.

9 Claims, 11 Drawing Sheets

(56) References Cited

U.S. PATENT DOCUMENTS

| | | |
|---|---|---|
| 6,849,411 B2 | 2/2005 | Knapp et al. |
| 6,864,626 B1 | 3/2005 | Weiss et al. |
| 6,911,345 B2 | 6/2005 | Quake et al. |
| 6,955,855 B2 | 10/2005 | Naasani |
| 6,960,437 B2 | 11/2005 | Enzelberger et al. |
| 6,982,146 B1 | 1/2006 | Schneider et al. |
| 7,033,762 B2 | 4/2006 | Nelson et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,078,499 B2 | 7/2006 | Odedra et al. |
| 7,125,671 B2 | 10/2006 | Sood et al. |
| 7,198,847 B2 | 4/2007 | Naasani |
| 7,205,048 B2 | 4/2007 | Naasani |
| 7,211,414 B2 | 5/2007 | Hardin et al. |
| 7,214,428 B2 | 5/2007 | Naasani |
| 7,217,562 B2 | 5/2007 | Cao et al. |
| 7,223,541 B2 | 5/2007 | Fuller et al. |
| 7,223,568 B2 | 5/2007 | Kondow et al. |
| 7,229,799 B2 | 6/2007 | Williams |
| 7,244,566 B2 | 7/2007 | Sood et al. |
| 7,244,602 B2 | 7/2007 | Frey et al. |
| 7,256,019 B2 | 8/2007 | Sood et al. |
| 7,264,934 B2 | 9/2007 | Fuller |
| 7,270,951 B1 | 9/2007 | Stemple et al. |
| 7,276,720 B2 | 10/2007 | Ulmer |
| 7,329,492 B2 | 2/2008 | Hardin et al. |
| 7,345,159 B2 | 3/2008 | Ju et al. |
| 7,361,466 B2 | 4/2008 | Korlach et al. |
| 7,368,086 B2 | 5/2008 | Naasani |
| 7,393,640 B2 | 7/2008 | Kumar et al. |
| 7,405,281 B2 | 7/2008 | Xu et al. |
| 7,416,844 B2 | 8/2008 | Korlach et al. |
| 7,427,673 B2 | 9/2008 | Balasubramanian et al. |
| 7,452,698 B2 | 11/2008 | Sood et al. |
| 7,456,954 B2 | 11/2008 | Weiss et al. |
| 7,485,424 B2 | 2/2009 | Korlach et al. |
| 7,501,245 B2 | 3/2009 | Quake et al. |
| 7,521,541 B2 | 4/2009 | Eigenbrot et al. |
| 7,541,444 B2 | 6/2009 | Milton et al. |
| 7,553,949 B2 | 6/2009 | Lee et al. |
| 7,599,059 B2 | 10/2009 | Laurence et al. |
| 7,611,907 B2 | 11/2009 | Dickson et al. |
| 7,668,697 B2 | 2/2010 | Volkov et al. |
| 7,670,770 B2 | 3/2010 | Chou et al. |
| 7,745,116 B2 | 6/2010 | Williams |
| 7,928,038 B2 | 4/2011 | Menchen et al. |
| 8,058,414 B2 | 11/2011 | Menchen et al. |
| 8,603,792 B2 | 12/2013 | Nikiforov et al. |
| 2002/0115092 A1 | 8/2002 | Rebek, Jr. |
| 2002/0132259 A1 | 9/2002 | Wagner, Jr. et al. |
| 2002/0197611 A1 | 12/2002 | Chagovetz |
| 2003/0044781 A1 | 3/2003 | Korlach et al. |
| 2003/0064366 A1 | 4/2003 | Hardin et al. |
| 2003/0087300 A1 | 5/2003 | Knapp et al. |
| 2003/0092005 A1 | 5/2003 | Levene et al. |
| 2004/0048300 A1 | 3/2004 | Sood et al. |
| 2004/0152119 A1 | 8/2004 | Sood et al. |
| 2004/0197800 A1 | 10/2004 | Borns |
| 2004/0197843 A1 | 10/2004 | Chou et al. |
| 2004/0244827 A1 | 12/2004 | Hatsukaiwa et al. |
| 2005/0003464 A1 | 1/2005 | Tibbe et al. |
| 2005/0042633 A1 | 2/2005 | Williams |
| 2005/0164255 A1 | 7/2005 | Korlach et al. |
| 2005/0244827 A1 | 11/2005 | Olsson et al. |
| 2005/0266424 A1 | 12/2005 | Hardin et al. |
| 2006/0003383 A1 | 1/2006 | Graham |
| 2006/0057565 A1 | 3/2006 | Ju et al. |
| 2006/0063264 A1 | 3/2006 | Turner et al. |
| 2006/0078937 A1 | 4/2006 | Korlach |
| 2006/0176479 A1 | 8/2006 | Laurence et al. |
| 2006/0177495 A1 | 8/2006 | Allen et al. |
| 2006/0275806 A1 | 12/2006 | Schwartz et al. |
| 2007/0009980 A1 | 1/2007 | Graham |
| 2007/0020772 A1 | 1/2007 | Cao et al. |
| 2007/0072196 A1 | 3/2007 | Xu et al. |
| 2007/0109536 A1 | 5/2007 | Weiss et al. |
| 2007/0111350 A1 | 5/2007 | Weiss et al. |
| 2007/0116868 A1 | 5/2007 | Weiss et al. |
| 2007/0128133 A1 | 6/2007 | Eid et al. |
| 2007/0161028 A1 | 7/2007 | Schwartz et al. |
| 2007/0172819 A1 | 7/2007 | Hardin et al. |
| 2007/0172858 A1 | 7/2007 | Hardin et al. |
| 2007/0172859 A1 | 7/2007 | Hardin et al. |
| 2007/0172860 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0172869 A1 | 7/2007 | Hardin et al. |
| 2007/0184475 A1 | 8/2007 | Hardin et al. |
| 2007/0196846 A1 | 8/2007 | Hanzel et al. |
| 2007/0250274 A1 | 10/2007 | Volkov et al. |
| 2007/0275395 A1 | 11/2007 | Hardin et al. |
| 2007/0292679 A1 | 12/2007 | Pellerite et al. |
| 2007/0292867 A1 | 12/2007 | Hardin et al. |
| 2008/0009100 A1 | 1/2008 | Davison |
| 2008/0091005 A1 | 4/2008 | Wang et al. |
| 2008/0108082 A1 | 5/2008 | Rank et al. |
| 2008/0131952 A1 | 6/2008 | Wu et al. |
| 2008/0132692 A1 | 6/2008 | Wu et al. |
| 2008/0176316 A1 | 7/2008 | Eid et al. |
| 2008/0176761 A1 | 7/2008 | Menchen et al. |
| 2008/0213910 A1 | 9/2008 | Jogikalmath |
| 2008/0219888 A1 | 9/2008 | Lawson et al. |
| 2008/0219890 A1 | 9/2008 | Lawson et al. |
| 2008/0261833 A1 | 10/2008 | Stemmer et al. |
| 2008/0274905 A1 | 11/2008 | Greene |
| 2008/0293071 A1 | 11/2008 | Gelfand et al. |
| 2009/0024331 A1 | 1/2009 | Tomaney et al. |
| 2009/0029385 A1 | 1/2009 | Christians et al. |
| 2009/0047699 A1 | 2/2009 | Graham |
| 2009/0061447 A1 | 3/2009 | Schneider |
| 2009/0081686 A1 | 3/2009 | Wu et al. |
| 2009/0176233 A1 | 7/2009 | Clark et al. |
| 2009/0275036 A1 | 11/2009 | Hardin et al. |
| 2009/0286245 A1 | 11/2009 | Bjornson et al. |
| 2009/0298075 A1 | 12/2009 | Travers et al. |
| 2009/0305248 A1 | 12/2009 | Lander et al. |
| 2009/0305278 A1 | 12/2009 | Hardin et al. |
| 2010/0216122 A1 | 8/2010 | Hardin et al. |
| 2010/0255463 A1 | 10/2010 | Harsin et al. |
| 2010/0255464 A1 | 10/2010 | Hardin et al. |
| 2010/0255487 A1 | 10/2010 | Beechem et al. |
| 2010/0261185 A1 | 10/2010 | Nikiforov |
| 2010/0304367 A1 | 12/2010 | Hardin et al. |
| 2010/0317005 A1 | 12/2010 | Hardin et al. |
| 2010/0330570 A1 | 12/2010 | Vander Horn et al. |
| 2011/0003343 A1 | 1/2011 | Nikiforov et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0184163 A1 | 7/2011 | Hardin et al. |
| 2011/0220844 A1 | 9/2011 | Tulsky et al. |
| 2011/0226995 A1 | 9/2011 | Tulsky et al. |
| 2011/0281740 A1 | 11/2011 | Beechem et al. |
| 2011/0306079 A1 | 12/2011 | Tulsky et al. |
| 2012/0322057 A1 | 12/2012 | Hendricks et al. |
| 2012/0329042 A1 | 12/2012 | Beechem et al. |

(56) References Cited

U.S. PATENT DOCUMENTS

| | | |
|---|---|---|
| 2013/0005020 A1 | 1/2013 | Peris et al. |
| 2013/0040363 A1 | 2/2013 | Nikiforov |
| 2013/0102050 A1 | 4/2013 | Hardin et al. |

FOREIGN PATENT DOCUMENTS

| | | |
|---|---|---|
| WO | WO-90/07576 | 7/1990 |
| WO | WO-91/01087 | 2/1991 |
| WO | WO-91/05060 | 4/1991 |
| WO | WO-91/06678 | 5/1991 |
| WO | WO-98/22615 | 5/1998 |
| WO | WO-98/31834 | 7/1998 |
| WO | WO-99/53034 | 12/1999 |
| WO | WO-00/17330 | 3/2000 |
| WO | WO-00/36151 | 6/2000 |
| WO | WO-00/36152 | 6/2000 |
| WO | WO-00/67698 | 11/2000 |
| WO | WO-00/70073 | 11/2000 |
| WO | WO-02/04680 | 1/2002 |
| WO | WO-02/44425 | 6/2002 |
| WO | WO-2007/070642 | 6/2007 |
| WO | WO-2008/030115 | 3/2008 |
| WO | WO-2008/154317 | 12/2008 |
| WO | WO-2009/017678 | 2/2009 |
| WO | WO-2009/091847 | 7/2009 |
| WO | WO-2010/002939 | 1/2010 |
| WO | WO-2010/039897 | 4/2010 |
| WO | WO-2010/040111 | 4/2010 |
| WO | WO-2010/048580 | 4/2010 |
| WO | WO-2010/048581 | 4/2010 |
| WO | WO-2010/096084 | 8/2010 |
| WO | WO-2010/111674 | 9/2010 |
| WO | WO-2010/111686 | 9/2010 |
| WO | WO-2010/111690 | 9/2010 |
| WO | WO-2010/111691 | 9/2010 |
| WO | WO-2010/111691 A3 | 9/2010 |
| WO | WO-2010/111691 A9 | 9/2010 |
| WO | WO-2010/151714 | 12/2010 |
| WO | WO-2010/111690 A3 | 3/2011 |
| WO | WO-2011/038158 | 3/2011 |
| WO | WO-2010/111686 A3 | 5/2011 |
| WO | WO-2011/078897 | 6/2011 |

OTHER PUBLICATIONS

Agard, N et al., "A Strain-Promoted [3+2]Azide-Alkyne Cycloaddition for Covalent Modification of Biomolecules in Living Systems", *J. Am. Chem Soc*, vol. 126(46), 2004, pp. 15046-15047.

Ahn, Jinwoo et al., "DNA Polymerase Beta: Structure-Fidelity Relationship from Pre-Steady-State Kinetic Analyses of All Possible Correct and Incorrect Base Pairs for Wild Type and R283A Mutant", *Biochemistry*, 36, 1997, 1100-1107.

Akerman, Maria E. et al., "Nanocrystal targeting in vivo", *Proceedings of the National Academy of Sciences (PNAS)*, vol. 99, No. 20, Oct. 1, 2002, 12617-12621.

Arenkov, Pavel et al., "Protein Microchips: Use for Immunoassay and Enzymatic Reactions", *Analytical Biochemistry*, vol. 278, 2000, 123-131.

Arion, Dominique et al., "HIV resistance to zidovudine: the role of pyrophosphorolysis", *Drug Resistance Updates*, vol. 2, No. 2, Apr. 1999, 91-95.

Arkin, A. P. et al., "An algorithm for protein engineering: Simulations of recursive ensemble mutagenesis", *PNAS USA*; vol. 89, 1992, pp. 7811-7815.

Arzumanov, Andrey A. et al., "γ-Phosphate-substituted 2'-Deoxynucleoside 5'-Triphosphates as Substrates for DNA Polymerases", *J. Biol. Chem.*, vol. 271(40), 1996, pp. 1996, pp. 24389-24394.

Bakhtina, Marina et al., "Contribution of the Reverse Rate of the Conformational Step to Polymerase B Fidelity", *Biochem.*, vol. 48, 2009, 3197-3208.

Barone, A. D. et al., "Novel Nucleoside Triphosphate Analogs for the Enzymatic labeling of Nucleic Acids", *Nucleosides, Nucleotides & Nucleic Acids*, 20(4-7), 2001, 1141-1145.

Barone, Anthony D. et al., "Photolithographic Synthesis of High-Density Oligonucleotide Probe Arrays", *Nucleosides, Nucleotides & Nucleic Acids*, vol. 20, Nos. 4-7, 2001, 525-531.

Beattie, W. G. et al., "Hybridization of DNA targets to glass-tethered oligonucleotide probes", *Mol. Biotechnology*, vol. 4(3), 1995, pp. 213-225.

Berman, Andrea J. et al., "Structures of phi29 DNA polymerase complexed with substrate: the mechanism of translocation in B-family polymerases", *The EMBO Journal*, vol. 26, 2007, 3494-3505.

Bernad, Antonio et al., "Structural and functional relationships between prokaryotic and eukaryotic DNA polymerases", *The EMBO Journal*, vol. 6 No. 13, 1987, 4219-4225.

Blanco, L. et al., "A general structure for DNA-dependent DNA polymerases", *Gene*, vol. 100, Elsevier Science Publishers B.V., 1991, 27-38.

Blasco, M. A. et al., "Phi29 D A polymerase active site. Residue ASP249 of co nserved amino acid motif "Dx2SLYP" is critical for synthetic activities", *The Journal of Biological Chemistry*. vol. 268 No. 32, Nov. 15, 1993, pp. 24106-24113.

Blasco, M. A., "Phi29 DNA polymerase active site. Mutants in conserved residues Tyr254 and Tyr290 are affected in dNTP binding",*The Journal of Biological Chemistry*. vol. 267 No. 27, Sep. 25, 1992, pp. 19427-19434.

Blasco, M. A. et al., "Primer terminus stabi l izat ion at the phi29 DNA polymer ase active site. Mutation analysis of conserved motif KXY", *The Journal of Biological Chemistry*. vol. 270 No. 6, Feb. 10, 1995, pp. 2735-2740.

Blasco, Maria et al., "Phi29 DNA Polymerase Active Site", *The Journal of Biological Chemistry*, vol. 268, No. 22,, 1993, 16763-16770.

Bouizar, et al., "Purification and Characterization of Calcitonin Receptors in Rat Kidney Membranes by Covalent Cross-Linking Techniques.", *European Journal of Biochemistry*, vol. 155, No. 1, 1986, 141-147.

Bowers, Jayson et al., "Virtual terminator nucleotides for next-generation DNA sequencing", *Nature Methods*, vol. 6, No. 8, 2009, 593-595.

Braslavsky, Ido et al., "Sequence information can be obtained from single DNA molecules",*Proc. Natl. Acad. Sci.*, vol. 100(7), 2003, pp. 3960-3964.

Brinkley, "A Brief Survey of Methods for Preparing Protein Conjugates with Dyes, Haptens, and Cross-Linking Reagents", *Bioconjugate Chemistry*, vol. 3, No. 1, 1992, 2-13.

Browning, et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Brustad, Eric et al., "A General and Efficient Method for the Site-Specific Dual-Labeling of Proteins for Single Molecule Fluorescence Resonance Energy Transfer", *J. Am. Chem. Soc.*, 130, 2008, 17664-17665.

Calogero, S. et al., "In vivo recombination and the production of hybrid genes", *FEMS Microbiology Letters*, vol. 97, 1992, pp. 41-44.

Campbell, A. K. et al., "A homogeneous immunoassay for cyclic nucleotides based on chemiluminescence energy transfer", *Biochem. J.*, vol. 216, 1983, pp. 185-194.

Caren, R. et al., "Efficient Sampling of Protein Sequence Space for Multiple Mutants", *Bio/Technology*, vol. 12, 1994, pp. 517-520.

Caspar, J. et al., "Photochemistry of Ru(bpy)3 2+. Solvent Effects", *J. Am. Chem. Soc.*, 105, 1983, 5583.

Caspar, Jonathan V. et al., "Application of the Energy Gap Law to Nonradiative, Excited-State Decay", *J. Phys. Chem.*, vol. 87, No. 6, 1983, pp. 952-957.

Castro, Christian et al., "Nucleic acid polymerases use a general acid for nucleotidyl transfer", *Nature Structural & Molecular Biology*, vol. 16 No. 2, 2009, 212-218.

Cha, Taewoon et al., "Enzymatic activity on a chip: The critical role of protein orientation", *Proteomics*, vol. 5, 2005, 416-419.

(56) References Cited

OTHER PUBLICATIONS

Cha, Taewoon et al., "Immobilization of oriented protein molecules on poly(ethylene glycol)-coated Si(111)", *Proteomics*, vol. 4, 2004, 1965-1976.
Choi, H. S. et al., "Nature Biotechnology", vol. 25, No. 10, Oct. 2007, pp. 1165-1170.
Chrisey, Linda A. et al., "Covalent attachment of synthetic DNA to self-assembled monolayer films", *Nucleic Acid Research*, vol. 24, No. 15, 1996, pp. 3031-3039.
Clapp, A.R. et al., "Fluorescence Resonance Energy Transfer Between Quantum Dot Donars and Dye-Labeled Protein Acceptors", *J. Am. Chem. Soc.*, 126, 2004, 301-310.
Clapp, Aaron et al., "Capping of CdSe—ZnS quantum dots with DHLA and subsequent conjugation with proteins", *Nature Protocols*, vol. 1 No. 3, 2006, 1258-1266.
Cull, Millard G. et al., "Screening for receptor ligands using large libraries of peptides linked to the C terminus of the lac repressor", *Proc. Natl. Acad. Sci. USA*, vol. 89, 1992, pp. 1865-1869.
Cwirla, Steven E. et al., "Peptides on phage: A vast library of peptides for identifying ligands", *PNAS*, vol. 87, 1990, pp. 6378-6382.
Dafni, H. et al., "Overexpression of Vascular Endothelial Growth Factor 165 Drives Peritumor Interstitial Convection and Induces Lymphatic Drain: Magnetic Resonance Imaging, Confocal Microscopy, and Histological Tracking of Triple-labeled Albumin", *Cancer Research*. vol. 62, No. 15, Nov. 15, 2002, pp. 6731-6739.
Dawson, Philip et al., "Synthesis of Native Proteins by Chemical Ligation", Annu. Rev. Biochem., 69:, 2000, 923-960.
Dawson, Philip E. et al., "Synthesis of Proteins by Native Chemical Ligation", *Science*, vol. 266, 1994, pp. 776-779.
De Graaf, Albert et al., "Nonnatural Amino Acids for Site-Specific Protein Conjugation", *Bioconjugate Chem.*, vol. 20, No. 7, 2009, 1281-1295.
De Vega, Miguel et al., "Primer-terminus stabilization at the 3'-5' exonuclease active site of Phi29 DNA polymerase. Involvement of two amino acid residues highly conserved in proofreading DNA polymerases", *The EMBO Journal*, vol. 15 No. 5, 1996, 1182-1192.
Decher, G. et al., "Buildup of ultrathin multilayer films by a self-assembly process: III. Consecutively alternating adsorption of anionic and cationic polyelectrolytes on charged surfaces", *Thin Solid Films*, vol. 210-211, Part 2, 1992, pp. 831-835.
Delagrave, Simon et al., "Recursive ensemble mutagenesis", *Protein Engineering*, vol. 6, No. 3, 1993, 327-331.
Delagrave, Simon et al., "Searching Sequence Space to Engineer Proteins: Exponential Ensemble Mutagenesis", *Bio/Technology*, vol. 11, 1993, pp. 1548-1552.
Derfus, A. M. er al., "Nano Letters.", vol. 4. No. I, Dec. 10, 2003, pp. 11-18.
Deuschle, Karen et al., "Construction and optimization of a family of genetically encoded metabolite sensors by semirational protein engineering", *Protein Science*, vol. 14, Iss. 9, 14, 2005, 2304-2314.
Dilgimen, Aydan Salman et al., "Water-soluble covalent conjugates of bovine serum albumin with anionic poly(N-isopropyl-acrylamide) and their immunogenicity", *Biomaterials*, 22, 2001, 2383-2392.
Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, 1995, pp. 175-185.
Drosopoulos, W. et al., "Virtues of being faithful: Can we limit the genetic variation in Human Immunodeficiency Virus", *J. Molecular Medicine*, vol. 76 (9), Aug. 1998, pp. 604-612.
Dryden, D.T.F. et al., "Nucleoside triphosphate-dependent restriction enzymes", *Nucleic Acids Research*, vol. 29, No. 18, 2001, 3728-3741.
Eigen, Manfred et al., "The fifth Paul Ehrlich lecture virus strains as models of molecular evolution", *Medicinal Research Reviews*, vol. 13, No. 4 (XP000430626), Jul. 1993, 385-398.
Eschenmoser, Albert, "Chemical Etiology of Nucleic Acid Structure", *Science*, vol. 284, 1999, 2118-2124.
Fasman, Gerald D., "UV Spectral Characteristics and Acidic Dissociation Constants of 280 Alkyl Bases. Nucleosides and Nucleotides", *Practical Handbook of Biochemistry and Molecular Biology*, CRC Press, Boca Raton, FL, 1989, pp. 385-394.
Fazio, Teresa et al., "DNA Curtains and Nanoscale Curtain Rods: High-Throughput Tools for Single Molecule Imaging", *Langmuir*, vol. 24, 2008, 10524-10531.
Ferrero, Miguel et al., "Biocatalytic Selective Modifications of Conventional Nucleosides, Carbocyclic Nucleosides, and C-Nucleosides", *Chem. Rev.*, vol. 100, No. 12, 2000, 4319-4348.
Flemer, Stevenson et al., "Strategies for the Solid-Phase Diversification of Poly-L-proline-Type II Peptide Mimic Scaffolds and Peptide Scaffolds Through Guanidinylation", *J. Org. Chem.*, vol. 73, 2008, 7593-7602.
Forster, T., "Intermolecular energy migration and fluorescence", *Annalen der Physik*, vol. 437(1-2), 1948, 55-75.
Fu, Dong-Jing et al., "Sequencing double-stranded DNA by strand displacement", *Nucleic Acids Research*, vol. 25 (3), Feb. 1997, pp. 677-679.
Furey, W. S. et al., "Use of Fluorescence Resonance Energy Transfer to Investigate the Conformation of DNA Substrates Bound to the Klenow Fragment", *Biochemistry*, vol. 37, No. 9, 1998, 2979-2990.
Ge, Hui, "UPA, a universal protein array system for quantitative detection of protein-protein, protein-DNA, protein-RNA and protein-ligand interaction", *Nucleic Acids Research*, vol. 28(2), 2000, pp. i-vii.
Ghadessy, Farid J. et al., "Generic expansion of the substrate spectrum of a DNA polymerase by directed evolution", *Nature Biotech.*, vol. 22, No. 6, 2004, 755-759.
Gheorghe, Alexandru et al., "Combination of Perfluoroalkyl and Triazole Moieties: A New Recovery Strategy for TEMPT", Organic Letters, vol. 10, No. 19, 2008, 4171-4174.
Givens, R. et al., "New Photoactivated Protecting Groups", *J. Am. Chem. Soc.*, vol. 119, 1997, pp. 8369-8370.
Goldman, E. et al., "An Algorithmically Optimized Combinatorial Library Screened by Digital Imaging Spectroscopy", *Bio/Technology*, vol. 10, 1992, pp. 1557-1561.
Goldman, E. R. et al., "Luminescent Quantum Dot-Adaptor Protein-Antibody Conjugates for Use in Fluoroimmunoassays", *phys. stat. sol. (b)*, 229, No. 1, 2002, 407-414.
Goldman, Ellen et al., "Avidin: A Natural Bridge for Quantum Dot-Antibody Conjugates", *J. Am. Chem. Soc.*, 124, 2002, 6378-6382.
Goldman, Ellen et al., "Conjugation of Luminescent Quantum Dots with Antibodies Using an Engineered Adaptor Protein to Provide New Reagents for Fluoroimmunoassays", *Anal. Chem.*, 74, 2002, 841-847.
Goldman, Ellen et al., "Self-assembled luminescent CdSe—ZnS quantum dot bioconjugates prepared using engineered poly-histidine terminated proteins", *Analytica Chimica Acta*, 534, 2005, 63-67.
Gram, Hermann et al., "In vitro selection and affinity maturation of antibodies from a naive combinatorial immunoglobulin library", *PNAS*. vol. 89, 1992, pp. 3576-3580.
Guo, Zhen et al., "Direct fluorescence analysis of genetic polymorphisms by hybridization with oligonucleotide arrays on glass supports", *Nucleic Acids Research*, vol. 22, No. 24, 1994, 5456-5465.
Ha, Taekjip et al., "Initiation and re-initiation of DNA unwinding by the *Escherichia coli* Rep helicase", *Nature*, vol. 419, 2002, 638-641.
Haab, Brian B. et al., "Protein microarrays for highly parallel detection and quantitation of specific proteins and antibodies in complex solutions", *Genome Biology*, vol. 2, No. 2, 2001, 1-13.
Hainfeld, James F. et al., "Ni-NTA-Gold Clusters Target His-Tagged Proteins", *Journal of Structural Biology*, 127, 1999, 185-198.
Han, et al., "Quantum-dot-tagged Microbeads for Multiplexed Optical Coding of Biomolecules,", *Nature Biotech*, vol. 19, Jul. 2001, 631-635.
Harris, Timothy D. et al., "Single-Molecule DNA Sequencing of a Viral Genome", *Science*, vol. 320, 2008, 106-109.
Hermes, J, et al., "Searching sequence space by definably random mutagenesis: Improving the catalytic potency of an enzyme", *PNAS*, vol. 87, 1990, pp. 696-700.
Howarth, Mark et al., "Targeting quantum dots to surface proteins in living cells with biotin ligase", *PNAS*, vol. 102, No. 21, 2005, 7583-7588.

(56) References Cited

OTHER PUBLICATIONS

Jaiswal, Jyoti et al., "Use of quantum dots for live cell imaging", *Nature Methods*, vol. 1, No. 1, 2004, 71-78.
Jares-Erijman, Elizabeth A. et al., "FRET imaging", *Nature Biotechnology*, vol. 21, No. 2003, 1387-1395.
Jauffred, Liselotte et al., "Three-Dimensional Optical Control of Individual Quantum Dots", *Nano Letter*, vol. 8, No. 10, 2008, 3376-3380.
Jeong, Lak S. et al., "Structure-activity relationships of .beta.-D-(2S,5R)- and .alpha.-D-(2S,5S)-1,3-oxathiolanyl nucleosides as potential anti-HIV agents", *J. Med. Chem.*, vol. 36, 1993, pp. 2627-2638.
Jewett, John et al., "Rapid Cu-Free Click Chemistry with Readily Synthesized Biarylazacyclooctynones", *J. Am. Chem. Soc.*, 132, 2010, 3688-3690.
Johnson, Erik et al., "Insights into the Mechanism and Catalysis of the Native Chemical Ligation Reaction", *J. Am. Chem. Soc.*, 128, 2006, 6640-6646.
Johnson, K., "Rapid kinetic analysis of mechanochemical adenosinetriphosphatases", *Methods Enzymol.*, vol. 134, 1986, pp. 677-705.
Joos, Beda et al., "Covalent Attachment of Hybridizable Oligonucleotides to Glass Supports", *Analytical Biochem.*, vol. 247(1), 1997, pp. 96-101.
Joshi, et al., "ATP Synthase Complex from Bovine Heart Mitochondria", *Journal of Biological Chemistry*, vol. 265, No. 24, 1990, 14518-14525.
Jung, et al., "Crosslinking of platelet glycoprotein lb by N-succinimidyl(4-azidophenyldithio)propionate and 3,3'-dithiobis(sulfosuccinimidyl propionate)", *Biochimica et Biophysica Acta*, vol. 761, No. 2, 1983, 152-162.
Kamiya, Mako et al., "Extension of the Applicable Range of Fluorescein: A Fluorescein-Based Probe for Western Blot Analysis", *Angew. Chem. Int. Ed.* vol. 44, 2005, 5439-5441.
Kamtekar, Satwik et al., "The phi29 DNA polymerase:protein-primer structure suggests a model for the initiation to elongation transition", *EMBO Journal*, vol. 25, No. 6, 2006, 1335-1343.
Kim, Hea O. et al., "1,3-Dioxolanylpurine nucleosides (2R,4R) and (2R,4S) with selective anti-HIV-1 activity in human lymphocytes", *J. Med. Chem.*, vol. 36, No. 1, 1993, 30-37.
Kiyonaka, Shigeki et al., "Semi-wet peptide/protein array using supramolecular hydrogel", *Nature Materials*, vol. 3, 2004, 58-64.
Kumar, Amarendra et al., "Inhibition of T7 RNA Polymerase: Transcription Initiation and Transition from Initiation to Elongation Are Inhibited by T7 Lysozyme via a Ternary Complex with RNA Polymerase and Promoter DNA", *Biochemistry*, vol. 36, No. 45, 1997, pp. 13954-13962.
Kumar, Shiv et al., "Terminal Phosphate Labeled Nucleotides: Synthesis, Applications, and Linker Effect on Incorporation by DNA Polymerases", *Nucleosides, Nucleotides and Nucleic Acids*, vol. 24, Nos. 5-7, 2005, 401-408.
Kunkel, Thomas A., "DNA replication fidelity", *Journal of Biological Chemistry*, vol. 267, No. 26, Sep. 15, 1992, 18251-18254.
Laitala, Ville et al., "Homogeneous Assay Based on Anti-Stokes' Shift Time-Resolved Fluorescence Resonance Energy-Transfer Measurement", *Analytical Chem.*, vol. 77, 2005, 1483-1487.
Lakowicz, J. R., "Energy Transfer", *Principles of Fluorescence Spectroscopy, 2nd Ed. Plenum Publishing Corp.*, New York, NY, 1999, 367-394.
Lamture, J. et al., "Direct detection of nucleic acid hybridization on the surface of a charge coupled device", *Nucleic Acids Research*, vol. 22(11), 1994, pp. 2121-2125.
Liu, Wenshe et al., "Genetic incorporation of unnatural amino acids into proteins in mammalian cells", *Nature Methods*, vol. 4, No. 3, 2007, 239-244.
Lundberg, Kelly S. et al., "High-fidelity amplification using a thermostabile DNA polymerase isolated from Pyrococcus furiosus", *Gene*, vol. 108, Elsevier Science Publishers B.V.,, 1991, 1-6.

Mac Beath, Gavin et al., "Printing Proteins as Microarrays for High-Throughput Function Determination", *Science*, vol. 289, 2000, 1760-1763.
Marshall, P. N., "Rules for the visible absorption spectra of halogenated Fluorescein dyes", *Histochemical Journal*, vol. 7, 1975, pp. 299-303.
Martinez, Carlos I. et al., "Acyclic nucleoside triphosphate analogs as terminators in biocatalytic DNA replication", *Bioorganic & Medicinal Chemistry Letters*, vol. 7(23), 1997, pp. 3013-3016.
Martinez, Carlos I. et al., "An allylic/acyclic adenosine nucleoside triphosphate for termination of DNA synthesis by DNA template-dependent polymerases", *Nucleic Acids Research*, vol. 27, No. 5, 1999, 1271-1274.
Matayoshi, et al., "Novel Fluoregenic Substrates for Assaying Retroviral Proteases by Resonance Energy Transfer", *Science*, vol. 247, Feb. 23, 1990, pp. 954-958.
Mathis, G., "Probing molecular interactions with homogeneous techniques based on rare earth cryptates and fluorescence energy transfer", *Clin. Chem.*, vol. 41, No. 9, 1995, pp. 1391-1397.
Matsumoto, et al., "Genbank Accession No. M33144", 1993.
Mattoussi, H. et al., "Bioconjugation of Highly Luminescent Colloidal CdSe—ZnS Quantum Dots with an Engineered Two-Domain Recombinant Protein", *Phys. Status Solido B-Basic Res.*, 224, No. 1, 2001, 277-283.
Mattoussi, H. et al., "Self-Assembly of CdSe—ZnS Quantum Dot Bioconjugates Using an Engineered Recombinant Protein", *J Am Chem Soc*, vol. 122, No. 49, Nov. 22, 2000, 12142-12150.
Mc Cafferty, J. et al., "Phage Antibodies: Filamentous Phage Displaying Antibody Variable Domains", *Nature*, vol. 348, 1990, pp. 552-554.
Medintz, et al., "A fluorescence resonance energy transfer-derived structure of a quantum dot-protein bioconjugate nanoassembly", *Proceedings of the National Academy of Sciences (PNAS)*, 101(26), 2004, 9612-9617.
Medintz, Igor L. et al., "Self-assembled nanoscale biosensors based on quantum dot FRET donors", *Nature Materials*, vol. 2, 2003, 630-638.
Megiatto, Jackson D. et al., "General Method for Synthesis of Functionalized Macrocycles and Catenanes Utilizing "Click" Chemistry", *J. Am. Chem. Soc.*, vol. 130, 2008, 12872-12873.
Meijer, Wilfried et al., "Phi29 Family of Phages", *Microbiology and Molecular Biology Reviews*, vol. 65, No. 2, 2001, 261-287.
Meisel, Andreas et al., "Type III restriction enzymes need two inversely oriented recognition sites for DNA cleavage", *Nature*, vol. 355, 1992, 467-469.
Moll, Jonathan R. et al., "Designed heterodimerizing leucine zippers with a ranger of pIs and stabilities up to 10-15 M", *Protein Science*, vol. 10, 2001, 649-655.
Murray, Noreen E., "Type I Restriction Systems: Sophisticated Molecular Machines (a Legacy of Bertani and Weigle)", *Microbiology and Molecular Biology Reviews*, vol. 64, No. 2, 2000, 412-434.
Nakaji-Hirabayashi, Tadashi et al., "Oriented immobilization of epidermal growth factor onto culture substrates for the selective expansion of neural stem cells", *Biomaterials*, vol. 28, No. 24. 2007, 3517-3529.
Nakanishi, Kazuhiro et al., "Recent Advances in Controlled Immobilization of Proteins onto the Surface of the Solid Substrate and Its Possible Application to Proteomics", *Current Proteomics*, vol. 5, 2008, 161-175.
Ngo, et al., "The Protein Folding Problem and Tertiary Structure Predict ion", Merz et al. (ed .), *Birkhauser*, Boston, MA, 1994, pp. 433 and 492-495.
Oliphant, Arnold R. et al., "Cloning of random-sequence oligodeoxynucleotides", *Gene*, vol. 44, Iss. 2-3, 1986, 177-183.
Park, et al., "Characterization of the Cell Surface Receptor for a Multi-Lineage Colony-Stimulating Factor (CSF-2alpha)", *Journal of Biological Chemistry*, vol. 261, No. 1, 1986, 205-210.
Park, Chan-Ho et al., "New Photoactivated Protecting Groups. 6. p-Hydroxyphenacyl: A Phototrigger for Chemical and Biochemical Probes1,2", *J. Am. Chem. Soc.*, vol. 119, No. 10, 1997, 2453-2463.
Patel, Smita et al., "Pre-Steady-State Kinetic Analysis of Processive DNA Replication Including Complete Characterization of an Exonuclease-Deficient Mutant", *Biochemistry*, 30, 1991, 511-525.

(56) References Cited

OTHER PUBLICATIONS

PCT/US01/21811, International Search Report mailed May 12, 2003.
PCT/US01/45819, International Search Report mailed Jun. 2, 2003.
PCTUS1028974, International Search Report and Written Opinion Received mailed on Jan. 26, 2011, 13 pgs.
PCTUS1050406, International Search Report and Written Opinion Received mailed on Feb. 21, 2011, 14pgs.
PCTUS2010028952, International Search Report and Written Opinion Received mailed on Mar. 29, 2011, 11 pgs.
PCTUS2010028967, International Search Report and Written Opinion Received mailed on Mar. 18, 2011, 10 pgs.
PCTUS2010028972, International Search Report and Written Opinion Received mailed on Jan. 21, 2011, 13 pgs.
Pease, Ann C. et al., "Light-Generated Oligonucleotide Arrays for Rapid DNA Sequence Analysis", *Proc. Natl. Acad. Sci.*, vol. 91, May 1994, 5022-5026.
Pecenkova, et al., "DNA Polymerase (Early Protein GP2)", *UniProt Accession* Q37882, Dec. 1998, 1-2.
Pecenkova, Tamara et al., "Bacteriophage B103: complete DNA sequence of its genome and relationship to other Bacillus phages", *Gene*, 199, 1997, 157-163.
Pingoud, Alfred et al., "Structure and function of type II restriction endonucleases", *Nucleic Acids Research*, vol. 29, No. 18, 2001, 3705-3727.
Piston, David W. et al., "Fluorescent protein FRET:the good, the bad and the ugly", *Trends Biochem. Sci.*, vol. 32, No. 9, 2007, 407-414.
Qu, Lianhua et al., "Alternative Routes Toward High Quality CdSe Nanocrystals", *Nano Letters*, vol. 1, No. 6, 2001, 333-337.
Rao, et al., "Oriented Immobilization of Proteins", *Mikrochim. Acta*, vol. 128, 1998, 127-143.
Richard, Jean-Alexandre et al., "7-Hydroxycoumarin—Hemicyanine Hybrids: A New Class of Far-Red Emitting Fluorogenic Dyes", *Organic Letters*, vol. 10, 2008, 4175-4178.
Rienitz, Axel et al., "On the fidelity of DNA polymerase alpha: the influence of alpha-thio dNTPs, Mn2+ and mismatch repair", *Nucleic Acids Research*, vol. 13, No. 15, 1985, 5685-5695.
Roettger, Michelle P. et al., "Mismatched and Matched dNTP Incorporation by DNA Polymerase #Proceed via Analogous Kinetic Pathways", *Biochemistry*, vol. 47, No. 37, 2008, 9718-9727.
Rogers, Yu-Hui et al., "Immobilization of Oligonucleotides onto a Glass Support via Disulfide Bonds: A Method for Preparation of DNA Microarrays", *Analytical Biochemistry*, vol. 266, 1999, 23-30.
Ronaghi, M et al., "Real-time DNA Sequencing Using Detection of Pyrophosphate Release", *Anal Biochem*, vol. 242(1), 1996, pp. 84-89.
Rothwell, Paul J. et al., "Structure and Mechanism of DNA Polymerases", *Advances in Protein Chemistry*, vol. 71, 2005, 401-440.
Sapsford, Kim E. et al., "Materials for Fluorescence Resonance Energy Transfer Analysis: Beyond Traditional Donor-Acceptor Combinations", *Angew. Chem. Int. Ed.*, vol. 45, 2006, 4562-4588.
Sarkez, A. et al., "A Fluorescence-based Assay for Analysis of Biotinylated Proteins and Nucleic Acids", *Biophysical Society 48th Annual Meeting*, Feb. 14, 2004, 1-6.
Schlageck, Joseph G. et al., "Spectroscopic techniques for study of phosphodiester bond formation of Escherichia coli RNA polymerase", *Journal of Biological Chemistry*, vol. 254, No. 23, Dec. 10, 1979, 12074-12077.
Schmitt, Christophe et al., "Kinetics of Formation and Functional Properties of Conjugates Prepared by Dry-State Incubation of Beta-Lactoglobulin/Acacia Gum Electrostatic Complexes", *J. Agric. Food Chem.*, 53, 2005, 9089-9099.
Schwartz, David C. et al., "Separation of Yeast Chromosome-Sized DNAs by Pulsed Field Gradient Gel Electrophoresis", *Cell*, vol. 37, 1984, 67-75.
Scott, Jamie K. et al., "Searching for Peptide Ligands with an Epitope Library", *Science*, vol. 249, 1990, 386-390.
Selvin, "Fluorescence Resonance Energy Transfer", *Methods in Enzymology*, vol. 246, 1995, 300-334.
Shao, Jun et al., "Unprotected Peptides as Building Blocks for the Synthesis of Peptide Dendrimers with Oxime, Hydrazone, and Thiazolidine Linkages", *J. Am. Chem. Soc.*, vol. 117, No. 14, 1995, 3893-3899.
Smith, J. J. et al., "Orthogonal Site-Specific Protein Modification by Engineering Reversible Thiol Protection Mechanisms", *Protein Science*, vol. 14, 2005, 64-73.
Soengas, Maria et al., "Site-directed mutagenesis at the Exo III motif of Phi29 DNA polymerase; overlapping structural domains for the 3'-5' exonuclease and strand-displacement activities", *The EMBO Journal*, vol. 1 1 No. 1 1, 1992, 4227-4237.
Sood, Anup et al., "Terminal Phosphate-Labeled Nucleotides with Improved Substrate Properties for Homogeneous Nucleic Acid Assays", *J. Am. Chem. Soc.*, vol. 127, No. 8, 2005, 2394-2395.
Steitz, Thomas, "DNA Polymerases: Structural Diversity and Common Mechanisms", *The Journal of Biological Chemistry*, vol. 274, No. 25, 1999, 17395-17398.
Stryer, "Fluorescence Energy Transfer as a Spectroscopic Ruler", *Annual Review of Biochemistry*, vol. 47, Jul. 1978, 819-846.
Sun, Lan et al., "Surface-Enhanced Raman Scattering Based Nonfluorescent Probe for Multiplex Detection", *Analytical Chemistry*, vol. 79, No. 11, 2007, 3981-3988.
Tolbert, Thomas et al., "Conjugation of Glycopeptide Thioesters to Expressed Protein Fragments", *Methods in Molecular Biology, Bioconjugation Protocols: Strategies and Methods*, 283, 2004, 255-266.
Tominaga, Jo et al., "An enzymatic strategy for site-specific immobilization of functional proteins using microbial transglutaminase", *Enzyme and Microbial Technology*, vol. 35, Iss. 6-7, 2004, 613-618.
Truniger, V. et al., "Phi29 DNA polymerase residue Leu384 , highly conserved in motif B of eukaryotic type DNA replicases, is involved in nucleotide insert ion fidelity", *The Journal of Biological Chemistry*. vol. 278 No. 35, Jun. 12, 2003, pp. 33482-33491.
Truniger, V. et al., "Two positively charged residues of phi29 DNA polymerase conserved in protein-primed DNA polymerases, are involved in stabil isation of the incoming nucleotide", *Journal of Molecular Biology*. vol. 335 No. 2, Jan. 9, 2004, pp. 481-494.
Tsai, Yu-Chih et al., "A New Paradigm for DNA Polymerase Specificity", *Biochemistry*, vol. 45, No. 32, 2006, 9675-9687.
Tsang, Shui Y. et al., "Copper-1,10-phenanthroline induces internucleosomal DNA fragmentation in HepG2 cells, resulting from direct oxidation by the hydroxyl radical", *Biochem. J.*, vol. 317, 1996, 13-16.
Tyagi, Sanjay et al., "Multicolor molecular beacons for allele discrimination", *Nature Biotechnology*, vol. 16, 1998, 49-53.
Tyagi, Sanjay, "Taking DNA probes into a protein world", *Nature Biotechnology*, vol. 14, 1996, 947-948.
Vallina-Garcia, Romina et al., "Oriented immobilisation of anti-pneumolysin Fab through a histidine tag for electrochemical immunosensors", *Biosensors and Bioelectronics*, vol. 23, Iss. 2, 2007, 210-217.
Watkins, Lucas P. et al., "Detection of Intensity Change Points in Time-Resolved Single-Molecule Measurements", *J. Phys. Chem. B.*, vol. 109(1), 2005, 617-628.
Werts, Michel P., "Mechanically Linked Polyrotaxanes: A Stepwise Approach", *Macromolecules*, vol. 36, Iss. 19, 2003, 7004-7013.
Wetmur, J. G., "DNA probes: applications of the principles of nucleic acid hybridization", *Crit. Rev. Biochem. Mol. Biol.*, vol. 26, Nos. 3-4, 1991, 227-259.
Williams, J. G. et al., "An artificial processivity clamp made with streptavidin facilitates oriented attachment of polymerase—DNA complexes to surfaces", *Nucleic Acid Research*. vol. 36. No. 18., Aug. 22, 2008, pp. e121.
Wong, Isaac et al., "An induced-fit kinetic mechanism for DNA replication fidelity: direct measurement by single-turnover kinetics", *Biochemistry*, vol. 30, No. 2, Jan. 1991, 526-537.
Wu, Felicia et al., "Synthesis and Properties of Adenosine-5'-triphosphoro-gamma-1-(5-sulfonic acid)naphthyl Ethylamidate: A Fluorescent Nucleotide Substrate for DNA-Dependent RNA Polymerase from Escherichia coli", *Archives of Biochemistry and Biophysics*, vol. 246, No. 2, 1986, 564-571.
Wu, P. et al., "Resonance Energy Transfer: Methods and Applications", *Anal. Biochem.*, vol. 218(1), 1994, pp. 1-13.

(56) References Cited

OTHER PUBLICATIONS

Xia, Jie et al., "Photolabile 'Caged' Fatty Acids Containing a 1-(2'Nitrophenyl)-1,2-Ethanediol Moiety", *Bioorganic & Medicinal Chemistry Letters*, vol. 7, Iss. 10, 1997, 1243-1248.

Xu, Yao et al., "Imaging protein interactions with bioluminescence resonance energy transfer (BRET) in plant and mammalian cells and tissues", *Proc. Natl. Acad. Sci.*, vol. 96, 1999, 151-156.

Yarbrough, L. R. et al., "Synthesis and properties of fluorescent nucleotide substrates for DNA-dependent RNA polymerases", *Journal of Biological Chemistry*, vol. 254, No. 23, Dec. 10, 1979, 12069-12073.

Yarbrough, Lynwood R., "Synthesis and Properties of a New Fluorescent Analog of ATP: Adenosine-5'-Triphosphoro-y-(5-SUlfonic Acid) Napthylamidate", *Biochemical and Biophysical Research Communications*, vol. 81, No. 1, Mar. 15, 1978, 35-41.

Yeo, Sanghak et al., "The patterned hydrophilic surfaces of glass slides to be applicable for the construction of protein chips", *Current Applied Physics*, vol. 6, 2006, 267-270.

Zarling, et al., "Mapping of Lymphocyte Surface Polypeptide Antigens by Chemical Cross-Linking with BSOCOES", *Journal of Immunology*, vol. 124, No. 2, 1980, 913-920.

Zhang, Kechun et al., "Artificial Polypeptide Scaffold for Protein Immobilization", *J. Am. Chem. Soc.*, vol. 127, No. 29, 2005, 10136-10137.

Zhu, Heng et al., "Analysis of Yeast Protein Kinases Using Protein Chips", *Nature Genetics*, vol. 26, 2000, 283-289.

Zhu, Heng et al., "Protein Chip Technology", *Curr. Opin. Chem. Biol.*, vol. 7, No. 1, 2003, 55-63.

SEQUENCE LISTING

```
<160> NUMBER OF SEQ ID NOS: 53

<210> SEQ ID NO 1
<211> LENGTH: 575
<212> TYPE: PRT
<213> ORGANISM: Bacillus sp.
<220> FEATURE:
<223> OTHER INFORMATION: Phage Phi-29

<400> SEQUENCE: 1
```

-continued

```
Met Lys His Met Pro Arg Lys Met Tyr Ser Cys Asp Phe Glu Thr Thr
 1               5                  10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                    100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
                195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415
```

```
Gly Glu Glu Glu Thr Lys Asp Pro Val Tyr Thr Pro Met Gly Val Phe
            420                 425                 430

Ile Thr Ala Trp Ala Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid

<400> SEQUENCE: 2

Asp Xaa Ser Leu Tyr Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 3

Lys Xaa Asn Ser Xaa Tyr Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus sequence
```

```
<400> SEQUENCE: 4

Tyr Gly Asp Thr Asp Ser
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid

<400> SEQUENCE: 5

Lys Xaa Tyr
1

<210> SEQ ID NO 6
<211> LENGTH: 572
<212> TYPE: PRT
<213> ORGANISM: Bacillus sp.
<220> FEATURE:
<223> OTHER INFORMATION: Phage Phi-29

<400> SEQUENCE: 6

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
```

```
                245                 250                 255
Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
            325                 330                 335

Tyr Glu Met Tyr Asn Val Glu Tyr Ile Asp Gly Phe Lys Phe Arg Glu
        340                 345                 350

Lys Thr Gly Leu Phe Lys Glu Phe Ile Asp Lys Trp Thr Tyr Val Lys
    355                 360                 365

Thr His Glu Lys Gly Ala Lys Lys Gln Leu Ala Lys Leu Met Phe Asp
370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
        420                 425                 430

Trp Ala Arg Phe Thr Thr Ile Thr Ala Ala Gln Ala Cys Tyr Asp Arg
    435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Ala Lys Glu Val Asp Gly Lys Leu Ile Glu
        500                 505                 510

Cys Ser Pro Asp Glu Ala Thr Thr Thr Lys Phe Ser Val Lys Cys Ala
    515                 520                 525

Gly Met Thr Asp Thr Ile Lys Lys Lys Val Thr Phe Asp Asn Phe Arg
530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 7
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30
```

```
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
 50                  55                  60
Ala Phe Ile Val Asn Trp Leu Glu His His Gly Phe Lys Trp Ser Asn
 65                  70                  75                  80
Glu Gly Leu Pro Asn Thr Tyr Asn Thr Ile Ile Ser Lys Met Gly Gln
                 85                  90                  95
Trp Tyr Met Ile Asp Ile Cys Phe Gly Tyr Lys Gly Lys Arg Lys Leu
            100                 105                 110
His Thr Val Ile Tyr Asp Ser Leu Lys Lys Leu Pro Phe Pro Val Lys
            115                 120                 125
Lys Ile Ala Lys Asp Phe Gln Leu Pro Leu Leu Lys Gly Asp Ile Asp
130                 135                 140
Tyr His Ala Glu Arg Pro Val Gly His Glu Ile Thr Pro Glu Glu Tyr
145                 150                 155                 160
Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
            195                 200                 205
Pro Lys Leu Ser Leu Pro Met Asp Lys Glu Ile Arg Arg Ala Tyr Arg
            210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
290                 295                 300
Pro Phe Phe Lys Gly Asn Glu Tyr Leu Lys Asn Ser Gly Ala Glu Pro
305                 310                 315                 320
Val Glu Leu Tyr Leu Thr Asn Val Asp Leu Glu Leu Ile Gln Glu His
                325                 330                 335
Tyr Glu Met Tyr Asn Val Glu Tyr Ile Asp Gly Phe Lys Phe Arg Glu
            340                 345                 350
Lys Thr Gly Leu Phe Lys Glu Phe Ile Asp Lys Trp Thr Tyr Val Lys
            355                 360                 365
Thr His Glu Lys Gly Ala Lys Lys Gln Leu Ala Lys Leu Met Leu Asn
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
```

-continued

```
                450                 455                 460
Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Arg
            530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 8
<211> LENGTH: 572
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240
```

Glu Gly Met Val Phe Asp Val Asn Ser Leu Tyr Pro Ser Gln Met Tyr
            245                 250                 255

Ser Arg Pro Leu Pro Tyr Gly Ala Pro Ile Val Phe Gln Gly Lys Tyr
        260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 9
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgcctcgca aaatgtttag ctgcgatttt gaaaccacca ccaaactgga tgattgtcgt    60
gtttgggcct atggctatat ggaaattggc aacctggata ttataaaaat cggcaatagc   120
ctggatgaat ttatgcagtg ggttatggaa attcaggccg atctgtattt tcataacctg   180

```
aaatttgatg gtgcctttat tgtgaattgg ctggaacatc atggctttaa atggtctaat      240
gaaggcctgc cgaataccta acaccatc attagcaaaa tgggccagtg gtatatgatt      300
gatatttgct ttggctataa aggcaaacgt aaactgcata ccgtgattta tgatagcctg      360
aaaaaactgc cgtttccggt gaaaaaaatc gccaaagatt tccaattacc tttactgaag      420
ggtgatattg attatcatgc agaacgtccg gttggtcatg aaattacacc ggaagaatat      480
gaatacatca agaatgatat tgaaattatt gcccgtgccc tggatattca gtttaaacag      540
ggtctggatc gtatgaccgc aggtagcgat tctctgaaag ctttaaaga tattctgagc      600 accaaaaaat taacaaagt gtttccgaaa ctgagcctgc cgatggataa agaaattcgt      660
cgtgcctatc gtggtggttt tacctggctg aatgataaat ataagaaaa agaaattggc      720 gaaggcatgg ttttgatgt taatagcctg tatccgagcc agatgtatag ccgtccgctg      780
ccgtatggtg caccgattgt gtttcagggc aaatatgaaa aagatgaaca gtatccgctg      840
tatattcagc gcatccgctt tgaatttgaa ctgaaagaag ctatatccc gaccatccag      900 attaaaaaaa atccgttttt taaaggcaac gaatatctga aaaatagcgg tgcagaaccg      960
gttgaactgt atctgaccaa tgtggatctg gaactgatcc aggaacatta tgaaatgtac     1020
aacgtggaat atattgatgg ttttaaattt cgcgaaaaaa ccggtctgtt taaagagttc     1080
attgataaat ggacctatgt gaaaacccat gaaaaaggtg caaaaaaaca gctggccaaa     1140
ctgatgttga attccctgta tggcaaattt gcaagcaatc cggatgttac cggtaaagtt     1200
ccgtatctga agaagatgg tagcctgggt tttcgtgttg gtgatgaaga atataaagat     1260
ccggtttata ccccgatggg tgttttttat accgcatggg cacgttttac caccattacc     1320
gcagcacagg catgttatga ccgcattatt tattgcgata ccgatagcat tcatctgacc     1380
ggcaccgaag ttccggaaat tattaaagat attgttgatc gaaaaaact gggttattgg     1440 gcacatgaaa gcacctttaa acgtgcaaaa tatctgcgcc agaaaaccta tattcaggat     1500
atttatgcca agaagtgga cggtaaactg attgaatgtt ctccggatga agcaaccacc     1560
acaaaattta gcgttaaatg cgcaggtatg accgatacca ttaaaaaaaa agtgacctt     1620 gataactttc gtgtgggttt tagcagcacc ggtaaaccga accggttca ggttaatggt     1680 ggtgttgttc tggttgatag cgtgtttacc attaaataa                            1719
```

<210> SEQ ID NO 10
<211> LENGTH: 1716
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgcctagaa aaatgtttag ttgtgacttt gagacgacta caaagttaga cgattgtcgt       60
gtatgggcat atggctatat ggaaatcggt aatctcgaca actacaagat tggaaatagc      120
ttagatgaat tcatgcagtg ggttatggaa attcaagctg atttatattt ccacaatcta      180
aaatttgacg tgctttcat tgtaaactgg ttagagcatc atggttttaa gtggtcaaac      240
gaagggttac cgaatactta aacacaata atatcaaaaa tgggtcaatg gtatatgatt      300
gacatatgtt tcggctataa gggaaaacgg aaattacata cagtgatata cgacagctta      360
aagaaattgc cgttcccagt aaagaaaata gcgaaagatt ttcaattacc gttattgaag      420
ggtgacattg attaccacgc tgaacgtcct gttggacatg agataacacc cgaagaatac      480
```

```
gagtatatta agaacgacat agaaattatc gcacgtgcac ttgacattca atttaaacag      540
ggtttagacc gaatgacagc tgggagcgat agccttaaag ggtttaagga catacttagc      600
accaagaaat ttaacaaggt gtttcctaag cttagcctac caatggataa agaaataagg      660
cgagcttatc gtggtggctt cacatggtta acgataaat acaaagaaaa agagattggt       720
gaaggtatgg tgtttgacgt taacagccta tacccagtc agatgtattc ccgaccactc       780
ccgtacggag cgccaatcgt attccaagga agtatgaga aagatgagca atatccgctc       840
tatatacagc gtatcagatt tgagtttgaa ttgaaagagg ctatatacc cacaattcag       900 attaagaaaa atccctttt taagggtaat gagtatctta aaaacagtgg cgctgagcct       960
gttgaactat atcttactaa tgtagattta gaattaatac aggaacacta cgaaatgtat      1020
aacgttgagt atattgacgg atttaaattc cgtgaaaaga ctggattatt caaagagttt      1080
attgataaat ggacatatgt aaaaactcat gaaaagggag ctaagaaaca attggctaag     1140
ctaatgttga atagtctcta tggtaaattt gcaagtaacc ctgacgttac aggtaaagtc      1200
ccttatttaa agaagatgg gagccttggt ttccgtgttg gtgatgagga atataaagac       1260 cctgttata cacctatggg tgtgtttata acggcatggg ctagatttac aactataaca       1320
gcggcacaag cgtgttacga tagaattata tattgtgaca ctgatagtat acatttaaca      1380
ggtacagaag taccagaaat aataaaggat attgttgatc caaaaaagtt agggtactgg      1440
gcgcatgaaa gcacatttaa gagagcaaaa tatttacgtc agaaaacgta tattcaagac     1500
atatatgcga aagaggttga cggtaaattg atagagtgtt cacctgatga agctacgaca      1560
actaaattca gtgtgaaatg tgccggaatg actgacacta tcaaaagaa agtcacattt       1620 gataacttta gagttggttt cagtagcacg ggtaaaccta aaccagttca agttaatggc      1680 gggggtagtgt tggttgatag tgtgtttacg attaaa                              1716

<210> SEQ ID NO 11
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgcctcgca aaatgtttag ctgcgatttt gaaaccacca ccaaactgga tgattgtcgt       60
gtttgggcct atggctatat ggaaattggc aacctggata attataaaat cggcaatagc      120
ctggatgaat ttatgcagtg ggttatggaa attcaggccg atctgtattt tcataacctg      180
aaatttgatg gtgcctttat tgtgaattgg ctggaacatc atggctttaa atggtctaat      240
gaaggcctgc cgaatacccta taacaccatc attagcaaaa tgggccagtg gtatatgatt     300
gatatttgct ttggctataa aggcaaacgt aaactgcata ccgtgattta tgatagcctg     360
aaaaaactgc cgtttccggt gaaaaaaatc gccaaagatt tccaattacc tttactgaag     420
ggtgatattg attatcatgc agaacgtccg gttggtcatg aaattacacc ggaagaatat     480
gaatacatca gaatgctat tgaattatt gcccgtgccc tggatattca gtttaaacag      540
ggtctggatc gtatgaccgc aggtagcgat tctctgaaag gctttaaaga tattctgagc     600
accaaaaaat ttaacaaagt gtttccgaaa ctgagcctgc cgatggataa agaaattcgt     660
cgtgcctatc gtggtggttt tacctggctg aatgataaat ataagaaaaa agaaattggc     720
gaaggcatgg ttttttgatgt taatagcctg tatccgagcc agatgtatag ccgtccgctg      780
```

```
ccgtatggtg caccgattgt gtttcagggc aaatatgaaa aagatgaaca gtatccgctg      840
tatattcagc gcatccgctt tgaatttgaa ctgaaagaag gctatatccc gaccatccag      900
attaaaaaaa atccgttttt taaaggcaac gaatatctga aaaatagcgg tgcagaaccg      960
gttgaactgt atctgaccaa tgtggatctg aactgatcc aggaacatta tgaaatgtac      1020
aacgtggaat atattgatgg ttttaaattt cgcgaaaaaa ccggtctgtt taaagagttc      1080
attgataaat ggacctatgt gaaaacccat gaaaaaggtg caaaaaaaca gctggccaaa      1140
ctgatgttga attccctgta tggcaaattt gcaagcaatc cggatgttac cggtaaagtt      1200
ccgtatctga agaagatgg tagcctgggt tttcgtgttg gtgatgaaga atataaagat       1260
ccggtttata ccccgatggg tgttttttatt accgcatggg cacgttttac caccattacc      1320
gcagcacagg catgttatga ccgcattatt tattgcgata ccgatagcat tcatctgacc       1380
ggcaccgaag ttccggaaat tattaaagat attgttgatc gaaaaaact gggttattgg       1440 gcacatgaaa gcacctttaa acgtgcaaaa tatctgcgcc agaaaaccta tattcaggat      1500
atttatgcca agaagtgga cggtaaactg attgaatgtt ctccggatga agcaaccacc       1560
acaaaattta gcgttaaatg cgcaggtatg accgatacca ttaaaaaaaa agtgaccttt       1620
gataactttc gtgtgggttt tagcagcacc ggtaaaccga aaccggttca ggttaatggt      1680
ggtgttgttc tggttgatag cgtgtttacc attaaataa                             1719

<210> SEQ ID NO 12
<211> LENGTH: 1716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgcctagaa aaatgtttag ttgtgacttt gagacgacta caaagttaga cgattgtcgt       60
gtatgggcat atggctatat ggaaatcggt aatctcgaca actacaagat tggaaatagc       120
ttagatgaat tcatgcagtg ggttatggaa attcaagctg attatatttt ccacaatcta       180
aaatttgacg gtgctttcat tgtaaactgg ttagagcatc atggttttaa gtggtcaaac      240
gaagggttac cgaatactta taacacaata atatcaaaaa tgggtcaatg gtatatgatt       300
gacatatgtt tcggctataa gggaaaacgg aaattacata cagtgatata cgacagctta      360
aagaaattgc cgttcccagt aaagaaaata gcgaaagatt ttcaattacc gttattgaag      420
ggtgacattg attccacgc tgaacgtcct gttggacatg agataacacc cgaagaatac      480
gagtatatta agaacgccat agaaattatc gcacgtgcac ttgacattca atttaaacag      540
ggtttagacc gaatgacagc tgggagcgat agccttaaag ggtttaagga catacttagc      600
accaagaaat ttaacaaggt gtttcctaag cttagcctac caatgataa agaaataagg       660 cgagcttatc gtggtggctt cacatggtta acgataaat acaagaaaa agagattggt        720 gaaggtatgg tgtttgacgt taacagccta taccccagtc agatgtattc ccgaccactc     780
ccgtacggag cgccaatcgt attccaagga agtatgaga aagatgagca atatccgctc     840
tatatacagc gtatcagatt tgagtttgaa ttgaaagagg gctatatacc cacaattcag       900
attaagaaaa tccctttttt taagggtaat gagtatctta aaaacagtgg cgctgagcct      960
gttgaactat atcttactaa tgtagattta gaattaatac aggaacacta cgaaatgtat      1020
aacgttgagt atattgacgg atttaaattc cgtgaaaaga ctggattatt caaagagttt     1080
```

```
attgataaat ggacatatgt aaaaactcat gaaaagggag ctaagaaaca attggctaag    1140
ctaatgttga atagtctcta tggtaaattt gcaagtaacc ctgacgttac aggtaaagtc    1200
ccttatttaa aagaagatgg gagccttggt ttccgtgttg gtgatgagga atataaagac    1260
cctgttaata cacctatggg tgtgtttata acggcatggg ctagatttac aactataaca    1320
gcggcacaag cgtgttacga tagaattata tattgtgaca ctgatagtat acatttaaca    1380
ggtacagaag taccagaaat aataaaggat attgttgatc aaaaaagtt agggtactgg     1440 gcgcatgaaa gcacatttaa gagagcaaaa tatttacgtc agaaaacgta tattcaagac    1500
atatatgcga aagaggttga cggtaaattg atagagtgtt cacctgatga agctacgaca    1560
actaaattca gtgtgaaatg tgccggaatg actgacacta tcaaaaagaa agtcacattt    1620
gataacttta gagttggttt cagtagcacg ggtaaaccta aaccagttca agttaatggc    1680
ggggtagtgt tggttgatag tgtgtttacg attaaa                               1716
```

<210> SEQ ID NO 13
<211> LENGTH: 572
<212> TYPE: PRT
<213> ORGANISM: Bacillus sp.
<220> FEATURE:
<223> OTHER INFORMATION: Phage M2Y

<400> SEQUENCE: 13

```
Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
```

245                 250                 255
Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
                355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
                435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
    515                 520                 525

Gly Met Thr Asp Thr Ile Lys Lys Lys Val Thr Phe Asp Asn Phe Ala
    530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 14
<211> LENGTH: 572
<212> TYPE: PRT
<213> ORGANISM: Bacillus sp.
<220> FEATURE:
<223> OTHER INFORMATION: Phage Nf

<400> SEQUENCE: 14

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val

```
                35                  40                  45
Met Glu Ile Gln Ala Asp Leu Tyr Phe His Asn Leu Lys Phe Asp Gly
 50                  55                  60

Ala Phe Ile Val Asn Trp Leu Glu Gln His Gly Phe Lys Trp Ser Asn
 65                  70                  75                  80

Glu Gly Leu Pro Asn Thr Tyr Asn Thr Ile Ser Lys Met Gly Gln
                 85                  90                  95

Trp Tyr Met Ile Asp Ile Cys Phe Gly Tyr Arg Gly Lys Arg Lys Leu
                100                 105                 110

His Thr Val Ile Tyr Asp Ser Leu Lys Lys Leu Pro Phe Pro Val Lys
                115                 120                 125

Lys Ile Ala Lys Asp Phe Gln Leu Pro Leu Leu Lys Gly Asp Ile Asp
            130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
                340                 345                 350

Lys Thr Gly Leu Phe Lys Asp Phe Ile Asp Lys Trp Thr Tyr Val Lys
            355                 360                 365

Thr His Glu Glu Gly Ala Lys Lys Gln Leu Ala Lys Leu Met Leu Asn
        370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460
```

Pro Glu Ile Ile Lys Asp Ile Val Asp Pro Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Ala
            530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 15
<211> LENGTH: 903
<212> TYPE: PRT
<213> ORGANISM: Unknown
<220> FEATURE:
<223> OTHER INFORMATION: Description of Unknown: Enterobacteria phage
      RB69

<400> SEQUENCE: 15

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met

-continued

```
                245                 250                 255
Tyr Gly Ser Arg Glu Ile Ile Thr Leu Phe Gly Ile Ser Val Leu Asp
                260                 265                 270
Tyr Ile Asp Leu Tyr Lys Lys Phe Ser Phe Thr Asn Gln Pro Ser Tyr
            275                 280                 285
Ser Leu Asp Tyr Ile Ser Glu Phe Glu Leu Asn Val Gly Lys Leu Lys
        290                 295                 300
Tyr Asp Gly Pro Ile Ser Lys Leu Arg Glu Ser Asn His Gln Arg Tyr
305                 310                 315                 320
Ile Ser Tyr Asn Ile Ile Asp Val Tyr Arg Val Leu Gln Ile Asp Ala
                325                 330                 335
Lys Arg Gln Phe Ile Asn Leu Ser Leu Asp Met Gly Tyr Tyr Ala Lys
            340                 345                 350
Ile Gln Ile Gln Ser Val Phe Ser Pro Ile Lys Thr Trp Asp Ala Ile
        355                 360                 365
Ile Phe Asn Ser Leu Lys Glu Gln Asn Lys Val Ile Pro Gln Gly Arg
    370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Leu Tyr
                405                 410                 415
Pro Ser Ile Ile Arg Gln Val Asn Ile Ser Pro Glu Thr Ile Ala Gly
            420                 425                 430
Thr Phe Lys Val Ala Pro Leu His Asp Tyr Ile Asn Ala Val Ala Glu
        435                 440                 445
Arg Pro Ser Asp Val Tyr Ser Cys Ser Pro Asn Gly Met Met Tyr Tyr
    450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
                485                 490                 495
Glu Ile Ile Lys Glu Ala Leu His Asn Pro Asn Leu Ser Val Asp Glu
            500                 505                 510
Pro Leu Asp Val Asp Tyr Arg Phe Asp Phe Ser Asp Glu Ile Lys Glu
        515                 520                 525
Lys Ile Lys Lys Leu Ser Ala Lys Ser Leu Asn Glu Met Leu Phe Arg
    530                 535                 540
Ala Gln Arg Thr Glu Val Ala Gly Met Thr Ala Gln Ile Asn Arg Lys
545                 550                 555                 560
Leu Leu Ile Asn Ser Leu Tyr Gly Ala Leu Gly Asn Val Trp Phe Arg
                565                 570                 575
Tyr Tyr Asp Leu Arg Asn Ala Thr Ala Ile Thr Thr Phe Gly Gln Met
            580                 585                 590
Ala Leu Gln Trp Ile Glu Arg Lys Val Asn Glu Tyr Leu Asn Glu Val
        595                 600                 605
Cys Gly Thr Glu Gly Glu Ala Phe Val Leu Tyr Gly Asp Thr Asp Ser
    610                 615                 620
Ile Tyr Val Ser Ala Asp Lys Ile Ile Asp Lys Val Gly Glu Ser Lys
625                 630                 635                 640
Phe Arg Asp Thr Asn His Trp Val Asp Phe Leu Asp Lys Phe Ala Arg
                645                 650                 655
Glu Arg Met Glu Pro Ala Ile Asp Arg Gly Phe Arg Glu Met Cys Glu
            660                 665                 670
```

```
Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
    690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
                740                 745                 750

Leu Gln Glu Gly Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Lys Val Tyr Val
                820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Leu Gly Ala Ala Lys Gly Ala Ala Lys Gly Ser Ala Ala
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Gly Gly Gly Ser Gly Gly Gly Ser Ala Ala Ala Gly
1               5                   10                  15

Ser Ala Ala

<210> SEQ ID NO 18
<211> LENGTH: 597
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Met Asn His Leu Val His His His His His Ile Glu Gly Arg His
1               5                   10                  15

Met Glu Leu Gly Thr Leu Glu Gly Ser Met Pro Arg Lys Met Phe Ser
            20                  25                  30

Cys Asp Phe Glu Thr Thr Thr Lys Leu Asp Asp Cys Arg Val Trp Ala
        35                  40                  45

Tyr Gly Tyr Met Glu Ile Gly Asn Leu Asp Asn Tyr Lys Ile Gly Asn
    50                  55                  60

Ser Leu Asp Glu Phe Met Gln Trp Val Met Glu Ile Gln Ala Asp Leu
65                  70                  75                  80

Tyr Phe His Asn Leu Lys Phe Asp Gly Ala Phe Ile Val Asn Trp Leu
                85                  90                  95

Glu His His Gly Phe Lys Trp Ser Asn Glu Gly Leu Pro Asn Thr Tyr
            100                 105                 110

Asn Thr Ile Ile Ser Lys Met Gly Gln Trp Tyr Met Ile Asp Ile Cys
        115                 120                 125

Phe Gly Tyr Lys Gly Lys Arg Lys Leu His Thr Val Ile Tyr Asp Ser
    130                 135                 140

Leu Lys Lys Leu Pro Phe Pro Val Lys Lys Ile Ala Lys Asp Phe Gln
145                 150                 155                 160

Leu Pro Leu Leu Lys Gly Asp Ile Asp Tyr His Ala Glu Arg Pro Val
                165                 170                 175

Gly His Glu Ile Thr Pro Glu Glu Tyr Glu Tyr Ile Lys Asn Asp Ile
            180                 185                 190

Glu Ile Ile Ala Arg Ala Leu Asp Ile Gln Phe Lys Gln Gly Leu Asp
        195                 200                 205

Arg Met Thr Ala Gly Ser Asp Ser Leu Lys Gly Phe Lys Asp Ile Leu
    210                 215                 220

Ser Thr Lys Lys Phe Asn Lys Val Phe Pro Lys Leu Ser Leu Pro Met
225                 230                 235                 240

Asp Lys Glu Ile Arg Arg Ala Tyr Arg Gly Gly Phe Thr Trp Leu Asn
                245                 250                 255

Asp Lys Tyr Lys Glu Lys Glu Ile Gly Glu Gly Met Val Phe Asp Val
            260                 265                 270

Asn Ser Leu Tyr Pro Ser Gln Met Tyr Ser Arg Pro Leu Pro Tyr Gly
        275                 280                 285

Ala Pro Ile Val Phe Gln Gly Lys Tyr Glu Lys Asp Glu Gln Tyr Pro
    290                 295                 300

Leu Tyr Ile Gln Arg Ile Arg Phe Glu Phe Glu Leu Lys Glu Gly Tyr
305                 310                 315                 320

Ile Pro Thr Ile Gln Ile Lys Lys Asn Pro Phe Phe Lys Gly Asn Glu
                325                 330                 335

Tyr Leu Lys Asn Ser Gly Ala Glu Pro Val Glu Leu Tyr Leu Thr Asn
            340                 345                 350

Val Asp Leu Glu Leu Ile Gln Glu His Tyr Glu Met Tyr Asn Val Glu
        355                 360                 365

Tyr Ile Asp Gly Phe Lys Phe Arg Glu Lys Thr Gly Leu Phe Lys Glu
    370                 375                 380

```
Phe Ile Asp Lys Trp Thr Tyr Val Lys Thr His Glu Lys Gly Ala Lys
385                 390                 395                 400

Lys Gln Leu Ala Lys Leu Met Leu Asn Ser Leu Tyr Gly Lys Phe Ala
                405                 410                 415

Ser Asn Pro Asp Val Thr Gly Lys Val Pro Tyr Leu Lys Glu Asp Gly
            420                 425                 430

Ser Leu Gly Phe Arg Val Gly Asp Glu Glu Tyr Lys Asp Pro Val Tyr
            435                 440                 445

Thr Pro Met Gly Val Phe Ile Thr Ala Trp Ala Arg Phe Thr Thr Ile
    450                 455                 460

Thr Ala Ala Gln Ala Cys Tyr Asp Arg Ile Ile Tyr Cys Asp Thr Asp
465                 470                 475                 480

Ser Ile His Leu Thr Gly Thr Glu Val Pro Glu Ile Ile Lys Asp Ile
            485                 490                 495

Val Asp Pro Lys Lys Leu Gly Tyr Trp Ala His Glu Ser Thr Phe Lys
            500                 505                 510

Arg Ala Lys Tyr Leu Arg Gln Lys Thr Tyr Ile Gln Asp Ile Tyr Ala
            515                 520                 525

Lys Glu Val Asp Gly Lys Leu Ile Glu Cys Ser Pro Asp Glu Ala Thr
            530                 535                 540

Thr Thr Lys Phe Ser Val Lys Cys Ala Gly Met Thr Asp Thr Ile Lys
545                 550                 555                 560

Lys Lys Val Thr Phe Asp Asn Phe Arg Val Gly Phe Ser Ser Thr Gly
                565                 570                 575

Lys Pro Lys Pro Val Gln Val Asn Gly Gly Val Val Leu Val Asp Ser
            580                 585                 590

Val Phe Thr Ile Lys
            595

<210> SEQ ID NO 19
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met His His His His His Lys His Met Pro Arg Lys Met Phe Ser
1               5                   10                  15

Cys Asp Phe Glu Thr Thr Thr Lys Leu Asp Asp Cys Arg Val Trp Ala
                20                  25                  30

Tyr Gly Tyr Met Glu Ile Gly Asn Leu Asp Asn Tyr Lys Ile Gly Asn
            35                  40                  45

Ser Leu Asp Glu Phe Met Gln Trp Val Met Glu Ile Gln Ala Asp Leu
50                  55                  60

Tyr Phe His Asn Leu Lys Phe Asp Gly Ala Phe Ile Val Asn Trp Leu
65                  70                  75                  80

Glu His His Gly Phe Lys Trp Ser Asn Glu Gly Leu Pro Asn Thr Tyr
                85                  90                  95

Asn Thr Ile Ile Ser Lys Met Gly Gln Trp Tyr Met Ile Asp Ile Cys
            100                 105                 110

Phe Gly Tyr Lys Gly Lys Arg Lys Leu His Thr Val Ile Tyr Asp Ser
            115                 120                 125

Leu Lys Lys Leu Pro Phe Pro Val Lys Lys Ile Ala Lys Asp Phe Gln
```

```
                130                 135                 140
Leu Pro Leu Lys Gly Asp Ile Asp Tyr His Ala Glu Arg Pro Val
145                 150                 155                 160

Gly His Glu Ile Thr Pro Glu Tyr Glu Tyr Ile Lys Asn Asp Ile
                165                 170                 175

Glu Ile Ile Ala Arg Ala Leu Asp Ile Gln Phe Lys Gln Gly Leu Asp
                180                 185                 190

Arg Met Thr Ala Gly Ser Asp Ser Leu Lys Gly Phe Lys Asp Ile Leu
                195                 200                 205

Ser Thr Lys Lys Phe Asn Lys Val Phe Pro Lys Leu Ser Leu Pro Met
210                 215                 220

Asp Lys Glu Ile Arg Arg Ala Tyr Arg Gly Gly Phe Thr Trp Leu Asn
225                 230                 235                 240

Asp Lys Tyr Lys Glu Lys Glu Ile Gly Glu Gly Met Val Phe Asp Val
                245                 250                 255

Asn Ser Leu Tyr Pro Ser Gln Met Tyr Ser Arg Pro Leu Pro Tyr Gly
                260                 265                 270

Ala Pro Ile Val Phe Gln Gly Lys Tyr Glu Lys Asp Glu Gln Tyr Pro
                275                 280                 285

Leu Tyr Ile Gln Arg Ile Arg Phe Glu Phe Glu Leu Lys Glu Gly Tyr
                290                 295                 300

Ile Pro Thr Ile Gln Ile Lys Lys Asn Pro Phe Phe Lys Gly Asn Glu
305                 310                 315                 320

Tyr Leu Lys Asn Ser Gly Ala Glu Pro Val Glu Leu Tyr Leu Thr Asn
                325                 330                 335

Val Asp Leu Glu Leu Ile Gln Glu His Tyr Glu Met Tyr Asn Val Glu
                340                 345                 350

Tyr Ile Asp Gly Phe Lys Phe Arg Glu Lys Thr Gly Leu Phe Lys Glu
                355                 360                 365

Phe Ile Asp Lys Trp Thr Tyr Val Lys Thr His Glu Lys Gly Ala Lys
                370                 375                 380

Lys Gln Leu Ala Lys Leu Met Leu Asn Ser Leu Tyr Gly Lys Phe Ala
385                 390                 395                 400

Ser Asn Pro Asp Val Thr Gly Lys Val Pro Tyr Leu Lys Glu Asp Gly
                405                 410                 415

Ser Leu Gly Phe Arg Val Gly Asp Glu Glu Tyr Lys Asp Pro Val Tyr
                420                 425                 430

Thr Pro Met Gly Val Phe Ile Thr Ala Trp Ala Arg Phe Thr Thr Ile
                435                 440                 445

Thr Ala Ala Gln Ala Cys Tyr Asp Arg Ile Ile Tyr Cys Asp Thr Asp
                450                 455                 460

Ser Ile His Leu Thr Gly Thr Glu Val Pro Glu Ile Ile Lys Asp Ile
465                 470                 475                 480

Val Asp Pro Lys Lys Leu Gly Tyr Trp Ala His Glu Ser Thr Phe Lys
                485                 490                 495

Arg Ala Lys Tyr Leu Arg Gln Lys Thr Tyr Ile Gln Asp Ile Tyr Ala
                500                 505                 510

Lys Glu Val Asp Gly Lys Leu Ile Glu Cys Ser Pro Asp Glu Ala Thr
                515                 520                 525

Thr Thr Lys Phe Ser Val Lys Cys Ala Gly Met Thr Asp Thr Ile Lys
                530                 535                 540

Lys Lys Val Thr Phe Asp Asn Phe Arg Val Gly Phe Ser Ser Thr Gly
545                 550                 555                 560
```

Lys Pro Lys Pro Val Gln Val Asn Gly Gly Val Val Leu Val Asp Ser
            565                 570                 575

Val Phe Thr Ile Lys
            580

<210> SEQ ID NO 20
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30

Met Tyr Ser Cys Ala Phe Glu Thr Thr Lys Val Glu Asp Cys Arg
            35                  40                  45

Val Trp Ala Tyr Gly Tyr Met Asn Ile Glu Asp His Ser Glu Tyr Lys
50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
            130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
            210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
            290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys

```
                325                 330                 335
Gly Asn Glu Tyr Leu Lys Ser Ser Gly Gly Glu Ile Ala Asp Leu Trp
            340                 345                 350
Leu Ser Asn Val Asp Leu Glu Leu Met Lys Glu His Tyr Asp Leu Tyr
        355                 360                 365
Asn Val Glu Tyr Ile Ser Gly Leu Lys Phe Lys Ala Thr Thr Gly Leu
    370                 375                 380
Phe Lys Asp Phe Ile Asp Lys Trp Thr Tyr Ile Lys Thr Thr Ser Glu
385                 390                 395                 400
Gly Ala Ile Lys Gln Leu Ala Lys Leu Met Leu Asn Ser Leu Tyr Gly
                405                 410                 415
Lys Phe Ala Ser Asn Pro Asp Val Thr Gly Lys Val Pro Tyr Leu Lys
            420                 425                 430
Glu Asn Gly Ala Leu Gly Phe Arg Leu Gly Glu Glu Thr Lys Asp
        435                 440                 445
Pro Val Tyr Thr Pro Met Gly Val Phe Ile Thr Ala Trp Ala Arg Tyr
    450                 455                 460
Thr Thr Ile Thr Ala Ala Gln Ala Cys Tyr Asp Arg Ile Ile Tyr Cys
465                 470                 475                 480
Asp Thr Asp Ser Ile His Leu Thr Gly Thr Glu Ile Pro Asp Val Ile
                485                 490                 495
Lys Asp Ile Val Asp Pro Lys Lys Leu Gly Tyr Trp Ala His Glu Ser
            500                 505                 510
Thr Phe Lys Arg Ala Lys Tyr Leu Arg Gln Lys Thr Tyr Ile Gln Asp
        515                 520                 525
Ile Tyr Met Lys Glu Val Asp Gly Lys Leu Val Glu Gly Ser Pro Asp
    530                 535                 540
Asp Tyr Thr Asp Ile Lys Phe Ser Val Lys Cys Ala Gly Met Thr Asp
545                 550                 555                 560
Lys Ile Lys Lys Glu Val Thr Phe Glu Asn Phe Lys Val Gly Phe Ser
                565                 570                 575
Arg Lys Met Lys Pro Lys Pro Val Gln Val Pro Gly Gly Val Val Leu
            580                 585                 590
Val Asp Asp Thr Phe Thr Ile Lys
        595                 600

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtactaagc ggccgcatg                                                   19

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tttttttcat gcggccgctt agtacc                                           26
```

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaaaaacat gcggccgctt agtacc                                          26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 cccccccat gcggccgctt agtacc                                           26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gggggggcat gcggccgctt agtacc                                          26

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctcgcagc cgtccaacca actcc                                           25

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cagtaacgga gttggttgga cggctgcgag gc                                   32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cagtaaggga gttggttgga cggctgcgag gc                                   32

```
<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cagtaaagga gttggttgga cggctgcgag gc                                        32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagtaatgga gttggttgga cggctgcgag gc                                        32

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttgcaaagg agcgggcg                                                        18

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgttccccgc ccgctccttt gcaac                                                25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgttccgcgc ccgctccttt gcaac                                                25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgttccacgc ccgctccttt gcaac                                                25

<210> SEQ ID NO 35
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cgttcctcgc ccgctccttt gcaac                                           25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcctcgcagc cgtccaacca actcc                                           25

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgccaccgga gttggttgga cggctgcgag gc                                   32

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttttttttac ccccgggtga caggtt                                          26

<210> SEQ ID NO 39
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tttttccccg acgatgcctc cccgacacgg aggttctatc atcgtcatcg tcatcgtcat     60
cg                                                                   62

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgatagaacc tccgtgtc                                                   18
```

```
<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggggaggcat cgtcgggaaa a                                              21

<210> SEQ ID NO 42
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

Met Ser His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Phe Ser Cys Asp Phe Glu Thr
        35                  40                  45

Thr Thr Lys Leu Asp Asp Cys Arg Val Trp Ala Tyr Gly Tyr Met Glu
50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His Gly Phe
            100                 105                 110

Lys Trp Ser Asn Glu Gly Leu Pro Asn Thr Tyr Asn Thr Ile Ile Ser
        115                 120                 125

Lys Met Gly Gln Trp Tyr Met Ile Asp Ile Cys Phe Gly Tyr Lys Gly
130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ala Arg
        195                 200                 205

Ala Leu Asp Ile Gln Phe Lys Gln Gly Leu Asp Arg Met Thr Ala Gly
        210                 215                 220

Ser Asp Ser Leu Lys Gly Phe Lys Asp Ile Leu Ser Thr Lys Phe
225                 230                 235                 240

Asn Lys Val Phe Pro Lys Leu Ser Leu Pro Met Asp Lys Glu Ile Arg
                245                 250                 255

Arg Ala Tyr Arg Gly Gly Phe Thr Trp Leu Asn Asp Lys Tyr Lys Glu
            260                 265                 270

Lys Glu Ile Gly Glu Gly Met Val Phe Asp Val Asn Ser Leu Tyr Pro
        275                 280                 285

Ser Gln Met Tyr Ser Arg Pro Leu Pro Tyr Gly Ala Pro Ile Val Phe
        290                 295                 300

Gln Gly Lys Tyr Glu Lys Asp Glu Gln Tyr Pro Leu Tyr Ile Gln Arg
305                 310                 315                 320

Ile Arg Phe Glu Phe Glu Leu Lys Glu Gly Tyr Ile Pro Thr Ile Gln
                325                 330                 335

Ile Lys Lys Asn Pro Phe Phe Lys Gly Asn Glu Tyr Leu Lys Asn Ser
            340                 345                 350

Gly Ala Glu Pro Val Glu Leu Tyr Leu Thr Asn Val Asp Leu Glu Leu
        355                 360                 365

Ile Gln Glu His Tyr Glu Met Tyr Asn Val Glu Tyr Ile Asp Gly Phe
370                 375                 380

Lys Phe Arg Glu Lys Thr Gly Leu Phe Lys Glu Phe Ile Asp Lys Trp
385                 390                 395                 400

Thr Tyr Val Lys Thr Arg Glu Lys Gly Ala Lys Lys Gln Leu Ala Lys
                405                 410                 415

Leu Met Leu Asn Ser Leu Tyr Gly Lys Phe Ala Ser Asn Pro Asp Val
            420                 425                 430

Thr Gly Lys Val Pro Tyr Leu Lys Glu Asp Gly Ser Leu Gly Phe Arg
        435                 440                 445

Val Gly Asp Glu Glu Tyr Lys Asp Pro Val Tyr Thr Pro Met Gly Val
450                 455                 460

Phe Ile Thr Ala Trp Ala Arg Phe Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Val Pro Glu Ile Ile Lys Asp Ile Val Asp Pro Lys Lys
            500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Ala Lys Glu Val Asp Gly
530                 535                 540

Lys Leu Ile Glu Cys Ser Pro Asp Glu Ala Thr Thr Thr Lys Phe Ser
545                 550                 555                 560

Val Lys Cys Ala Gly Met Thr Asp Thr Ile Lys Lys Lys Val Thr Phe
                565                 570                 575

Asp Asn Phe Arg Val Gly Phe Ser Ser Thr Gly Lys Pro Lys Pro Val
            580                 585                 590

Gln Val Asn Gly Gly Val Val Leu Val Asp Ser Val Phe Thr Ile Lys
        595                 600                 605

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tttttttgca ggtgacaggt ttttcctgtc acctgc                                 36

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgttaaccgc ccgctccttt gcaac                                    25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gttgcaaagg agcgggcg                                            18

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cagtaacgga gttggttgga cggctgcgag gc                            32

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctcgcagc cgtccaacca actcc                                    25

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 48

His His His His His His
1               5

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttcctgtcac cc                                                  12

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 50
gggggtaaaa aaaa                                                   14

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Asn His Leu Val His His His His His Ile Glu Gly Arg His
1               5                   10                  15

Met Glu Leu Gly Thr Leu Glu Gly Ser
            20                  25

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met His His His His His His Lys His
1               5

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Leu Asn Asp Ile Phe Glu Ala Gln Lys Ile Glu Trp His Glu
1               5                   10                  15
```

POLYMERASE COMPOSITIONS AND METHODS

CROSS-REFERENCE TO RELATED APPLICATIONS

This application is a continuation of U.S. Nonprovisional application Ser. No. 13/540,935, filed Jul. 3, 2012, which is a continuation of U.S. Nonprovisional application Ser. No. 12/748,359, filed Mar. 26, 2010 and now abandoned, which claims the filing date benefit of U.S. Provisional Application Nos. 61/164,324, filed on Mar. 27, 2009; 61/184,770, filed on Jun. 5, 2009; 61/242,771, filed on Sep. 15, 2009; 61/245,457, filed on Sep. 24, 2009; 61/263,974, filed on Nov. 24, 2009; 61/289,388; filed on Dec. 22, 2009; 61/293,618, filed on Jan. 8, 2010; 61/293,616, filed on Jan. 8, 2010; 61/299,919, filed on Jan. 29, 2010; 61/299,917, filed on Jan. 29, 2010; 61/307,356, filed on Feb. 23, 2010. The contents of each of the foregoing patent applications are incorporated by reference in their entirety.

The instant application contains a Sequence Listing which has been submitted electronically in ASCII format and is hereby incorporated by reference in its entirety. Said ASCII copy, created on Apr. 21, 2015, is named LT00052CON_SL.txt and is 78,446 bytes in size.

FIELD

The disclosure relates generally to polymerase compositions and methods. More particularly, the disclosure relates to modified polymerases and their use in biological applications including, for example, nucleotide incorporation, primer extension and single molecule sequencing reactions.

BACKGROUND

The polymerases typically catalyze nucleic acid synthesis against an existing polynucleotide template using Watson-Crick base pairing interactions, and are useful in a variety of biological applications. Such applications frequently involve the use of labels to visualize one or more components or products of the polymerase reaction. For example, "sequencing by synthesis" applications typically involve the monitoring of polymerase activity in real time by detecting signals emitted by labels associated with one or more components of the polymerase reaction. However, many labels cannot be employed in such assays because their presence inhibits polymerase activity. For example, although nanoparticles can exhibit superior quantum yield, size tunability, brightness and resistance to photobleaching compared to conventional organic, e.g., dye, labels, their utility in polymerase-based assays is hampered by the sensitivity of many polymerases to the presence of nanoparticles. Furthermore, many polymerases can also exhibit loss of polymerase activity upon exposure to excitation radiation, thus hampering their use in assays involving labels that require excitation to be detectable. This problem can be exacerbated in the presence of nanoparticles, resulting in further loss of polymerase activity.

Yet another set of problems revolves around the kinetic behavior of the polymerase towards nucleotide substrates. Analysis of polymerase activity can be complicated by undesirable behavior such as, for example, the tendency of a given polymerase to dissociate from the template; to bind and/or incorporate the incorrect, e.g., non Watson-Crick base-paired, nucleotide; or to release the correct, e.g., Watson-Crick based paired, nucleotide without incorporation. In addition, some applications may require the use of polymerases exhibiting increased residence times or branching ratios for particular nucleotides, so as to increase the duration during which labeled nucleotide incorporation can be detected. Finally, although many biological applications require the use of labeled nucleotides, many polymerases do not incorporate such nucleotides efficiently, thus limiting the utility of such polymerase-nucleotide combinations in these applications. These and other desirable properties can be enhanced via suitable selection, engineering and/or modification of a polymerase of choice.

It is therefore desirable to develop polymerases having increased tolerance for the presence of both organic (e.g., conventional dye) and inorganic (e.g., nanoparticle-based) labels, as well as polymerases that retain higher levels of polymerase activity following exposure to excitation radiation. There is also a need for polymerases that exhibit improved reaction kinetics with a particular set of labeled nucleotides. Accordingly, there remains a need in the art for improved polymerase compositions, and methods of use thereof, which can permit polynucleotide synthesis with higher efficiency while allowing the use of an expanded repertoire of excitation and/or labeling strategies.

SUMMARY

Provided herein are novel polymerase compositions, methods of making such compositions and methods of using such compositions in various biological applications.

In some embodiments, the present disclosure relates to a modified DNA polymerase having a photostability that is at least about 80% under standard photostability assay conditions.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard photostability assay conditions.

In some embodiments, the present disclosure relates to a modified DNA polymerase having a nanoparticle tolerance that is at least about 80% under standard nanoparticle tolerance assay conditions.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard nanoparticle tolerance assay conditions.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard nanoparticle tolerance assay conditions.

In some embodiments, the disclosure relates to a nucleic acid molecule encoding any one, some or all of the modified DNA polymerases of the present disclosure. The nucleic acid molecule can optionally be DNA or RNA.

In some embodiments, the disclosure relates to a vector comprising a DNA encoding any one, some or all of the modified DNA polymerases as provided herein.

In some embodiments, the disclosure relates to an isolated host cell comprising a vector including a DNA encoding any one, some or all of the modified DNA polymerases of the present disclosure.

In some embodiments, the disclosure relates to a method for obtaining the modified DNA polymerases of the present disclosure. Optionally, the method comprises purifying the modified DNA polymerase from an isolated host cell comprising a vector including a DNA encoding a modified DNA polymerase of the present disclosure.

In some embodiments, the disclosure relates to a method for performing a primer extension reaction, comprising: contacting a modified DNA polymerase as provided herein with a nucleic acid molecule and a nucleotide under conditions where the nucleotide is incorporated into the nucleic acid molecule by the modified DNA polymerase. Optionally, the nucleotide is a labeled nucleotide, and the label of the nucleotide emits a signal during incorporation of the at least one nucleotide. Optionally, the method further comprises detecting the signal emitted by the nucleotide label. Optionally, the method further comprises analyzing the detected signal to determine the identity of the incorporated nucleotide.

In some embodiments, the disclosure relates to a modified DNA polymerase having an increased branching ratio in the presence of labeled nucleotides relative to a DNA polymerase having the amino acid sequence of SEQ ID NO: 7. In some embodiments, the modified DNA polymerase comprising an amino acid sequence that is at least about 95% identical to the amino acid sequence of SEQ ID NO: 7. Optionally, the modified DNA polymerase further includes the amino acid mutation H370R.

DETAILED DESCRIPTION OF THE DRAWINGS

The following figures form part of the present specification and are included to further demonstrate certain aspects of the disclosure by way of illustrating non-limiting embodiments and examples. The disclosure may be better understood by reference to one or more of these figures in combination with the detailed description of specific embodiments presented herein.

Figure 3:
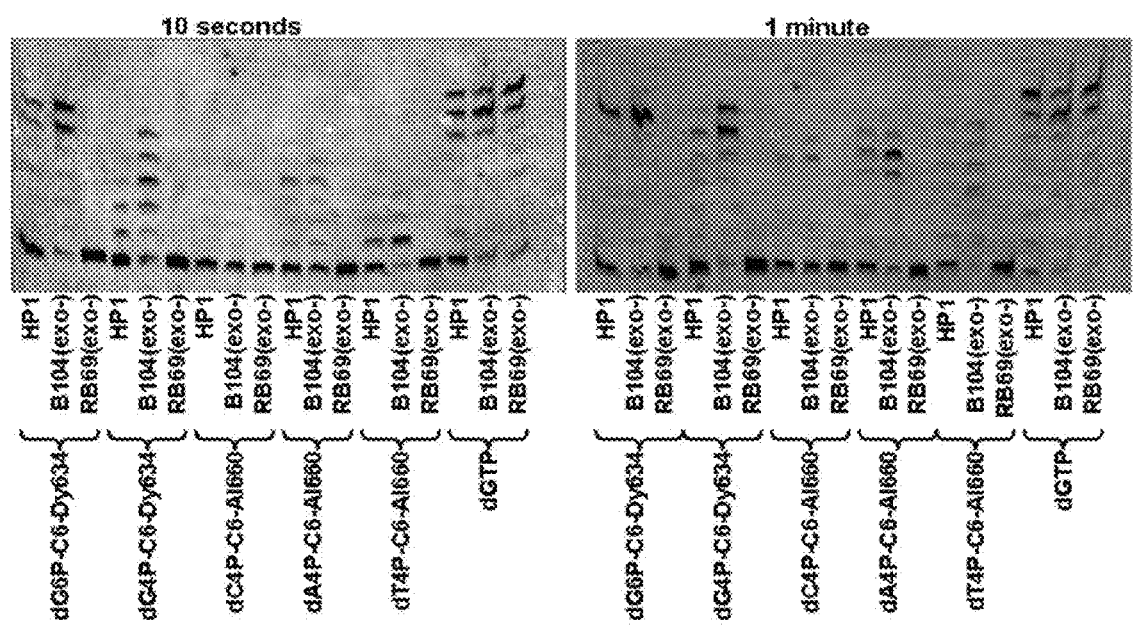

FIG. 3 depicts the results of an assay measuring the fractional extension activity, i.e., the fraction of nucleic acid templates that are extended by at least one nucleotide in a polymerase reaction, of an exemplary modified polymerase comprising the amino acid sequence of SEQ ID NO: 8, and two exemplary reference polymerases comprising the amino acid sequences of SEQ ID NO: 15 and SEQ ID NO: 20, respectively.

Figure 4:
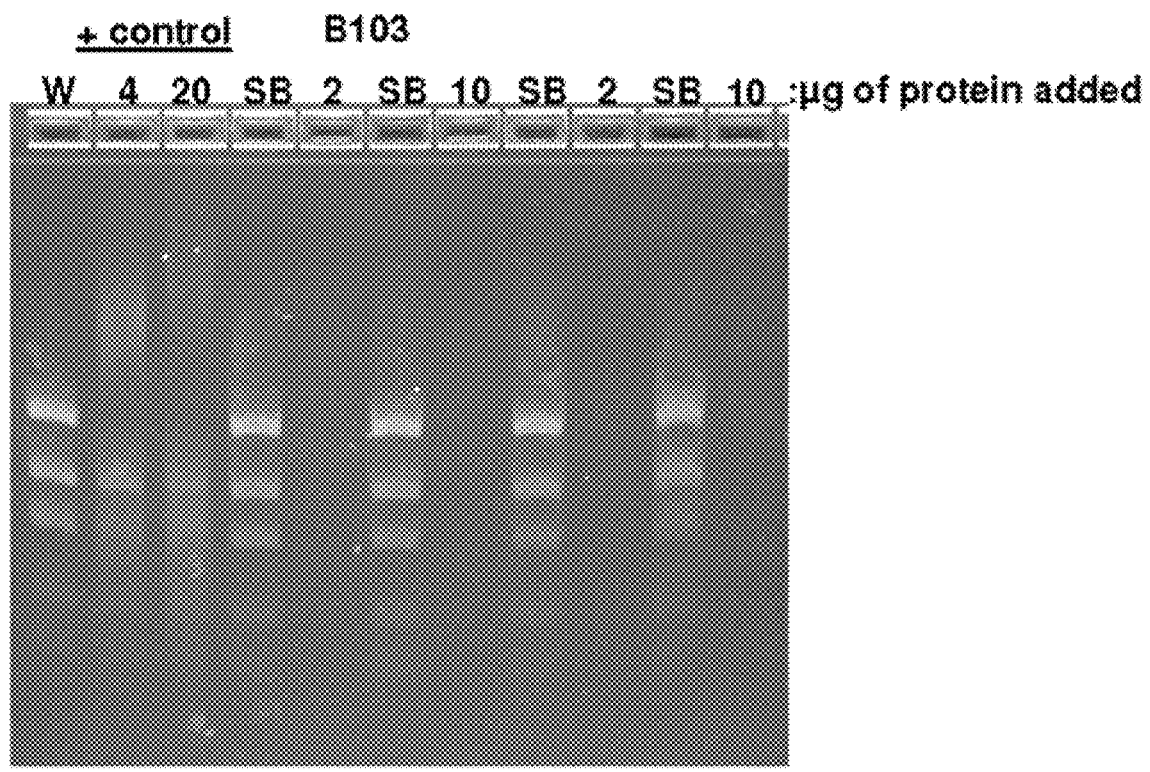

FIG. 4 depicts the results of an assay measuring the exonuclease activity of T7 DNA polymerase, an exemplary reference polymerase, and of an exemplary modified variant comprising the amino acid sequence of SEQ ID NO: 7.

Figure 5:
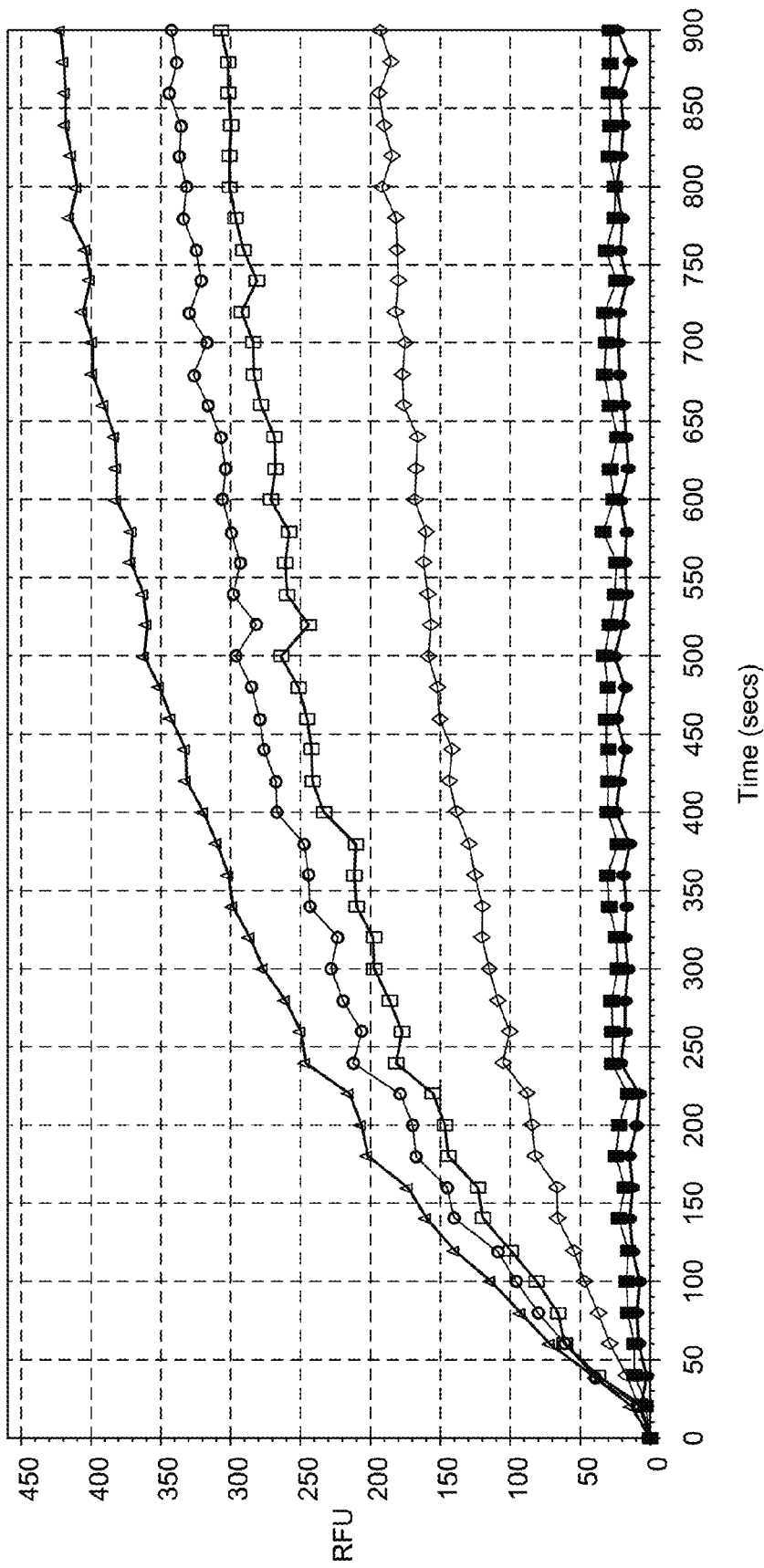

FIG. 5 depicts the results of an assay measuring the nanoparticle tolerance of an exemplary modified polymerase comprising the amino acid sequence of SEQ ID NO: 19, and an exemplary reference polymerase comprising the amino acid sequence of SEQ ID NO: 20.

Figure 6A:
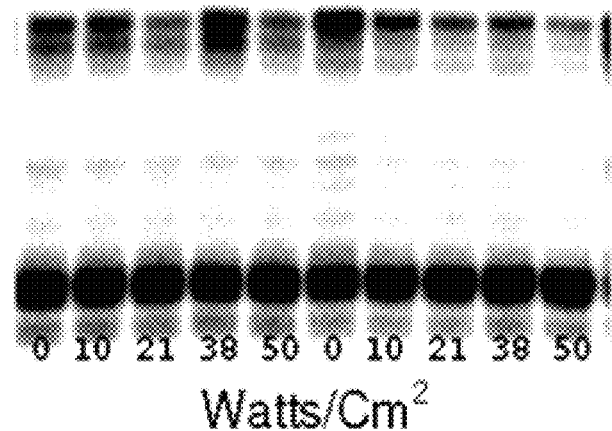
Figure 6B:
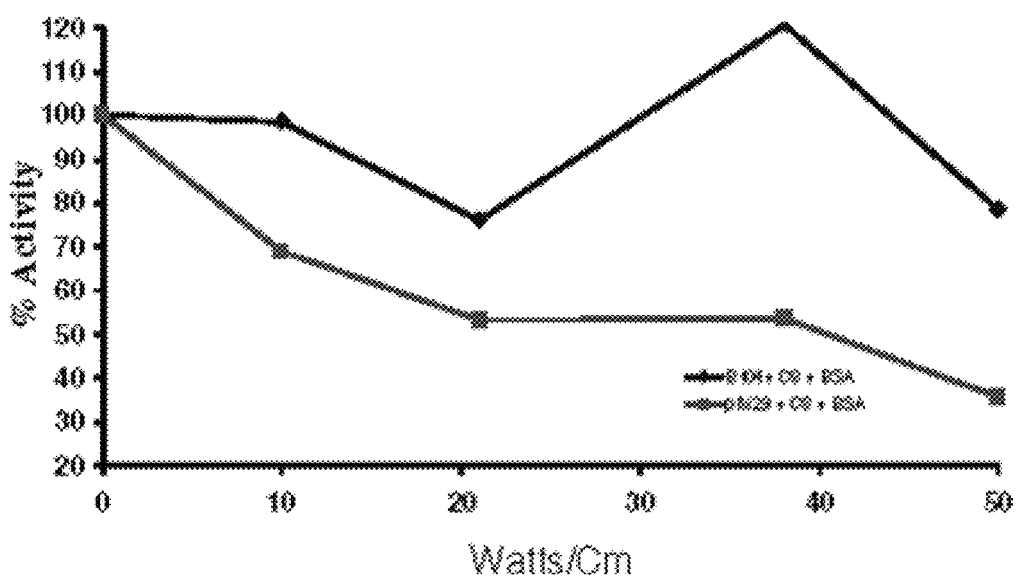

FIG. 6A depicts the results of an assay measuring the photostability of an exemplary modified polymerase comprising the amino acid sequence of SEQ ID NO: 19, and an exemplary reference polymerase comprising the amino acid sequence of SEQ ID NO: 20. FIG. 6A shows a polyacrylamide gel loaded with primer extension reactions of B104 and phi29 polymerases exposed to excitation radiation. FIG. 6B also depicts the results of an assay measuring the photostability of an exemplary modified polymerase comprising the amino acid sequence of SEQ ID NO: 19, and an exemplary reference polymerase comprising the amino acid sequence of SEQ ID NO: 20. FIG. 6B shows a graph of the primer extension reactions of B104 and phi29 polymerases exposed to excitation radiation.

Figure 7A:
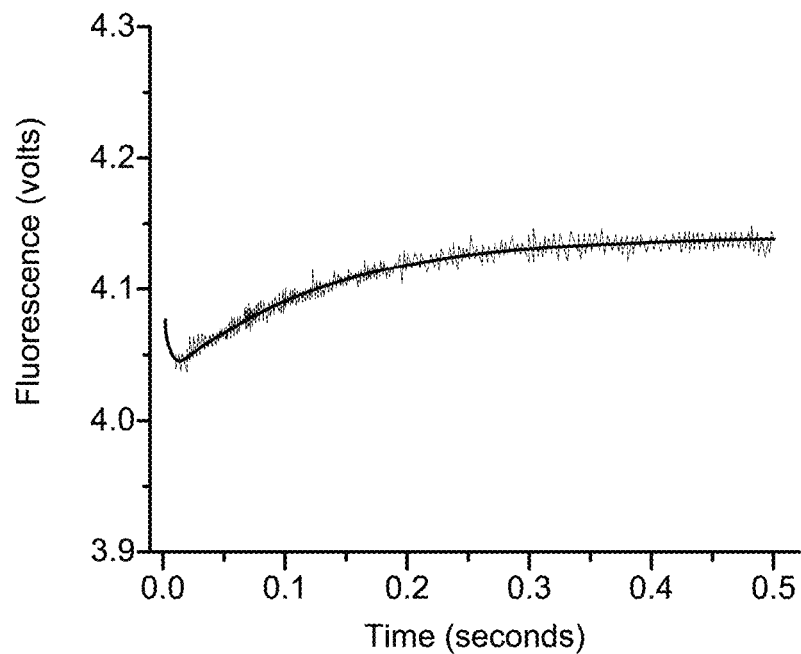
Figure 7B:
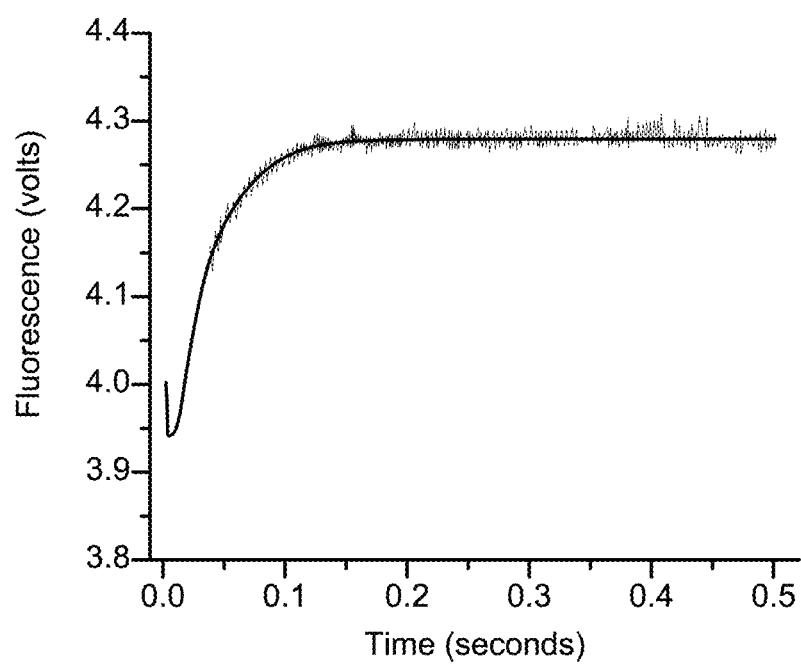
Figure 7C:
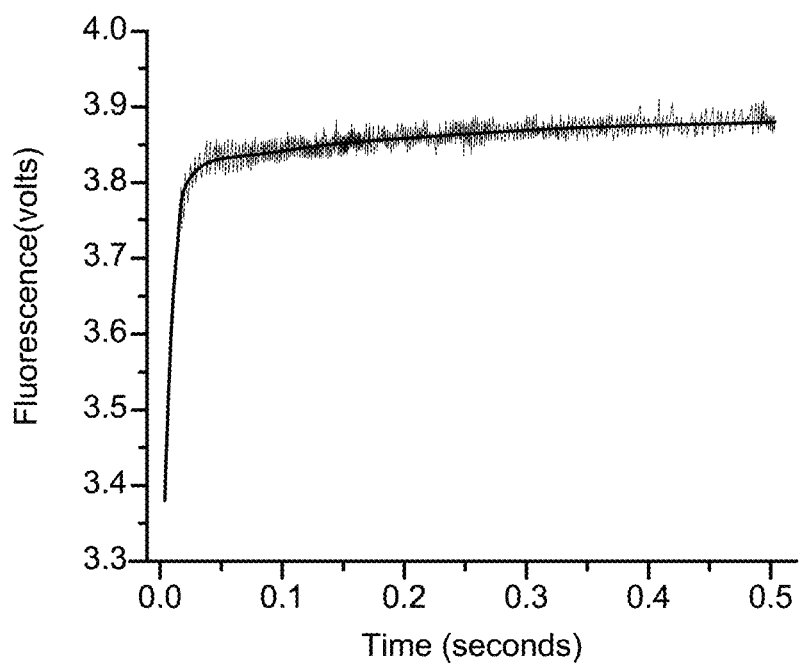

FIG. 7A depicts time traces of fluorescence at 550 nm from three different stopped-flow assay systems, each comprising a mutant Phi-29 polymerase. FIG. 7A shows a time trace of a mutant Phi-29 polymerase and terminally labeled nucleotide triphosphates. FIG. 7B depicts time traces of fluorescence at 550 nm from three different stopped-flow assay systems, each comprising a mutant Phi-29 polymerase. FIG. 7B shows a time trace of a mutant Phi-29 polymerse and a terminally labeled nucleotide tetraphosphates. FIG. 7C depicts time traces of fluorescence at 550 nm from three different stopped-flow assay systems, each comprising a mutant Phi-29 polymerase. FIG. 7C shows a time trace of a mutant Phi-29 polymerase and a terminally labeled nucleotide hexaphosphates.

Figure 8A:
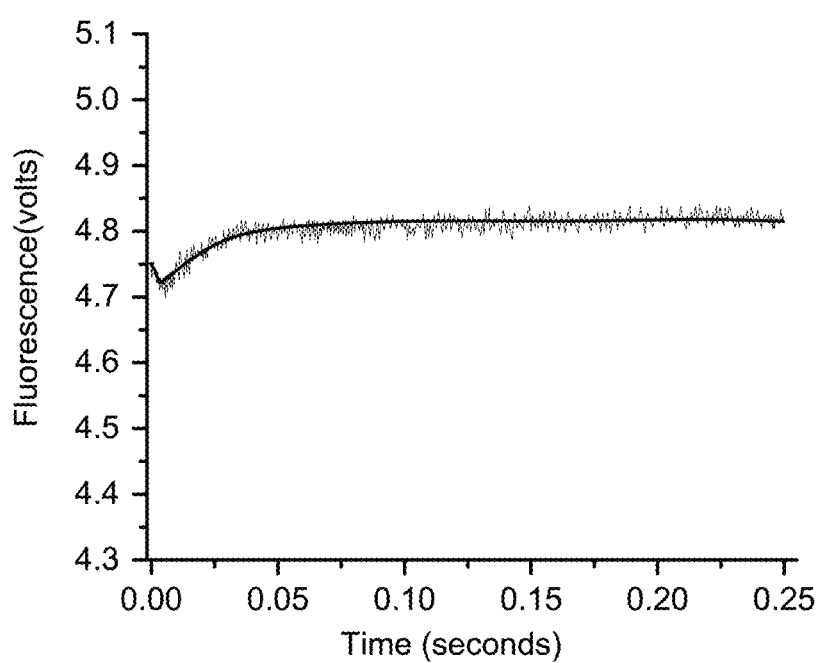
Figure 8B:
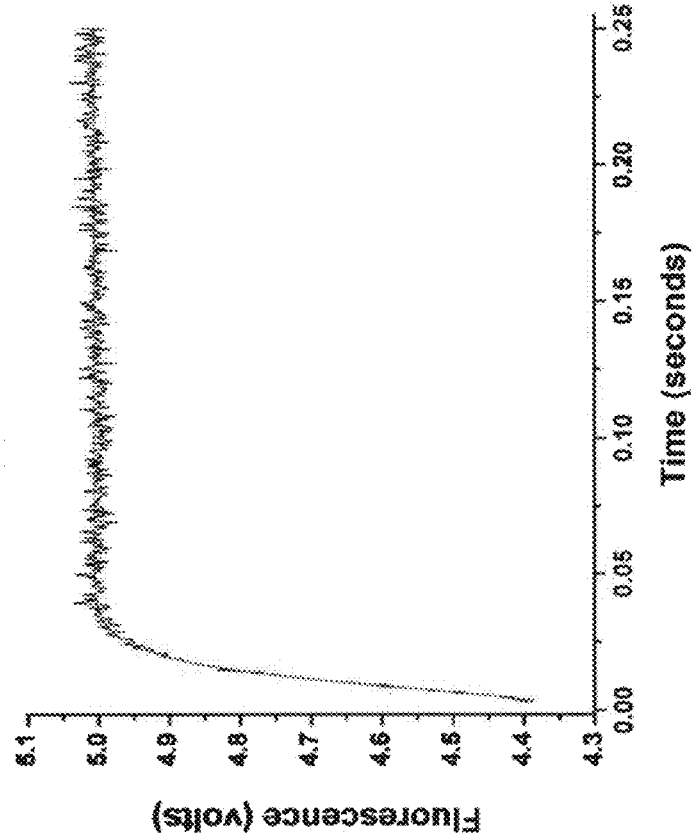

FIG. 8A depicts time traces of fluorescence at 550 nm from two different stopped-flow assay systems, each comprising different mutant Phi-29 polymerase. FIG. 8A shows a time trace of a mutant Phi-29 polymerase and terminally labeled nucleotide hexaphosphates. FIG. 8B depicts time traces of fluorescence at 550 nm from two different stopped-flow assay systems, each comprising different mutant Phi-29 polymerase. FIG. 8B shows a time trace of a mutant Phi-29 polymerase and terminally labeled nucleotide hexaphosphates.

Figure 9:
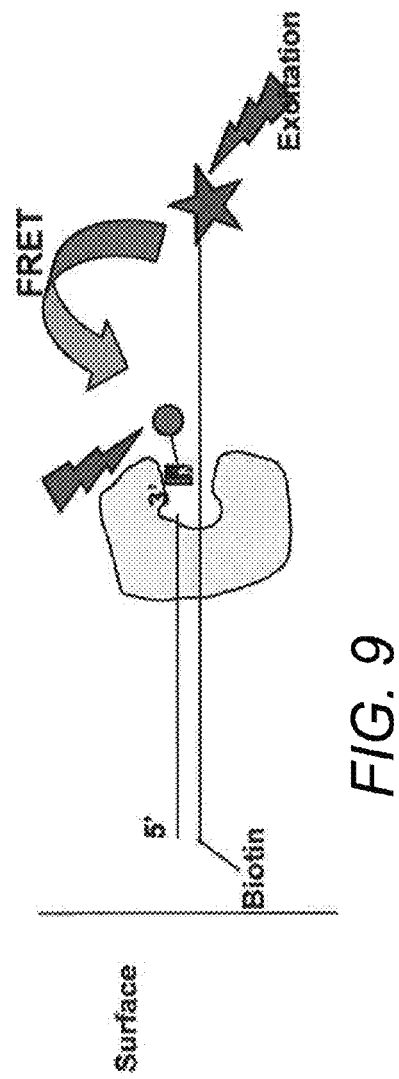

FIG. 9 provides a graphical depiction of the various reaction components included in the real-time single molecule sequencing reaction of Example 10.

Figure 10:
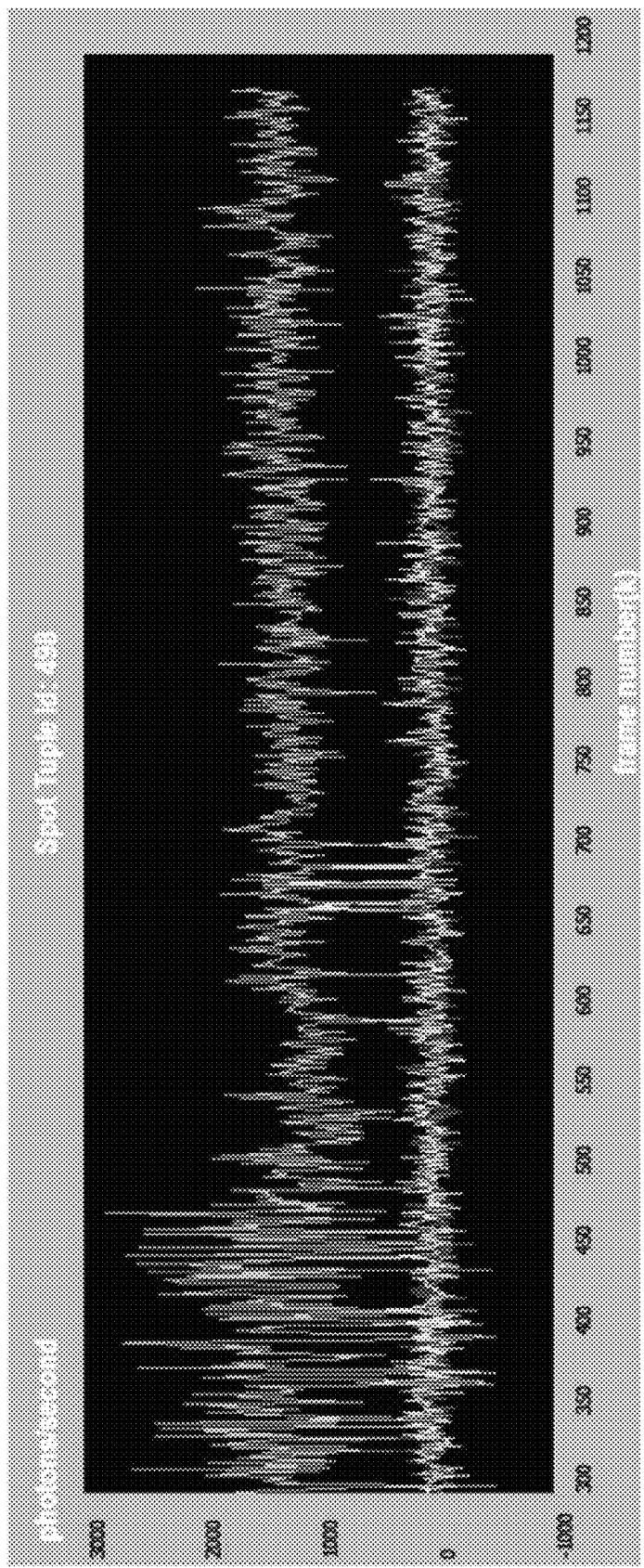

FIG. 10 depicts exemplary portions of fluorescence time traces detected at 550 and 647 nm from a single-molecule real time sequencing reaction comprising a mutant Phi-29 polymerase and terminally-labeled nucleotide hexaphosphates.

Figure 11:
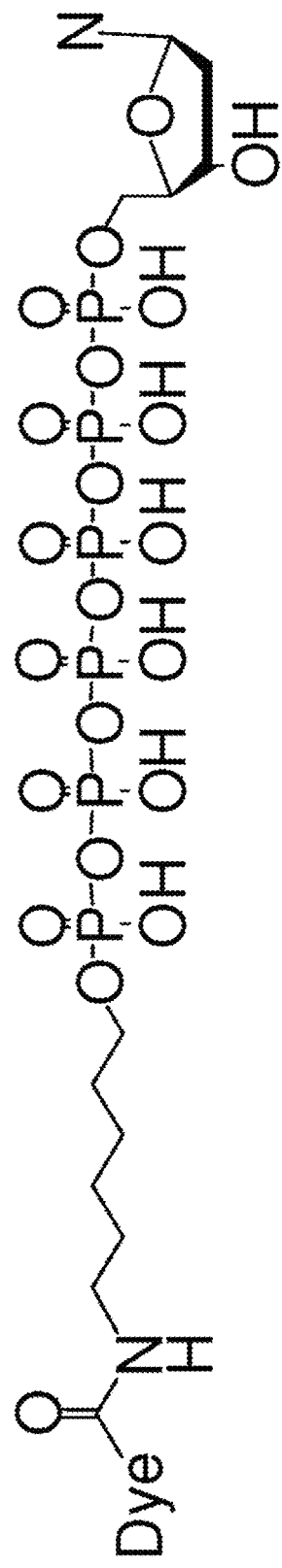

FIG. 11 depicts the general structure of a dye-labeled nucleotide hexaphosphate that can be used in conjunction with the labeled polymerase conjugates disclosed herein.

DETAILED DESCRIPTION OF THE SEQUENCE LISTINGS

SEQ ID NO: 1 comprises the amino acid sequence of an exemplary polymerase of the bacteriophage Phi-29.

SEQ ID NO: 2 comprises the amino acid sequence of a consensus motif named Motif 1, also known as Motif A, which can be found within various polymerases including polymerases isolated from bacteriophages of the family of Phi-29-like bacteriophages.

SEQ ID NO: 3 comprises the amino acid sequence of a consensus motif named Motif 2a, also known as Motif B, which can be found within various polymerases including polymerases isolated from bacteriophages of the family of Phi-29-like bacteriophages.

SEQ ID NO: 4 comprises the amino acid sequence of a consensus motif named Motif 3, also known as Motif C, which can be found within various polymerases including polymerases isolated from bacteriophages of the family of Phi-29-like bacteriophages.

SEQ ID NO: 5 comprises the amino acid sequence of a consensus motif named Motif 4, we can be found within various polymerases including polymerases isolated from bacteriophages of the family of Phi-29-like bacteriophages.

SEQ ID NO: 6 comprises the amino acid sequence of an exemplary polymerase of the bacteriophage B103, a member of the Phi-29-like family of bacteriophages SEQ ID NO: 7 comprises the amino acid sequence of an exemplary modified polymerase according to the present disclosure.

SEQ ID NO: 8 comprises the amino acid sequence of another exemplary modified polymerase according to the present disclosure.

SEQ ID NO: 9 comprises the nucleotide sequence of an exemplary polynucleotide encoding the modified polymerase comprising the amino acid sequence of SEQ ID NO: 7.

SEQ ID NO: 10 comprises the nucleotide sequence of a second exemplary polynucleotide encoding the modified polymerase comprising the amino acid sequence of SEQ ID NO: 7.

SEQ ID NO: 11 comprises the nucleotide sequence of an exemplary polynucleotide encoding the modified polymerase comprising the amino acid sequence of SEQ ID NO: 8.

SEQ ID NO: 12 comprises the nucleotide sequence of a second exemplary polynucleotide encoding the modified polymerase comprising the amino acid sequence of SEQ ID NO: 8.

SEQ ID NO: 13 comprises the amino acid sequence of a polymerase of the bacteriophage M2Y, a member of the Phi-29-like family of bacteriophages.

SEQ ID NO: 14 comprises the amino acid sequence of a polymerase of the bacteriophage Nf, a member of the Phi-29-like family of bacteriophages.

SEQ ID NO: 15 comprises the amino acid sequence of a polymerase of RB69.

SEQ ID NO: 16 comprises the amino acid sequence of an exemplary peptide linker, named "H-linker", useful in linking tags or labels to a protein sequence of interest.

SEQ ID NO: 17 comprises the amino acid sequence of another exemplary peptide linker, named "F-linker", useful in linking tags or labels to a protein sequence of interest.

SEQ ID NO: 18 comprises the amino acid sequence of an exemplary His-tagged version of a protein comprising the amino acid sequence of SEQ ID NO: 7.

SEQ ID NO: 19 comprises the amino acid sequence of another exemplary His-tagged version of a protein comprising the amino acid sequence of SEQ ID NO: 7.

SEQ ID NO: 20 comprises the amino acid sequence of HP1, a Phi-29 polymerase peptide that lacks exonuclease activity and comprises an N-terminal His-tag, an intervening linker sequence, and the D12A and D66A mutations.

SEQ ID NO: 21 comprises the nucleotide sequence of an exemplary oligonucleotide primer used to construct a primer:template duplex for use in assays for fractional extension activity as disclosed, for example, in Example 3.

SEQ ID NOS: 22-25 each comprises the nucleotide sequence of an exemplary polynucleotide template used to construct a primer:template duplex for use in assays for fractional extension activity as disclosed, for example, in Example 3.

SEQ ID NO: 26 comprises the nucleotide sequence of an exemplary oligonucleotide primer used to construct a primer: template duplex for use in nucleotide incorporation assays to evaluate polymerase reaction kinetics as disclosed, for example, in Example 7.

SEQ ID NOS: 27-30 each comprises the nucleotide sequence of an exemplary polynucleotide template used to construct a primer:template duplex for use in nucleotide incorporation assays as disclosed, for example, in Example 7.

SEQ ID NO: 31 comprises the nucleotide sequence of an exemplary oligonucleotide primer used to construct a primer: template duplex for use in nucleotide incorporation assays to evaluate polymerase reaction kinetics as disclosed, for example, in Example 8.

SEQ ID NOS: 32-35 each comprise the nucleotide sequence of an exemplary polynucleotide template used to construct a primer:template duplex for use in nucleotide incorporation assays as disclosed, for example, in Example 8.

SEQ ID NO: 36 comprises the nucleotide sequence of an exemplary oligonucleotide primer used to construct a primer-template duplex for use in a real time single molecule sequencing assay, as disclosed, for example, in Example 10.

SEQ ID NO: 37 comprises the nucleotide sequence of an exemplary polynucleotide template used to construct a primer-template duplex for use in a real time single molecule sequencing assay, as disclosed, for example, in Example 10.

SEQ ID NO: 38 comprises the nucleotide sequence of an exemplary hairpin template used for three-color nucleotide incorporation reaction as described, for example, in Example 11.

SEQ ID NO: 39 comprises the nucleotide sequence of an exemplary polynucleotide template used for a four-color nucleotide incorporation reaction as described, for example, in Example 11.

SEQ ID NO: 40 comprises the nucleotide sequence of an exemplary oligonucleotide primer used for a four-color nucleotide incorporation reaction as described, for example, in Example 11.

SEQ ID NO: 41 comprises the predicted nucleotide sequence that will be synthesized in a four-color nucleotide incorporation reaction using the primer of SEQ ID NO: 40 in conjunction with the template of SEQ ID NO: 39 as described, for example, in Example 11.

SEQ ID NO: 42 comprises the amino acid sequence of a modified B103 polymerase comprising the amino acid sequence of SEQ ID NO: 8 and further including the mutation H370R as well as a biotinylation site and His tag fused to the N-terminus of the polymerase.

SEQ ID NO: 43 comprises the nucleotide sequence of a fluorescein-labeled oligonucleotide primer used to measure primer extension activity of a polymerase sample according to an exemplary assay, as described in Example 13.

SEQ ID NO: 44 comprises the nucleotide sequence of an exemplary polynucleotide template used in a stopped-flow assay for nucleotide incorporation kinetics as described, for example, in Example 12.

SEQ ID NO: 45 comprises the nucleotide sequence of an exemplary oligonucleotide primer used in a stopped-flow assay for nucleotide incorporation kinetics as described, for example, in Example 12.

SEQ ID NO: 46 comprises the nucleotide sequence of an exemplary polynucleotide template used in a stopped-flow assay for nucleotide incorporation kinetics as described, for example, in Example 12.

SEQ ID NO: 47 comprises the nucleotide sequence of an exemplary oligonucleotide primer used in a stopped-flow assay for nucleotide incorporation kinetics as described, for example, in Example 12.

DETAILED DESCRIPTION

The present disclosure provides for compositions, methods and systems relating to modified polymerases and their use in various biological applications. More particularly, provided herein are novel polymerases having altered polymerase activity, label tolerance, photostability and/or nucleotide incorporation kinetics as compared to their unmodified counterparts, which can be useful in a wide variety of biological applications.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference. The citation of any publication is for its disclosure prior to the filing date and should not be construed as an admission that the present invention is not entitled to antedate such publication by virtue of prior invention.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, *Molecular Cloning: A Laboratory Manual*, Third Edition; Ausubel, F. M., et al., eds., 2002, *Short Protocols In Molecular Biology*, Fifth Edition.

Unless otherwise indicated, the numbering of any amino acid residues described herein will be relative to the sequence of a B103 polymerase having the amino acid sequence of SEQ ID NO: 6. However, the skilled artisan will appreciate that the actual position within a modified polymerase according to the present disclosure may vary. For example, the modified polymerase may comprise one or more deletions or additions within its sequence, thereby altering the numbering of the corresponding amino acid residue in the modified polymerase relative to the B103 polymerase having SEQ ID NO: 6.

Throughout this disclosure, various amino acid mutations, including, for example, amino acid substitutions are referenced using the amino acid single letter code, and indicating the position of the residue within a reference amino acid sequence. In the case of amino acid substitutions, the identity of the substituent is also indicated using the amino acid single letter code. For example, the amino acid substitution F383L, wherein the numbering is relative to the amino acid sequence of SEQ ID NO: 6, indicates an amino acid substitution wherein a leucine (L) residue is substituted for the normally occurring phenylalanine (F) residue at amino acid position 383 of the amino acid sequence of SEQ ID NO: 6.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; and the like. Some examples of linkages can be found, for example, in Hermanson, G., *Bioconjugate Techniques*, Second Edition (2008); Aslam, M., Dent, A., *Bioconjugation: Protein Coupling Techniques for the Biomedical Sciences*, London: Macmillan (1998); Aslam, M., Dent, A., *Bioconjugation: Protein Coupling Techniques for the Biomedical Sciences*, London: Macmillan (1998).

As used herein, the term "linker" and its variants comprises any composition, including any molecular complex or molecular assembly, that serves to link two or more compounds.

As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and *E. coli* DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. One exemplary embodiment of such a polymerase is Phusion® DNA polymerase (New England Biolabs), which comprises a *Pyrococcus*-like polymerase fused to a processivity-enhancing domain as described, for example, in U.S. Pat. No. 6,627,424.

As used herein, the term "polymerase activity" and its variants, when used in reference to a given polymerase, comprises any in vivo or in vitro enzymatic activity characteristic of a given polymerase that relates to catalyzing the polymerization of nucleotides into a nucleic acid strand, e.g., primer extension activity, and the like. Typically, but not necessarily such nucleotide polymerization occurs in a template-dependent fashion. In addition to such polymerase activity, the polymerase can typically possess other enzymatic activities, for example, 3' to 5' exonuclease activity.

As used herein, the term "nucleotide" and its variants comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprises polymerization of one or more nucleotides into a nucleic acid strand.

As used herein, the term "biological activity" and its variants, when used in reference to a biomolecule (such as, for example, an enzyme) refers to any in vivo or in vitro activity that is characteristic of the biomolecule itself, including the interaction of the biomolecule with one or more targets. For example, biological activity can optionally include the selective binding of an antibody to an antigen, the enzymatic activity of an enzyme, and the like. Such activity can also include, without limitation, binding, fusion, bond formation, association, approach, catalysis or chemical reaction, optionally with another biomolecule or with a target molecule.

As used herein, the term "biologically active fragment" and its variants refers to any fragment, derivative or analog of a biomolecule that possesses an in vivo or in vitro activity that is characteristic of the biomolecule itself. For example, the biomolecule can be an antibody that is characterized by antigen-binding activity, or an enzyme characterized by the ability to catalyze a particular biochemical reaction, etc. Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells. Because biomolecules often exhibit a range of physiological properties and because such properties can be attributable to different portions of the biomolecule, a useful biologically active fragment can be a fragment of a biomolecule that exhibits a biological activity in any biological assay. In some embodiments, the fragment or analog possesses 10%, 40%, 60%, 70%, 80% or 90% or greater of the activity of the biomolecule in any in vivo or in vitro assay of interest.

The term "modification" or "modified" and their variants, as used herein with reference to a protein, comprise any change in the structural, biological and/or chemical properties of the protein, particularly a change in the amino acid sequence of the protein. In some embodiments, the modification can comprise one or more amino acid mutations, including without limitation amino acid additions, deletions and substitutions (including both conservative and non-conservative substitutions).

As used herein, the terms "identical" or "percent identity," and their variants, when used in the context of two or more nucleic acid or polypeptide sequences, refer to two or more sequences or subsequences that are the same or have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "*A general method applicable to the search for similarities in the amino acid sequence of two proteins" Journal of Molecular Biology* 48 (3):443-53); Smith-Waterman (see, e.g., Smith, Temple F.; and Waterman, Michael S., "*Identification of Common Molecular Subsequences"* (1981) *Journal of Molecular Biology* 147:195-197); or BLAST (Basic Local Alignment Search Tool; see, e.g., Altschul S F, Gish W, Miller W, Myers E W, Lipman D J, "*Basic local alignment search tool*" (1990) *J Mol Biol* 215 (3):403-410).

The terms "resonance energy transfer" and "RET" and their variants, as used herein, refer to a radiationless transmission of excitation energy from a first moiety, termed a donor moiety, to a second moiety termed an acceptor moiety. One type of RET includes Forster Resonance Energy Transfer (FRET), in which a fluorophore (the donor) in an excited state transfers its energy to a proximal molecule (the acceptor) by nonradiative dipole-dipole interaction. See, e.g., Forster, T. "Intermolecular Energy Migration and Fluorescence", *Ann. Phys.*, 2:55-75, 1948; Lakowicz, J. R., Principles of Fluorescence Spectroscopy, 2nd ed. Plenum, New York. 367-394, 1999. RET also comprises luminescence resonance energy transfer, bioluminescence resonance energy transfer, chemiluminescence resonance energy transfer, and similar types of energy transfer not strictly following the Forster's theory, such as nonoverlapping energy transfer occurring when non-overlapping acceptors are utilized. See, for example, Anal. Chem. 2005, 77: 1483-1487.

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, isoleucine or proline) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

The term "primer extension activity" and its variants, as used herein, when used in reference to a given polymerase, comprises any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. The primer extension activity is typically quantified as the total number of nucleotides incorporated (as measured by, e.g., radiometric or other suitable assay) by a unit amount of polymerase (in moles) per unit time (seconds) under a particular set of reaction conditions.

The terms "His tag" or "His-tag" and their variants as used herein refers to a stretch of amino acids comprising multiple histidine residues. Typically, the His tag can bind to metal ions, for example, $Zn^{2+}$, $Ni^{2+}$, $Co^{2+}$, or $Cu^{2+}$ ions. Optionally, the His tag comprises 2, 3, 4, 5, 6, 7, 8 or more histidine residues. In some embodiments, the His tag is fused to the N- or C-terminus of a protein; alternatively, it can be fused at any suitable location within the protein.

As used herein, the term "biotin moiety" and its variants comprises biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-∈-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like. "Biotin moiety" also comprises biotin variants that can specifically bind to an avidin moiety.

The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

The terms "avidin" and "avidin moiety" and their variants, as used herein, comprises the native egg-white glycoprotein avidin, as well as any derivatives, analogs and other non-native forms of avidin, that can specifically bind to biotin moieties. In some embodiments, the avidin moiety can comprise deglycosylated forms of avidin, bacterial streptavidins produced by selected strains of Streptomyces, e.g., Streptomyces avidinii, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety.

As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-14}$ to $10^{-15}$ mol/L. Typically, such binding occurs via non-covalent interactions.

The term "label" and its variants, as used herein, comprises any optically detectable moiety and includes any moiety that can be detected using, for example, fluorescence, luminescence and/or phosphorescence spectroscopy, Raman scattering, or diffraction. Exemplary labels according to the present disclosure include fluorescent and luminescent moieties as well as quenchers thereof. Some typical labels include without limitation nanoparticles and organic dyes.

The present disclosure relates to compositions and methods comprising modified polymerases derived from Phi-29 and/or Phi-29-like phages, wherein the modified polymerases exhibit altered polymerase activity, photostability, label tolerance, kinetics for nucleotide binding and/or nucleotide incorporation kinetics. For example, in some embodiments the disclosure relates to polymerase compositions, methods of making such compositions and methods of using such compositions in various biological applications. The compositions and related methods described herein represent significant advances over the art. For example, in some embodiments, the disclosed compositions and methods can permit nucleic acid synthesis with improved kinetics for real-time visualization of polymerase activity. In some embodiments, the disclosed compositions and methods can permit polymerization of nucleotides (including labeled nucleotide analogs) with increased tolerance for the presence of labeled moieties, for example nanoparticles. In some embodiments, the disclosed compositions and methods can permit increased primer extension activity in conjunction with use of higher intensities or duration of exposure to excitation radiation. Such compositions and methods can facilitate, for example, applications involving nucleic acid synthesis, including applications requiring direct monitoring of polymerase activity in vitro or in vivo, such as real-time single molecule sequencing.

In some embodiments, the present disclosure relates to a modified DNA polymerase having a photostability that is at least about 80% under standard photostability assay conditions. In some embodiments, the modified DNA polymerase comprises an amino acid sequence that is at least about 80%, 85%, 90%, 95%, 97%, 98% or 99% identical to the amino acid sequence of SEQ ID NO: 7.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard photostability assay conditions.

In some embodiments, the disclosure relates to a modified DNA polymerase comprising an amino acid sequence that is at least about 80%, 85%, 90%, 95%, 97%, 98% or 99% identical to the amino acid sequence of SEQ ID NO: 7, and further including one or more amino acid mutations that increase the photostability of the enzyme. In some embodiments, the one or more amino acid mutations increase the photostability of the modified DNA polymerase by at least about 5%, 10%, 25%, 50%, 75%, 100%, 125%, 250%, 500%, 750% or 1000%.

In some embodiments, the present disclosure relates to a modified DNA polymerase having a nanoparticle tolerance that is at least about 80% under standard nanoparticle tolerance assay conditions. In some embodiments, the modified DNA polymerase comprises an amino acid sequence that is at least about 80%, 85%, 90%, 95%, 97%, 98% or 99% identical to the amino acid sequence of SEQ ID NO: 7 or SEQ ID NO: 8.

In some embodiments, the disclosure relates to a modified DNA polymerase comprising an amino acid sequence that is at least about 80%, 85%, 90%, 95%, 97%, 98% or 99% identical to the amino acid sequence of SEQ ID NO: 7, and further including one or more amino acid mutations that increase the nanoparticle tolerance of the enzyme. In some embodiments, the one or more amino acid mutations increase the nanoparticle tolerance of the modified DNA polymerase by at least about 5%, 10%, 25%, 50%, 75%, 100%, 125%, 250%, 500%, 750% or 1000%.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard nanoparticle tolerance assay conditions.

In some embodiments, the disclosure relates to a modified DNA polymerase comprising an amino acid sequence that is at least about 80%, 85%, 90%, 95%, 97%, 98% or 99% identical to the amino acid sequence of SEQ ID NO: 7, and further including one or more amino acid mutations that increase the primer extension activity of the enzyme. In some embodiments, the one or more amino acid mutations increase the primer extension activity of the modified DNA polymerase by at least about 5%, 10%, 25%, 50%, 75%, 100%, 125%, 250%, 500%, 750% or 1000%.

In some embodiments, the present disclosure relates to a modified DNA polymerase comprising an amino acid sequence that is at least about 85%, 90%, 95%, 97% or 99% identical to the amino acid sequence of SEQ ID NO: 7 or SEQ ID NO: 8. In some embodiments, the modified DNA polymerase has a nanoparticle tolerance that is at least about 80% under standard nanoparticle tolerance assay conditions. In some embodiments, the modified DNA polymerase has a photostability that is at least about 80% under standard photostability assay conditions.

In some embodiments, the present disclosure relates to a modified DNA polymerase having a primer extension activity that is at least about 105%, 110%, 125%, 150%, 175%, 200%, 250%, 375%, 500%, 750% or 1000% relative to the primer extension activity of a wild type Phi-29 polymerase comprising the amino acid sequence of SEQ ID NO: 1 under standard nanoparticle tolerance assay conditions.

In some embodiments, the present disclosure relates to a modified DNA polymerase comprising an amino acid sequence that is at least about 85%, 90%, 95%, 97% or 99% identical to the amino acid sequence of SEQ ID NO: 7 or SEQ ID NO: 8. The modified DNA polymerases of the present disclosure can further comprise one or more amino acid substitutions selected from the group consisting of: D9A, E11A, E11I, T12I, H58R, N59D, D63A, Y162F, Y162C, D166A, Q377A, S385G, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7.

Optionally, the modified DNA polymerases of the present disclosure can further comprise a mutation reducing 3' to 5' exonuclease activity. The mutation reducing 3' to 5' exonuclease activity of the modified DNA polymerase can optionally include one or more amino acid substitutions at positions selected from the group consisting of: 2, 9, 11, 12, 58, 59, 63, 162, 166, 377 and 385. In some embodiments, the one or more amino acid substitutions can be selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

In some embodiments, the modified DNA polymerases of the present disclosure can further comprise a mutation increasing the branching ratio of the polymerase in the presence of a labeled nucleotide. Optionally, the modified DNA polymerase comprises an amino acid sequence that is at least about 80%, 85%, 90%, 95%, 97%, 98% or 99% identical to the amino acid sequence of SEQ ID NO: 7, and further comprises one or more mutations increasing the branching ratio of the modified DNA polymerase. In some embodiments, the one or more mutations comprise one or more amino acid substitutions at positions selected from the group consisting of: 370, 371, 372, 373, 374, 375, 376 and 377. In some embodiments, the one or more mutations can be selected from the group consisting of: H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. In some embodiments, the modified DNA polymerase comprises an amino acid sequence that is at least about 85%, 90%, 95%, 97% or 99% identical to the amino acid sequence of SEQ ID NO: 7 or SEQ ID NO: 8 and further includes the amino acid substitution H370R. In some embodiments, the presence of the amino acid substitution H370R increases the branching ratio of the modified polymerase by at least about 5%, 10%, 25%, 50%, 75%, 100%, 150%, 200%, 250%, 500%, 750%, 1000% or greater.

In some embodiments, the modified DNA polymerases of the present disclosure can further comprise a mutation increasing the primer extension activity. Optionally, the mutation increasing the primer extension activity of the modified DNA polymerase comprises one or more amino acid substitutions at positions selected from the group consisting of: 129 and 339, wherein the numbering is relative to the amino acid sequence of SEQ ID NO: 7.

In some embodiments, the modified DNA polymerases of the present disclosure can further comprise a mutation that increases the nucleotide binding affinity of the polymerase for a particular labeled nucleotide. Optionally, the mutation increasing the nucleotide binding affinity for a particular labeled nucleotide comprises one or more amino acid substitutions at positions selected from the group consisting of: 370, 371, 372, 373, 374, 375, 376, 507 and 509. In some embodiments, the one or more amino acid substitutions can be selected from the group consisting of: H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7.

In some embodiments, the disclosure relates to a nucleic acid molecule encoding any one, some or all of the modified DNA polymerases of the present disclosure. The nucleic acid molecule can optionally be DNA or RNA.

In some embodiments, the disclosure relates to a vector comprising a DNA encoding any one, some or all of the modified DNA polymerases of the present disclosure.

In some embodiments, the disclosure relates to an isolated host cell comprising a vector including a DNA encoding any one, some or all of the modified DNA polymerases of the present disclosure.

In one embodiment, the disclosure relates to compositions and methods relating to modified polymerases comprising one or more modifications relative to a reference polymerase. In some embodiments, the reference polymerase is a Phi-29 polymerase comprising the amino acid sequence of SEQ ID NO: 1 or SEQ ID NO: 20. In some embodiments, the reference polymerase is a B103 polymerase comprising the amino acid sequence of SEQ ID NO: 6.

In some embodiments, the modified polymerase is an isolated variant of a B103 polymerase comprising the amino acid sequence of SEQ ID NO: 6, wherein the variant comprises an amino acid sequence that is at least 80%, 85%, 90%, 95%, 97%, 98% or 99% identical to the amino acid sequence of SEQ ID NO: 7.

In some embodiments, the modified polymerase comprises an amino acid sequence that is at least 80%, 85%, 90%, 95%, 97%, 98% or 99% identical to the amino acid sequence of SEQ ID NO: 7 or SEQ ID NO: 8.

In some embodiments, the modified polymerase comprises an amino acid sequence that is at least 85%, 90%, 95% or 99% identical to the amino acid sequence of SEQ ID NO: 7 or SEQ ID NO: 8, and further comprises any one, two, three or more modifications at amino acid positions 2, 9, 12, 14, 15, 58, 59, 63, 129, 166, 246, 247, 339, 370, 371, 372, 373, 374, 375, 376, 377, 380, 383, 384, 385, 455, 507 and 509, or any combinations thereof, wherein the numbering is relative to the amino acid sequence of SEQ ID NO: 7. In some embodiments, the modifications can include deletions, additions and substitutions. The substitutions can be conservative or non-conservative substitutions.

In some embodiments, the modified polymerase comprises an amino acid sequence that is at least 85%, 90%, 95% or 99% identical to the amino acid sequence of SEQ ID NO: 7 and comprises any one, two, three or more mutations selected from the group consisting of: D9A, E11A, E11I, T12I, H58R, N59D, D63A, Y162F, Y162C, D166A, Q377A, S385G, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. In some embodiments, the modified polymerase comprises any one, two, three or more of these amino acid substitutions.

In some embodiments, the modified polymerase comprises one or more amino acid substitutions selected from the group consisting of: D9A, E11A, E11I, T12I, H58R, N59D, D63A, Y162F, Y162C, D166A, Q377A and S385G, and further comprises one or more amino acid substitutions selected from the group consisting of: H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the sequence of SEQ ID NO: 7.

In some embodiments, the modified polymerase comprises one or more modifications resulting in an alteration (for example, an increase or decrease) in polymerase activity relative to the polymerase activity of a reference polymerase.

In some embodiments, the modified polymerase comprises one or more modifications resulting in a change in the kinetic behavior of the polymerase in vitro or in vivo. For example, the modification(s) may result in a change (for example, an increase or decrease) in one or more of the following activities or properties of the polymerase, relative to the corresponding activity or property of a reference polymerase: specific activity as measured in a primer extension assay; specific activity as measured in a nucleotide incorporation assay (including assays for incorporation of naturally occurring nucleotides and nucleotide analogs); exonuclease activity (including, for example, 3' to 5' exonuclease activity); ability to bind one or more substrates (including naturally occurring nucleotides and nucleotide analogs); yield of synthesized nucleic acid product; processivity; fidelity of nucleic acid synthesis; rate of nucleic acid synthesis; binding affinity for one or more particular nucleotides (including naturally occurring nucleotides and nucleotide analogs); $K_m$ for one or more substrates (including naturally occurring nucleotides, nucleotide analogs and/or template strand); $k_{cat}$ or $V_{max}$, $t_{pol}$, $t_{-1}$, $k_{pol}$, or $k_{-1}$ for one or more nucleotides (including naturally occurring nucleotides and nucleotide analogs); binding affinity for one or more nucleotides (including naturally occurring nucleotides and nucleotide analogs); residence time of one or more nucleotides (including naturally occurring nucleotides and nucleotide analogs) within one or more polymerase active sites; rate of binding for one or more nucleotides (including naturally occurring nucleotides and nucleotide analogs); rate of nucleotide release (in either altered or unaltered state) from the polymerase active site, including, for example, rate of product release; average template read length in presence of nucleotides (including naturally occurring nucleotides and nucleotide analogs); stability of the polymerase under a given set of conditions, including photostability and chemical stability; tolerance for the presence of labels (including both organic labels, e.g., dyes, and inorganic labels, e.g., nanoparticles); and photostability.

In some embodiments, the modification(s) result in an alteration (e.g., increase or decrease) of any one, some or all of the above activities or properties or properties relative to the corresponding activity or property of a reference polymerase.

The reference polymerase can be any suitable polymerase whose polymerase activity can be measured and compared to the activity of a modified polymerase of the present disclosure. In some embodiments, the reference polymerase can be the unmodified counterpart of the modified polymerase. In some embodiments, the reference polymerase is a naturally occurring polymerase. The naturally occurring polymerase can in some embodiments be derived from Phi-29 or the Phi-29-like family of bacteriophages, including Phi-29, B103 and RB69; alternatively, it can be a non-Phi-29-like polymerase, including, for example, T7 DNA polymerase, Taq DNA polymerase or E. coli DNA polymerase. In some embodiments, the reference polymerase can be a Phi-29 polymerase. (See, for example, U.S. Pat. Nos. 5,001,050; 5,198,543 and 5,576,204 to Blanco et al.). In some embodiments, the reference polymerase is wild type Phi-29 polymerase having the amino acid sequence of SEQ ID NO: 1, or a His-tagged version of Phi-29 polymerase having the amino acid sequence of SEQ ID NO: 20. In some embodiments, the reference polymerase can be a B103 polymerase comprising the amino acid sequence of SEQ ID NO: 6. In some embodiments, the reference polymerase can be a variant of a B103 polymerase comprising the amino acid sequence of SEQ ID NO: 7 or SEQ ID NO: 8. In some embodiments, the reference polymerase is an RB69 polymerase having the amino acid sequence of SEQ ID NO: 15. In some embodiments, the reference polymerase can comprise the amino acid sequence of SEQ ID NO: 13. In some embodiments, the reference polymerase can comprise the amino acid sequence of SEQ ID NO: 14. (See, for example, Meijer et al., "Phi-29 family of phages" Microbiol. & Mol. Biol. Revs. 65(2):261-287 (2001)).

In some embodiments, the reference polymerase is the same polymerase in unmodified form. In some embodiments, the reference polymerase is a polymerase having the amino acid sequence of SEQ ID NO: 1 or SEQ ID NO: 20. In some embodiments, the reference polymerase comprises the amino acid sequence of SEQ ID NO: 6. In some embodiments, the reference polymerase is RB69 polymerase comprising the amino acid sequence of SEQ ID NO: 15.

In some embodiments, the modified polymerase exhibits an increase or decrease in the branching ratio in the presence of a particular nucleotide, for example, a labeled nucleotide analog, relative to the unmodified polymerase, or relative to any other reference polymerase such as, for example, a Phi-29 polymerase having the amino acid sequence of SEQ ID NO: 1.

In some embodiments, the modified polymerase exhibits an increase in the $t_{-1}$ value for a particular nucleotide, for example, a labeled nucleotide analog, relative to an unmodified counterpart.

In some embodiments, the modified polymerase exhibits a $t_{-1}$ value for a labeled nucleotide that is equal to or greater than the $t_{-1}$ value for the same nucleotide of a reference Phi-29 polymerase comprising the amino acid sequence of SEQ ID NO: 1.

In some embodiments, the modified polymerase exhibits an increase in the $t_{pol}$ value for a particular nucleotide, for example, a labeled nucleotide analog, relative to an unmodified counterpart.

In some embodiments, the modified polymerase exhibits a $t_{pol}$ value for a labeled nucleotide that is equal to or lesser than the $t_{pol}$ value for the same nucleotide of a reference Phi-29 polymerase comprising the amino acid sequence of SEQ ID NO: 1.

In some embodiments, the modified polymerase exhibits an increase in residence time for a particular nucleotide, for example, a labeled nucleotide analog, relative to an unmodified counterpart.

In some embodiments, the modified polymerase exhibits a residence time for a labeled nucleotide that is equal to or greater than the residence time for the same nucleotide of a reference Phi-29 polymerase comprising the amino acid sequence of SEQ ID NO: 1.

In some embodiments, the modified polymerase exhibits an increase in photostability relative to an unmodified counterpart.

In some embodiments, the modified polymerase exhibits a photostability that is greater than the photostability of a reference Phi-29 polymerase comprising the amino acid sequence of SEQ ID NO: 1.

In some embodiments, the modified polymerase exhibits an increase in nanoparticle tolerance relative to an unmodified counterpart.

In some embodiments, the modified polymerase exhibits a nanoparticle tolerance that is greater than the nanoparticle tolerance of a reference Phi-29 polymerase comprising the amino acid sequence of SEQ ID NO: 1.

In some embodiments, the modified polymerase is operably linked to a detectable label. In some embodiments, the detectable label is a nanoparticle.

Also provided herein are polynucleotides encoding the modified polymerases of the present disclosure, and isolated host cells comprising one or more of these polynucleotides.

Also provided herein are vectors comprising one or more polynucleotides encoding the modified polymerases of the present disclosure, and isolated host cells comprising these vectors. In some embodiments, the vectors further comprise a promoter operably linked to the polynucleotide encoding the modified polymerase. The promoter can be constitutive or inducible. The host cell comprising the polynucleotide encoding the modified polymerase can be eukaryotic or prokaryotic.

Also provided are methods for producing one or more modified polymerases of the present disclosure, comprising: culturing a host cell comprising a polynucleotide that encodes a modified polymerase under conditions that are suitable for the host cell to produce the active modified polymerase. Optionally, the method can include the step of purifying the modified polymerase from the isolated host cells. Also disclosed herein is an active modified polymerase produced by this method.

Also provided herein are methods for nucleotide incorporation, comprising: contacting a modified polymerase of the present disclosure with a target nucleic acid molecule and with at least one nucleotide under conditions where the at least one labeled nucleotide is incorporated by the modified polymerase into an extending nucleic acid molecule. In some embodiments, the modified polymerase can comprise an amino acid sequence at least 90%, 95%, 97,%, 98% or 99% identical to the amino acid sequence of SEQ ID NO: 7 or SEQ ID NO: 8. In some embodiments, the at least one nucleotide can be a labeled nucleotide. In some embodiments, the labeled nucleotide comprises a nucleotide operably linked to a detectable label, referred to herein as a nucleotide label. In some embodiments, the nucleotide label can emits one or more signals indicative of incorporation of the labeled nucleotide. In some embodiments, the method can further comprise the step of detecting the incorporation of the labeled nucleotide by detecting the one or more signals emitted by the nucleotide label. In some embodiments, the incorporation is a productive or non-productive incorporation.

Also provided herein is a method for determining a nucleotide sequence of a single nucleic acid molecule, comprising: (a) conducting a nucleotide polymerization reaction comprising a target nucleic acid molecule, a modified polymerase and at least one labeled nucleotide, which reaction results in the incorporation of one or more labeled nucleotides by the modified polymerase and the generation of one or more detectable signals indicative of one or more nucleotide incorporations; (b) detecting a time sequence of nucleotide incorporations; and (c) determining the identity of one or more incorporated nucleotides, thereby determining some or all of the nucleotide sequence of the target nucleic acid molecule. In some embodiments, the determination of nucleotide sequence can occur in real or near real time. In some embodiments, the modified polymerase comprises an amino acid sequence that is at least 80%, 85%, 90%, 95%, 97%, 98% or 99% identical to the amino acid sequence of SEQ ID NO: 8, and can optionally further include one or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Typically, this modified polymerase can exhibit increase branching ratio and/or increased photostability and/or increased nanoparticle tolerance relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

Also disclosed herein is a method for determining a nucleotide sequence of a single nucleic acid molecule, comprising the steps of: (a) conducting a polymerase reaction comprising a polymerase and at least one labeled nucleotide, such that one or more labeled nucleotides interact successively with the polymerase, thereby generating or causing to be generated one or more detectable signals indicative of one or more polymerase-nucleotide interactions, and where the polymerase comprises the amino acid sequence of SEQ ID NO: 7 or SEQ ID NO: 8; (b) detecting a time sequence of polymerase-nucleotide interactions; and (c) determining the identity of the one or more labeled nucleotides that interact with the polymerase during the one or more polymerase-nucleotide interactions, thereby determining some or all of the nucleotide sequence of a single nucleic acid molecule. In some embodiments, the determination of nucleotide sequence can occur in real or near real time. In some embodiments, the modified polymerase can comprise an amino acid sequence that is at least 80%, 85%, 90%, 95%, 97%, 98% or 99% identical to the amino acid sequence of SEQ ID NO: 8. In some embodiments, the modified polymerase can further comprise one or more amino acid substitutions selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Typically, this modified polymerase can exhibit increase branching ratio and/or increased photostability and/or increased nanoparticle tolerance relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

In some embodiments, the modified polymerase can comprise an amino acid sequence that is at least 80%, 85%, 90%, 95%, 97%, 98% or 99% identical to the amino acid sequence of SEQ ID NO: 1, and further comprise one or more amino acid substitutions increasing the branching ratio of the enzyme. Optionally, the one or more amino acid substitutions can include replacement of the lysine residue at position 373 of SEQ ID NO: 1 with any amino acid other than lysine.

In some embodiments of the methods of the present disclosure, the modified polymerase can exhibit a $t_{-1}$ value for a labeled nucleotide that is equal to or greater than the $t_{-1}$ value for the same nucleotide of a reference Phi-29 polymerase comprising the amino acid sequence of SEQ ID NO: 1.

In some embodiments of the methods of the present disclosure, the modified polymerase can exhibit a $t_{pol}$ value for a labeled nucleotide that is equal to or lesser than the $t_{pol}$ value for the same nucleotide of a reference Phi-29 polymerase comprising the amino acid sequence of SEQ ID NO: 1.

In some embodiments of the methods of the present disclosure, the modified polymerase can exhibit a residence time for a labeled nucleotide that is equal to or greater than the residence time for the same nucleotide of a reference Phi-29 polymerase comprising the amino acid sequence of SEQ ID NO: 1.

In some embodiments of the methods of the present disclosure, the modified polymerase can exhibit a photostability that is equal to or greater than the photostability of a reference Phi-29 polymerase comprising the amino acid sequence of SEQ ID NO: 1.

In some embodiments of the methods of the present disclosure, the modified polymerase can exhibit a nanoparticle tolerance that is equal to or greater than the nanoparticle tolerance of a reference Phi-29 polymerase comprising the amino acid sequence of SEQ ID NO: 1.

In some embodiments of the methods of the present disclosure, the labeled nucleotide can comprise a nucleotide label operably linked to the nucleotide. In some embodiments, the nucleotide label can be operably linked to the base, sugar or phosphate group of the nucleotide.

In some embodiments of the methods of the present disclosure, the labeled nucleotide can be a reversible terminator. In some embodiments, the modified polymerase can be operably linked to a detectable label. In some embodiments, the label of the modified polymerase and the nucleotide label can be capable of undergoing FRET with each other. Typically, FRET between the polymerase label and the nucleotide label results in the emission of one or more FRET signals. Optionally, the one or more FRET signals can be detected and analyzed to determine the occurrence of a polymerase-nucleotide interaction, or the base identity of the underlying nucleotide.

Although the polymerases differ from organism to organism, such polymerases are typically capable of template-dependent nucleic acid synthesis and share several highly conserved domains. Various studies have examined the phylogenetic relationships among various polymerases. See, e.g., Bernad, A., et al., "Structural and functional relationships between prokaryotic and eukaryotic DNA polymerases" EMBO J. 6(13):4219-4225 (1987); Braithwaite, D. K. & Ito, J., "Compilation, alignment, and phylogenetic relationships of DNA polymerases" Nucl. Acids Res. 21:787-802 (1993); Steitz et al., "DNA polymerases: structural diversity and common mechanisms" J. Biol. Chem. 274:17395-17398 (1999). Based on such studies, polymerases have been classified into the Family A DNA polymerases (based on homology to the product of the polA gene encoding E. coli DNA polymerase I); the Family B DNA polymerases (based on homology to the product of the polB gene encoding E. coli DNA polymerase II); and the Family C DNA polymerases (based on homology to the product of the polC gene encoding E. coli DNA polymerase III alpha subunit). The Family B DNA polymerases can include the DNA polymerase of the bacteriophage Phi-29, (also known as Φ29 or phi29) of the Podoviridae family of phages.

In some embodiments, the modified polymerase can be a modified Phi-29-like polymerase comprising an amino acid sequence that is at least 80%, 85%, 90%, 95%, or 99% identical to the amino acid sequence of SEQ ID NO: 1:

```
                                            (SEQ ID NO: 1)
MKHMPRKMYS CDFETTTKVE DCRVWAYGYM NIEDHSEYKI 70         80
GNSLDEFMAW VLKVQADLYF HNLKFDGAFI INWLERNGFK 90        100        110        120
WSADGLPNTY NTIISRMGQW YMIDICLGYK GKRKIHTVIY 130        140        150        160
DSLKKLPFPV KKIAKDFKLT VLKGDIDYHK ERPVGYKITP 170        180        190        200
EEYAYIKNDI QIIAEALLIQ FKQGLDRMTA GSDSLKGFKD 210        220        230        240
IITTKKFKKV FPTLSLGLDK EVRYAYRGGF TWLNDRFKEK 250        260        270        280
EIGEGMVFDV NSLYPAQMYS RLLPYGEPIV FEGKYVWDED
```

-continued
```
       290        300        310        320
YPLHIQHIRC EFELKEGYIP TIQIKRSRFY KGNEYLKSSG 330        340        350        360
GEIADLWLSN VDLELMKEHY DLYNVEYISG LKFKATTGLF 370        380        390        400
KDFIDKWTYI KTTSEGAIKQ LAKLMLNSLY GKFASNPDVT 410        420        430        440
GKVPYLKENG ALGFRLGEEE TKDPVYTPMG VFITAWARYT 450        460        470        480
TITAAQACYD RIIYCDTDSI HLTGTEIPDV IKDIVDPKKL 490        500        510        520
GYWAHESTFK RAKYLRQKTY IQDIYMKEVD GKLVEGSPDD 530        540        550        560
YTDIKFSVKC AGMTDKIKKE VTFENFKVGF SRKMKPKPVQ

570
VPGGVVLVDD TFTIK
```

In some embodiments, the reference polymerase can comprise an amino acid sequence that is at least 70%, 80%, 85%, 90%, 95%, 99% or 100% identical to the amino acid sequence of SEQ ID NO: 1.

In some embodiments, the polymerase can be a mutant Phi-29 polymerase that retains nucleotide polymerization activity but lacks the 3'→5' or 5'→3' exonuclease activity. For example, mutant Phi-29 polymerases having exonuclease-minus activity, or reduced exonuclease activity, can include the amino acid sequence of SEQ ID NO: 1 and further comprise one or more amino acid substitutions at positions selected from the group consisting of: 12, 14, 15, 62, 66, 165 and 169 (wherein the numbering is relative to the amino acid sequence of wild type Phi-29). In some embodiments, the polymerase is a phi29 polymerase comprising the amino acid sequence of SEQ ID NO: 1 and one or more of the following amino acid substitutions: D12A, E14I, E14A, T15I, N62D, D66A, Y165F, Y165C, and D169A, wherein the numbering is relative to SEQ ID NO: 1. In some embodiments, the reference polymerase can comprise an amino acid sequence that is at least 70%, 80%, 85%, 90%, 95%, 99% or 100% identical to the amino acid sequence of SEQ ID NO: 1 and further comprise one or more of the following amino acid substitutions: D12A, E14I, E14A, T15I, N62D, D66A, Y165F, Y165C, and D169A, wherein the numbering is relative to SEQ ID NO: 1. In some embodiments, the polymerase is a phi29 polymerase comprising the amino acid sequence of SEQ ID NO: 1 and one or both of the following amino acid substitutions: D12A and D66A. In some embodiments, the reference polymerase can comprise an amino acid sequence that is at least 70%, 80%, 85%, 90%, 95%, 99% or 100% identical to the amino acid sequence of SEQ ID NO: 1 and further comprise one or both of the following amino acid substitutions: D12A and D66A, wherein the numbering is relative to SEQ ID NO: 1. See, e.g., Blanco, U.S. Pat. Nos. 5,001,050, 5,198,543, and 5,576,204; and Hardin PCT/US2009/31027 with an International filing date of Jan. 14, 2009. Optionally, the polymerase can further include a biotinylation site or His tag as described herein.

In some embodiments, the modified polymerase can comprise an amino acid sequence that is at least 70%, 80%, 85%, 90%, 95%, 99% or 100% identical to the amino acid sequence of SEQ ID NO: 1 and further include one or more amino acid mutations at positions selected from the group consisting of: 132, 135, 250, 266, 332, 342, 368, 370, 371, 372, 373, 375, 379, 380, 383, 387, 390, 458, 478, 480, 484, 486, and 512, wherein the numbering is relative to the amino acid sequence of SEQ ID NO: 1. In some embodiments, the modified polymerase can comprise an amino acid deletion, wherein the deletion includes some of all of the amino acids spanning positions 306 to 311.

In some embodiments, the reference polymerase can comprise an amino acid sequence that is at least 70%, 80%, 85%, 90%, 95%, 99% or 100% identical to the amino acid sequence of SEQ ID NO: 1 and further include one or more amino acid mutations at positions selected from the group consisting of: 132, 135, 250, 266, 332, 342, 368, 371, 375, 379, 380, 383, 387, 390, 458, 478, 480, 484, 486, 510 and 512, wherein the numbering is relative to the amino acid sequence of SEQ ID NO: 1.

In some embodiments, the modified polymerase comprises an amino acid sequence that is at least 70%, 80%, 85%, 90%, 95%, 99% or 100% identical to the amino acid sequence of SEQ ID NO: 1 and further includes one or more amino acid mutations selected from the group consisting of: K132A, K135A, K135D, K135E, V250A, V250C, Y266F, D332Y, L342G, T368D, T368E, T368F, K370A, K371E, T372D, T372E, T372R, T372K, E375A, E375F, E375H, E375K, E375Q, E375R, E375S, E375W, E375Y, K379A, Q380A, K383E, K383H, K383L, K383R, N387Y, Y390F, D458N, K478D, K478E, K478R, L480K, L480R, A484E, E486A, E486D, K512A K512D, K512E, K512R, K512Y, K371E/ K383E/N387Y/D458N, Y266F/Y390F, Y266F/Y390F/ K379A/Q380A, K379A/Q380A, E375Y/Q380A/K383R, E375Y/Q380A/K383H, E375Y/Q380A/K383L, E375Y/ Q380A/V250A, E375Y/Q380A/V250C, E375Y/K512Y/ T368F, E375Y/K512Y/T368F/A484E, K379A/E375Y, K379A/K383R, K379A/K383H, K379A/K383L, K379A/ Q380A, V250A/K379A, V250A/K379A/Q380A, V250C/ K379A/Q380A, K132A/K379A and deletion of some or all of the amino acid residues spanning R306 to K311, wherein the numbering is relative to the amino acid sequence of SEQ ID NO: 1.

Also disclosed herein is a method for single molecule sequencing in real time, comprising: contacting a modified Phi-29 polymerase according to the present disclosure with labeled nucleotide under conditions where the labeled nucleotides are incorporated by the polymerase onto the end of an extending nucleic acid molecule, accompanied by the emission of a signal indicative of a nucleotide incorporation; detecting a time sequence of nucleotide incorporations; and analyzing the time sequence of nucleotide incorporations to determine a polynucleotide sequence.

In some embodiments, the reference polymerase comprises an amino acid sequence that is at least 70%, 80%, 85%, 90%, 95%, 99% or 100% identical to the amino acid sequence of SEQ ID NO: 1 and further includes one or more amino acid mutations selected from the group consisting of: K132A, K135A, K135D, K135E, V250A, V250C, Y266F, D332Y, L342G, T368D, T368E, T368F, K370A, K371E, T372D, T372E, T372R, T372K, T373A, T373F, T373H, T373K, T373Q, T373R, T373S, T373W, T373Y, T373E, E375A, E375F, E375H, E375K, E375Q, E375R, E375S, E375W, E375Y, K379A, Q380A, K383E, K383H, K383L, K383R, N387Y, Y390F, D458N, K478D, K478E, K478R, L480K, L480R, A484E, E486D, K510A, K510F, K510H, K510K, K510Q, K510R, K510S, K510W, K510Y, K510E, K512A K512D, K512E, K512R, K512Y, K371E/K383E/ N387Y/D458N, Y266F/Y390F, Y266F/Y390F/K379A/ Q380A, K379A/Q380A, E375Y/Q380A/K383R, E375Y/ Q380A/K383H, E375Y/Q380A/K383L, E375Y/Q380A/ V250A, E375Y/Q380A/V250C, E375Y/K512Y/T368F, E375Y/K512Y/T368F/A484E, K379A/E375Y, K379A/ K383R, K379A/K383H, K379A/K383L, K379A/Q380A, V250A/K379A, V250A/K379A/Q380A, V250C/K379A/ Q380A, K132A/K379A and deletion of some or all of the amino acid residues spanning R306 to K311, wherein the numbering is relative to the amino acid sequence of SEQ ID NO: 1.

Without being bound to any particular theory, it is thought that the domain comprising amino acid residues 304-314 of the amino acid sequence of SEQ ID NO: 3 (Phi-29 polymerase), or homologs thereof, can reduce or otherwise interfere with DNA initiation and/or elongation by inhibiting access to the Phi-29 polymerase active site, and that this region must be displaced in order to allow access to the active site. See, e.g., Kamtekar et al., "The Φ29 DNA polymerase: protein primer structure suggests a model for the initiation to elongation transition", EMBO J., 25:1335-1343 (2005).

In some embodiments, the modified polymerase is derived from a polymerase of any member of the Phi-29-like family of phages. The Phi-29-like phages are a genus of phages that are related to Phi-29 that includes the phages PZA, Φ15, BS32, B103, M2Y (M2), Nf1 and GA-1. Phages of this group have been sub-classified into three groups based on serological properties, DNA and/or polymerase maps and partial or complete DNA sequences, and share several characteristics in common. For example, such phages can typically undergo protein-primed DNA replication. See, for example, Meijer et al., "Phi-29 family of phages" Microbiol. & Mol. Biol. Revs. 65(2):261-287 (2001).

The genome of the Phi-29-like phage B103, including a gene encoding a B103 DNA polymerase, has been sequenced. See, e.g., Pecenkova et al., "Bacteriophage B103: complete DNA sequence of its genome and relationship to other *Bacillus* phages" Gene 199:157-163 (1999). The DNA polymerase of B103 is homologous to the DNA polymerase of Phi-29 and of other Phi-29-like phages. Collectively, these polymerases share several highly conserved regions. See, e.g., Meijer et al., "Phi-29 family of phages" Microbiol. & Mol. Biol. Revs. 65(2):261-287 (2001). These conserved regions are typically characterized by several conserved amino acid motifs. See, e.g., Blanco et al., Gene 100:27-38 (1991); Blasco et al., "Φ29 DNA polymerase Active Site" J. Biol. Chem. 268: 16763-16770 (1993) (describing regions of sequence homology and mutational analysis of consensus regions of Phi-29 and Phi-29-like DNA polymerases); Berman et al., "Structures of phi29 DNA polymerase complexed with substrate: the mechanism of translocation in B-family polymerases", EMBO J., 26:3494-3505 (2007). Site-directed mutagenesis indicates that these three regions can include an evolutionarily conserved polymerase active site.

Collectively, the polymerases of these phages share several highly conserved regions. See, e.g., Meijer et al., "Phi-29 family of phages" Microbiol. & Mol. Biol. Revs. 65(2):261-287 (2001). The conserved regions are typically characterized by the following amino acid motifs:

Dx$_2$SLYP (SEQ ID NO: 2)

The consensus sequence of SEQ ID NO: 2 represents the consensus amino acid sequence for a motif known as region 1, also named motif A.

Kx$_3$NSxYG (SEQ ID NO: 3)

The consensus sequence of SEQ ID NO: 3 represents the consensus amino acid sequence for the motif known as region 2a, also named motif B.

YGDTDS (SEQ ID NO: 4)

The consensus sequence of SEQ ID NO: 4 represents the consensus amino acid sequence for the motif known as region 3, also named motif C.

KxY (SEQ ID NO: 5)

The consensus sequence of SEQ ID NO: 5 represents the consensus amino acid sequence for the motif known as region 4. See, e.g., Blanco et al., Gene 100:27-38 (1991); Blasco et al., "Φ29 DNA polymerase Active Site" J. Biol. Chem. 268: 16763-16770 (1993) (describing regions of sequence homology and mutational analysis of consensus regions of Phi-29 and Phi-29-like DNA polymerases).

Site-directed mutagenesis indicates that these motifs can include one or more evolutionarily conserved polymerase active sites.

In some embodiments, the modified polymerase is

In some embodiments, the modified polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 6 as follows:

```
                                                                (SEQ ID NO: 6)
  1 mprkmfscdf etttklddcr vwaygymeig nldnykigns idefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyikndieii araldiqfkg 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmfdslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the modified polymerase is derived from a polymerase of the Phi-29-like phages and comprises an amino acid sequence that is at least 70%, 80%, 85%, 90%, 95%, 97%, 98%, 99% or 100% identical to the amino acid sequence, wherein the modified polymerase comprises an amino acid sequence that is at least 80%, 85%, 90%, 95%, 97%, 98% or 99% identical to the amino acid sequence of SEQ ID NO: 6, or any biologically active fragment thereof.

In some embodiments, the modified polymerase is homologous to a polymerase of one or more of the following organisms: B103, Phi-29, GA-1, PZA, Phi-15, BS32, M2Y, Nf, G1, Cp-1, PRD1, PZE, SF5, Cp-5, Cp-7, PR4, PR5, PR722, or L17. See, e.g., Meijer et al., "Phi-29 family of phages," Microbiol. & Mol. Biol. Revs. 65(2):261-287 (2001).

In some embodiments, the modified polymerase is derived from a B103 polymerase having the amino acid sequence of SEQ ID NO: 6 and further comprises one or more mutations in the amino acid sequence of SEQ ID NO: 6. In some embodiments, the one or more mutations can include, for example, substitution, chemical modification, addition, deletion and/or inversion of one or more amino acid residues, or any combination of the foregoing.

For example, in some embodiments, the modified polymerase comprises the amino acid sequence of SEQ ID NO: 6, and further comprises one or more amino acid mutations (e.g., amino acid substitutions, additions, deletions) that increases polymerase activity, reduces 3' to 5' exonuclease activity, increases the branching ratio of the polymerase with a particular labeled nucleotide, and/or increases the residence time of a particular labeled nucleotide within the polymerase active site. The modification can include, for example, one or more amino acid substitutions, additions, deletions or chemical modifications.

For example, in some embodiments, the modified polymerase includes one or more amino acid mutations that increase the polymerase activity of the modified polymerase relative to a reference polymerase having the amino acid sequence of SEQ ID NO: 6. For example, in some embodiments, the modified polymerase comprises an amino acid mutation at position 383, at position 384, or at both positions 383 and 384, wherein the numbering is relative to the amino acid sequence of SEQ ID NO: 6. In some embodiments, the modified polymerase comprises the amino acid substitutions F383L and D384N, and exhibits increased polymerase activity relative to the reference polymerase having the amino acid sequence of SEQ ID NO: 6. Typically, such mutants exhibit increased polymerase activity relative to the unmodified protein having the amino acid sequence of SEQ ID NO: 6.

In some embodiments, the modified polymerase having increased polymerase activity relative to the reference polymerase of SEQ ID NO: 6 comprises an amino acid sequence that is at least 80%, 85%, 90%, 95%, 97%, 98% or 99% identical to the amino acid sequence of SEQ ID NO: 6, or any biologically active fragment thereof, wherein the amino acid at position 383 is not phenylalanine (F), where the numbering is relative to the amino acid sequence of SEQ ID NO: 6.

In some embodiments, the modified polymerase comprises the amino acid sequence of SEQ ID NO: 6, and further comprises an amino acid substitution at position 383, wherein the numbering is relative to a B103 polymerase having the amino acid sequence of SEQ ID NO: 6. In some embodiments, the modified polymerase is a variant of B103 polymerase that comprises an amino acid sequence that is at least 80%, 85%, 90%, 95%, 97%, 98% or 99% identical to the amino acid sequence of SEQ ID NO: 6, or any biologically active fragment thereof, wherein the modified polymerase further comprises the amino acid mutation F383L.

In some embodiments, the modified polymerase is a variant of a B103 polymerase that comprises an amino acid sequence that is at least 80%, 85%, 90%, 95%, 97%, 98% or 99% identical to the amino acid sequence of SEQ ID NO: 6, or any biologically active fragment thereof, wherein the amino acid at position 384 is not aspartic acid (D), where the numbering is relative to the amino acid sequence of SEQ ID NO: 6.

In some embodiments, the modified polymerase comprises the amino acid sequence of SEQ ID NO: 6 and further comprises an amino acid substitution at position 384, wherein the numbering is relative to a B103 polymerase having the amino acid sequence of SEQ ID NO: 6. In some embodiments, the modified polymerase is a variant of B103 polymerase that comprises an amino acid sequence that is at least 80%, 85%, 90%, 95%, 97%, 98% or 99% identical to the amino acid sequence of SEQ ID NO: 6, or any biologically active fragment thereof, wherein the modified polymerase further comprises the amino acid mutation D384N. In some embodiments, the modified polymerase is a variant of B103 polymerase, or any biologically active fragment thereof, having the amino acid sequence of SEQ ID NO: 6, wherein the modified variant further comprises amino acid substitutions at positions 383 and 384, wherein the numbering is relative to the amino acid sequence of SEQ ID NO: 6. In some embodiments, the modified polymerase comprises the amino acid substitutions F383L and D384N, wherein the numbering is relative to the amino acid sequence of SEQ ID NO: 6. The amino acid sequence of this modified polymerase can be represented as follows:

```
                                                          (SEQ ID NO: 7)
  1 mprkmfscdf etttkldcr  vwaygymeig nldnykigns idefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyikndieii araldiqfkg 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmlnslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the modified B103 polymerase comprises an amino acid sequence that is at least 80%, 85%, 90%, 95%, 97%, 98% or 99% identical to the amino acid sequence of SEQ ID NO: 7, or any biologically active fragment thereof. Typically, a modified polymerase having the amino acid sequence of SEQ ID NO: 7 will exhibit increased polymerase activity (e.g., primer extension activity) relative to the unmodified reference polymerase having the amino acid sequence of SEQ ID NO: 6.

In some embodiments, the modified polymerase comprises one or more modifications resulting in altered exonuclease activity (for example 3' to 5' exonuclease activity) as compared to a reference polymerase (for example, an unmodified counterpart). In some embodiments, the modification comprises an amino acid substitution. In some embodiments, the modified polymerase lacks 3' to 5' exonuclease activity, or lacks 5' to 3' exonuclease activity, or both.

Mutations that reduce or eliminate 3' to 5' exonuclease activity have been described, for example, in Phi-29 polymerase at various residues. See, e.g., de Vega et al., "Primer-terminus stabilization at the 3'-5' exonuclease active site of Φ29 DNA polymerase. Involvement of two amino acid residues highly conserved in proofreading DNA polymerases" EMBO J., 15(5):1182-1192 (1996); Soengas et al., "Site-directed mutagenesis at the Exo III motif of Φ29 DNA polymerase; overlapping structural domains for the 3'-5' exonuclease and strand-displacement activities" EMBO J., 11(11): 4227-4237 (1992); Blanco et al., U.S. Pat. Nos. 5,001,050, 5,198,543 and 5,576,204.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more amino acid substitutions, additions or deletions at one or more positions selected from the group consisting of: 2, 9, 11, 12, 58, 59, 63, 162, 166, 377 and 385, wherein the numbering is relative to SEQ ID NO: 6. In some embodiments, this modified polymerase can exhibit reduced exonuclease activity relative to an unmodified counterpart.

In some embodiments, the modified polymerase comprises an amino acid sequence that is at least 70%, 75%, 85%, 90%, 95% or 99% identical to any one of the amino acid sequences SEQ ID NO: 6 or SEQ ID NO: 7, or to any biologically active fragment thereof, and further comprises the amino acid mutation D166A, wherein the numbering is relative to SEQ ID NO: 6. In some embodiments, this modified polymerase can exhibit reduced 3' to 5' exonuclease activity relative to a reference polymerase having the amino acid sequence of SEQ ID NO: 7.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: D9A, E11A, E11I, T12I, H58R, N59D, D63A, Y162F, Y162C, D166A, Q377A and S385G, wherein the numbering is relative to SEQ ID NO: 6. In some embodiments, this modified polymerase can exhibit reduced exonuclease activity relative to an unmodified counterpart.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: D9A, E11A, E11I, T12I, H58R, N59D, D63A, Y162F, Y162C, Q377A and S385G, wherein the numbering is relative to SEQ ID NO: 6. Typically, this modified polymerase can exhibit reduced 3' to 5' exonuclease activity relative to an unmodified counterpart.

In some embodiments, the modified polymerase comprises an amino acid sequence that is at least 85%, 90%, 95% or 99% identical to the amino acid sequence of SEQ ID NO: 6 and further comprises an amino acid substitution wherein the amino acid residue at position 9 is replaced with an alanine ("A") residue, wherein the numbering is relative to the amino acid sequence of SEQ ID NO: 6.

In some embodiments, the modified polymerase comprises an amino acid sequence that is at least 85%, 90%, 95% or 99% identical to the amino acid sequence of SEQ ID NO: 6 and further comprises one or more of the amino acid substitutions D9A, E11A, T12I, H58R, N59D, D63A, D166A, Q377A, S385G, or any combination thereof, wherein the numbering is relative to the amino acid sequence of SEQ ID NO: 6. In some embodiments, the modified polymerase comprises any one, two, three, four, five or all of these mutations. In some embodiments, the modified polymerase comprises the amino acid substitutions D9A and D63A. In some embodiments, the modified polymerase comprises the amino acid substitutions N59D and T12I. Typically, this polymerase will exhibit reduced 3' to 5' exonuclease activity relative to an unmodified counterpart.

In some embodiments, the modified polymerase comprises an amino acid sequence that is at least 85%, 90%, 95% or 99% identical to the amino acid sequence of SEQ ID NO: 6, SEQ ID NO: 7 or SEQ ID NO: 8 and comprises any one, two, three or more of the mutations described herein.

Optionally, the modification(s) reducing 3' to 5' exonuclease activity can be combined with additional modification(s) that increase polymerase activity. Modifications increasing polymerase activity include, for example, the amino acid substitutions F383L and D384N.

In one embodiment, the modified polymerase comprises the amino acid sequence of SEQ ID NO: 6 and further comprises the amino acid substitution D166A, which reduces the 3' to 5' exonuclease activity, in combination with the amino acid substitutions F383L and D384N, which increase the polymerase activity of the modified polymerase, relative to the unmodified protein having the amino acid sequence of SEQ ID NO: 6. The amino acid sequence of this triple mutant polymerase is the amino acid sequence of SEQ ID NO: 8, below:

```
                                                              (SEQ ID NO: 8)
  1 mprkmfscdf etttkldder vwaygymeig nldnykigns ldefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyiknaieii araldiqfkg 181 gldrmtagsd slkgfkdils tkkfnkvfpk lslpmdkeir rayrggftwl ndkykekeig 241 egmvfdvnsl ypsqmysrpl pygapivfqg kyekdeqypl yiqrirfefe lkegyiptiq 301 ikknpffkgn eylknsgaep velyltnvdl eliqehyemy nveyidgfkf rektglfkef 361 idkwtyvkth ekgakkqlak lmlnslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

In some embodiments, the modified polymerase comprises an amino acid sequence that is at least 70%, 75%, 80%, 85%, 90%, 95%, 97%, 98% or 99% identical to the amino acid sequence of SEQ ID NO: 8, or any biologically active fragment thereof. Typically, the modified polymerase of SEQ ID NO: 8 will exhibit reduced exonuclease activity relative to a reference polymerase comprising the amino acid sequence of SEQ ID NO: 1, SEQ ID NO: 6, SEQ ID NO: 7 or SEQ ID NO: 13.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more modifications resulting in altered (e.g., increased or decreased) branching ratio and/or nucleotide binding affinity ($K_D$) as compared to a reference polymerase. For example, mutations that may affect branching ratio and/or nucleotide binding affinity can include mutations (e.g., amino acid substitutions, additions or deletions) at positions selected from the group consisting of: 370, 371, 372, 373, 374, 375, 376 and 377, wherein the numbering is relative to the amino acid sequence of SEQ ID NO: 6. In some embodiments, the mutation comprises one or more of the amino acid substitutions selected from the group consisting of H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the sequence of SEQ ID NO: 6.

In some embodiments, the polymerase further comprises one or more mutations reducing the exonuclease activity as described herein such as, for example, the amino acid substitution D166A.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more modifications resulting in altered (e.g., increased or decreased) primer extension activity as compared to a reference polymerase. For example, mutations that may affect primer extension activity can include mutations (e.g., amino acid substitutions, additions or deletions) at positions selected from the group consisting of: 129 and 339, wherein the numbering is relative to the amino acid sequence of SEQ ID NO: 6. In some embodiments, the mutation comprises one or more of the amino acid substitutions selected from the group consisting of: In some embodiments, the polymerase further comprises one or more mutations reducing the exonuclease activity as described herein such as, for example, the amino acid substitution D166A.

In some embodiments, the modified polymerase comprises an amino acid sequence that is at least 70%, 75%, 85%, 90%, 95% or 99% identical to any one of the amino acid sequences SEQ ID NO: 6, SEQ ID NO: 7 and SEQ ID NO: 8, or to any biologically active fragment thereof, and further comprises one or more modifications resulting in altered (e.g., increased or decreased) $t_{pol}$ or $k_{pol}$ values as compared to a reference polymerase. For example, mutations that may affect $t_{pol}$ or $k_{pol}$ values can include mutations (e.g., amino acid substitutions, additions or deletions) at position 380, wherein the numbering is relative to the amino acid sequence of SEQ ID NO: 6. In some embodiments, the mutation comprises one or more of the amino acid substitutions selected from the group consisting of: K380E, K380T, K380S, K380R, K380A, K380Q, K380W, K380Y and K380F, and results in an increased $t_{pol}$ value (or decreased $k_{pol}$ value) relative to the unmodified counterpart. In some embodiments, the polymerase further comprises one or more mutations reducing the exonuclease activity as described herein such as, for example, the amino acid substitution D166A.

In some embodiments, the modified polymerase is a variant of a B103 polymerase comprising the amino acid sequence of SEQ ID NO: 6, SEQ ID NO: 7 or SEQ ID NO: 8, wherein the variant further comprises any one, two, three or more modifications at amino acid positions 2, 9, 12, 14, 15, 58, 59, 63, 129, 166, 246, 247, 339, 370, 371, 372, 373, 374, 375, 376, 377, 380, 383, 384, 385, 455, 507, 509, or any combinations thereof, wherein the numbering is relative to the amino acid sequence of SEQ ID NO: 6. In some embodiments, the modifications can include deletions, additions and substitutions. The substitutions can be conservative or non-conservative substitutions.

In some embodiments, the modified polymerase is a variant of a B103 polymerase comprising the amino acid sequence of SEQ ID NO: 6, SEQ ID NO: 7 or SEQ ID NO: 8, wherein the variant further comprises any one, two, three or more modifications at amino acid positions selected from the group consisting of: 2, 9, 12, 14, 15, 58, 59, 61, 63, 98, 129, 166, 176, 185, 186, 187, 195, 208, 246, 247, 248, 251, 252, 256, 300, 302, 310, 339, 357, 360, 362, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 552, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio, increased nucleotide binding affinity, increased photostability and/or increased nanoparticle tolerance relative to a reference polymerase having the amino acid sequence of SEQ ID NO: 7.

In some embodiments, the modified polymerase comprises one or more amino acid substitutions at any one, two, three or more positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises a modification at residue at position 2, wherein the numbering is relative to a B103 polymerase having the amino acid sequence of SEQ ID NO: 6. The modification can include, for example, one or more amino acid substitutions, additions, deletions or chemical modifications. In some embodiments, the modified polymerase comprises a proline (P) residue at position 2.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 370, wherein the numbering is relative to a B103 polymerase having the amino acid sequence of SEQ ID NO: 6. In some embodiments, the amino acid at position 370 is any amino acid other than threonine (T) or histidine (H). In some embodiments, the amino acid at position 370 of the modified polymerase is glutamic acid (E), serine (S), lysine (K), arginine (R), alanine (A), glutamine (Q), tryptophan (W), tyrosine (Y), phenylalanine (F) or any other natural or non-natural amino acid, other than threonine (T). modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid substitution selected from the group consisting of: H370E, H370K, H370G, H370T, H370S, H370K, H370R, H370A, H370Q, H370W, H370Y and H370F, wherein the numbering is relative to the amino acid sequence of SEQ ID NO: 6.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 371, wherein the numbering is relative to a B103 polymerase having the amino acid sequence of SEQ ID NO: 7. The modification can include, for example, one or more amino acid substitutions, additions, deletions or chemical modifications. In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, wherein the amino acid at position 371 is any amino acid other than serine (S). In some embodiments, the modified polymerase comprises a glutamic acid (E) residue at position 371. In some embodiments, the amino acid at position 371 is any amino acid other than serine (S) or glutamic acid (E). In some embodiments, the amino acid at position 371 of the modified polymerase is glycine (G), histidine (H), lysine (K), arginine (R), alanine (A), glutamine (Q), tryptophan (W), tyrosine (Y), phenylalanine (F) or any other natural or non-natural amino acid, other than serine (S). In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of E371G, E371H, E371T, E371S, E371K, E371R, E371A, E371Q, E371W, E371Y and E371F, wherein the numbering is relative to the amino acid sequence of SEQ ID NO: 6.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 372, wherein the numbering is relative to a B103 polymerase having the amino acid sequence of SEQ ID NO: 7. The modification can include, for example, one or more amino acid substitutions, additions, deletions or chemical modifications. In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, wherein the amino acid at position 372 is any amino acid other than glutamic acid (E). In some embodiments, the modified polymerase comprises a lysine (K) residue at position 372. In some embodiments, the amino acid at position 372 is any amino acid other than glutamic acid (E) or lysine (K). In some embodiments, the amino acid at position 372 of the modified polymerase is glycine (G), histidine (H), serine (S), arginine (R), alanine (A), glutamine (Q), tryptophan (W), tyrosine (Y), phenylalanine (F) or any other natural or non-natural amino acid, other than glutamic acid (E). In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: K372G, K372E, K372T, K372S, K372R, K372A, K372Q, K372W, K372Y and K372F, wherein the numbering is relative to the amino acid sequence of SEQ ID NO: 6.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 380, wherein the numbering is relative to a B103 polymerase having the amino acid sequence of SEQ ID NO: 7. The modification can include, for example, one or more amino acid substitutions, additions, deletions or chemical modifications. In some embodiments, the amino acid at position 380 can be any amino acid other than lysine (K). In some embodiments, the amino acid at position 380 of the modified polymerase is glycine (G), histidine (H), serine (S), arginine (R), alanine (A), glutamine (Q), tryptophan (W), tyrosine (Y), phenylalanine (F) or any other natural or non-natural amino acid, other than lysine (K). In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: K380E, K380T, K380S, K380R, K380A, K380Q, K380W, K380Y and K380F, wherein the numbering is relative to the amino acid sequence of SEQ ID NO: 6.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 507, wherein the numbering is relative to a B103 polymerase having the amino acid sequence of SEQ ID NO: 7. The modification can include, for example, one or more amino acid substitutions, additions, deletions or chemical modifications. In some embodiments, the amino acid at position 507 can be any amino acid other than aspartic acid (D). In some embodiments, the modified polymerase comprises a histidine (H) residue at position D. In some embodiments, the amino acid at position 380 of the modified polymerase is glycine (G), histidine (H), serine (S), arginine (R), alanine (A), glutamine (Q), tryptophan (W), tyrosine (Y), phenylalanine (F) or any other natural or non-natural amino acid, other than aspartic acid (D). In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: D507H, D507G, D507E, D507T, D507S, D507R, D507A, D507R, D507Q, D507W, D507Y and D507F, wherein the numbering is relative to the amino acid sequence of SEQ ID NO: 6.

In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises an amino acid modification at position 509, wherein the numbering is relative to a B103 polymerase having the amino acid sequence of SEQ ID NO: 7. The modification can include, for example, one or more amino acid substitutions, additions, deletions or chemical modifications. In some embodiments, the amino acid at position 509 can be any amino acid other than lysine (K). In some embodiments, the amino acid at position 509 of the modified polymerase is glycine (G), histidine (H), serine (S), arginine (R), alanine (A), glutamine (Q), tryptophan (W), tyrosine (Y), phenylalanine (F) or any other natural or non-natural amino acid, other than lysine (K). In some embodiments, the modified polymerase is a variant of B103 polymerase that comprises an amino acid sequence that is at least 70%, 75%, 80%, 85%, 90%, 95%, 97%, 98% or 99% identical to any one of the amino acid sequences SEQ ID NO: 6, SEQ ID NO: 7 and SEQ ID NO: 8, or to any biologically active fragment thereof, and further comprises one or more amino acid substitutions selected from the group consisting of: K509H, K509G, K509D, K509R, K509E, K509T, K509S, K509R, K509A, K509Q, K509W, K509Y and K509F, wherein the numbering is relative to the amino acid sequence of SEQ ID NO: 6.

In some embodiments, the modified polymerase comprises an amino acid sequence that is at least 85%, 90%, 95% or 99% identical to the amino acid sequence of SEQ ID NO: 6, SEQ ID NO: 7 or SEQ ID NO: 8 and comprises any one, two, three or more of the mutations selected from the group consisting of: D9A, E11A, T12I, H58R, N59D, D63A, D166A, Q377A, S385G, T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, F383L, D384N, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6, 7 or 8, respectively.

In some embodiments, the modified polymerase comprises one or more amino acid substitutions selected from the group consisting of: D9A, E11A, E11I, T12I, H58R, N59D, D63A, Y162F, Y162C, D166A, Q377A and S385G, and further includes one or more amino acid substitutions selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, F383L, D384N, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the sequence of SEQ ID NO: 6.

In some embodiments, the modified polymerase comprises one or more amino acid substitutions selected from the group consisting of: D9A, E11A, T12I, H58R, N59D, D63A, D166A, Q377A and S385G, and further comprises amino acid substitutions at two or more positions selected from the group consisting of: 370, 372 and 507.

In some embodiments, the modified polymerase comprises one or more amino acid substitutions selected from the group consisting of: D9A, E11A, T12I, H58R, N59D, D63A, D166A, Q377A and S385G, and further comprises the amino acid substitutions K372Y and D507H.

In some embodiments, the modified polymerase comprises one or more amino acid substitutions selected from the group consisting of: D9A, E11A, T12I, H58R, N59D, D63A, D166A, Q377A and S385G, and further comprises the amino acid substitutions H370R and D507H.

In some embodiments, the modified polymerase comprises one or more amino acid substitutions selected from the group consisting of: D9A, E11A, T12I, H58R, N59D, D63A, D166A, Q377A and S385G, and further comprises two or more amino acid substitutions selected from the group consisting of: H370R, K372Y and D507H.

In some embodiments, the modified polymerase comprises an amino acid sequence that is at least 85%, 90%, 95%, 97%, 98% or 99% identical to the amino acid sequence of SEQ ID NO: 7 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 6. Typically, such a modified polymerase will exhibit reduced 3' to 5' exonuclease activity relative to reference polymerase having the amino acid sequence of SEQ ID NO: 7.

In some embodiments, the modified polymerase comprises an amino acid sequence that is at least 85%, 90%, 95%, 97%, 98% or 99% identical to the amino acid sequence of SEQ ID NO: 7 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6. In some embodiments, the modified polymerase comprises any one, two, three, four, five or all of these mutations. In some embodiments, the modified polymerase comprises the amino acid substitution D166A. In some embodiments, the modified polymerase comprises the amino acid substitutions D9A and D63A. In some embodiments, the modified polymerase comprises the amino acid substitutions N59D and T12I. Typically, such modified polymerases will exhibit reduced 3' to 5' exonuclease activity relative to reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further comprises an amino acid substitution at one or more positions selected from the group consisting of: 2, 73, 107, 147, 221, 318, 339, 359, 372, 405, 503, 511, 544 and 550, wherein the numbering is relative to the amino acid sequence of SEQ ID NO: 6. Typically, this modified polymerase can exhibit increased photostability and/or increased nanoparticle tolerance relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 6. Optionally, this modified polymerase comprises the amino acid mutation H370R. Typically, this modified polymerase can exhibit an increased branching ratio and/or increased nucleotide binding affinity relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes a mutation at position 365, wherein the numbering is relative to the amino acid sequence of SEQ ID NO: 6. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 6. Optionally, this modified polymerase comprises the amino acid mutation T365F. Typically, this modified polymerase can exhibit an increased branching ratio and/or increased nucleotide binding affinity relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes a mutation at position 372, wherein the numbering is relative to the amino acid sequence of SEQ ID NO: 6. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 6. Optionally, this modified polymerase comprises the amino acid mutation K372Y. Typically, this modified polymerase can exhibit an increased branching ratio and/or increased nucleotide binding affinity relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes a mutation at position 481, wherein the numbering is relative to the amino acid sequence of SEQ ID NO: 6. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 6. Optionally, this modified polymerase comprises the amino acid mutation A481E. Typically, this modified polymerase can exhibit an increased branching ratio and/or increased nucleotide binding affinity relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes a mutation at position 509, wherein the numbering is relative to the amino acid sequence of SEQ ID NO: 6. In some embodiments, the mutation is selected from the group consisting of: K509E, K509F, K509O, K509S, K509R, K509K, K509A, K509T, K509Q, K509W and K509Y, wherein the numbering is relative to the amino acid sequence of SEQ ID NO: 6. Optionally, this modified polymerase comprises the amino acid mutation K509Y. Typically, this modified polymerase can exhibit an increased branching ratio and/or increased nucleotide binding affinity relative to a reference polymerase having the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio and/or increased nucleotide binding affinity relative to a reference polymerase having the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further comprises an amino acid mutation at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio, increased nucleotide binding affinity, increased photostability and/or increased nanoparticle tolerance relative to a reference polymerase having the amino acid sequence of SEQ ID NO: 7.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, F383L, D384N, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. In some embodiments, the modified polymerase comprises the amino acid mutations Typically, this modified polymerase can exhibit an increased branching ratio and/or increased nucleotide binding affinity relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 80%, 85%, 90%, 95%, 97%, 98%, 99% or 100% identical to the amino acid sequence of SEQ ID NO: 7 and further includes amino acid mutations at positions 372 and 509, wherein the numbering is relative to the amino acid sequence of SEQ ID NO: 7. In some embodiments, the modified polymerase comprises an amino acid sequence that is at least 80%, 85%, 90%, 95%, 97%, 98%, 99% or 100% identical to the amino acid sequence of SEQ ID NO: 7 and further includes the amino acid substitutions E372Y and K509Y, wherein the numbering is relative to the amino acid sequence of SEQ ID NO: 7. In some embodiments, the modified polymerase comprises an amino acid sequence that is at least 80%, 85%, 90%, 95%, 97%, 98%, 99% or 100% identical to the amino acid sequence of SEQ ID NO: 7 and further includes amino acid mutations at positions 365, 372 and 509, wherein the numbering is relative to the amino acid sequence of SEQ ID NO: 7. In some embodiments, the modified polymerase comprises an amino acid sequence that is at least 80%, 85%, 90%, 95%, 97%, 98%, 99% or 100% identical to the amino acid sequence of SEQ ID NO: 7 and further includes the amino acid substitutions T365F, E372Y and K509Y, wherein the numbering is relative to the amino acid sequence of SEQ ID NO: 7. In some embodiments, the modified polymerase comprises an amino acid sequence that is at least 80%, 85%, 90%, 95%, 97%, 98%, 99% or 100% identical to the amino acid sequence of SEQ ID NO: 7 and further includes amino acid mutations at positions 365, 372, 481 and 509, wherein the numbering is relative to the amino acid sequence of SEQ ID NO: 7. In some embodiments, the modified polymerase comprises an amino acid sequence that is at least 80%, 85%, 90%, 95%, 97%, 98%, 99% or 100% identical to the amino acid sequence of SEQ ID NO: 7 and further includes the amino acid substitutions T365F, E372Y, A481E and K509Y, wherein the numbering is relative to the amino acid sequence of SEQ ID NO: 6. Typically, such modified polymerases can exhibit an increased branching ratio and/or increased nucleotide binding affinity relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 7. Typically, this modified polymerase can exhibit an increase $t_{-1}$ value in the presence of the dye-labeled nucleotides relative to a reference polymerase having the amino acid sequence of SEQ ID NO: 7. In some embodiments, the $t_{-1}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 7. In some embodiments, the $t_{-1}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation H370R, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 7. Typically, this modified polymerase can exhibit an increased $t_{pol}$ value in the presence of the dye-labeled nucleotides relative to a reference polymerase having the amino acid sequence of SEQ ID NO: 7. In some embodiments, the $t_{pol}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. In some embodiments, the $t_{pol}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation K380R, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. Optionally, the modified polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 1 and further includes an amino acid mutation selected from the group: T373G, T373E, T373T, T373S, T373R, T373A, K T373Q, T373W, T373Y and T373F, wherein the numbering is relative to the amino acid sequence of SEQ ID NO: 1. Typically, this modified polymerase can exhibit an increased $t_{-1}$ value in the presence of the dye-labeled nucleotides relative to a reference polymerase having the amino acid sequence of SEQ ID NO: 1. In some embodiments, the $t_{-1}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D12A, E14I, E14A, T15I, N62D, D66A, Y165F, Y165C, and D169A, wherein the numbering is relative to the amino acid sequence of SEQ ID NO: 1. In some embodiments, the $t_{-1}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation T373R, wherein the numbering is relative to the amino acid sequence of SEQ ID NO: 1. In some embodiments, the modified polymerase further includes the mutations D12A and D66A.

Also disclosed herein are exemplary nucleotide sequences (polynucleotides) encoding the modified polymerases of the present disclosure.

In some embodiments, the nucleotide sequence encodes a modified polymerase having or comprising an amino acid sequence that is at least 80%, 85%, 90%, 95%, 97%, 98% or 99% identical to the amino acid sequence of SEQ ID NO: 7.

In some embodiments, the nucleotide sequence encoding the modified polymerase having the amino acid sequence of SEQ ID NO: 7 comprises the following nucleotide sequence:

(SEQ ID NO: 9)
```
atgcctcgcaaaatgtttagctgcgattttgaaaccaccaccaaactgga
tgattgtcgtgtttgggcctatggctatatggaaattggcaacctggata
attataaaatcggcaatagcctggatgaatttatgcagtgggttatggaa
attcaggccgatctgtattttcataacctgaaatttgatggtgcctttat
tgtgaattggctggaacatcatggctttaaatggtctaatgaaggcctgc
cgaatacctataacaccatcattagcaaaatgggccagtggtatatgatt
gatatttgctttggctataaaggcaaacgtaaactgcataccgtgattta
tgatagcctgaaaaaactgccgtttccggtgaaaaaaatcgccaaagatt
tccaattacctttactgaagggtgatattgattatcatgcagaacgtccg
gttggtcatgaaattacaccggaagaatatgaatacatcaagaatgatat
tgaaattattgcccgtgccctggatattcagtttaaacagggtctggatc
gtatgaccgcaggtagcgattctctgaaaggctttaaagatattctgagc
accaaaaaatttaacaaagtgtttccgaaactgagcctgccgatggataa
agaaattcgtcgtgcctatcgtggtggttttacctggctgaatgataaat
ataaagaaaaagaaattggcgaaggcatggttttttgatgttaatagcctg
tatccgagccagatgtatagccgtccgctgccgtatggtgcaccgattgt
gtttcagggcaaatatgaaaaagatgaacagtatccgctgtatattcagc
gcatccgctttgaatttgaactgaaagaaggctatatcccgaccatccag
attaaaaaaaatccgtttttttaaaggcaacgaatatctgaaaaatagcgg
tgcagaaccggttgaactgtatctgaccaatgtggatctggaactgatcc
aggaacattatgaaatgtacaacgtggaatatattgatggttttaaattt
cgcgaaaaaaccggtctgtttaaagagttcattgataaatggacctatgt
gaaaacccatgaaaaaggtgcaaaaaaacagctggccaaactgatgttga
attccctgtatggcaaatttgcaagcaatccggatgttaccggtaaagtt
ccgtatctgaaagaagatggtagcctgggttttcgtgttggtgatgaaga
atataaagatccggtttataccccgatgggtgttttttattaccgcatggg
cacgttttaccaccattaccgcagcacaggcatgttatgaccgcattatt
tattgcgataccgatagcattcatctgaccggcaccgaagttccggaaat
tattaaagatattgttgatccgaaaaaactgggttattgggcacatgaaa
gcacctttaaacgtgcaaaatatctgcgccagaaaacctatattcaggat
atttatgccaaagaagtggacggtaaactgattgaatgttctccggatga
agcaaccaccacaaaatttagcgttaaatgcgcaggtatgaccgatacca
ttaaaaaaaagtgaccctttgataactttcgtgtgggttttagcagcacc
ggtaaaccgaaaccggttcaggttaatggtggtgttgttctggttgatag
cgtgtttaccattaaataa
```

In some embodiments, the nucleotide sequence of the modified polymerase comprises a polynucleotide that is at least 80%, 85%, 90%, 95%, 97%, 98% or 99% identical to the nucleotide sequence of SEQ ID NO: 9.

In some embodiments, the modified polymerase comprising the amino acid sequence of SEQ ID NO: 7 can be encoded by the following nucleotide sequence:

(SEQ ID NO: 10)
ATGCCTAGAAAAATGTTTAGTTGTGACTTTGAGACGACTACAAAGTTAGA
CGATTGTCGTGTATGGGCATATGGCTATATGGAAATCGGTAATCTCGACA
ACTACAAGATTGGAAATAGCTTAGATGAATTCATGCAGTGGGTTATGGAA
ATTCAAGCTGATTTATATTTCCACAATCTAAAATTTGACGGTGCTTTCAT
TGTAAACTGGTTAGAGCATCATGGTTTTAAGTGGTCAAACGAAGGGTTAC
CGAATACTTATAACACAATAATATCAAAAATGGGTCAATGGTATATGATT
GACATATGTTTCGGCTATAAGGGAAAACGGAAATTACATACAGTGATATA
CGACAGCTTAAAGAAATTGCCGTTCCCAGTAAAGAAAATAGCGAAAGATT
TTCAATTACCGTTATTGAAGGGTGACATTGATTACCACGCTGAACGTCCT
GTTGGACATGAGATAACACCCGAAGAATACGAGTATATTAAGAACGACAT
AGAAATTATCGCACGTGCACTTGACATTCAATTTAAACAGGGTTTAGACC
GAATGACAGCTGGGAGCGATAGCCTTAAAGGGTTTAAGGACATACTTAGC
ACCAAGAAATTTAACAAGGTGTTTCCTAAGCTTAGCCTACCAATGGATAA
AGAAATAAGGCGAGCTTATCGTGGTGGCTTCACATGGTTAAACGATAAAT
ACAAAGAAAAGAGATTGGTGAAGGTATGGTGTTTGACGTTAACAGCCTA
TACCCCAGTCAGATGTATTCCCGACCACTCCCGTACGGAGCGCCAATCGT
ATTCCAAGGAAAGTATGAGAAAGATGAGCAATATCCGCTCTATATACAGC
GTATCAGATTTGAGTTTGAATTGAAAGAGGGCTATATACCCACAATTCAG
ATTAAGAAAAATCCCTTTTTTAAGGGTAATGAGTATCTTAAAAACAGTGG
CGCTGAGCCTGTTGAACTATATCTTACTAATGTAGATTTAGAATTAATAC
AGGAACACTACGAAATGTATAACGTTGAGTATATTGACGGATTTAAATTC
CGTGAAAAGACTGGATTATTCAAAGAGTTTATTGATAAATGGACATATGT
AAAAACTCATGAAAAGGGAGCTAAGAAACAATTGGCTAAGCTAATGTTGA
ATAGTCTCTATGGTAAATTTGCAAGTAACCCTGACGTTACAGGTAAAGTC
CCTTATTTAAAAGAAGATGGGAGCCTTGGTTTCCGTGTTGGTGATGAGGA
ATATAAAGACCCTGTTTATACACCTATGGGTGTGTTTATAACGGCATGGG
CTAGATTTACAACTATAACAGCGGCACAAGCGTGTTACGATAGAATTATA
TATTGTGACACTGATAGTATACATTTAACAGGTACAGAAGTACCAGAAAT
AATAAAGGATATTGTTGATCCAAAAAAGTTAGGGTACTGGGCGCATGAAA
GCACATTTAAGAGAGCAAAATATTTACGTCAGAAAACGTATATTCAAGAC
ATATATGCGAAAGAGGTTGACGGTAAATTGATAGAGTGTTCACCTGATGA
AGCTACGACAACTAAATTCAGTGTGAAATGTGCCGGAATGACTGACACTA
TCAAAAAGAAAGTCACATTTGATAACTTTAGAGTTGGTTTCAGTAGCACG
GGTAAACCTAAACCAGTTCAAGTTAATGGCGGGGTAGTGTTGGTTGATAG
TGTGTTTACGATTAAA

In some embodiments, the nucleotide sequence of the modified polymerase comprises a polynucleotide that is at least 80%, 85%, 90%, 95%, 97%, 98% or 99% identical to the nucleotide sequence of SEQ ID NO: 10.

In some embodiments, the polynucleotide encodes a modified polymerase having or comprising an amino acid sequence that is at least 80%, 85%, 90%, 95%, 97%, 98% or 99% identical to the amino acid sequence of SEQ ID NO: 7.

In some embodiments, the modified polymerase comprising the amino acid sequence of SEQ ID NO: 8 can be encoded by the following nucleotide sequence:

(SEQ ID NO: 11)
atgcctcgcaaaatgtttagctgcgattttgaaaccaccaccaaactgga
tgattgtcgtgtttgggcctatggctatatggaaattggcaacctggata
attataaaatcggcaatagcctggatgaatttatgcagtgggttatggaa
attcaggccgatctgtattttcataacctgaaatttgatggtgcctttat
tgtgaattggctggaacatcatggctttaaatggtctaatgaaggcctgc
cgaatacctataacaccatcattagcaaaatgggccagtggtatatgatt
gatatttgctttggctataaaggcaaacgtaaactgcataccgtgattta
tgatagcctgaaaaaactgccgtttccggtgaaaaaaatcgccaaagatt
ccaattacctttactgaagggtgatattgattatcatgcagaacgtccg
gttggtcatgaaattacaccggaagaatatgaatacatcaagaatgctat
tgaaattattgcccgtgccctggatattcagtttaaacagggtctggatc
gtatgaccgcaggtagcgattctctgaaaggctttaaagatattctgagc
accaaaaaatttaacaaagtgtttccgaaactgagcctgccgatggataa
agaaattcgtcgtgcctatcgtggtggttttacctggctgaatgataaat
ataaagaaaagaaattggcgaaggcatggttttttgatgttaatagcctg
tatccgagccagatgtatagccgtccgctgccgtatggtgcaccgattgt
gtttcagggcaaatatgaaaagatgaacagtatccgctgtatattcagc
gcatccgctttgaatttgaactgaaagaaggctatatcccgaccatccag
attaaaaaaaatccgttttttaaaggcaacgaatatctgaaaaatagcgg
tgcagaaccggttgaactgtatctgaccaatgtggatctggaactgatcc
aggaacattatgaaatgtacaacgtggaatatattgatggttttaaattt
cgcgaaaaaaccggtctgtttaaagagttcattgataaatggacctatgt
gaaaacccatgaaaaaggtgcaaaaaaacagctggccaaactgatgttga
attccctgtatggcaaatttgcaagcaatccggatgttaccggtaaagtt
ccgtatctgaaagaagatggtagcctgggttttcgtgttggtgatgaaga
atataaagatccggtttatacccgatgggtgtttttattaccgcatggg
cacgttttaccaccattaccgcagcacaggcatgttatgaccgcattatt
tattgcgataccgatagcattcatctgaccggcaccgaagttccggaaat
tattaaagatattgttgatccgaaaaaactgggttattgggcacatgaaa
gcacctttaaacgtgcaaaatatctgcgccagaaaacctatattcaggat
atttatgccaaagaagtggacggtaaactgattgaatgttctccggatga
agcaaccaccacaaaatttagcgttaaatgcgcaggtatgaccgatacca
ttaaaaaaaagtgacctttgataactttcgtgtgggttttagcagcacc
ggtaaaccgaaaccggttcaggttaatggtggtgttgttctggttgatag
cgtgtttaccattaaataa In some embodiments, the nucleotide sequence of the modified polymerase comprises a polynucleotide that is at least 80%, 85%, 90%, 95%, 97%, 98% or 99% identical to the nucleotide sequence of SEQ ID NO: 11.

In some embodiments, the modified polymerase comprising the amino acid sequence of SEQ ID NO: 8 can be encoded by the following nucleotide sequence:

(SEQ ID NO: 12)
```
ATGCCTAGAAAAATGTTTAGTTGTGACTTTGAGACGACTACAAAGTTAGA
CGATTGTCGTGTATGGGCATATGGCTATATGGAAATCGGTAATCTCGACA
ACTACAAGATTGGAAATAGCTTAGATGAATTCATGCAGTGGGTTATGGAA
ATTCAAGCTGATTTATATTTCCACAATCTAAAATTTGACGGTGCTTTCAT
TGTAAACTGGTTAGAGCATCATGGTTTTAAGTGGTCAAACGAAGGGTTAC
CGAATACTTATAACACAATAATATCAAAAATGGGTCAATGGTATATGATT
GACATATGTTTCGGCTATAAGGGAAAACGGAAATTACATACAGTGATATA
CGACAGCTTAAAGAAATTGCCGTTCCCAGTAAAGAAAATAGCGAAAGATT
TTCAATTACCGTTATTGAAGGGTGACATTGATTACCACGCTGAACGTCCT
GTTGGACATGAGATAACACCCGAAGAATACGAGTATATTAAGAACGCCAT
AGAAATTATCGCACGTGCACTTGACATTCAATTTAAACAGGGTTTAGACC
GAATGACAGCTGGGAGCGATAGCCTTAAAGGGTTAAGGACATACTTAGC
ACCAAGAAATTTAACAAGGTGTTTCCTAAGCTTAGCCTACCAATGGATAA
AGAAATAAGGCGAGCTTATCGTGGTGGCTTCACATGGTTAAACGATAAAT
ACAAAGAAAAGAGATTGGTGAAGGTATGGTGTTTGACGTTAACAGCCTA
TACCCCAGTCAGATGTATTCCCGACCACTCCCGTACGGAGCGCCAATCGT
ATTCCAAGGAAAGTATGAGAAAGATGAGCAATATCCGCTCTATATACAGC
GTATCAGATTTGAGTTTGAATTGAAAGAGGGCTATATACCCACAATTCAG
ATTAAGAAAAATCCCTTTTTTAAGGGTAATGAGTATCTTAAAAACAGTGG
CGCTGAGCCTGTTGAACTATATCTTACTAATGTAGATTTAGAATTAATAC
AGGAACACTACGAAATGTATAACGTTGAGTATATTGACGGATTTAAATTC
CGTGAAAAGACTGGATTATTCAAAGAGTTTATTGATAAATGGACATATGT
AAAAACTCATGAAAAGGGAGCTAAGAAACAATTGGCTAAGCTAATGTTGA
ATAGTCTCTATGGTAAATTTGCAAGTAACCCTGACGTTACAGGTAAAGTC
CCTTATTTAAAAGAAGATGGGAGCCTTGGTTTCCGTGTTGGTGATGAGGA
ATATAAAGACCCTGTTTATACACCTATGGGTGTGTTTATAACGGCATGGG
CTAGATTTACAACTATAACAGCGGCACAAGCGTGTTACGATAGAATTATA
TATTGTGACACTGATAGTATACATTTAACAGGTACAGAAGTACCAGAAAT
AATAAAGGATATTGTTGATCCAAAAAAGTTAGGGTACTGGGCGCATGAAA
GCACATTTAAGAGAGCAAAATATTTACGTCAGAAAACGTATATTCAAGAC
ATATATGCGAAAGAGGTTGACGGTAAATTGATAGAGTGTTCACCTGATGA
AGCTACGACAACTAAATTCAGTGTGAAATGTGCCGGAATGACTGACACTA
TCAAAAAGAAAGTCACATTTGATAACTTTAGAGTTGGTTTCAGTAGCACG
GGTAAACCTAAACCAGTTCAAGTTAATGGCGGGGTAGTGTTGGTTGATAG
TGTGTTTACGATTAAA
```

In some embodiments, the nucleotide sequence of the modified polymerase comprises a polynucleotide that is at least 80%, 85%, 90%, 95%, 97%, 98% or 99% identical to the nucleotide sequence of SEQ ID NO: 12.

In some embodiments, the polynucleotide encodes a modified polymerase having or comprising an amino acid sequence that is at least 80%, 85%, 90%, 95%, 97%, 98% or 99% identical to the amino acid sequence of SEQ ID NO: 8, wherein the modified polymerase comprises any residue other than aspartic acid (D) at position 166, the numbering being relative to the amino acid sequence of SEQ ID NO: 8. In some embodiments, the residue at position 166 is alanine (A).

In some embodiments, the polynucleotide encodes a modified polymerase having or comprising an amino acid sequence that is at least 80%, 85%, 90%, 95%, 97%, 98% or 99% identical to the amino acid sequence of SEQ ID NO: 8.

As the skilled artisan will appreciate, due to the degeneracy of the genetic code, many different polynucleotides can encode the modified polymerases disclosed herein, all of which are within the scope of the present disclosure. An exemplary list of the various nucleotide "codons" or "triplets" that may encode a given amino acid is provided in Table 1, below:

TABLE 1

| Amino Acid | SLC | DNA codons |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Stop codons | Stop | TAA, TAG, TGA |

Table 1 lists the twenty naturally occurring amino acids commonly found in proteins, along with the single-letter code ("SLC") typically used to represent these amino acids in protein databases. The nucleotide codons that typically encode each amino acid are also listed. As shown in Table 1, 3 of the 64 possible 3-letter combinations of the nucleic acid coding units T, C, A and G can be used to encode one of the three stop codons (TAA, TAG and TGA) that typically signals the end of a sequence. The remaining 61 combinations can be used to encode one of the twenty naturally-occurring amino acids, as indicated in Table 1. As the skilled artisan will readily appreciate, the corresponding peptide sequence encoded by any given polynucleotide sequence can typically be determined unambiguously. Because most amino acids have multiple codons, however, a number of different polynucleotide sequences can encode the same protein sequence.

As indicated in Table 1, most of the naturally occurring amino acids are coded for by multiple codons. Because codon preference can vary from species to species, selection or synthesis of a polynucleotide sequence, and its expression in a given species can optionally be optimized by selecting for codons that are highly preferred, or provide optimal translation efficiency or overall expression levels, in the species of choice. See, for example, Kudla et al., Science 324:255-258 (2009). In some embodiments the polynucleotide may be homologous to polynucleotides having the nucleotide sequence of SEQ ID NO: 9, 10, 11 or 12, and contain "silent" or "synonymous" mutations that do not alter the peptide sequence of the encoded peptide product.

In some embodiments, the polynucleotide is an artificial or recombinant nucleic acid molecule that hybridizes to a nucleic acid molecule having the nucleotide sequence of SEQ ID NO: 9, SEQ ID NO: 10, SEQ ID NO: 11 or SEQ ID NO: 12 under highly stringent conditions over substantially the entire length of the nucleic acid molecule. Hybridization, or association of nucleic acid molecules due to hydrogen bonding, base stacking, solvent exclusion and the like are well known in the art and have been extensively described. See, e.g., Hanes et al., *Gene Probes* (Oxford University Press 1995); Tijssen, *Laboratory Techniques in Biochemistry and Molecular Biology* (Elsevier, 1993). In one exemplary method, the polynucleotide is greater than 100 nucleotides in length and is subjected to high-stringency hybridization conditions comprising 50% formalin with 1 mg of heparin at 42° C. overnight. In some embodiments, the polynucleotide can also be subjected to a high-stringency wash following hybridization. In some embodiments, the high stringency wash can comprise one wash with 0.2×.SSC at 65° C. for 15 minutes. In some embodiments, the polynucleotide can be subjected to extremely stringent conditions selected to be equal to the thermal melting point ($T_m$) for a particular polynucleotide sequence. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

In some embodiments, disclosed herein is a polynucleotide encoding modified polymerases, wherein the polynucleotide specifically hybridizes to a probe nucleic acid having the nucleotide sequence of SEQ ID NO: 9, SEQ ID NO: 10, SEQ ID NO: 11 or SEQ ID NO: 12 under stringent, highly stringent or extremely stringent conditions. A polynucleotide is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5-10 times as high as that observed for hybridization to any of the unmatched target nucleic acids.

The skilled artisan will also appreciate that many variants of the disclosed nucleotide and/or amino acid sequences are within the scope and spirit of the present disclosure. For example, modified polymerases comprising one or more conservative mutations of the disclosed amino acid sequences and are functionally similar to the modified polymerases explicitly disclosed herein are also disclosed. In some embodiments, the modified polymerases of the present disclosure can be a variant of the various modified polymerases disclosed herein and additionally contain one or more conservative mutations.

In some embodiments, the modified polymerase is a variant of a polymerase comprising the amino acid sequence of SEQ ID NO: 7, wherein the variant polymerase further comprises one or more amino acid substitutions within one or more amino acid motifs selected from the group consisting of: a motif comprising the amino acid sequence of SEQ ID NO: 2; a motif comprising the amino acid sequence of SEQ ID NO: 3; a motif comprising the amino acid sequence of SEQ ID NO: 4; and a motif comprising the amino acid sequence of SEQ ID NO: 5. In some embodiments, the one or more substitutions are conservative mutations. In some embodiments, the one or more substitutions are non-conservative mutations.

In some embodiments, the modified polymerase is derived from a M2 polymerase (also known as M2Y DNA polymerase) having the amino acid sequence of the SEQ ID NO: 13 as follows:

```
                                                      (SEQ ID NO: 13)
  1 msrkmfscdf etttklddcr vwaygymeig nldnykigns ldefmqwvme iqadlyfhnl 61 kfdgafivnw leqhgfkwsn eglpntynti iskmgqwymi dicfgykgkr klhtviydsl 121 kklpfpvkki akdfqlpllk gdidyhterp vgheitpeey eyikndieii araldiqfkg 181 gldrmtagsd slkgfkdils tkkfnkvfpk lslpmdkeir kayrggftwl ndkykekeig 241 egmvfdvnsl ypsqmysrpl pygapivfqg kyekdeqypl yiqrirfefe lkegyiptiq 301 ikknpffkgn eylknsgvep velyltnvdl eliqehyely nveyidgfkf rektglfkdf 361 idkwtyvkth eegakkqlak lmlnslygkf asnpdvtgkv pylkddgslg frvgdeeykd 421 pvytpmgvfi tawarfttit aaqacydrii ycdtdsihlt gtevpeiikd ivdpkklgyw 481 ahestfkrak ylrqktyiqd iyvkevdgkl kecspdeatt tkfsvkcagm tdtikkkvtf 541 dnfavgfssm gkpkpvqvng gvvlvdsvft ik
```

In some embodiments, the modified polymerase can comprise an amino acid sequence that is at least 85%, 90%, 95%, 97%, 98% or 99% or 100% identical to the amino acid of SEQ ID NO: 13. In some embodiments, the modified polymerase can have a nanoparticle tolerance that is at least about 5%, 10%, 25%, 37.5%, 50%, 75%, 100%, 110%, 125%, 150%, 200%, 250%, 500%, 750%, 1,000%, 5,000% or 10,000 relative to the nanoparticle tolerance of a reference Phi-29 polymerase having the amino acid sequence of SEQ ID NO: 1. In some embodiments, the modified polymerase has a photostability that is at least about 5%, 10%, 25%, 37.5%, 50%, 75%, 100%, 110%, 125%, 150%, 200%, 250%, 500%, 750%, 1,000%, 5,000% or 10,000 relative to the photostability of a reference Phi-29 polymerase having the amino acid sequence of SEQ ID NO: 1.

In some embodiments, the modified polymerase comprises an amino acid sequence that is at least 85%, 90%, 95%, 97%, 98% or 99% identical to the amino acid sequence of SEQ ID NO: 13 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 6. Typically, such a modified polymerase will exhibit reduced 3' to 5' exonuclease activity relative to reference polymerase having the amino acid sequence of SEQ ID NO: 13.

In some embodiments, the modified polymerase comprises an amino acid sequence that is at least 85%, 90%, 95%, 97%, 98% or 99% identical to the amino acid sequence of SEQ ID NO: 13 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6. In some embodiments, the modified polymerase comprises any one, two, three, four, five or all of these mutations. In some embodiments, the modified polymerase comprises the amino acid substitution D166A. In some embodiments, the modified polymerase comprises the amino acid substitutions D9A and D63A. In some embodiments, the modified polymerase comprises the amino acid substitutions N59D and T12I. Typically, such modified polymerases will exhibit reduced 3' to 5' exonuclease activity relative to reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further comprises an amino acid substitution at one or more positions selected from the group consisting of: 2, 73, 147, 221, 318, 339, 359, 372, 405, 503, 511, 544 and 550, wherein the numbering is relative to the amino acid sequence of SEQ ID NO: 6. Typically, this modified polymerase can exhibit increased photostability and/or increased nanoparticle tolerance relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 6. Optionally, this modified polymerase comprises the amino acid mutation H370R. Typically, this modified polymerase can exhibit an increased branching ratio and/or increased nucleotide binding affinity relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes a mutation at position 365, wherein the numbering is relative to the amino acid sequence of SEQ ID NO: 6. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 6. Optionally, this modified polymerase comprises the amino acid mutation T365F. Typically, this modified polymerase can exhibit an increased branching ratio and/or increased nucleotide binding affinity relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes a mutation at position 372, wherein the numbering is relative to the amino acid sequence of SEQ ID NO: 6. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 6. Optionally, this modified polymerase comprises the amino acid mutation K372Y. Typically, this modified polymerase can exhibit an increased branching ratio and/or increased nucleotide binding affinity relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes a mutation at position 481, wherein the numbering is relative to the amino acid sequence of SEQ ID NO: 6. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 6. Optionally, this modified polymerase comprises the amino acid mutation A481E. Typically, this modified polymerase can exhibit an increased branching ratio and/or increased nucleotide binding affinity relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes a mutation at position 509, wherein the numbering is relative to the amino acid sequence of SEQ ID NO: 6. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 6. Optionally, this modified polymerase comprises the amino acid mutation K509Y. Typically, this modified polymerase can exhibit an increased branching ratio and/or increased nucleotide binding affinity relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes any one, two, three or more amino acid mutations selected from the group consisting of: S2P, Q73H, T147A, K221R, V318A, L339M, D359E, E372K, D405E, V503A, K511I, A544R and M550T, wherein the numbering is relative to the amino acid sequence of SEQ ID NO: 6. Typically, this modified polymerase can exhibit increased photostability and/or increased nanoparticle tolerance relative to a reference polymerase having the amino acid sequence of SEQ ID NO: 13.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio and/or increased nucleotide binding affinity relative to a reference polymerase having the amino acid sequence of SEQ ID NO: 13.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further comprise amino acid mutations at any one, two, three or more positions selected from the group consisting of: 2, 9, 12, 14, 15, 58, 59, 61, 63, 73, 98, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio, increased nucleotide binding affinity, increased photostability and/or increased nanoparticle tolerance relative to a reference polymerase having the amino acid sequence of SEQ ID NO: 13.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. In some embodiments, the modified polymerase comprises the amino acid mutations Typically, this modified polymerase can exhibit an increased branching ratio and/or increased nucleotide binding affinity relative to a reference polymerase having the amino acid sequence of SEQ ID NO: 13. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 80%, 85%, 90%, 95%, 97%, 98%, 99% or 100% identical to the amino acid sequence of SEQ ID NO: 13 and further includes amino acid mutations at positions 372 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 13 and further includes the amino acid substitutions E372Y and K509Y, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 13 and further includes amino acid mutations at positions 365, 372 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 13 and further includes the amino acid substitutions T365F, E372Y and K509Y, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 13 and further includes amino acid mutations at positions 365, 372, 481 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 13 and further includes the amino acid substitutions T365F, E372Y, A481E and K509Y, wherein the numbering is relative to the amino acid sequence of SEQ ID NO: 6. Typically, such modified polymerases can exhibit an increased branching ratio and/or increased nucleotide binding affinity relative to a reference polymerase having the amino acid sequence of SEQ ID NO: 13. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 13. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further includes the amino acid mutation H370R, wherein the numbering is relative to the amino acid sequence of SEQ ID NO: 6. In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. Optionally, the modified polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 13. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 7. Typically, this modified polymerase can exhibit an increase $t_{-1}$ value in the presence of the dye-labeled nucleotides relative to a reference polymerase having the amino acid sequence of SEQ ID NO: 13. In some embodiments, the $t_{-1}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. In some embodiments, the $t_{-1}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation H370R, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 13 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 7. Typically, this modified polymerase can exhibit an increased $t_{pol}$ value in the presence of the dye-labeled nucleotides relative to a reference polymerase having the amino acid sequence of SEQ ID NO: 13. In some embodiments, the $t_{pol}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 7. In some embodiments, the $t_{pol}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation K380R, wherein the numbering is relative to the amino acid sequence of SEQ ID NO: 7.

In some embodiments, the modified polymerase is derived from a bacteriophage Nf polymerase having the amino acid sequence of the SEQ ID NO: 14 as follows:

```
                                                                (SEQ ID NO: 14)
  1 msrkmfscdf etttklddcr vwaygymeig nldnykigns ldefmqwvme iqadlyfhnl 61 kfdgafivnw leqhgfkwsn eglpntynti iskmgqwymi dicfgyrgkr klhtviydsl 121 kklpfpvkki akdfqlpllk gdidyhterp vgheitpeey eyikndieii araldiqfkg 181 gldrmtagsd slkgfkdils tkkfnkvfpk lslpmdkeir kayrggftwl ndkykekeig 241 egmvfdvnsl ypsqmysrpl pygapivfqg kyekdeqypl yiqrirfefe lkegyiptiq 301 ikknpffkgn eylknsgvep velyltnvdl eliqehyely nveyidgfkf rektglfkdf 361 idkwtyvkth eegakkqlak lmlnslygkf asnpdvtgkv pylkddgslg frvgdeeykd 421 pvytpmgvfi tawarfttit aaqacydrii ycdtdsihlt gtevpeiikd ivdpkklgyw 481 ahestfkrak ylrqktyiqd iyvkevdgkl kecspdeatt tkfsvkcagm tdtikkkvtf 541 dnfavgfssm gkpkpvqvng gvvlvdsvft ik
```

In some embodiments, the modified polymerase can comprise an amino acid sequence that is at least 85%, 90%, 95%, 97%, 98% or 99% or 100% identical to the amino acid of SEQ ID NO: 14. In some embodiments, the modified polymerase can have a nanoparticle tolerance that is at least about 5%, 10%, 25%, 37.5%, 50%, 75%, 100%, 110%, 125%, 150%, 200%, 250%, 500%, 750%, 1,000%, 5,000% or 10,000 relative to the nanoparticle tolerance of a reference Phi-29 polymerase having the amino acid sequence of SEQ ID NO: 1. In some embodiments, the modified polymerase has a photostability that is at least about 5%, 10%, 25%, 37.5%, 50%, 75%, 100%, 110%, 125%, 150%, 200%, 250%, 500%, 750%, 1,000%, 5,000% or 10,000 relative to the photostability of a reference Phi-29 polymerase having the amino acid sequence of SEQ ID NO: 1.

In some embodiments, the modified Nf polymerase comprises an amino acid sequence that is at least 85%, 90%, 95%, 97%, 98% or 99% identical to the amino acid sequence of SEQ ID NO: 14 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 6. Typically, such a modified polymerase will exhibit reduced 3' to 5' exonuclease activity relative to reference polymerase having the amino acid sequence of SEQ ID NO: 14.

In some embodiments, the modified polymerase comprises an amino acid sequence that is at least 85%, 90%, 95%, 97%, 98% or 99% identical to the amino acid sequence of SEQ ID NO: 14 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6. In some embodiments, the modified polymerase comprises any one, two, three, four, five or all of these mutations. In some embodiments, the modified polymerase comprises the amino acid substitution D166A. In some embodiments, the modified polymerase comprises the amino acid substitutions D9A and D63A. In some embodiments, the modified polymerase comprises the amino acid substitutions N59D and T12I. Typically, such modified polymerases will exhibit reduced 3' to 5' exonuclease activity relative to reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further comprises an amino acid substitution at one or more positions selected from the group consisting of: 2, 73, 107, 147, 221, 318, 339, 359, 372, 405, 503, 511, 544 and 550, wherein the numbering is relative to the amino acid sequence of SEQ ID NO: 6. Typically, this modified polymerase can exhibit increased photostability and/or increased nanoparticle tolerance relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 6. Optionally, this modified polymerase comprises the amino acid mutation H370R. Typically, this modified polymerase can exhibit an increased branching ratio and/or increased nucleotide binding affinity relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes a mutation at position 365, wherein the numbering is relative to the amino acid sequence of SEQ ID NO: 6. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 6. Optionally, this modified polymerase comprises the amino acid mutation T365F. Typically, this modified polymerase can exhibit an increased branching ratio and/or increased nucleotide binding affinity relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes a mutation at position 372, wherein the numbering is relative to the amino acid sequence of SEQ ID NO: 6. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 6. Optionally, this modified polymerase comprises the amino acid mutation K372Y. Typically, this modified polymerase can exhibit an increased branching ratio and/or increased nucleotide binding affinity relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes a mutation at position 481, wherein the numbering is relative to the amino acid sequence of SEQ ID NO: 6. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 6. Optionally, this modified polymerase comprises the amino acid mutation A481E. Typically, this modified polymerase can exhibit an increased branching ratio and/or increased nucleotide binding affinity relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes a mutation at position 509, wherein the numbering is relative to the amino acid sequence of SEQ ID NO: 6. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 6. Optionally, this modified polymerase comprises the amino acid mutation K509Y. Typically, this modified polymerase can exhibit an increased branching ratio and/or increased nucleotide binding affinity relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes any one, two, three or more amino acid mutations selected from the group consisting of: S2P, Q73H, R107K, T147A, K221R, V318A, L339M, D359E, E372K, D405E, V503A, K511I, A544R and M550T, wherein the numbering is relative to the amino acid sequence of SEQ ID NO: 6. Typically, this modified polymerase can exhibit increased photostability and/or increased nanoparticle tolerance relative to a reference polymerase having the amino acid sequence of SEQ ID NO: 14.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio and/or increased nucleotide binding affinity relative to a reference polymerase having the amino acid sequence of SEQ ID NO: 14.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further comprise amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 6. In some embodiments, the modifications can include deletions, additions and substitutions. The substitutions can be conservative or non-conservative substitutions. Optionally, this modified polymerase comprises the amino acid substitution H370R. In some embodiments, the polymerase further comprises one or more mutations reducing the exonuclease activity as described herein such as, for example, the amino acid substitution D166A. Typically, this modified polymerase can exhibit increased branching ratio, increased nucleotide binding affinity, increased photostability and/or increased nanoparticle tolerance relative to a reference polymerase having the amino acid sequence of SEQ ID NO: 14.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. In some embodiments, the modified polymerase comprises the amino acid mutations Typically, this modified polymerase can exhibit an increased branching ratio and/or increased nucleotide binding affinity relative to a reference polymerase having the amino acid sequence of SEQ ID NO: 14. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 80%, 85%, 90%, 95%, 97%, 98%, 99% or 100% identical to the amino acid sequence of SEQ ID NO: 14 and further includes amino acid mutations at positions 372 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 14 and further includes the amino acid substitutions E372Y and K509Y, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 14 and further includes amino acid mutations at positions 365, 372 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 14 and further includes the amino acid substitutions T365F, E372Y and K509Y, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 14 and further includes amino acid mutations at positions 365, 372, 481 and 509, wherein the numbering is relative to the amino acid sequence of SEQ ID NO: 6. In some embodiments, the modified polymerase comprises an amino acid sequence that is at least 80%, 85%, 90%, 95%, 97%, 98%, 99% or 100% identical to the amino acid sequence of SEQ ID NO: 14 and further includes the amino acid substitutions T365F, E372Y, A481E and K509Y, wherein the numbering is relative to the amino acid sequence of SEQ ID NO: 6. Typically, such modified polymerases can exhibit an increased branching ratio and/or increased nucleotide binding affinity relative to a reference polymerase having the amino acid sequence of SEQ ID NO: 14. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 14.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further includes the amino acid mutation H370R, wherein the numbering is relative to the amino acid sequence of SEQ ID NO: 6. In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. Optionally, the modified polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 6. Typically, this modified polymerase can exhibit increase branching ratio and/or increased photostability and/or increased nanoparticle tolerance relative to a reference polymerase having the amino acid sequence of SEQ ID NO: 14. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 6.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 7. Typically, this modified polymerase can exhibit an increase $t_{-1}$ value in the presence of the dye-labeled nucleotides relative to a reference polymerase having the amino acid sequence of SEQ ID NO: 14. In some embodiments, the $t_{-1}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 7. In some embodiments, the $t_{-1}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further includes the amino acid mutation H370R, wherein the numbering is relative to the amino acid sequence of SEQ ID NO: 7.

In some embodiments, the modified polymerase comprises an amino acid sequence that is at least 70%, 80%, 85%, 90%, 95%, 97%, 98%, 99% or 100% identical to the amino acid sequence of SEQ ID NO: 14 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 7. Typically, this modified polymerase can exhibit an increased $t_{pol}$ value in the presence of the dye-labeled nucleotides relative to a reference polymerase having the amino acid sequence of SEQ ID NO: 14. In some embodiments, the $t_{pol}$ value of the modified polymerase is increased by at least about 105%, 110%, 125%, 150%, 175%, 200%, 250%, 500%, 750%, or 1000% relative to the reference polymerase. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, the modified polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 6. In some embodiments, the $t_{pol}$ value is increased in the presence of the dye-labeled nucleotide AF647-C6-dG6P. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes the amino acid mutation K380R, wherein the numbering is relative to the amino acid sequence of SEQ ID NO: 7.

In some embodiments, the modified polymerase is derived from an RB69 polymerase having the amino acid sequence of the SEQ ID NO: 15 as follows:

```
                                        (SEQ ID NO: 15)
MKEFYLTVEQIGDSIFERYIDSNGRERTREVEYKPSLFAHCPESQATKYF

DIYGKPCTRKLFANMRDASQWIKRMEDIGLEALGMDDFKLAYLSDTYNYE

IKYDHTKIRVANFDIEVTSPDGFPEPSQAKHPIDAITHYDSIDDRFYVFD

LLNSPYGNVEEWSIEIAAKLQEQGGDEVPSEIIDKIIYMPFDNEKELLME

YLNFWQQKTPVILTGWNVESFDIPYVYNRIKNIFGESTAKRLSPHRKTRV

KVIENMYGSREIITLFGISVLDYIDLYKKFSFTNQPSYSLDYISEFELNV

GKLKYDGPISKLRESNHQRYISYNIIDVYRVLQIDAKRQFINLSLDMGYY

AKIQIQSVFSPIKTWDAIIFNSLKEQNKVIPQGRSHPVQPYPGAFVKEPI

PNRYKYVMSFDLTSLYPSIIRQVNISPETIAGTFKVAPLHDYINAVAERP

SDVYSCSPNGMMYYKDRDGVVPTEITKVFNQRKEHKGYMLAAQRNGEIIK

EALHNPNLSVDEPLDVDYRFDFSDEIKEKIKKLSAKSLNEMLFRAQRTEV

AGMTAQINRKLLINSLYGALGNVWFRYYDLRNATAITTFGQMALQWIERK

VNEYLNEVCGTEGEAFVLYGDTDSIYVSADKIIDKVGESKFRDTNHWVDF

LDKFARERMEPAIDRGFREMCEYMNNKQHLMFMDREAIAGPPLGSKGIGG

FWTGKKRYALNVWDMEGTRYAEPKLKIMGLETQKSSTPKAVQKALKECIR

RMLQEGEESLQEYFKEFEKEFRQLNYISIASVSSANNIAKYDVGGFPGPK

CPFHIRGILTYNRAIKGNIDAPQVVEGEKVYVLPLREGNPFGDKCIAWPS

GTEITDLIKDDVLHWMDYTVLLEKTFIKPLEGFTSAAKLDYEKKASLFDM

FDF
```

In some embodiments, the modified polymerase can comprise an amino acid sequence that is at least 85%, 90%, 95%, 97%, 98% or 99% identical to the amino acid of SEQ ID NO: 15.

In some embodiments, the modified polymerases disclosed herein, as well as the modified polymerases encoded by the polynucleotides of the present disclosure, can exhibit (or can be further engineered or evolved to exhibit) an altered polymerase activity in a particular biological assay of interest as compared to a reference counterpart. Some examples of evolved polymerases having altered functions or activities can be found, for example, in U.S. Provisional Application No. 61/020,995, filed Jan. 14, 2008; International PCT Application No. WO 2008/091847, published Jul. 23, 2009; U.S. Publication No. 2007/0196846 A1, published Aug. 23, 2007; U.S. Publication No. 2008/0108082, published May 8, 2008; and U.S. Publication No. 2009/0176233, published Jul. 9, 2009.

In some embodiments, a vector comprises a polynucleotide encoding a modified polymerase of the present disclosure. In some embodiments, the vector is a cosmid, plasmid, virus, phage or the like. In some embodiments, the vector is an expression vector. In some embodiments, the modified polymerases of the present disclosure can be produced by a suitable expression vector/host cell system. For example, a modified polymerase can be encoded by suitable recombinant expression vectors carrying inserted sequences of the modified polymerase. The polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker that confers resistance to drugs (e.g., kanamycin, ampicillin, tetracycline, chloramphenicol, or the like) or a requirement for a nutrient. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, virus, phage, and the like. The expression vector can enter a host cell which can replicate the vector, produce an RNA transcript of the inserted sequence, and/or produce protein encoded by the inserted sequence. Methods for preparing suitable recombinant expression vectors and expressing the RNA and/or protein encoded by the inserted sequences are well known (Sambrook et al, *Molecular Clon-*

*ing* (1989)). In some embodiments, the polynucleotide comprises the nucleotide sequence of SEQ ID NO: 9, SEQ ID NO: 10, SEQ ID NO: 11 or SEQ ID NO: 12, or a nucleotide sequence that is at least 80%, 85%, 90%, 95%, 97% or 99% identical to any of these nucleotide sequences. In some embodiments, the polynucleotide is cloned into the expression vector pTTQ, which allows expression of the polypeptide encoded by the polynucleotide from the pTAC promoter (Stark, J. J. R., Gene, 51, pp. 255-267, 1987).

In some embodiments, the modified polymerase can be homologous to a naturally occurring polymerase; alternatively, it can be a biologically active fragment, mutant or other derivative of a naturally occurring polymerase. Typically, the polymerase will elongate a pre-existing nucleic acid, for example, a primer, by polymerizing nucleotides on to the 3' end of the molecule; for example, the polymerase can catalyze transfer of a nucleoside monophosphate from a nucleoside triphosphate (or analog thereof) to the 3' hydroxyl group of the polymerization initiation site. The polymerase can bind a target nucleic acid molecule, which may or may not be base-paired with a polymerization initiation site (e.g., primer). The polymerase can bind a nucleotide. The polymerase can mediate incorporation of a nucleotide (or analog thereof) on to a polymerization initiation site (e.g., terminal 3'OH of a primer). The polymerase can mediate cleavage between the $\alpha$ and $\beta$ phosphate groups. The polymerase can mediate phosphodiester bond formation. The polymerase can mediate release of the polyphosphate product.

In some embodiments, the modified polymerase can be linked to a label to form a labeled polymerase that retains polymerase activity. In some embodiments, the label is an organic label. In some embodiments, the label is an inorganic label, for example a nanoparticle. The nanoparticle can be a nanocrystal or a quantum dot. In some embodiments, the nanoparticle or quantum dot, or populations thereof, can comprise a surface layer including multiple functional groups such as, for example, dipeptides, tripeptides, monodentate thiols, or polydentate thiols as well as mixtures of dipeptides, tripeptides, monodentate thiols, or polydentate thiols with hydrophobic ligands like TDPA, OPA, TOP, and/or TOPO.

In some embodiments, the modified polymerase is linked to an energy transfer moiety. The energy transfer moiety can in some embodiments be a RET or FRET moiety. In some embodiments, the energy transfer moiety is a donor moiety. Exemplary methods of attaching labels to a polymerase can be found, for example, in U.S. Provisional Application No. 61/184,770, filed Jun. 5, 2009.

In some embodiments, the polymerase can be further modified to comprise intact subunits, biologically-active fragments and/or fusion variants of any polymerases disclosed herein, as well as mutated, truncated, modified, genetically engineered or fusion variants of such polymerases. The modifications of a modified polymerase can include amino acid substitutions, insertions, or deletions. In some embodiments, the modified polymerases can be isolated from a cell, or generated using recombinant DNA technology or chemical synthesis methods. In another embodiment, the modified polymerases can be expressed in prokaryote, eukaryote, viral, or phage organisms. In some embodiments, the modified polymerases can be post-translationally modified proteins or fragments thereof.

The polymerases disclosed herein can also be derived from any subunits, mutated, modified, truncated, genetically engineered or fusion variants of a polymerase having the amino acid sequence of SEQ ID NO: 7 or SEQ ID NO: 8 (wherein the mutation involves the replacement of one or more or many amino acids with other amino acids, the insertion or deletion of one or more or many amino acids, or the conjugation of parts of one or more polymerases).

In some embodiments, the modified polymerase is a fusion protein comprising some or all of the amino acid sequence of SEQ ID NO: 7 or SEQ ID NO: 8.

In some embodiments, the modified polymerase can be attached, fused or otherwise associated with a moiety that facilitates purification of the polymerase, isolation of the polymerase and/or linkage of the polymerase to one or more labels. For example, in some embodiments the moiety can be an enzymatic recognition site, an epitope or an affinity tag that facilitates purification of the polymerase. In some embodiments, the tag is an affinity tag. The affinity tag can be selected from: a His tag, a GST tag, an HA tag, a SNAP-tag, and the like. In some embodiments, the modified polymerase can comprise a plurality of 6-His tags (SEQ ID NO: 48), a plurality of GST tags, a plurality of HA tags, and combinations thereof. Such tags can be inserted into any suitable position within the polymerase sequence. In some embodiments, the modified polymerase comprises one or more tags that are fused in-frame with the polymerase amino acid sequence at the N-terminal, the C-terminal end, or anywhere in between. Typically, the presence of the tag does not affect polymerase activity.

In some embodiments, the affinity tag is a His tag. For example, in some embodiments the His tag can include a stretch of amino acids comprising multiple histidine residues. In some embodiments, the His tag comprises a 6-His tag (SEQ ID NO: 48) (hexahistidine tag [SEQ ID NO: 48]). The His tag can optionally bind to one or more metal atom of a label. In one exemplary embodiment, the His tag binds to bound metal ions on the surface of a nanoparticle, for example, $Ni^{2+}$, $Co^{2+}$, or $Cu^{2+}$ ions, thus linking the polymerase to the nanoparticle. In some embodiments, the His tag comprises 2, 3, 4, 5, 6, 7, 8 or more histidine residues. In some embodiments, the His tag is fused to the N- or C-terminus of the protein; alternatively, it can be fused at any suitable location within the open reading frame of the protein.

In some embodiments, the His tag may be fused directly with the protein; alternatively, a linker comprising various lengths of amino acid residues can be placed between the protein and the His tag. The linker can be flexible or rigid.

In some embodiments, the His tag can facilitate purification of the polymerase. For example, His tagged polymerase can be purified from a raw bacterial lysate by contacting the lysate with any suitable affinity medium comprising bound metal ions to which the histidine residues of the His tag can chelate. The bound metal ions can comprise either nickel or cobalt, to which the polyhistidine-tag binds with micromolar affinity. Suitable affinity media include Ni Sepharose (such as, for example, that provided by GE Healthcare), NTA-agarose (such as, for example, that provided by Qiagen), HisPur® resin (Thermo Scientific, Pierce Protein Products, Rockford, Ill.), or Talon® resin (Clontech, Mountain View, Calif.). The affinity matrix can be washed with suitable buffers, e.g., phosphate buffers, to remove proteins that do not specifically interact with the cobalt or nickel ion. Washing efficiency can be improved by the addition of 20 mM imidazole. In some embodiments, the protein(s) can be eluted from the matrix. In some embodiments, the proteins can be eluted with 150-300 mM imidazole). The purity and amount of purified polymerase can be assessed using suitable methods, e.g., SDS-PAGE, size exclusion chromatography, mass spectrometry and/or Western blotting.

In some embodiments, the His tag can be followed by a suitable amino acid sequence that facilitates removal of the His tag using a suitable endopeptidase. Alternatively, the His tag may be removed using a suitable exopeptidase, for example the Qiagen TAGZyme exopeptidase.

In addition to facilitating purification of the polymerase, the His tag can also facilitate binding of the His tagged polymerase to the nanoparticle comprising one or more bound metal ions via chelation bonding. Exemplary methods of conjugation of a His tagged polymerase to a nanoparticle are described, for example, in U.S. Provisional Application No. 61/184,770, filed Jun. 5, 2009.

In some embodiments, the amino acid sequence of a modified polymerase fused to a peptide sequence that encodes a stretch of amino acid acids capable of functioning as a peptide linker to facilitate the formation of a linkage between the modified polymerase and another reactive moiety. This peptide linker sequence can be fused to the N-terminus, the C-terminus or any suitable position between the N-terminus and the C-terminus of the modified polymerase.

In some embodiments, the peptide linker can comprise the amino acid sequence: LLGAAAKGAAAKGSAA (SEQ ID NO: 16).

This linker is hereinafter referred to as the "H-linker". Without being bound to any particular theory of operation, it has been suggested that this linker comprises a helix-forming peptide that can effectively separate different functional domains of a fusion protein or conjugate. See, for example, Arai et al., Protein Engineering 14(8): 529-532 (2001); Marqusee & Baldwin, Proc. Natl. Acad. Sci. USA, 84: 8898-8902 (1987).

In some embodiments, the peptide linker can comprise the amino acid sequence: LLGGGGSGGGGSAAAGSAA (SEQ ID NO: 17). In some embodiments, the peptide linker can comprise the amino acid sequence: MNHLVHHHHHHIEGRHMELGTLEGS (SEQ ID NO: 51). In some embodiments, the peptide linker can comprise the amino acid sequence: MHHHHHHKH (SEQ ID NO: 52). In some embodiments, the peptide linker can comprise the amino acid sequence: GLNDIF-EAQKIEWHE (SEQ ID NO:53).

This linker is hereinafter referred to as the "F-linker". See, for example, Arai et al., Protein Engineering 14(8): 529-532 (2001); Alfthan et al., Protein Engineering 8(7): 725-731 (1995).

In some embodiments, the modified polymerase comprises a modified N-terminal His tagged version of a B103 polymerase, wherein the modified polymerase comprises the following amino acid sequence:

```
                                          (SEQ ID NO: 18)
        10         20         30         40
MNHLVHHHHH HIEGRHMELG TLEGSMPRKM FSCDFETTTK 50         60         70         80
LDDCRVWAYG YMEIGNLDNY KIGNSLDEFM QWVMEIQADL 90        100        110        120
YFHNLKFDGA FIVNWLEHHG FKWSNEGLPN TYNTIISKMG 130        140        150        160
QWYMIDICFG YKGKRKLHTV IYDSLKKLPF PVKKIAKDFQ 170        180        190        200
LPLLKGDIDY HAERPVGHEI TPEEYEYIKN DIEIIARALD 210        220        230        240
IQFKQGLDRM TAGSDSLKGF KDILSTKKFN KVFPKLSLPM 250        260        270        280
DKEIRRAYRG GFTWLNDKYK EKEIGEGMVF DVNSLYPSQM
```

```
-continued
       290        300        310        320
YSRPLPYGAP IVFQGKYEKD EQYPLYIQRI RFEFELKEGY 330        340        350        360
IPTIQIKKNP FFKGNEYLKN SGAEPVELYL TNVDLELIQE 370        380        390        400
HYEMYNVEYI DGFKFREKTG LFKEFIDKWT YVKTHEKGAK 410        420        430        440
KQLAKLMLNS LYGKFASNPD VTGKVPYLKE DGSLGFRVGD 450        460        470        480
EEYKDPVYTP MGVFITAWAR FTTITAAQAC YDRIIYCDTD 490        500        510        520
SIHLTGTEVP EIIKDIVDPK KLGYWAHEST FKRAKYLRQK 530        540        550        560
TYIQDIYAKE VDGKLIECSP DEATTTKFSV KCAGMTDTIK 570        580        590
KKVTFDNFRV GFSSTGKPKP VQVNGGVVLV DSVFTIK
```

In some embodiments, the modified polymerase can comprise an amino acid sequence that is at least 70%, 80%, 85%, 90%, 95%, 99% or 100% identical to the amino acid sequence of SEQ ID NO: 18. In some embodiments, the modified polymerase further comprises the amino acid substitution D191A, wherein the numbering is relative to SEQ ID NO: 18.

In some embodiments, the modified polymerase comprises an amino acid sequence that is at least 85%, 90%, 95% or 99% identical to the amino acid sequence of SEQ ID NO: 18 and comprises any one, two, three or more of the mutations described herein.

In some embodiments, the modified polymerase comprises an amino acid sequence that is at least 85%, 90%, 95% or 99% identical to the amino acid sequence of SEQ ID NO: 18 and further comprises one or more amino acid substitutions selected from the group consisting of: D34A, E36A, H83R, N84D, D88A, D191A, Q402A and S410G, and further comprises one or more amino acid substitutions selected from the group consisting of: H395G, H395T, H395S, H395K, H395R, H395A, H395Q, H395W, H395Y, H395F, E396G, E396H, E396T, E396S, E396K, E396R, E396A, E396Q, E396W, E396Y, E396F, K397G, K397E, K397T, K3975, K397R, K397A, K397Q, K397W, K397Y, K397F, K405E, K405T, K405S, K405R, K405A, K405Q, K405W, K405Y, K405F, D532H, D532G, D532E, D532T, D532S, D532R, D532A, D532R, D532Q, D532W, D532Y, D532F, K534H, K534G, K534D, K534R, K534E, K534T, K534S, K534R, K534A, K534Q, K534W, K534Y and K534F, wherein the numbering is relative to the sequence of SEQ ID NO: 18.

In some embodiments, the modified polymerase comprising the amino acid sequence of SEQ ID NO: 18 further comprises one or more amino acid substitutions selected from the group consisting of: D34A, E36A, H83R, N84D, D88A, D191A, Q402A and S410G, and further comprises amino acid substitutions at two or more positions selected from the group consisting of: 395, 397 and 532, wherein the numbering is relative to the amino acid sequence of SEQ ID NO: 18.

In some embodiments, the modified polymerase comprises the amino acid sequence of comprises one or more amino acid substitutions selected from the group consisting of: D34A, E36A, H83R, N84D, D88A, D191A, Q402A and S410G, and further comprises the amino acid substitutions K397Y and D532H, wherein the numbering is relative to the amino acid sequence of SEQ ID NO: 18.

In some embodiments, the modified polymerase comprises one or more amino acid substitutions selected from the group consisting of: D34A, E36A, H83R, N84D, D88A, D191A, Q402A and S410G, and further comprises the amino acid substitutions H395R and D532H, wherein the numbering is relative to the amino acid sequence of SEQ ID NO: 18.

In some embodiments, the modified polymerase comprises one or more amino acid substitutions selected from the group consisting of: D34A, E36A, H83R, N84D, D88A, D191A, Q402A and S410G, and further comprises two or more amino acid substitutions selected from the group consisting of: H395R, K397Y and D532H, wherein the numbering is relative to the amino acid sequence of SEQ ID NO: 18.

In some embodiments, the modified polymerase comprises a modified N-terminal His tagged version of a B103 polymerase, wherein the modified polymerase comprises the following amino acid sequence:

```
                                            (SEQ ID NO: 19)
          10         20         30         40
MHHHHHHKHM PRKMFSCDFE TTTKLDDCRV WAYGYMEIGN 50         60         70         80
LDNYKIGNSL DEFMQWVMEI QADLYFHNLK FDGAFIVNWL 90        100        110        120
EHHGFKWSNE GLPNTYNTII SKMGQWYMID ICFGYKGKRK 130        140        150        160
LHTVIYDSLK KLPFPVKKIA KDFQLPLLKG DIDYHAERPV 170        180        190        200
GHEITPEEYE YIKNDIEIIA RALDIQFKQG LDRMTAGSDS 210        220        230        240
LKGFKDILST KKFNKVFPKL SLPMDKEIRR AYRGGFTWLN 250        260        270        280
DKYKEKEIGE GMVFDVNSLY PSQMYSRPLP YGAPIVFQGK 290        300        310        320
YEKDEQYPLY IQRIRFEFEL KEGYIPTIQI KKNPFFKGNE 330        340        350        360
YLKNSGAEPV ELYLTNVDLE LIQEHYEMYN VEYIDGFKFR 370        380        390        400
EKTGLFKEFI DKWTYVKTHE KGAKKQLAKL MLNSLYGKFA 410        420        430        440
SNPDVTGKVP YLKEDGSLGF RVGDEEYKDP VYTPMGVFIT 450        460        470        480
AWARFTTITA AQACYDRIIY CDTDSIHLTG TEVPEIIKDI 490        500        510        520
VDPKKLGYWA HESTFKRAKY LRQKTYIQDI YAKEVDGKLI 530        540        550        560
ECSPDEATTT KFSVKCAGMT DTIKKKVTFD NFRVGFSSTG 570        580
KPKPVQVNGG VVLVDSVFTI K
```

In some embodiments, the modified polymerase can comprise an amino acid sequence that is at least 70%, 80%, 85%, 90%, 95%, 99% or 100% identical to the amino acid sequence of SEQ ID NO: 19. In some embodiments, the modified polymerase further comprises the amino acid substitution D175A, wherein the numbering is relative to SEQ ID NO: 19.

In some embodiments, the modified polymerase comprises an amino acid sequence that is at least 85%, 90%, 95% or 99% identical to the amino acid sequence of SEQ ID NO: 19 and comprises any one, two, three or more of the mutations described herein.

In some embodiments, the modified polymerase comprises an amino acid sequence that is at least 85%, 90%, 95% or 99% identical to the amino acid sequence of SEQ ID NO: 19 and further comprises any one, two, three or more of the mutations selected from the group consisting of: D18A, E20A, H67R, N68D, D72A, D175A, Q386A, S394G, H379G, H379T, H379S, H379K, H379R, H379A, H379Q, H379W, H379Y, H379F, E379G, E380H, E380T, E380S, E380K, E380R, E380A, E380Q, E380W, E380Y, E380F, K381G, K381E, K381T, K381S, K381R, K381A, K381Q, K381W, K381Y, K381F, K389E, K389T, K389S, K389R, K389A, K389Q, K389W, K389Y, K389F, D516H, D516G, D516E, D516T, D516S, D516R, D516A, D516R, D516Q, D516W, D516Y D516F, K518H, K518G, K518D, K518R, K518E, K518T, K518S, K518R, K518A, K518Q, K518W, K518Y and K518F, wherein the numbering is relative to the amino acid sequence of SEQ ID NO: 19.

In some embodiments, the modified polymerase comprises one or more amino acid substitutions selected from the group consisting of: D18A, E20A, H67R, N68D, D72A, D175A, Q386A and S394G, and further comprises one or more amino acid substitutions selected from the group consisting of: H379G, H379T, H379S, H379K, H379R, H379A, H379Q, H379W, H379Y, H379F, E379G, E380H, E380T, E380S, E380K, E380R, E380A, E380Q, E380W, E380Y, E380F, K381G, K381E, K381T, K381S, K381R, K381A, K381Q, K381W, K381Y, K381F, K389E, K389T, K389S, K389R, K389A, K389Q, K389W, K389Y, K389F, D516H, D516G, D516E, D516T, D516S, D516R, D516A, D516R, D516Q, D516W, D516Y D516F, K518H, K518G, K518D, K518R, K518E, K518T, K518S, K518R, K518A, K518Q, K518W, K518Y and K518F, wherein the numbering is relative to the sequence of SEQ ID NO: 19.

In some embodiments, the modified polymerase comprises one or more amino acid substitutions selected from the group consisting of: D18A, E20A, H67R, N68D, D72A, D175A, Q386A and S394G and further comprises amino acid substitutions at two or more positions selected from the group consisting of: 379, 380 and 516, wherein the numbering is relative to the sequence of SEQ ID NO: 19.

In some embodiments, the modified polymerase comprises one or more amino acid substitutions selected from the group consisting of: D18A, E20A, H67R, N68D, D72A, D175A, Q386A and S394G, and further comprises the amino acid substitutions K381Y and D516H, wherein the numbering is relative to the sequence of SEQ ID NO: 19.

In some embodiments, the modified polymerase comprises one or more amino acid substitutions selected from the group consisting of: D18A, E20A, H67R, N68D, D72A, D175A, Q386A and S394G, and further comprises the amino acid substitutions H379R and D516H, wherein the numbering is relative to the sequence of SEQ ID NO: 19.

In some embodiments, the modified polymerase comprises one or more amino acid substitutions selected from the group consisting of: D18A, E20A, H67R, N68D, D72A, D175A, Q386A and S394G, and further comprises two or more amino acid substitutions selected from the group consisting of: H379R, K381Y and D516H, wherein the numbering is relative to the sequence of SEQ ID NO: 19.

In some embodiments, one or more activities or properties of a modified polymerase comprising an amino acid sequence that is at least %, 90%, 95% or 99% identical to the amino acid sequence of SEQ ID NO: 7, SEQ ID NO: 8, SEQ ID NO: 18 or SEQ ID NO: 19 can be altered (e.g., increased or decreased) relative to the corresponding one or more activities or properties of an exemplary reference polymerase having an amino acid sequence that is at least 70%, 80%, 85%, 90%, 95%, 99% or 100% identical to the following amino acid sequence:

```
                                            (SEQ ID NO: 20)
MNHLVHHHHH  HIEGRHMELG  TLEGSMKHMP  RKMYSCAFET 70          80
TTKVEDCRVW  AYGYMNIEDH  SEYKIGNSLD  EFMAWVLKVQ 90         100         110         120
ADLYFHNLKF  AGAFIINWLE  RNGFKWSADG  LPNTYNTIIS 130         140         150         160
RMGQWYMIDI  CLGYKGKRKI  HTVIYDSLKK  LPFPVKKIAK 170         180         190         200
DFKLTVLKGD  IDYHKERPVG  YKITPEEYAY  IKNDIQIIAE 210         220         230         240
ALLIQFKQGL  DRMTAGSDSL  KGFKDIITTK  KFKKVFPTLS 250         260         270         280
LGLDKEVRYA  YRGGFTWLND  RFKEKEIGEG  MVFDVNSLYP 290         300         310         320
AQMYSRLLPY  GEPIVFEGKY  VWDEDYPLHI  QHIRCEFELK 330         340         350         360
EGYIPTIQIK  RSRFYKGNEY  LKSSGGEIAD  LWLSNVDLEL 370         380         390         400
MKEHYDLYNV  EYISGLKFKA  TTGLFKDFID  KWTYIKTTSE 410         420         430         440
GAIKQLAKLM  LNSLYGKFAS  NPDVTGKVPY  LKENGALGFR 450         460         470         480
LGEEETKDPV  YTPMGVFITA  WARYTTITAA  QACYDRIIYC 490         500         510         520
DTDSIHLTGT  EIPDVIKDIV  DPKKLGYWAH  ESTFKRAKYL 530         540         550         560
RQKTYIQDIY  MKEVDGKLVE  GSPDDYTDIK  FSVKCAGMTD 570         580         590         600
KIKKEVTFEN  FKVGFSRKMK  PKPVQVPGGV  VLVDDTFTIK
```

This fusion polymerase of amino acid sequence of SEQ ID NO: 20 is herein variously referred to as "HP1" or "HP-1". See, e.g., U.S. Provisional Application No. 61/184,770, filed Jun. 5, 2009. This reference polymerase typically comprises a Phi-29 polymerase peptide that lacks exonuclease activity and comprises an N-terminal His-tag, an intervening linker sequence, and the D12A and D66A mutations.

In some embodiments, the reference polymerase comprises an amino acid sequence that is at least 70%, 80%, 85%, 90%, 95%, 99% or 100% identical to the amino acid sequence of SEQ ID NO: 20 (HP-1).

In one embodiment, the polymerase can be a fusion protein comprising the amino acid sequence of a nucleic acid-dependent polymerase (the polymerase portion) linked to the amino acid sequence of a second enzyme or a biologically active fragment thereof (the second enzyme portion). The second enzyme portion of the fusion protein may be linked to the amino or carboxyl end of the polymerase portion, or may be inserted within the polymerase portion. The polymerase portion of the fusion protein may be linked to the amino or carboxyl end of the second enzyme portion, or may be inserted within the second enzyme portion. In some embodiments, the polymerase and second enzyme portions can be linked to each other in a manner which does not significantly interfere with polymerase activity of the fusion or with the ability of the fusion to bind nucleotides, or does not significantly interfere with the activity of the second enzyme portion. In the fusion protein, the polymerase portion or the second enzyme portions can be linked with at least one energy transfer donor moiety. The fusion protein can be a recombinant protein having a polymerase portion and a second enzyme portion. In some embodiments, the fusion protein can include a polymerase portion chemically linked to the second enzyme portion.

In some embodiments, the polymerase can be a modified polymerase having certain desired characteristics, such as an evolved polymerase selected from a directed or non-directed molecular evolution procedure. The evolved polymerase can exhibit modulated characteristics or functions, such as changes in: affinity, specificity, or binding rates for substrates (e.g., target molecules, polymerization initiation sites, or nucleotides); binding stability to the substrates (e.g., target molecules, polymerization initiation sites, or nucleotides); nucleotide incorporation rate; nucleotide analog permissiveness; exonuclease activity (e.g., 3'→5' or 5'→3'); rate of extension; processivity; fidelity; stability; or sensitivity and/or requirement for temperature, chemicals (e.g., DTT), salts, metals, pH, or electromagnetic energy (e.g., excitation or emitted energy). Many examples of evolved polymerases having altered functions or activities can be found in U.S. provisional patent application No. 61/020,995, filed Jan. 14, 2008.

Methods for creating and selecting proteins and enzymes having the desired characteristics are known in the art, and include: oligonucleotide-directed mutagenesis in which a short sequence is replaced with a mutagenized oligonucleotide; error-prone polymerase chain reaction in which low-fidelity polymerization conditions are used to introduce point mutations randomly across a sequence up to about 1 kb in length (R. C. Caldwell, et al., 1992 PCR Methods and Applications 2:28-33; H. Gramm, et al., 1992 Proc. Natl. Acad. Sci. USA 89:3576-3580); and cassette mutagenesis in which a portion of a sequence is replaced with a partially randomized sequence (A. R. Oliphant, et al., 1986 Gene 44:177-183; J. D. Hermes, et al., 1990 Proc. Natl. Acad. Sci. USA 87:696-700; A. Arkin and D. C. Youvan 1992 Proc. Natl. Acad. Sci. USA 89:7811-7815; E. R. Goldman and D. C. Youvan 1992 Bio/Technology 10:1557-1561; Delagrave et al., 1993 Protein Engineering 6: 327-331; Delagrave et al., 1993 Bio/Technology 11: 1548-155); and domain shuffling.

Methods for creating evolved antibody and antibody-like polypeptides can be adapted for creating evolved polymerases, and include applied molecular evolution formats in which an evolutionary design algorithm is applied to achieve specific mutant characteristics. Many library formats can be used for evolving polymerases including: phage libraries (J. K. Scott and G. P. Smith 1990 Science 249:386-390; S. E. Cwirla, et al. 1990 Proc. Natl. Acad. Sci. USA 87:6378-6382; J. McCafferty, et al. 1990 Nature 348:552-554) and lad (M. G. Cull, et al., 1992 Proc. Natl. Acad. Sci. USA 89:1865-1869).

Another adaptable method for evolving polymerases employs recombination (crossing-over) to create the mutagenized polypeptides, such as recombination between two different plasmid libraries (Caren et al. 1994 Bio/Technology 12: 517-520), or homologous recombination to create a hybrid gene sequence (Calogero, et al., 1992 FEMS Microbiology Lett. 97: 41-44; Galizzi et al., WO91/01087). Another recombination method utilizes host cells with defective mismatch repair enzymes (Radman et al., WO90/07576). Other methods for evolving polymerases include random fragmentation, shuffling, and re-assembly to create mutagenized polypeptides (published application No. U.S. 2008/0261833, Stemmer). Adapting these mutagenesis procedures to generate evolved polymerases is well within the skill of the art.

In some embodiments, the polymerase can be fused with, or otherwise engineered to include, DNA-binding or other domains from other proteins that are capable of modulating DNA polymerase activity. For example, fusion of suitable portions of the Single-Stranded DNA Binding Protein (SSBP), thioredoxin and/or T7 DNA polymerase to bacterial or viral DNA polymerases has been shown to enhance both the processivity and fidelity of the DNA polymerase. Similarly, other groups have described efforts to engineer polymerases so as to broaden their substrate range. See, e.g., Ghadessy et al, Nat. Biotech., 22 (6):755-759 (2004). Similarly, the conjugates of the present disclosure can optionally comprise any polymerase engineered to provide suitable performance characteristics, including for example a polymerase fused to intact SSBP or fragments thereof, or to domains from other DNA-binding proteins (such as the herpes simplex virus UL42 protein.)

In some embodiments, a blend of different conjugates, each of which comprises a polymerase of unique sequence and characteristics, can be used according to the methods described herein. Use of such conjugate blends can additionally increase the fidelity and processivity of DNA synthesis. For example, use of a blend of processive and non-processive polymerases has been shown to result in increased overall read length during DNA synthesis, as described in U.S. Published App. No. 2004/0197800. Alternatively, conjugates comprising polymerases of different affinities for specific acceptor-labeled nucleotides can be used so as to achieve efficient incorporation of all four nucleotides.

In some embodiments, the polymerase can comprise the amino acid sequence of any polymerase disclosed in U.S. Provisional Application Nos. 61/242,771, filed on Sep. 15, 2009; 61/263,974, filed on Nov. 24, 2009 and 61/299,919, filed on Jan. 29, 2010, or any variant thereof.

In some embodiments, the polymerases of the present disclosure can be isolated from a cell, or generated using recombinant DNA technology or chemical synthesis methods. In another embodiment, the polymerases can be expressed in prokaryote, eukaryote, viral, or phage organisms. In another embodiment, the polymerases can be post-translationally modified proteins or fragments thereof.

In some embodiments, the polymerases of the present disclosure can be recombinant proteins that are produced by a suitable expression vector/host cell system. The polymerases can be encoded by suitable recombinant expression vectors carrying inserted nucleotide sequences of the polymerases. In some embodiments, the polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker which confers resistance to drugs (e.g., kanamycin, ampicillin, tetracycline, chloramphenicol, or the like), or confers a nutrient requirement. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. The recombinant polymerase can include an affinity tag for enrichment or purification, including a poly-amino acid tag (e.g., poly His tag), GST, and/or HA sequence tag. Methods for preparing suitable recombinant expression vectors and expressing the RNA and/or protein encoded by the inserted sequences are well known (Sambrook et al, *Molecular Cloning* (1989)).

In some embodiments, the present disclosure relates to modified polymerases exhibiting altered kinetics of nucleotide binding, nucleotide incorporation and/or primer extension. For example, in some embodiments, the modified polymerases of the present disclosure comprise one or more modifications resulting in a change in the kinetic behavior of the polymerase in vitro or in vivo. For example, the modification(s) may result in a change (for example, an increase or decrease) in one or more of the following activities or properties of the polymerase, relative to the corresponding activity or property of a reference polymerase: specific activity as measured in a primer extension assay; specific activity as measured in a nucleotide incorporation assay (including assays for incorporation of naturally occurring nucleotides and nucleotide analogs); exonuclease activity (including, for example, 3' to 5' exonuclease activity); ability to bind one or more substrates (including naturally occurring nucleotides and nucleotide analogs); yield of synthesized nucleic acid product; processivity; fidelity of nucleic acid synthesis; rate of nucleic acid synthesis; binding affinity for one or more particular nucleotides (including naturally occurring nucleotides and nucleotide analogs); $K_m$ for one or more substrates (including naturally occurring nucleotides, nucleotide analogs and/or template strand); $k_{cat}$ or $V_{max}$, $t_{pol}$, $t_{-1}$, $k_{pol}$, or $k_{-1}$ for one or more nucleotides (including naturally occurring nucleotides and nucleotide analogs); residence time of one or more nucleotides (including naturally occurring nucleotides and nucleotide analogs) within one or more polymerase active sites; rate of binding for one or more nucleotides (including naturally occurring nucleotides and nucleotide analogs); rate of nucleotide release (in either altered or unaltered state) from the polymerase active site, including, for example, rate of product release; average template read length in presence of nucleotides (including naturally occurring nucleotides and nucleotide analogs); nucleotide binding specificity for one or more particular nucleotides (including naturally occurring nucleotides and nucleotide analogs); accessibility of one or more polymerase active sites by one or more nucleotides (including naturally occurring nucleotides and nucleotide analogs); steric inhibition of nucleotide entry into a polymerase active site (including, for example, inhibition of entry of naturally occurring nucleotides and nucleotide analogs); complementarity of a polymerase active site with one or more natural, unnatural or non-complementary nucleotides (including naturally occurring nucleotides and nucleotide analogs) as compared to that of complementary nucleotides; ability to discriminate between correct and incorrect nucleotides (including naturally occurring nucleotides and nucleotide analogs); frequency of incorporation of non-complementary nucleotides as compared to that of complementary nucleotides (including naturally occurring nucleotides and nucleotide analogs); branching ratio for one or more nucleotides (including naturally occurring nucleotides and nucleotide analogs); stability, for example at elevated temperatures; observed performance in a particular biological assay; complementarity with one or more natural or non-natural features of a nucleotide (including naturally occurring nucleotides and nucleotide analogs); tolerance of the polymerase for various chemical and/or physical stresses, as well as the stability of the polymerase under a given set of conditions, including photostability and chemical stability; tolerance for the presence of labels (including both organic labels, e.g., dyes, and inorganic labels, e.g., nanoparticles); and photostability.

In some embodiments, the modified polymerases and/or polynucleotides of the present disclosure can exhibit an altered kinetic behavior with one or more nucleotide substrates, including, for example, labeled nucleotide analogs, relative to an unmodified counterpart. For example, in some embodiments, the modified polymerase can exhibit altered kinetics of polymerization, including, for example, polymerization of substrates comprising labeled nucleotide analogs. In some embodiments, the modified polymerase can exhibit an altered $K_m$ value for a substrate, particularly a labeled nucleotide analog. In some embodiments, the polymerase can be engineered to exhibit altered $k_{cat}/K_m$ and/or $V_{max}/K_m$ for a substrate, particularly a labeled nucleotide analog. In some embodiments, the $k_{cat}/K_m$, the $V_{max}/K_m$, or both, are increased relative to the wild type polymerase. In some embodiments, the modified polymerase can exhibit an altered $K_m$, $K_D$, $t_{-1}$, $t_{pol}$, nucleotide residence time for one or more nucleotides, for example a labeled nucleotide analog.

The kinetic activity of an enzyme can be modeled using various methods. Some exemplary theories of enzyme kinetics and associated models can be found, for example, in Berg at al., Biochemistry, 5th Ed. (W.H. Freeman, 2007); Fersht, *Enzyme Structure & Mechanism,* 5th Ed. (W.H. Freeman, 1985). Without being bound by any particular theory, the Michaelis-Menten theory provides an non-limiting exemplary theoretical model for enzymatic activity. This model is based on the assumption that an enzyme-substrate reaction typically proceeds as follows:

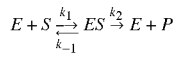

Where E=free enzyme; S=free substrate; P=product and ES=enzyme-substrate complex, $k_1$ is the rate constant for the association of substrate (S) and enzyme (E) to form an enzyme-substrate complex (ES); $k_2$ is the rate constant for the dissociation of the enzyme-substrate complex (ES) into product (i.e., altered substrate) and free enzyme, and $k_{-1}$ is the rate constant for the dissociation of the enzyme-substrate complex, ES, into unaltered substrate and enzyme.

The equilibrium dissociation constant for the dissociation of the enzyme-substrate complex, ES, into unaltered substrate and enzyme, $K_D$, can be determined as the ratio of $k_{-1}$ and $k_1$. Mathematically, this relationship can be represented as:

$$K_D = k_{-1}/k_1$$

$K_D$ can also be expressed as a ratio of the equilibrium concentrations of enzyme, substrate and enzyme-substrate complex:

$$K_D = [E][S]/[ES]$$

The Michaelis-Menten equation describes the rate of initial enzymatic activity, v, as a function of substrate concentration:

$$v = V_{max}[S]/(k_m + [S])$$

where the variables can be defined as follows:
v is the reaction rate, measured as amount of product formed per time interval.
[S] is the concentration of uncombined, i.e., free, substrate.
$V_{max}$ is maximal enzyme velocity, extrapolated to maximum substrate concentrations, i.e., rate when enzyme is saturated with substrate (also referred to as enzymatic "rate"); and $K_m$ is the so-called Michaelis-Menten constant, can be defined as $(k_2+k_{-1})/k_1$. $K_m$ is typically related to the dissociation constant, and provides an indication of the affinity of the enzyme for a particular substrate (and hence the stability of the enzyme-substrate complex). In the most simple case, when $k_2 \ll k_1$, product formation is very slow compared to the rate of formation of enzyme-substrate complex (ES), i.e., product formation is the rate limiting step, then $K_m$ can equal or approximate the equilibrium dissociation constant of the enzyme-substrate complex, $K_D$, and thus can describe the binding affinity of the substrate for the enzyme. Typically, $K_m$ can be measured as the substrate concentration at which the reaction rate is half the maximum enzyme velocity, $V_{max}$.

$V_{max}$, $k_{cat}$ and $E_T$, the total enzyme concentration (i.e., the concentration of active sites), can be mathematically related in the following equation: $k_{cat} = V_{max}/E_T$ For a polymerase reaction involving incorporation of a nucleotide onto the end of an extending nucleic acid molecule, the enzyme-substrate interactions can be more complex because they involve enzymatic interactions with the nucleic acid molecule as well as the nucleotide. A typical exemplary reaction can be represented by the following pathway:

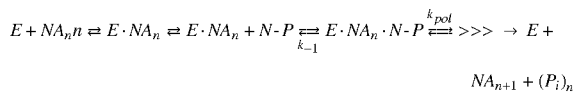

Figure 1:
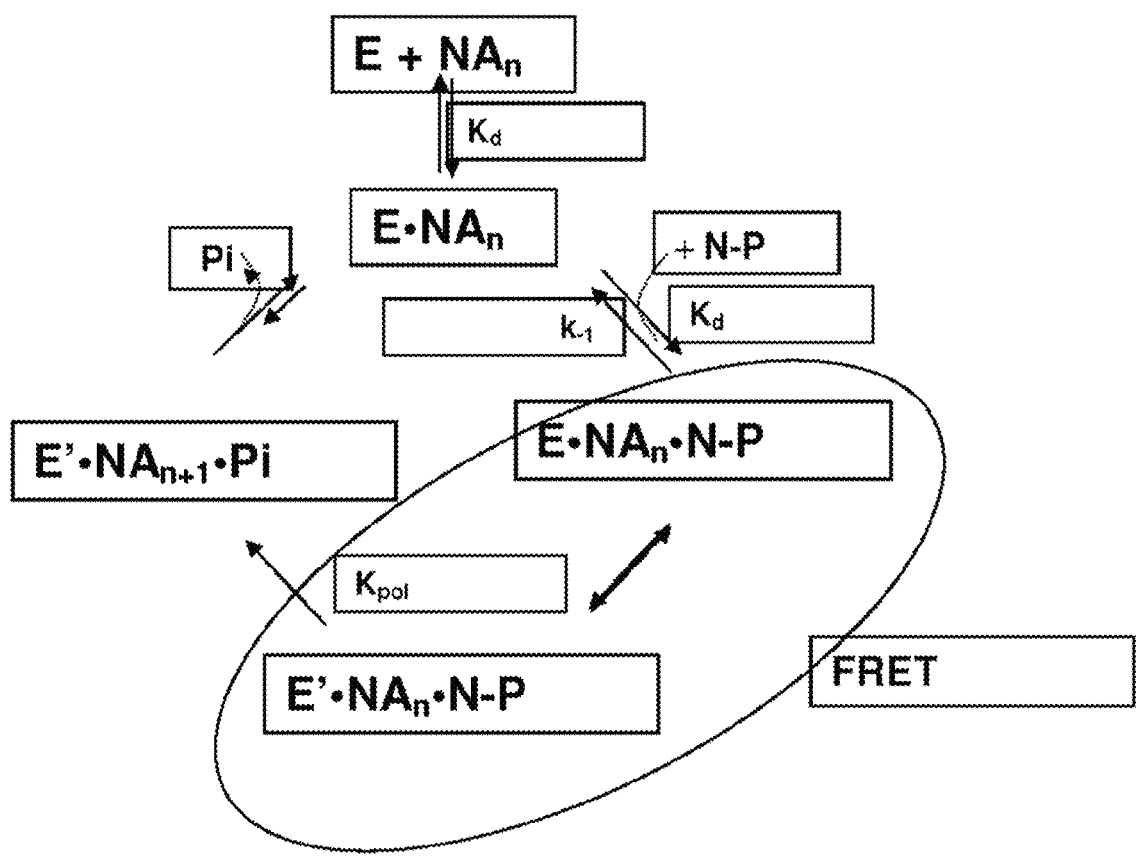
FIG. 1 depicts one exemplary theoretical model of the various stages in binding of a polymerase to a nucleic acid molecule and a nucleotide substrate, followed by dissociation of the nucleotide substrate in unaltered state (i.e., a non-productive event) or by incorporation of the nucleotide into the nucleic acid molecule.

A more detailed representation of this exemplary theoretical model is also depicted in FIG. 1. As depicted above and in FIG. 1, the nucleotide incorporation reaction pathway can typically begin with the initial association of the enzyme with a nucleic acid molecule comprising "n" nucleotide subunits (represented above and in FIG. 1 as "$NA_n$") to form an enzyme-nucleic acid complex, represented as E•$NA_n$. The E•$NA_n$ complex can also associate with a nucleotide, represented above and in FIG. 1 as "N-P" although this representation is in no way intended to restrict the nucleotide to any particular structure or any particular number of phosphate groups, as opposed to other forms of nucleotides and nucleotide analogs, which are also included. This association of the E•$NA_n$ complex with the nucleotide results in the formation of a ternary complex, represented as E•$NA_n$•N-P. This ternary complex can in some instances dissociate with rate constant $k_{-1}$ to yield an enzyme-nucleic acid complex, E•$NA_n$, comprising enzyme bound to nucleic acid, and unaltered nucleotide, N-P (a so-called "non-productive incorporation"). Alternatively, in some instances the ternary complex can undergo a productive incorporation wherein the nucleic acid molecule is extended by one nucleotide moiety with the liberation of a polyphosphate moiety. During this productive incorporation, the polymerase can undergo a conformational change from the so-called "open" form to the "closed" form wherein the nucleotide is positioned in the polymerase active site; the resulting complex comprising the polymerase in "closed" conformation is represented as E•$NA_n$•N-P. This complex can give rise to an intermediate complex comprising the "closed"-form polymerase, an extended nucleic acid and a polyphosphate group; this intermediate complex can be represented as E•$NA_{n+1}$•$(Pi)_n$, wherein the polyphosphate moiety is represented herein and in FIG. 1 as $(Pi)_n$. The polymerase of the complex can undergo a reverse conformational change from the "closed" to "open" form, resulting in a complex comprising "open"-form polymerase, extended nucleic acid and polyphosphate moiety (E•NA$_{n+1}$•(Pi)$_n$). Release of the polyphosphate moiety ((Pi)$_n$) results in a complex comprising polymerase and extended nucleic acid, which can in some instances associate with another nucleotide to form a ternary complex that can undergo another productive incorporation.

Although the polyphosphate moiety is represented herein and in FIG. 1 as (Pi)$_n$, this representation is in no way intended to restrict the polyphosphate moiety to monophosphates or inorganic phosphate. In some embodiments, for example, the nucleotide can be a phosphate-labeled nucleotide analog and the liberated moiety can comprise any one, two, three, four, five, six, seven, eight, nine, ten or more phosphate groups linked to a label, e.g., a dye moiety. The number of phosphate groups in the liberated polyphosphate will depend on the number of phosphates in the polyphosphate chain of the nucleotide substrate. A more complete description of this theoretical model of polymerase activity can be found, for example, in Patel et al., "Pre-Steady-State Kinetic Analysis of Processive DNA Replication Including Complete Characterization of an Exonuclease-Deficient Mutant" Biochemistry 30:511-525 (1991).

In FIG. 1, the step involving productive incorporation is further depicted as separated into three sub-steps, with the first sub-step involving formation of the ternary complex, E•NA$_n$•N-P, and the second sub-step involves the conversion of E•NA$_n$•N-P to E*•NA$_n$•N-P$_n$, wherein the enzyme has undergone a conformational change from "open" form (E) to "closed" form (E*). The third sub-step, the so-called "chemistry" step, typically involves the conversion of E*•NA$_n$•N-P to E*•NA$_{n+1}$•(Pi)$_n$, wherein the nucleic acid is extended by a single nucleotide moiety, with the formation of a polyphosphate by-product, denoted as (Pi)$_n$. In some embodiments, the E'•NA$_{n+1}$•(Pi)$_n$ complex can dissociate to form free enzyme, extended nucleic acid, and free polyphosphate (E+NA$_{n+1}$+(Pi)$_n$); alternatively, the polyphosphate may dissociate from the complex while the enzyme remains associated with the extended nucleic acid and can in some embodiments catalyze a subsequent nucleotide incorporation. FIG. 1 also depicts a window wherein FRET activity can occur using embodiments wherein any suitable combination of components selected from the group consisting of the nucleic acid molecule, the nucleotide, the primer and the polymerase are labeled with moieties capable of undergoing FRET with each other. In some embodiments, the polymerase is labeled with one member of a FRET donor:acceptor pair and the incoming nucleotide is labeled with another member of the FRET pair.

In some embodiments, the above reaction involves a polymerase, any suitable nucleic acid molecule (represented above as NA$_n$) and any suitable nucleotide. In some embodiments, the nucleotide can be a polyphosphate-comprising nucleotide, represented above as N-P. Any suitable polyphosphate-comprising nucleotide can be used, including, for example labeled deoxynucleotide polyphosphates comprising tri-, tetra-, penta-hexa-phosphate, hepta-phosphate, octa-phosphate, nona-phosphate, deca-phosphate, and undeca-phosphate moieties, as well as deoxynucleotide polyphosphates comprising twelve or more phosphate groups.

Theoretically, each step of this reaction pathway is associated with specific rate constants, dissociation constants, and associated kinetic parameters. In one exemplary embodiment, one or more of these kinetic parameters can be measured in a "stopped-flow" assay using suitable techniques. See, for example, M. P. Roettger, Biochemistry 47:9718-9727 (2008); M. Bakhtina Biochemistry 48:3197-320 (2009); Ahn et al, Biochemistry 36:1100-1107 (1997).

Without intending to be bound to any particular theory of reaction mechanism, it can be surmised that in some cases k$_{-1}$, which indicates the rate of dissociation of the ternary complex (E•NA$_n$•N-P) into enzyme-nucleic acid complex (E•NA$_n$) and free, unaltered nucleotide (N-P), is significantly lower than k$_{pol}$, which indicates the rate at which the ternary complex (E•NA$_n$•N-P) converts to the intermediate complex (E*•NA$_{n+1}$•(Pi)$_n$), then it can be expected that non-productive incorporation events will predominate over productive incorporation events. Conversely, when k$_{pol}$ is significantly lower than k$_{-1}$ then it can be expected that productive incorporations will predominate over non-productive incorporations.

In some embodiments, the polymerases, nucleotides, and reaction conditions, can be screened for their suitability for use in the disclosed nucleotide binding, nucleotide incorporation and/or primer extension methods, using well known screening techniques. For example, the suitable polymerase may be capable of binding nucleotides and/or incorporating nucleotides. In some embodiments, the reaction kinetics for nucleotide binding, association, incorporation, and/or dissociation rates, can be determined using rapid kinetics techniques (e.g., stopped-flow or quench flow techniques). Using stopped-flow or quench flow techniques, the binding kinetics of a nucleotide can be estimated by calculating the 1/k$_d$ value. Stopped-flow techniques which analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494). Nucleotide incorporation by a polymerase can also be analyzed by gel separation of the primer extension products.

In some embodiments, the modified polymerase exhibits altered (e.g., increased or decreased) levels of primer extension activity. For example, the modified polymerase may exhibit increased primer extension activity in the presence of labeled nucleotides, relative to an unmodified counterpart. In some embodiments, the primer extension activity of the modified polymerase is at least about 5%, 10%, 25%, 37.5%, 50%, 75%, 100%, 110%, 125%, 150%, 200%, 250%, 500%, 750%, 1,000%, 5,000% or 10,000% of the primer extension activity of a reference polymerase under identical reaction conditions. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the modified polymerase comprises the amino acid sequence of SEQ ID NO: 7, SEQ ID NO: 8, or any other variant form of the polymerase having the amino acid sequence of SEQ ID NO: 7. In some embodiments, the nucleotide substrate is a natural nucleotide. In some embodiments, the nucleotide substrate is a labeled nucleotide analog. The polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

The primer extension activity can be measured using any suitable assay that provides a quantitative indication of the amount of extension product obtained using defined reaction conditions comprising a known concentration of polymerase. Regardless of which assay is used, differences in primer extension activity between two samples, when obtained using identical reaction conditions, can be evaluated by simply comparing levels of observed primer activity obtained from each sample. Optionally, the observed primer extension activity can normalized for amount of polymerase by dividing the amount of incorporated radioactivity by the polymerase concentration in the reaction mixture, to allow comparison between reactions containing different polymerase concentrations.

In one exemplary embodiment, the primer extension activity of a polymerase can be measured using a radiometric assay that measures incorporation of a radioactively labeled nucleotide into acid-insoluble material in a polymerase reaction. The amount of incorporated radioactivity indicates the total number of nucleotides incorporated. See, e.g., Wu et al., Gene Biotechnology, 2nd Ed., CRC Press; Sambrook, J., Fritsch, E F, and Maniatis, T. (1989) Molecular Cloning A Laboratory Manual, 2nd ed., Cold Spring Harbor Laboratory Press, Cold Spring Harbor, N.Y.

In another exemplary embodiment, levels of primer extension activity in a sample can be measured by monitoring the fluorescence intensity change over time during extension of a fluorescein-labeled hairpin oligonucleotide. One such exemplary assay is described in Example 13, herein.

In another exemplary embodiment, the primer extension activity can be quantified by quantifying the amount of pyrophosphate liberated after performing primer extension under standard tolerance assay conditions for 5 minutes. One such exemplary assay is described in Example 5.

In another exemplary embodiment, the primer extension activity can be quantified by measuring the fraction of extended primer within a population of primer-template duplexes. One such exemplary assay using standard photostability assay conditions is provided in Example 6. In this exemplary embodiment, the template comprised a radioactive ($^{32}$P) moiety or fluorescent (TAMRA) label to permit visualization of polymerase reaction products (e.g., extended primer). Primer extension products were resolved on a gel, and the primer extension activity was quantified as the proportion (%) of extended primer relative to total starting primer by adding the intensities of all bands observed within a single lane as measured by densitometric analysis.

In some embodiments, the modified polymerase exhibits an altered (e.g., increased or decreased) $K_m$ value for any particular nucleotide substrate of interest, for example a labeled nucleotide analog, relative to an unmodified counterpart. In some embodiments, the modified polymerase exhibits a $K_m$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $K_m$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the modified polymerase comprises the amino acid sequence of SEQ ID NO: 7, SEQ ID NO: 8, or any other variant form of the polymerase having the amino acid sequence of SEQ ID NO: 7. In some embodiments, the nucleotide substrate is a natural nucleotide. In some embodiments, the nucleotide substrate is a labeled nucleotide analog. The polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509Q, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase comprises one or more modifications that alter the $t_{-1}$ value of the modified polymerase for a given nucleotide, for example a labeled nucleotide analog, as compared to the $t_{-1}$ value of an unmodified counterpart for the same nucleotide. In some embodiments, the $t_{-1}$ value can be defined as the average time required for the nucleotide (e.g., a labeled nucleotide analog) to dissociate in unaltered form from the enzyme-template-nucleotide ternary complex (E•NA$_n$•N-P) during nucleic acid polymerization, wherein the dissociation can be represented through the following reaction:

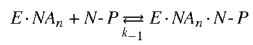

Typically, $t_{-1}$ can be calculated as the reciprocal of $k_{-1}$, the rate constant for the dissociation reaction, and thus $t_{-1}$ can be mathematically represented as $1/k_{-1}$. In some embodiments, the modified polymerase comprises one, two or more modifications that increase the $t_{-1}$ value of the polymerase for a particular nucleotide substrate, particularly a labeled nucleotide analog. Such increase in the $t_{-1}$ value typically correlates with a decreased rate of dissociation of the enzyme-template-nucleotide ternary complex, which can in some cases increase the duration during which the nucleotide remains associated with the polymerase and template in the ternary complex. This can be helpful in various biological applications, including nucleic acid sequencing, which require or otherwise involve visualization of the labeled nucleotide analog when in proximity with or bound to the polymerase active site.

A variety of methods are available to measure the rate of nucleotide dissociation, $k_{-1}$ (and the corresponding $t_{-1}$ value). Typically, the $k_{-1}$ value is measured using stopped-flow fluorescence measurements, and fitting the resulting fluorescence traces to a single exponential function of the form:

$$\text{Fluorescence} = A_1 * e^{-k-1*t} + C \quad \text{[Equation(1)]}$$

where $A_1$ represents the corresponding fluorescence amplitude, C is an offset constant, and $k_{-1}$ is the observed rate constant for the fluorescence transition. See, e.g., Bakhtina, Biochemistry 48:3197-3208 (2009).

In one exemplary method, a non-extendible primed template is formed by annealing a primer comprising a dideoxynucleotide at its 3' end with a template oligonucleotide that further protrudes a few nucleotides downstream from the 3' end of the primer, and comprises a donor fluorophore at its 5' end. This non-extendible primed template is then contacted with a nucleotide comprising an acceptor fluorophore attached to the terminal phosphate group (also referred to herein as the "omega" phosphate group) to form a ternary complex. The ternary complex is then contacted with unlabeled ("cold") nucleotides, and the dissociation of the omega-labeled nucleotide from the ternary complex is monitored as a function of donor fluorescence where typically dissociation is correlated with an increase in donor fluorescence. The fluorescence traces are then fitted into a function of the form of Equation (1) to determine the $k_{-1}$ and the corresponding $t_{-1}$ values for the polymerase.

In some embodiments, the modified polymerase exhibits an altered (e.g., increased or decreased) $t_{-1}$ value for a given nucleotide substrate, for example a labeled nucleotide analog, relative to an unmodified counterpart. In some embodiments, the modified polymerase exhibits a $t_{pol}$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $t_{-1}$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8 or any other variant form of the polymerase having the amino acid sequence of SEQ ID NO: 7. In some embodiments, the modified polymerase is at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 370, 371, 372, 373, 374, 375, 376, 377, 380, 383, 384, 385, 455, 507 and 509, or any combinations thereof.

In one exemplary assay, the $t_{-1}$ value of the modified polymerase is measured with respect to an exemplary labeled nucleotide analog comprising a fluorophore, e.g., an Alexa Fluor 647 moiety, attached to the terminal phosphate of a deoxynucleotide tetraphosphate via a suitable linker. Some non-limiting examples of labeled nucleotides and methods of using such nucleotides in polymerase-based applications can be found, inter alia, in U.S. Pat. No. 7,244,566 issued Jul. 17, 2007; U.S. Pat. No. 7,223,541 issued May 29, 2007; U.S. Pat. No. 7,052,839 issued May 30, 2006; U.S. Pat. No. 7,244,566 issued Jul. 17, 2007; U.S. Pat. No. 7,393,640 issued Jul. 1, 2008; U.S. Pat. No. 7,033,762 issued Apr. 25, 2006; U.S. Pat.

No. 7,256,019 issued Aug. 14, 2007; U.S. Pat. No. 7,041,812 issued May 9, 2006; U.S. Pat. No. 7,452,698 issued Nov. 18, 2008 and U.S. Pat. No. 7,078,499 issued Jul. 18, 2006; as well as in U.S. Published Application Nos. 2004/0048300 published Mar. 11, 2004; 2008/0132692 published Jun. 5, 2008; 2009/0081686, published Mar. 26, 2009; 2008/0131952, published Jun. 5, 2008; and 2007/0292679, published Dec. 20, 2007.

In some embodiments, the modified polymerase has a $t_{-1}$ value for a nucleotide substrate that is greater than or equal to the $t_{-1}$ value for the same nucleotide substrate of a Phi-29 polymerase comprising the amino acid sequence of SEQ ID NO: 1 and further comprising an amino acid substitution at one or more residues selected from the group consisting of: 132, 250, 342, 373, 375, 379, 380, 383, 510 and 512, wherein the numbering is relative to the amino acid of SEQ ID NO: 1. In some embodiments, the modified polymerase has a $t_{-1}$ value for a given nucleotide that is greater than or equal to the $t_{-1}$ for the same nucleotide of a Phi-29 polymerase comprising the amino acid sequence of SEQ ID NO: 1 and further comprising one or more amino acid substitutions selected from the group consisting of: K132A, V250A, L342G, T373R, E375Y, T373R, K379A, Q380A, D510H and K512Y.

In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase is at least 80%, 85%, 97%, 98% or 99% identical to the amino acid sequence of SEQ ID NO: 7 and can in some embodiments comprise an amino acid substitutions at one or more positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

Another useful parameter of enzymatic activity is $k_{cat}$, also known as the turnover number. Typically, $k_{cat}$ equals the number of times each enzyme site converts substrate to product per unit time, i.e., the maximal number of molecules of substrate converted to product per enzyme active site per unit time (e.g., second).

In some embodiments, the modified polymerase exhibits an altered (e.g., increased or decreased) $k_{cat}$ value for a given nucleotide substrate, for example a labeled nucleotide analog, relative to an unmodified counterpart. In some embodiments, the modified polymerase exhibits a $k_{cat}$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $k_{cat}$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant form of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits an altered (e.g., increased or decreased) specificity for a given nucleotide substrate, for example a labeled nucleotide analog, relative to an unmodified counterpart. In some embodiments, the modified polymerase exhibits a specificity for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the specificity of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant form of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 370, 371, 372, 373, 374, 375, 376, 377, 380, 383, 384, 385, 455, 507 and 509, or any combinations thereof.

Without being bound to any particular theory, according to some theories the specificity of the enzyme can be defined mathematically as the ratio $k_{cat}/K_m = k_{cat} \cdot k_1/(k_{-1}+k_2)$. It has the dimension $M^{-1} s^{-1}$, with large values typically indicating high specificity. In some embodiments, the modified polymerase exhibits an altered (e.g., increased or decreased) $k_{cat}/K_m$ ratio for a given nucleotide substrate, for example a labeled nucleotide analog, relative to an unmodified counterpart. In some embodiments, the modified polymerase exhibits a $k_{cat}/K_m$ ratio for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $k_{cat}/K_m$ ratio of a reference polymerase for the same nucleotide substrate. In some embodiments, the reference polymerase is the unmodified counterpart of the modified polymerase. In some, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits an altered (e.g., increased or decreased) $V_{max}/K_m$ value for a given nucleotide substrate, for example a labeled nucleotide analog, relative to an unmodified counterpart. In some embodiments, the modified polymerase exhibits a $V_{max}/K_m$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $V_{max}/K_m$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase comprises one or more modifications that alter the $t_{pol}$ value of the modified polymerase for a given nucleotide, for example a labeled nucleotide analog, as compared to the $t_{pol}$ value of an unmodified counterpart for the same nucleotide. The $t_{pol}$ value can be defined as the average time for the incorporation reaction to occur from the enzyme-template-nucleotide ternary complex according to the following reaction:

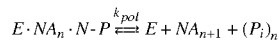

Typically, $t_{pol}$ can be calculated as the reciprocal of $k_{pol}$, the rate constant for the above reaction, and thus $t_{pol}$ can be mathematically represented as $1/k_{pol}$. In some embodiments, the modified polymerase comprises one, two or more modifications that decrease the $t_{pol}$ value of the polymerase for a particular nucleotide substrate, particularly a labeled nucleotide analog. Such decrease in the $t_{pol}$ value typically correlates with an increased rate of the forward reaction in which the enzyme-template-nucleotide ternary complex undergoes a productive incorporation, thereby producing an extended nucleic acid molecule. This increase in forward rate can be helpful in various biological applications, including nucleic acid sequencing, which require or otherwise involve visualization of the labeled nucleotide analog when in proximity with or bound to the polymerase active site.

A variety of methods are available to measure $k_{pol}$ (and the corresponding $t_{pol}$ value). In one exemplary method as taught in MP Roettger (2008 Biochemistry 47:9718-9727); M. Bakhtina 2009 Biochemistry 48:3197-320), the $k_{pol}$ value of a polymerase can be measured in a stopped-flow experiment by fitting the fluorescence trace data to a general double exponential function of the form:

$$\text{Fluorescence} = A_1 * e^{-k1*t} + A_2 * e^{-kpol*t} + C \quad \text{[Equation (2)]}$$

where $A_1$ and $A_2$ represent corresponding fluorescence amplitudes, C is an offset constant, and $k_1$ and $k_{pol}$ are the observed rate constants for the fast and slow phases of the reaction, respectively. Plotting the concentration dependence of the rates and amplitudes for the fast and slow phases can afford a definition of the rate constants $k_1$ and $k_{pol}$ in a two-step binding process.

In one exemplary stopped-flow method, the an extendible primed template is formed by annealing a primer with a template oligonucleotide that extends a further few nucleotides downstream from the 3' end of the primer, and comprises a donor fluorophore at its 5' end. This extendible primed template is contacted with a nucleotide comprising an acceptor fluorophore attached to the terminal ("omega") phosphate group to initiate the nucleotide incorporation reaction. The reaction progress is monitored as a function of donor fluorescence where typically the reaction progress is correlated with an initial dip in donor fluorescence followed by a recovery in donor fluorescence. Based on these fluorescence measurements, the $k_{pol}$ value can be determined by fitting the fluorescence traces to a function having the form of Equation (2), and the $t_{pol}$ value can be calculated as the reciprocal of the $k_{pol}$ value.

In some embodiments, the modified polymerase exhibits an altered (e.g., increased or decreased) $t_{pol}$ value for a given nucleotide substrate, for example a labeled nucleotide analog, relative to an unmodified counterpart. In some embodiments, the modified polymerase exhibits a $t_{pol}$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $t_{pol}$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

Any suitable method of measuring $t_{pol}$ may be used. In one exemplary assay, the $t_{pol}$ value of the modified polymerase is measured with respect to an exemplary labeled nucleotide analog comprising an Alexa Fluor 647 moiety attached to the terminal ("omega") phosphate of a deoxynucleotide tetraphosphate via a 6-carbon linker. See, for example, U.S. Pat. No. 7,041,812, issued May 9, 2006.

In some embodiments, the modified polymerase has a $t_{pol}$ value for a nucleotide that is less than or equal to the $t_{pol}$ value for the same nucleotide of a Phi-29 polymerase comprising the amino acid sequence of SEQ ID NO: 1 and further comprising an amino acid substitution at one or more positions selected from the group consisting of: 132, 250, 342, 373 375, 379, 380, 383, 510 and 512, wherein the numbering is relative to the amino acid of SEQ ID NO: 1. In some embodiments, the modified polymerase has a $t_{pol}$ value for a given nucleotide that is greater than or equal to the $t_{pol}$ value for the same nucleotide of a Phi-29 polymerase comprising the amino acid sequence of SEQ ID NO: 1 and further comprising one or more amino acid substitutions selected from the group consisting of: K132A, V250A, L342G, T373R, E375Y, K379A, Q380A, D510H and K512Y.

In some embodiments, the ratio of $t_{-1}/t_{pol}$ values for the modified polymerase is at least about 0.5, more typically at least about 1.0, even more typically at least about 1.2, 1.3, 1.5, 1.75, 2.0, 2.5, 5.0, 7.5, 10, 12.5, 25, 50, or 100. In some embodiments, the modified polymerase exhibits an altered (e.g., increased or decreased) ratio of $t_{-1}/t_{pol}$ values for a given nucleotide substrate, for example a labeled nucleotide analog, relative to an unmodified counterpart. In some embodiments, the modified polymerase exhibits a $t_{-1}/t_{pol}$ ratio for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $t_{-1}/t_{pol}$ ratio of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase comprises an amino acid sequence that is at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In one embodiment, stopped-flow techniques can be used to screen and select mutant polymerases having a $t_{pol}$ value (e.g., $1/k_{pol}$) for a particular labeled nucleotide that is less than the $t_{-1}$ (e.g., $1/k_{-1}$) value of the polymerase for the same labeled nucleotide. In some embodiments, the modified polymerase comprises an amino acid sequence that is at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the polymerase comprises the amino acid sequence of SEQ ID NO: 8, and optionally further comprises the amino acid substitution H370R. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

For example, some Phi-29 or B103 polymerases (wild-type or mutant) exhibit $t_{pol}$ values which are less than $t_{-1}$ values, in the presence of nucleotide tetraphosphate or hexaphosphate molecules.

In another embodiment, polymerases can be modified by binding it to a chemical compound or an antibody, in order to inhibit nucleotide incorporation.

In some embodiments, the modified polymerase exhibits an altered (e.g., increased or decreased) ratio of $k_{cat}/K_d$ value values for a given nucleotide substrate, for example a labeled nucleotide analog, relative to an unmodified counterpart. In some embodiments, the modified polymerase exhibits a $k_{cat}/K_d$ ratio for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $k_{cat}/K_d$ ratio of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog.

In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase comprises an amino acid sequence that is at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the polymerase can be selected to exhibit a reduced $K_{sub}$ for a substrate, particularly a labeled nucleotide analog. In some embodiments, the polymerase can comprise one or more mutations resulting in altered $K_{cat}/K_{sub}$ and/or $V_{max}/K_{sub}$ for a particular labeled nucleotide. In some embodiments, the $K_{cat}/K_{sub}$, the $V_{max}/K_{sub}$, or both, are increased as compared to the wild type polymerase.

In some embodiments, the modified polymerase exhibits a $K_{cat}/K_{sub}$ and/or $V_{max}/K_{sub}$ ratio for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $K_{cat}/K_{sub}$ and/or $V_{max}/K_{sub}$ ratio of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog.

In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase comprises an amino acid sequence that is at least 80%, 85%, 90%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to exhibit either increased or decreased residence times for one or more nucleotides, particularly for a labeled nucleotide analog. The residence time indicates the duration for which the nucleotide dwells within the active site of the polymerase.

In some embodiments, the modified polymerase exhibits an altered (e.g., increased or decreased) residence for a given nucleotide substrate, for example a labeled nucleotide analog, relative to an unmodified counterpart. In some embodiments, the modified polymerase exhibits a residence time for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the residence time of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase has a residence time for a particular nucleotide substrate that is between about 20 msec and about 300 msec, typically between about 55 msec and about 100 msec. In some embodiments, the residence time of the selected, mutated, modified, evolved or otherwise engineered polymerase for the nucleotide substrate can be between about 1.5 and about 4 times the residence time of a reference polymerase for the same nucleotide substrate. Some exemplary polymerases exhibiting altered residence times for labeled nucleotides are disclosed in U.S. Pub. No. 20080108082, published May 8, 2008.

In some embodiments, the modified polymerase exhibits an altered (e.g., increased or decreased) $1/(k_{pol}+k_{-1})$ value for a given nucleotide substrate, for example a labeled nucleotide analog, relative to an unmodified counterpart. In some embodiments, the modified polymerase exhibits a $1/(k_{pol}+k_{-1})$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $1/(k_{pol}+k_{-1})$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits an altered (e.g., increased or decreased) rate of binding for a given nucleotide substrate, for example a labeled nucleotide analog, relative to an unmodified counterpart. In some embodiments, the modified polymerase exhibits a rate of binding for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the rate of binding of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to exhibit an altered branching ratio for one or more nucleotide substrates, particularly for labeled nucleotide analogs. The term "branching" and its variants, when used in reference to a polymerase, typically refers to binding of the appropriate nucleotide to the polymerase without productive incorporation of the nucleotide into an extending nucleic acid molecule by the polymerase. In some applications, for example single molecule sequencing, such behavior can be undesirable because it can complicate analysis of the reaction as it progresses and/or render it difficult to distinguish between productive and non-productive incorporations, and it is therefore desirable to alter the branching ratio to minimize such complications. The complications posed by branching behavior during single molecule sequencing analysis are described, for example, in Rank, U.S. Published Patent Application No. 2008/0108082; Hanzel, U.S. Published Patent Application No. 2007/0196846; Clark, U.S. Published Patent Application No. 2009/0176233; and Bjornsen, U.S. Published Patent Application No. 2009/0286245.

Without being bound to any particular theory, in some embodiments, the branching ratio can be defined as the fraction (expressed as a percentage ratio) of events involving the formation of an enzyme-template-nucleotide ternary complex, E•NA•N-P, that actually result in productive incorporation of the nucleotide into an extending nucleic acid molecule. Alternatively, in some embodiments, the branching ratio can be defined as the fraction of the nucleotides that bind to, and dissociate from, the polymerase active site without being incorporated to the extending nucleic acid molecule.

One exemplary mathematical measure for branching ratio can be represented as follows:

Branching ratio=$k_{pol}/(k_{pol}+k_{-1})$

Without intending to be bound to any particular theory, in some cases this measure of branching ratio, $k_{pol}/(k_{pol}+k_{-1})$, can provides an indication of the fraction (expressed as a percentage) of nucleotide binding events (i.e., events wherein the nucleotide binds to the polymerase to form a ternary enzyme-template-nucleotide complex) that result in productive incorporation. In some applications, it can be desirable to increase the branching ratio as much as possible, ideally to 1.0 (wherein a value of 1.0 indicates that every bound nucleotide becomes incorporated into the extending nucleic acid molecule).

In some embodiments, the branching ratio (measured as $k_{pol}/(k_{pol}+k_{-1})$) of the modified polymerase for a particular nucleotide substrate, for example, a labeled nucleotide analog, can be between about 0.25 and 1.00, typically between about 0.6 and about 0.99. In some embodiments, the branching ratio of the modified polymerase for a particular nucleotide substrate, for example a labeled nucleotide analog, is greater than 0.95, typically greater than about 0.97, 0.98, 0.99 or 0.999.

In some embodiments, the modified polymerase exhibits an altered (e.g., increased or decreased) branching ratio for a given nucleotide substrate, for example a labeled nucleotide analog, relative to an unmodified counterpart. In some embodiments, the modified polymerase exhibits a branching ratio for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the branching ratio of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits an altered (e.g., increased or decreased) $k_{pol}/(k_{pol}+k_{-1})$ value for a given nucleotide substrate, for example a labeled nucleotide analog, relative to an unmodified counterpart. In some embodiments, the modified polymerase exhibits a $k_{pol}/(k_{pol}+k_{-1})$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $k_{pol}/(k_{pol}+k_{-1})$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to exhibit either increased or decreased processivity for one or more nucleotide substrates, particularly for labeled nucleotide analogs. The processivity is the number of nucleotides incorporated for a single binding event between the polymerase and the target molecule base-paired with the polymerization initiation site.

In some embodiments, the processivity of the modified polymerase with one or more labeled nucleotide analogs can be between about 10 and 10,000 nucleotides, typically between about 10 and 100 nucleotides. For example, the processivity of the modified polymerase may be about 1, 5, 10, 20, 25, 50, 100, 250, 500, 750, 1000, 2000, 5000, or 10,000 or more nucleotides incorporated with a single binding event.

In some embodiments, the modified polymerase exhibits an altered (e.g., increased or decreased) processivity for a given nucleotide substrate, for example a labeled nucleotide analog, relative to an unmodified counterpart. In some embodiments, the modified polymerase exhibits a processivity for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the processivity of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof.

Without being bound to any particular theory, under some models one exemplary mathematical expression for processivity can be represented as follows:

$$\text{Processivity} = k_{pol}/(k_{-1(E \cdot DNA)})$$

In some embodiments, the modified polymerase exhibits an altered (e.g., increased or decreased) $k_{pol}/(k_{-1\ (E \cdot DNA)})$ value for a given nucleotide substrate, for example a labeled nucleotide analog, relative to an unmodified counterpart. In some embodiments, the modified polymerase exhibits a $k_{pol}/(k_{-1\ (E \cdot DNA)})$ value for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the $k_{pol}/(k_{-1(E \cdot DNA)})$ value of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to extend an increased or decreased fractional extension activity, defined as fraction of nucleic acid templates that are extended by at least one nucleotide in a polymerase reaction under defined reaction conditions. In a typical embodiment, fractional extension efficiency is determined using reaction conditions comprising 50 mM Tris, pH 7.5, 50 mM NaCl, 5 mM DTT, 100 nM polymerase, 100 nM primer-template duplex, 2 mM $MnCl_2$ and 5 µM of nucleotides at 37° C. (for eukaryotic or bacterial polymerases) or 23° C. (for B103-like and Phi29-like polymerases) for 30 seconds. In some embodiments, the extended fraction can be measured as the percentage of total primed nucleic acid templates that are extended by one or more nucleotides under such reaction conditions. In some embodiments, the fractional extension activity of the modified polymerase is increased or decreased relative to the fractional extension activity of a reference polymerase under identical reaction conditions. In some embodiments, the reference polymerase can be a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof, and exhibits increased or decreased fractional extension activity as compared to a reference polymerase, e.g., an unmodified counterpart. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to exhibit either increased or decreased ease of entry of nucleotides, particularly labeled nucleotide analogs, into the polymerase active site. In some embodiments, the modified polymerase exhibits an altered (e.g., increased or decreased) degree of steric inhibition of nucleotide entry to the active site relative to the degree of steric inhibition exhibited by a reference polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In some embodiments, the modified polymerase exhibits, or can be further modified, selected, mutated, evolved or otherwise engineered to exhibit either increased or decreased rate of incorporation of one or more nucleotide substrates, particularly for labeled nucleotide analogs. In some embodiments, the rate of nucleotide incorporation of the modified polymerase with one or more nucleotide substrates is greater than or equal to one nucleotide per second, 5 nucleotides per second, 10 nucleotides per second, 20 nucleotides per second, 30 nucleotides per second, 40 nucleotides per second, 50 nucleotides per second, 100 nucleotides, or 200 nucleotides per second. In some embodiments, the rate of nucleotide incorporation is one nucleotide per 2, 3, 4, or 5 seconds.

In some embodiments, the modified polymerase exhibits an altered (e.g., increased or decreased) rate of nucleotide incorporation for a given nucleotide substrate, for example a labeled nucleotide analog, relative to an unmodified counterpart. In some embodiments, the modified polymerase exhibits a rate of nucleotide incorporation for a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the rate of nucleotide incorporation of a reference polymerase for the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

In one embodiment, polymerases exhibiting reduced nucleotide incorporation rates include mutant phi29 polymerase having lysine substituted with leucine, arginine, histidine or other amino acids (Castro 2009 Nature Structural and Molecular Biology 16:212-218). In some embodiments, the polymerase can be selected to exhibit either reduced or enhanced rates of incorporation for polyphosphate-comprising nucleotides comprising a label bonded to the terminal phosphate.

In some embodiments, the polymerase can be selected, mutated, modified, evolved or otherwise engineered to exhibit high fidelity with low error rates. The fidelity of a polymerase may be measured using assays well known in the art (Lundburg et al., 1991 Gene, 108:1-6). Typically, the fidelity of a polymerase is measured as the error rate, i.e., the frequency of incorporation of a nucleotide in a manner that violates the widely known Watson-Crick base pairing rules. The accuracy or fidelity of DNA polymerization can be influenced not only by the polymerase activity of a given enzyme, but also by the 3'-5' exonuclease activity of a polymerase. The error rate of the polymerase can be one error per about 100, or about 250, or about 500, or about 1000, or about 1500 incorporated nucleotides. High fidelity polymerases include those exhibiting error rates of about 5×10⁻⁶ per base pair or lower rates. By suitable selection and engineering of the polymerase, the error rate of the single-molecule sequencing methods disclosed herein can be further improved. In some embodiments, the polymerase can be further engineered or modified, e.g., via glycosylation, so as to enhance peptide stability and/or performance.

In some embodiments, the selection of the polymerase can be determined by the level of fidelity desired, such as the error rate per nucleotide incorporation. The frequency of misincorporation ($f_{mis}$) can be defined as the ratio between the $k_{cat}/K_d$ values for correct and incorrect nucleotides. Fidelity, i.e. the number of correct incorporation events before a mismatch occurs, can be expressed as $1/f_{mis}$.

In some embodiments, the modified polymerase exhibits an altered (e.g., increased or decreased) fidelity in the presence of a given nucleotide substrate, for example a labeled nucleotide analog, relative to an unmodified counterpart. In some embodiments, the modified polymerase exhibits a fidelity in the presence of a particular nucleotide substrate that is at least about 5%, 10%, 25%, 37.5%, 50%, 75%, 100%, 110%, 125%, 150%, 200%, 250%, 500%, 750%, 1,000%, 5,000% or 10,000% as high as the fidelity exhibited by a reference polymerase in the presence of the same nucleotide substrate. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof. In some embodiments, the modified polymerase comprises an amino acid sequence that is at least 70%, 80%, 85%, 90%, 95%, 97%, 98%, 99% or 100% identical to the amino acid sequence of SEQ ID NO: 7 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 7. In some embodiments, the modifications can include deletions, additions and substitutions. The substitutions can be conservative or non-conservative substitutions. In some embodiments, the modified polymerase comprises an amino acid sequence that is at least 80%, 85%, 90%, 95%, 97%, 98%, 99% or 100% identical to the amino acid sequence of SEQ ID NO: 7 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 7. Optionally, the modified polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 7. Optionally, this modified polymerase comprises the amino acid substitution H370R.

Each the kinetic parameters of the modified polymerase, including the various parameters described above, can be measured with respect to a given substrate of the polymerase, including, for example, one or more particular nucleotides. In some embodiments, the nucleotide is a labeled nucleotide analog, for example, a base-, sugar- or phosphate-labeled analog. The labeled nucleotide analog can comprise one or more phosphate groups. In some embodiments, the nucleotide analog comprises a triphosphate, tetraphosphate, pentaphosphate, hexaphosphate, heptaphosphate, octaphosphate, nonaphosphate or decaphosphate moieties. The labeled nucleotide analog can comprise an organic dye attached to the omega or terminal phosphate of the labeled nucleotide analog. In some embodiments, the organic dye is an Alexa Fluor moiety.

Disclosed herein are modified polymerases exhibiting altered levels of tolerance for the presence of specific labels, particularly inorganic labels such as nanoparticles. The word "tolerance" and its variants, as used herein with reference to a particular polymerase, refers to the average primer extension activity retained by the polymerase in the presence of a particular label (e.g., dye or nanoparticle) under defined reaction conditions, as compared to the average primer extension activity of the polymerase in the absence of the label but under otherwise identical reaction conditions.

In some embodiments, the modified polymerase exhibits increased tolerance for one or more particular labels as compared to its unmodified counterpart. Such increased tolerance can be desirable because it allows high levels of primer extension activity in reactions comprising labeled components, such as single molecule sequencing reactions. The labels included in the reaction mixture can optionally be attached to the polymerase, to the nucleotides, and/or to any other component of the reaction mixture. The labels can be organic (e.g., dyes) or inorganic (e.g., nanoparticles). Typically, the tolerance can vary depending on the reaction conditions, including the type(s) and concentration of any label(s) present in the reaction mixture. The lower the decrease in primer extension activity in the presence of the label(s), the greater the tolerance of the polymerase for the particular label(s).

The tolerance of a polymerase for a particular label is typically measured by first obtaining the tolerance ratio for the polymerase under defined reaction conditions. The tolerance ratio is the ratio of the average primer extension activity of the polymerase in the presence of one or more types of label under defined reaction conditions (termed "$A_{pol-label}$")

and the average primer extension activity of the polymerase in the absence of the label but under otherwise identical reaction conditions (termed "$A_{pol\text{-}}$"). This relationship can be expressed mathematically as follows:

Tolerance ratio=$A_{pol\text{-}label}/A_{pol}$

The tolerance is then calculated by converting the tolerance ratio into a percentage value (%), which can be obtained by multiplying the tolerance ratio, $A_{pol\text{-}label}/A_{pol}$, by 100. This relationship can be represented as follows:

Tolerance (%)=$(A_{pol,\text{-}label}/A_{pol}) \times 100$

For example, a polymerase that has about 90% tolerance for a particular type of label will retain on average about 90% of its average primer extension activity in a defined reaction mixture including a particular concentration of label, where the average primer extension activity of the polymerase in the absence of label under otherwise identical reaction conditions is arbitrarily set as 100%.

In a typical embodiment, tolerance is measured using defined reaction conditions (referred to herein as "standard tolerance assay conditions") comprising 50 mM Tris, pH 7.5, 50 mM NaCl, 5 mM DTT, 100 nM polymerase, 100 nM primer-template duplex, 2 mM MnCl$_2$ and 5 µM of nucleotides, and 100 nM of label for 5 minutes at 23° C. The observed primer extension activity is measured and compared to the primer extension activity of the same polymerase in the absence of any label but under otherwise identical reaction conditions (control reaction), which is arbitrarily defined as having 100% primer extension activity.

Depending on the biological application of interest, however, the tolerance can also be determined under different, i.e., non-standard, assay conditions, for example by measuring the average primer extension activity of the polymerase under different reaction conditions including higher or lower concentrations of the label, and comparing this activity to the average primer extension activity of the polymerase in the absence of the label but under otherwise identical reaction conditions. In some embodiments, the reaction conditions can optionally include exposure to excitation radiation of defined intensity, frequency and duration.

In some embodiments, the label is a nanoparticle and the tolerance of the polymerase for the nanoparticle is referred to as the "nanoparticle tolerance". The nanoparticle tolerance of a polymerase can vary with the nature of the nanoparticle label itself.

In one exemplary and non-limiting embodiment, the nanoparticle tolerance can be measured under standard tolerance assay conditions as follows: a polymerase reaction mixture comprising 50 mM Tris, pH 7.5, 50 mM NaCl, 5 mM DTT, 100 nM polymerase, 100 nM primer-template duplex and 2 mM MnCl$_2$ is prepared, as well as a second aliquot of the identical reaction mixture further comprising 100 nM of test nanoparticle. The polymerase reaction is then initiated by the addition of 5 µM of labeled nucleotide to both mixtures, and the resulting primer extension activity is measured after 5 minutes. All reactions are performed at 23° C. The nanoparticle tolerance ratio is calculated by dividing the average primer extension activity exhibited by the modified polymerase in reactions comprising 100 nM nanoparticles ($A_{pol,np}$) by the observed primer extension activity of the polymerase in control reactions lacking nanoparticles ($A_{pol}$), as expressed in the following equation:

Nanoparticle tolerance ratio=$(A_{pol,np}/A_{pol})$

The nanoparticle tolerance is then calculated by converting the nanoparticle tolerance ratio into a percentage value, by multiplying the nanoparticle tolerance ratio, $A_{pol,np}/A_{pol}$, by 100. This relationship can be expressed as follows:

Nanoparticle tolerance (%)=$(A_{pol,np}/A_{pol}) \times 100$.

In some embodiments, the present disclosure relates to modified polymerases having a nanoparticle tolerance ($A_{pol\text{-}label}/A_{pol} \times 100$), of up to about 5%, 10%, 15%, 20%, 25%, 30%, 35%, 40%, 45%, 50%, 55%, 60%, 65%, 70%, 80% or 90% as measured using standard tolerance assay conditions, as described herein. In some embodiments, the nanoparticle tolerance of the modified polymerase is at least about 5%, 10%, 25%, 50%, 70%, 75%, 80%, 90%, 100%, 125%, 250%, 500%, 750% or 1,000% as measured using standard tolerance assay conditions.

In some embodiments, the modified polymerase exhibits an altered, e.g., increased or decreased, nanoparticle tolerance ($A_{pol,np}/A_{pol} \times 100$) relative to an unmodified counterpart. In some embodiments, the modified polymerase exhibits a photostability ($A_{pol,np}/A_{pol} \times 100$) that is at least about 5%, 10%, 25%, 37.5%, 50%, 75%, 100%, 110%, 125%, 150%, 200%, 250%, 500%, 750%, 1,000%, 5,000% or 10,000% of the photostability of a reference polymerase under identical reaction conditions. In some embodiments, the reaction conditions can comprise standard tolerance assay conditions, as described herein.

In some embodiments, the modified polymerase has a primer extension activity ($A_{pol\text{-}np}$) under standard tolerance assay conditions that is at least about that is at least about 5%, 10%, 25%, 37.5%, 50%, 75%, 100%, 110%, 125%, 150%, 200%, 250%, 500%, 750%, 1,000%, 5,000% or 10,000% of the primer extension activity of a reference polymerase under identical reaction conditions.

In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase having altered nanoparticle tolerance comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof.

In some embodiments the nanoparticle tolerance, expressed as a percentage value ($A_{pol,np}/A_{pol} \times 100$) of the modified polymerase can be about 70%, whereas the $A_{pol,np}/A_{pol} \times 100$ value of a reference Phi-29 polymerase comprising the amino acid sequence of SEQ ID NO: 1 under identical reaction conditions is about 60%. In some embodiments the ($A_{pol,np}/A_{pol} \times 100$) value of the modified polymerase can be at least about 85%, whereas the ($A_{pol,np}/A_{pol} \times 100$) value of a reference Phi-29 polymerase comprising the amino acid sequence of SEQ ID NO: 1 is no greater than about 55% under identical reaction conditions. In some embodiments the ($A_{pol,np}/A_{pol} \times 100$) value of the modified polymerase can be about 90%, whereas the $A_{pol,np}/A_{pol} \times 1000$ value of a reference Phi-29 polymerase comprising the amino acid sequence of SEQ ID NO: 1 under identical reaction conditions is about 50%.

Disclosed herein are modified polymerases exhibiting altered (e.g., increased or decreased) levels of photostability following exposure to excitation radiation. The word "photostability" and its variants, as used herein with reference to a particular polymerase, refers to the average primer extension activity retained by the polymerase following exposure to excitation radiation under defined reaction conditions, as compared to the average primer extension activity of the polymerase in the absence of such exposure but under otherwise identical reaction conditions.

In some embodiments, the modified polymerase exhibits increased photostability as compared to its unmodified counterpart, thus increasing its utility in methods and systems involving labels requiring excitation in order to be detectable. For example, increased photostability can be desirable because it allows high levels of primer extension activity in reactions involving the use of excitation radiation, such as single molecule sequencing reactions.

Typically, the photostability will vary depending on the reaction conditions employed, including the intensity, wavelength and duration of the excitation radiation. The lower the decrease in primer extension activity following exposure to excitation radiation, the greater the photostability of the polymerase.

The photostability of a polymerase is typically measured by first obtaining the photostability ratio of the polymerase under defined reaction conditions. The photostability ratio is the ratio of the average primer extension activity of the polymerase following exposure to excitation radiation under defined reaction conditions (termed "$A_{pol-R}$") and the average primer extension activity of the polymerase without exposure to any excitation radiation but under otherwise identical reaction conditions (termed "$A_{pol}$"). This relationship can be expressed mathematically as follows:

Photostability ratio=$A_{pol-R}/A_{pol}$

The photostability can then be calculated by converting the photostability ratio into a percentage value (%), which can be obtained by multiplying the ratio $A_{pol-R}/A_{pol}$ by 100. This relationship can be represented as follows:

Photostability (%)=$(A_{pol-R}/A_{pol}) \times 100$

For example, a polymerase that has about 90% photostability will retain on average about 90% of its average primer extension activity under defined reaction conditions (including exposure to excitation radiation of a defined intensity, wavelength and duration), where the average primer extension activity of the polymerase in the absence of any exposure to excitation radiation but under otherwise identical reaction conditions is arbitrarily set as 100%.

In a typical embodiment, the photostability of a polymerase is measured using defined reaction conditions (referred to herein as "standard photostability assay conditions") comprising 50 mM Tris, pH 7.5, 50 mM NaCl, 1 mM DTT, 2 mM $MnCl_2$, 0.3% BSA, 200 nM His-tagged polymerase, 100 nM primed template and 100 nM nanoparticles and further including exposure to excitation radiation of 50 W/$cm^2$ intensity at 405 nm wavelength and 5 minutes duration. Following such irradiation, the primer extension reaction is initiated by adding nucleotides to a final concentration of 5 µM and primer extension is performed at 23° C. for 30 seconds. The resulting primer extension activity is measured after 30 seconds by arresting the reaction (e.g., via addition of 10 mM EDTA). The primer extension activity is then measured and then compared to the primer extension activity of control sample (i.e., no exposure to excitation radiation) under otherwise identical reaction conditions.

In one exemplary embodiment, the primer extension activity was measured by resolving the extension products on a 8M urea, 24% polyacrylamide, and calculating the concentration of fully extended product relative to total concentration for all extension products. The observed primer extension activity is compared to the primer extension activity of the same polymerase in the absence of any label but under otherwise identical reaction conditions (control reaction), which is arbitrarily defined as having 100% primer extension activity.

Depending on the biological application of interest, however, the photostability can also be determined under different, i.e., non-standard, assay conditions, for example by measuring the average primer extension activity of the polymerase under different reaction conditions including higher or lower intensities, wavelengths and/or durations of excitation, and comparing this activity to the average primer extension activity of the polymerase in the absence of the label but under otherwise identical reaction conditions. In some embodiments, the reaction conditions can optionally include the presence of one or more labels, e.g., nanoparticles in the reaction mixture.

In some embodiments, the present disclosure relates to modified polymerases having a photostability ($A_{pol-R}/A_{pol} \times 100$) of up to about 5%, 10%, 15%, 20%, 25%, 30%, 35%, 40%, 45%, 50%, 55%, 60%, 65%, 70%, 80% or 90% under standard photostability assay conditions, as described herein. In some embodiments, the photostability of the modified polymerase is at least about 5%, 10%, 25%, 50%, 70%, 75%, 80%, 90%, 100%, 125%, 250%, 500%, 750% or 1,000% under standard photostability assay conditions.

In some embodiments, the modified polymerase exhibits an altered, e.g., increased or decreased, photostability ($A_{pol-R}/A_{pol} \times 100$) relative to an unmodified counterpart. In some embodiments, the modified polymerase exhibits a photostability ($A_{pol-R}/A_{pol} \times 100$) that is at least about 5%, 10%, 25%, 37.5%, 50%, 75%, 100%, 110%, 125%, 150%, 200%, 250%, 500%, 750%, 1,000%, 5,000% or 10,000% as high as the photostability of a reference polymerase under identical reaction conditions. In some embodiments, the reaction conditions can comprise standard photostability assay conditions, as described herein.

In some embodiments, the modified polymerase has a primer extension activity ($A_{pol-R}$) under standard photostability assay conditions that is at least about that is at least about 5%, 10%, 25%, 37.5%, 50%, 75%, 100%, 110%, 125%, 150%, 200%, 250%, 500%, 750%, 1,000%, 5,000% or 10,000% of the primer extension activity of a reference polymerase under identical reaction conditions.

In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase having altered photostability comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof.

In some embodiments, the excitation radiation comprises light of 405 nm wavelength. The intensity of excitation radiation can be about 10 W/cm$^2$, 20 W/cm$^2$ or 50 W/cm$^2$ or any other suitable value. In some embodiments, the duration of exposure to excitation radiation can be less than or equal to 0.1, 0.25, 0.3, 0.4, 0.5, 0.75, 1, 2.5, 5, 10, 15, 20, 30, 45 or 60 minutes. In some embodiments, the $A_{pol-R}/A_{pol}$ value of the modified polymerase is at least 50%, 60%, 70%, 80%, 90%, 95% or 99% following exposure to excitation radiation at 20 W/cm$^2$ for 5 minutes. In some embodiments, the $A_{pol-R}/A_{pol}$ value of the modified polymerase is at least 50%, 60%, 70%, 80%, 90%, 95% or 99% following exposure to excitation radiation at 50 W/cm$^2$ for 30 seconds.

In some embodiments, the modified polymerase exhibits an altered (e.g., increased or decreased) $A_{pol-R}/A_{pol}$ value relative to an unmodified counterpart. In some embodiments, the modified polymerase exhibits $A_{pol-R}/A_{pol}$ value that is at least about 5%, 10%, 25%, 37.5%, 50%, 75%, 100%, 110%, 125%, 150%, 200%, 250%, 500%, 750%, 1,000%, 5,000% or 10,000% as high as the $A_{pol-R}/A_{pol}$ value of a reference polymerase under identical reaction conditions. In some embodiments, the reference polymerase is the unmodified counterpart of the modified polymerase. In some embodiments, the reference polymerase is a Phi-29 polymerase having the amino acid sequence of SEQ ID NO: 1. In some embodiments, the reference polymerase is a B103 polymerase having the amino acid sequence of SEQ ID NO: 6, SEQ ID NO: 7 or SEQ ID NO: 8. In some embodiments, the nucleotide substrate is a natural nucleotide. In some embodiments, the nucleotide substrate is a labeled nucleotide analog. In some embodiments, the modified polymerase comprises the amino acid sequence of SEQ ID NO: 7, SEQ ID NO: 8, or any other variant of the polymerase having the amino acid sequence of SEQ ID NO: 7. In some embodiments, the modified polymerase can be at least 80%, 85%, 97%, 98% or 99% identical to the amino acid sequence of SEQ ID NO: 7 or SEQ ID NO: 8. In some embodiments, the modified polymerase comprises one or more amino acid substitutions at positions selected from the group consisting of: 2, 9, 12, 58, 59, 63, 129, 166, 246, 247, 339, 370, 371, 372, 373, 374, 375, 376, 377, 380, 383, 384, 385, 455, 507 and 509, or any combinations thereof.

Also disclosed herein are kits comprising one or more modified polymerases of the present disclosure for use in primer extension or single molecule sequencing reactions. For example, in some embodiments, the kit can comprise one or more modified polymerases and one or more nucleotides packaged in a fashion to enable use of the polymerase to incorporate one or more nucleotides of the kit. The modified polymerase can be a polymerase having or comprising the amino acid sequence of SEQ ID NO: 7 or SEQ ID NO: 8, or a polymerase comprising an amino acid sequence that is at least 80%, 85%, 90%, 95%, 97%, 98% or 99% identical to the amino acid sequence of SEQ ID NO: 7 or SEQ ID NO: 8. The nucleotide can be a labeled nucleotide analog. The label can be linked to the sugar, base, phosphate or any other moiety of the nucleotide analog. In some embodiments, the nucleotide is a reversible terminator.

In some embodiments, the kit can comprise a modified polymerases according to the present disclosure linked to one or more labels to form a labeled polymerase conjugates. Some methods of making and using labeled polymerase conjugates are disclosed, for example, in U.S. provisional application No. 61/184,770, filed Jun. 5, 2009; 61/245,457, filed on Sep. 24, 2009; and 61/299,919, filed on Jan. 29, 2010, as well as U.S. application Ser. No. _____ titled "Conjugates of Biomolecules to Nanoparticles" and filed concurrently herewith; and U.S. application Ser. No. _____ titled "Labeled Enzyme Compositions, Methods & Systems" and filed concurrently herewith. In some embodiments, the one or more labels of the labeled polymerase conjugate are capable of undergoing FRET with the label of the nucleotide bound to the active site of the polymerase. Optionally, such FRET can occur with a FRET efficiency of at least about 10% or 20%.

In some embodiments, the kit can further comprise additional reagents, such as additional nucleotides, including labeled and unlabeled nucleotides; divalent metal cations; nucleic acid molecules (for example, for use as primer and/or template); buffer solutions; salt solutions, and the like. Typically, the kit will also comprise instructions for use of the contents in a variety of applications such as, for example, nucleotide incorporation, primer extension and single molecule sequencing.

Also provided herein are methods of isolating or preparing the modified polymerases of the present disclosure. In some embodiments, the polymerase can be a recombinant protein which is produced by a suitable expression vector/host cell system. The polymerases can be encoded by suitable recombinant expression vectors carrying inserted sequences of the polymerases. The polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker that confers resistance to drugs (e.g., kanamycin, ampicillin, tetracycline, chloramphenicol, or the like) or requirement for nutrients. The suitable expression vector can have one or more restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. Methods for preparing suitable recombinant expression vectors and expressing the RNA and/or protein encoded by the inserted sequences are well known. See, e.g., Sambrook et al., *Molecular Cloning* (1989).

As the skilled artisan will readily appreciate, the scope of the present disclosure encompasses not only the specific amino acid and/or nucleotide sequences disclosed herein, but also, for example, too many related sequences encoding genes and/or peptides with the functional properties described herein. For example, nucleotide and amino acid sequences encoding conservative variants of the various modified polymerases disclosed herein are also within the scope of the present disclosure.

Also provided herein are methods of using the modified polymerase compositions of the present disclosure.

In some embodiments, the modified polymerases of the present disclosure can polymerize one or more nucleotides, including, for example, labeled and unlabeled nucleotides.

In some embodiments, the disclosure relates to a method for performing a primer extension reaction, comprising: contacting a modified DNA polymerase as provided herein with a nucleic acid molecule and a nucleotide under conditions where the nucleotide is incorporated into the nucleic acid molecule by the modified DNA polymerase. Optionally, the modified DNA polymerase comprises an amino acid sequence that is at least 80%, 85%, 90%, 95%, 97%, 98% or 99% identical to the amino acid sequence of SEQ ID NO: 7.

Optionally, the nucleotide is a labeled nucleotide, and the label of the nucleotide emits a signal during incorporation of the at least one nucleotide. Optionally, the method further comprises detecting the signal emitted by the nucleotide label. Optionally, the method further comprises analyzing the detected signal to determine the identity of the incorporated nucleotide.

Optionally, the modified DNA polymerase can exhibit a $t_{-1}$ value for a labeled nucleotide that is equal to or greater than the $t_{-1}$ value of a reference Phi-29 polymerase comprising the amino acid sequence of SEQ ID NO: 1 for the same nucleotide. Optionally, the modified polymerase exhibits a $t_{pol}$ value for a labeled nucleotide that is equal to or greater than the $t_{pol}$ value of a reference Phi-29 polymerase comprising the amino acid sequence of SEQ ID NO: 1 for the same nucleotide. Optionally, the modified DNA polymerase exhibits a residence time for a labeled nucleotide that is equal to or greater than the residence time of a reference Phi-29 polymerase comprising the amino acid sequence of SEQ ID NO: 1 for the same nucleotide. In some embodiments, the modified DNA polymerase has a photostability of at least about 80% under standard photostability assay conditions. In some embodiments, the modified polymerase has a nanoparticle tolerance of at least about 80% under standard tolerance assay conditions.

Optionally, the nucleotide is a labeled nucleotide. In some embodiments, the labeled nucleotide comprises a nucleotide label linked to the base, sugar or phosphate group of the nucleotide. In some embodiments, the labeled nucleotide is a reversible terminator. Optionally, the modified DNA polymerase can be linked to a label. The label can be a dye or a nanoparticle. Optionally, the label of the modified polymerase and the nucleotide label are capable of undergoing FRET with each other. Such FRET can optionally occur with a FRET efficiency of at least 20%.

Disclosed herein are methods for incorporation of one or more nucleotides onto the end of a nucleic acid molecule, comprising: contacting a nucleic acid molecule with a modified polymerase provided for herein and one or more nucleotides under conditions where at least one nucleotide is incorporated by the modified polymerase. The nucleic acid molecule can be any suitable target nucleic acid molecule of interest. In some embodiments, the modified polymerase can be a polymerase having or comprising the amino acid sequence of SEQ ID NO: 7 or SEQ ID NO: 8. In some embodiments, the at least one nucleotide can be become incorporated onto the 3' end of an extending nucleic acid molecule by the polymerase. In some embodiments, the at least one nucleotide can be a labeled nucleotide analog. The labeled nucleotide analog can comprise a label linked to the base, sugar, phosphate or any other portion of the nucleotide analog. In some embodiments, the nucleotide can also comprise a blocking group that inhibits, slows down or blocks further incorporation of nucleotides onto the end of the nucleic acid molecule until the blocking group is removed from the nucleotide. In some embodiments, the nucleotide comprising a blocking group is a reversible terminator for nucleic acid synthesis, as described further below. In some embodiments, the blocking group can be removed from the nucleotide by chemical, enzymatic, or photocleaving reactions.

In some embodiments, the method further includes the step of adding one or more divalent cations to the polymerase reaction mixture in an amount sufficient for inhibiting further incorporation of nucleotides onto the end of the nucleic acid molecule by the modified polymerase. In some embodiments, the divalent cation that inhibits nucleotide incorporation is calcium. In another embodiment, omitting, reducing, or chelating cations that permit nucleotide incorporation (e.g, manganese and/or magnesium) can be employed. Such methods are described, for example, in U.S. Provisional Application 61/242,762, filed Sep. 15, 2009; and in U.S. Provisional Application No. 61/184,774, filed on Jun. 5, 2009. In some embodiments, the polymerase can be linked to a label, as, for example, disclosed in U.S. Provisional Application No. 61/184,770, filed Jun. 5, 2009.

Also provided herein is a method for detecting one or more nucleotide incorporations onto the end of a single nucleic acid molecule, comprising: contacting a target nucleic acid molecule with a modified polymerase provided for herein and one or more labeled nucleotides under conditions where at least one labeled nucleotide is incorporated by the polymerase onto the end of an extending nucleic acid molecule and where the label of at least one labeled nucleotide emits one or more signals indicative of nucleotide incorporation; and detecting the one or more signals indicative of nucleotide incorporation. In some embodiments, the method can further include the step of analyzing the one or more detected signals indicative of nucleotide incorporation to determine the presence of a target nucleic acid molecule. In some embodiments, the detecting can be performed in real or near real time. In some embodiments, the method can further include the step of analyzing the one or more detected signals indicative of nucleotide incorporation to determine the identity of the target nucleic acid molecule. In some embodiments, the method can further include the step of analyzing the one or more detected signals indicative of nucleotide incorporation to determine the identity of one or more incorporated nucleotides. In some embodiments, a time series of nucleotide incorporations can be detected and analyzed to determine some or all of the sequence of the target nucleic acid molecule.

Also disclosed herein is a method for determining a nucleotide sequence of a single nucleic acid molecule, comprising: (a) conducting a polymerase reaction comprising a modified polymerase provided for herein and at least one labeled nucleotides, which reaction results in the incorporation of one or more labeled nucleotides by the polymerase and the generation of one or more signals indicative of one or more nucleotide incorporations; (b) detecting a time sequence of nucleotide incorporations; and (c) determining the identity of one or more incorporated nucleotides, thereby determining some or all of the nucleotide sequence of a single nucleic acid molecule.

Also provided herein are methods of sequencing a nucleic acid molecule, comprising: (a) conducting a polymerase reaction comprising a modified polymerase and at least one labeled nucleotide, which reaction results in the incorporation of one or more labeled nucleotides by the polymerase and the generation of one or more signals indicative of one or more nucleotide incorporations; (b) detecting a time sequence of nucleotide incorporations; and (c) determining the identity of one or more incorporated nucleotides, thereby determining some or all of the nucleotide sequence of a single nucleic acid molecule.

In some embodiments, the polymerase can bind a target nucleic acid molecule, which may or may not be base-paired with a polymerization initiation site (e.g., primer).

The polymerization initiation site is used by the polymerase (e.g., DNA or RNA polymerase) to initiate nucleotide polymerization. In some embodiments, the polymerization initiation site can be a terminal 3' OH group. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication. The polymerization initiation site can be provided by an accessory protein (e.g., RNA polymerase or helicase/primase). The polymerization initiation site can be provided by a terminal protein which can be bound (covalently or non-covalently) to the end of the target nucleic, including terminal protein (e.g., TP) found in phage (e.g., TP from phi29 phage). Thus, the polymerization initiation site may be at a terminal end or within a base-paired nucleic acid molecule.

In other embodiments, the polymerization initiation site used by some polymerases (e.g., RNA polymerase) may not include a 3'OH group.

The portion of the target molecule which is base paired with the primer or with the oligonucleotide, or the self-primed portion of the target molecule, can form hydrogen bonding by Watson-Crick or Hoogstein binding to form a duplex nucleic acid structure. The primer, oligonucleotide, and self-priming sequence may be complementary, or partially complementary, to the nucleotide sequence of the target molecule. The complementary base pairing can be the standard A-T or C-G base pairing, or can be other forms of base-pairing interactions.

The polymerization initiation site can be in a position on the target nucleic acid molecule to permit successive nucleotide incorporation events in a direction away from, or towards, the solid surface.

The primer molecule can hybridize with the target nucleic acid molecule. The sequence of the primer molecule can be complementary or non-complementary with the sequence of the sequence of the target molecule. The 3' terminal end of the primer molecule can provide the polymerization initiation site.

The primers can be modified with a chemical moiety to protect the primer from serving as a polymerization initiation site or as a restriction enzyme recognition site. The chemical moiety can be a natural or synthetic amino acid linked through an amide bond to the primer.

The primer, oligonucleotide, or self-priming portion, may be naturally-occurring, or may be produced using enzymatic or chemical synthesis methods. The primer, oligonucleotide, or self-priming portion may be any suitable length including 5, 10, 15, 20, 25, 30, 40, 50, 75, or 100 nucleotides or longer in length. The primer, oligonucleotide, or self-priming portion may be linked to an energy transfer moiety (e.g., donor or acceptor) or to a reporter moiety (e.g., a dye) using methods well known in the art.

The primer molecule, oligonucleotide, and self-priming portion of the target molecule, may comprise ribonucleotides, deoxyribonucleotides, ribonucleotides, deoxyribonucleotides, peptide nucleotides, modified phosphate-sugar backbone nucleotides including phosphorothioate and phosphoramidate, metallonucleosides, phosphonate nucleosides, and any variants thereof, or combinations thereof.

In one embodiment, the primer molecule can be a recombinant DNA molecule. The primer can be linked at the 5' or 3' end, or internally, with at least one binding partner, such as biotin. The biotin can be used to immobilize the primer molecule to the surface (via an avidin-like molecule), or for attachment to a reporter moiety. The primer can be linked to at least one energy transfer moiety, such as a fluorescent dye or a nanoparticle, or to a reporter moiety. The primer molecule can hybridize to the target nucleic acid molecule. The primer molecule can be used as a capture probe to immobilize the target molecule.

Typically, the polymerase can selectively bind to a nucleotide. Such nucleotide binding can occur in a template-dependent or non-template-dependent manner. Typically, the polymerase can mediate cleavage of the bound nucleotide. Typically, such cleavage of the nucleotide results in the formation of at least two nucleotide cleavage products. For polyphosphate-comprising nucleotides, such cleavage will typically occur between the $\alpha$ and $\beta$ phosphate groups. Typically, the polymerase can mediate incorporation of one of the nucleotide cleavage products into a nucleic acid molecule, and release of another nucleotide cleavage product. When used in conjunction with polyphosphate-comprising nucleotides, the released nucleotide cleavage product can comprise one or more phosphates (for example, a polyphosphate chain); for nucleotides that are non-phosphate-comprising analogs, the nucleotide cleavage product may not comprise any phosphorus.

In some embodiments, the polymerase can mediate incorporation of a nucleotide on to a polymerization initiation site (e.g., terminal 3'OH of a primer).

The compositions, methods, systems and kits of the present disclosure have particular use in single molecule sequencing reactions. Typically, such applications comprise the performance of a polymerase reaction using the a conjugate comprising a polymerase linked to a label and having polymerase activity according to the present disclosure.

In one exemplary embodiment, the temporal order of nucleotide incorporations during the polymerase reaction is detected and monitored in real time based on detection of FRET signals resulting from FRET between the labeled polymerase conjugates and the nucleotide label of an incorporating acceptor-labeled nucleotide.

In some embodiments, the polymerase is linked to a FRET donor and contacted with a nucleotide comprising a FRET acceptor. In some embodiments, the donor performs FRET with the acceptor when the polymerase and nucleotide are bought into sufficient proximity (for example, during a productive incorporation, a non-productive incorporation or during association of a nucleotide with the polymerase active site), resulting in the emission of a FRET signal. The FRET signal can optionally be detected and analyzed to determine the occurrence of a polymerase-nucleotide interaction.

In some embodiments, the FRET can occur prior to, during or after productive incorporation of the nucleotide into a nucleic acid molecule. Alternatively, the FRET can occur prior to binding of the nucleotide to the polymerase active site, or while the nucleotide resides within the polymerase active site, during a non-productive incorporation.

In some embodiments, the FRET acceptor moiety can in some embodiments be attached to, or comprise part of, the nucleotide sugar, the nucleobase, or analogs thereof. In some embodiments, the FRET acceptor is attached to a phosphate group of the nucleotide that is cleaved and released upon incorporation of the underlying nucleotide into the primer strand, for example the γ-phosphate, the β-phosphate or some other terminal phosphate of the incoming nucleotide. When this acceptor-labeled nucleotide polyphosphate is incorporated by the labeled polymerase conjugate into a nucleic acid molecule, the polymerase cleaves the bond between the alpha and beta phosphate, thereby releasing a pyrophosphate moiety comprising the acceptor that diffuses away. Thus, in these embodiments, a signal indicative of nucleotide incorporation is generated through FRET between the nanoparticle and the acceptor bonded to the gamma, beta or other terminal phosphate as each incoming nucleotide is incorporated into the newly synthesized strand. By releasing the label upon incorporation, successive incorporation of labeled nucleotides can each be detected without interference from nucleotides previously incorporated into the complementary strand. Alternatively, the nucleotide may be labeled with a FRET acceptor moiety on an internal phosphate, for example, the alpha phosphate, the beta phosphate, or another internal phosphate. Although such alpha-phosphate adducts are not cleaved and released during the polymerization process, they can be removed and/or rendered inoperable through appropriate treatments, e.g., chemical cleavage or photobleaching, later in the sequencing process.

The polymerase reaction conditions can comprise any suitable reaction conditions that permit nucleotide polymerization by labeled polymerase conjugates of the present disclosure. In one non-limiting example of nucleotide polymerization, the steps of polymerization can comprise: (1) complementary base-pairing of a target DNA molecule (e.g., a template molecule) with a primer molecule having a terminal 3' OH (the terminal 3' OH provides the polymerization initiation site for the polymerase); (2) binding of the polymerase of the conjugate to the base-paired target DNA/primer duplex to form a complex (e.g., open complex); (3) binding of the candidate nucleotide by the polymerase of the conjugate, which polymerase interrogates the candidate nucleotide for complementarity with the template nucleotide on the target DNA molecule; (4) catalysis of nucleotide polymerization by the polymerase of the conjugate.

In one embodiment, the polymerase of the conjugate comprises cleavage of the incorporating nucleotide by the polymerase, accompanied by liberation of a nucleotide cleavage product. When the nucleotide is a phosphate-comprising nucleotide, the cleavage product can include one or more phosphate groups. In other embodiments, where the polymerase incorporates a nucleotide analog having substituted phosphate groups, the cleavage product may include one or more substituted phosphate groups.

The candidate nucleotide may or may not be complementary to the template nucleotide on the target molecule. The candidate nucleotide may dissociate from the polymerase. If the candidate nucleotide dissociates from the polymerase, it can be liberated; in some embodiments, the liberated nucleotide carries intact polyphosphate groups. When the candidate nucleotide dissociates from the DNA polymerase, the event is known as a "non-productive binding" event. The dissociating nucleotide may or may not be complementary to the template nucleotide on the target molecule.

The incorporated nucleotide may or may not be complementary to the template nucleotide on the target. When the candidate nucleotide binds the DNA polymerase and is incorporated, the event is a "productive binding" event. The incorporated nucleotide may or may not be complementary to the template nucleotide on the target molecule.

The length of time, frequency, or duration of the binding of the complementary candidate nucleotide to the polymerase can differ from that of the non-complementary candidate nucleotide. This time difference can be used to distinguish between the complementary and non-complementary nucleotides, and/or can be used to identify the incorporated nucleotide, and/or can be used to deduce the sequence of the target molecule.

The signal (or change in signal) generated by the energy transfer donor and/or acceptor can be detected before, during, and/or after any nucleotide incorporation event.

In some embodiments, the polymerase reaction includes RNA polymerization which does not require a 3' polymerization initiation site. Polymerase reactions involving RNA polymerization are well known in the art.

Productive and Non-Productive Binding

Also provided herein are energy transfer compositions and methods for distinguishing between the productive and non-productive binding events. The compositions and methods can also provide base identity information during nucleotide incorporation. The compositions include nucleotides and polymerases each attached to a energy transfer moiety.

The compositions and methods provided herein can be used to distinguish events such as productive and non-productive nucleotide binding to the polymerase. In a productive binding event, the nucleotide can bind/associate with the polymerase for a time period which is distinguishable (e.g., longer or shorter time period), compared to a non-productive binding event. In a non-productive binding event, the nucleotide can bind/associate with the polymerase and then dissociate. The donor and acceptor energy transfer moieties produce detectable signals when they are in proximity to each other and can be associated with productive and non-productive binding events. Thus, the time-length difference between signals from the productive and non-productive binding events can provide distinction between the two types of events.

The detectable signals can be classified into true positive and false positive signals. For example, the true positive signals can arise from productive binding in which the nucleotide binds the polymerase and is incorporated. The incorporated nucleotide can be complementary to the template nucleotide. In another example, the false positive signals can arise from different binding events, including: non-specific binding, non-productive binding, and any event which brings the energy transfer donor and acceptor into sufficient proximity to induce a detectable signal.

Optionally, polymerase reactions performed using the methods, systems, compositions and kits of the present disclosure can be performed under any conditions which are suitable for: forming the complex (target/polymerase or target/initiation site/polymerase); binding the nucleotide to the polymerase; permitting the energy transfer and reporter moieties to generate detectable signals when the nucleotide binds the polymerase; incorporating the nucleotide; permitting the energy transfer and reporter moieties to generate a signal upon close proximity and/or nucleotide incorporation; and/or detecting the signal, or change in the signal, from the energy transfer or reporter moieties. The suitable conditions include well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. The buffer can include Tris, Tricine, HEPES, MOPS, ACES, or MES, which can provide a pH range of about 5.0 to about 9.5. The buffer can include chelating agents such as EDTA and EGTA, and the like.

Reducing Photo-Damage

The suitable polymerase reaction conditions can also include compounds which reduce photo-damage. For example, the compounds may reduce oxygen-damage or photo-damage. Illuminating the nucleotide binding and/or nucleotide incorporation reactions with electromagnetic radiation at an excitation wavelength can induce formation of reactive oxygen species from the fluorophore or other components in the reaction. The reactive oxygen species can cause photo-damage to the fluorophores, polymerases, or any other component of the binding or incorporation reactions. The nucleotide binding or nucleotide incorporation reactions can include compounds which are capable of reducing photo-damage, including: protocatechuate-3,4-dioxygenase, protocatechuic acid; 6-Hydroxy-2,5,7,8-tetramethylchroman-2-carboxylic Acid (TROLOX); or cyclooctatetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazobicyclooctane (DABCO), dithiothreitol (DTT), ergothioneine, glucose oxidase/catalase (GO/Cat), glutathione, glutathione peroxidase, hydrazine ($N_2H_4$), hydroxylamine, lycopene, lutein, polyene dialdehydes, melatonin, methionine, mercaptopropionylglycine, 2-mercaptoethane sulfonate (MESNA), pyridoxinel and its derivatives, mercaptoethylamine (MEA), β-mercaptoethanol (BME), n-propyl gallate, p-phenylenediamene (PPD), hydroquinone, sodium azide ($NaN_3$), sodium sulfite ($Na_2SO_3$), superoxide dismutase, tocopherols, α-tocopheryl succinate and its analogs, and zeaxanthin.

Also provided herein are methods of using the labeled biomolecule conjugates of the present disclosure.

For example, disclosed herein are methods for incorporation of one or more nucleotides onto the end of a nucleic acid molecule, comprising: contacting a conjugate including a polymerase linked to a label with a nucleotide under conditions where the nucleotide is incorporated into a nucleic acid molecule by the conjugate. The nucleic acid molecule can be any suitable target nucleic acid molecule of interest. In some embodiments, the labeled polymerase can be a polymerase having or comprising the amino acid sequence of SEQ ID NO: 7 or SEQ ID NO: 8. In some embodiments, the nucleotide can be become incorporated onto the 3' end of an extending nucleic acid molecule by the polymerase. In some embodiments, the nucleotide can be a labeled nucleotide analog. The labeled nucleotide analog can further comprise a label linked to the base, sugar, phosphate or any other portion of the nucleotide analog. In some embodiments, the nucleotide can also comprise a blocking group that inhibits, slows down or blocks further incorporation of nucleotides onto the end of the nucleic acid molecule until the blocking group is removed from the nucleotide. In some embodiments, the nucleotide comprising a blocking group is a reversible terminator for nucleic acid synthesis, as described further below. In some embodiments, the blocking group can be removed from the nucleotide by chemical, enzymatic, or photocleaving reactions.

In some embodiments, the method further includes the step of adding one or more divalent cations to the polymerase reaction mixture in an amount sufficient for inhibiting further incorporation of nucleotides onto the end of the nucleic acid molecule by the labeled polymerase. In some embodiments, the divalent cation that inhibits nucleotide incorporation is calcium. In another embodiment, omitting, reducing, or chelating cations that permit nucleotide incorporation (e.g, manganese and/or magnesium) can be employed. Such methods are described, for example, in U.S. Provisional Application 61/242,762, filed Sep. 15, 2009; and in U.S. Provisional Application No. 61/184,774, filed on Jun. 5, 2009. In some embodiments, the polymerase can be linked to a label, as, for example, disclosed herein and in U.S. Provisional Application No. 61/184,770, filed Jun. 5, 2009.

Also provided herein is a method for detecting one or more nucleotide incorporations, comprising: contacting a conjugate including a polymerase linked to a label with a labeled nucleotide under conditions where the labeled nucleotide is incorporated by the conjugate into a nucleic acid molecule, and where the label of the labeled nucleotide emits a signal indicative of such nucleotide incorporation; and detecting the signal indicative of such nucleotide incorporation. In some embodiments, the detecting can be performed in real or near real time. In some embodiments, the method can further include analyzing the detected signal indicative of nucleotide incorporation to determine the identity of the incorporated nucleotide. In some embodiments, the labeled polymerase conjugate catalyzes a time series of nucleotide incorporations, which can collectively be detected and analyzed to determine some or all of the sequence of the target nucleic acid molecule.

Also disclosed herein is a method for determining a nucleotide sequence of a single nucleic acid molecule, comprising: (a) conducting a polymerase reaction comprising a labeled biomolecule conjugate and a labeled nucleotide under conditions where the conjugate incorporates the labeled nucleotide into a nucleic acid molecule and a signal indicative of such nucleotide incorporation is generated; (b) detecting the signal indicative of such nucleotide incorporation; and (c) analyzing the signal to determine the identity of the incorporated nucleotide. Optionally, a time series of nucleotide incorporation signals can be detected and analyzed, thereby determining some or all of the nucleotide sequence of a single nucleic acid molecule.

Also provided herein are methods of sequencing a nucleic acid molecule, comprising: (a) performing a polymerase reaction comprising a labeled polymerase conjugate and labeled nucleotides under conditions resulting in a series of labeled nucleotide incorporations by the polymerase and the generation of a signal indicative of each nucleotide incorporation the series; (b) detecting a time sequence of nucleotide incorporations; and (c) determining the identity of one or more incorporated nucleotides, thereby determining some or all of the nucleotide sequence of a single nucleic acid molecule.

In some embodiments, the polymerase is attached to or associated with a substrate or surface. In some embodiments, the polymerase can be attached to or associated with a nucleic acid molecule (termed a template), and polymerize one or more nucleotides in a template-dependent fashion. In some embodiments, the template can be attached to or associated with a substrate or surface. In some embodiments, the polymerase, template, nucleotide, substrate or surface, or some combination thereof, can also be labeled.

In some embodiments, the methods of the present disclosure can be performed in multiplex and/or "high-throughput" format wherein multiple units of the labeled polymerase conjugates of the present disclosure can each be visualized and monitored in parallel with each other. For example, in some embodiments, multiple labeled polymerase conjugates may be positioned, associated with, or attached to different locations on a substrate, and a polymerase activity of one or more of these polymerases may be detected in isolation. In some embodiments, the polymerase or the template nucleic acid molecule are associated with or attached to a substrate or surface in array format. The array can be spatially addressable.

In some embodiments, the sequencing reaction can be performed using buffer conditions comprising 50 mM Tris buffer pH 7.5, 50 mM NaCl, 0-10 mM MgCl$_2$, 2 mM MnCl$_2$, 330 nM polymerase, 100 nM primed template and 4 µM labeled nucleotide hexaphosphate. Optionally, 0.3% BSA and/or 0.05% Tween20 can be included in the reaction mix. In some embodiments, the reaction mix is further supplemented with 2 mM DTT and/or single stranded binding protein (SSBP) at a concentration of 100 µg/ml.

Alternatively, in some embodiments the sequencing reaction can be performed using buffer conditions comprising 50 mM Tris pH 8.0, 50 mM NaCl and 10 mM MgCl$_2$.

In one exemplary embodiment, a nucleic acid sequencing system can comprise a template nucleic acid molecule attached to a substrate, a labeled polymerase conjugate comprising a FRET donor label linked to a polymerase, and labeled nucleotides each comprising a nucleotide linked to one or more FRET acceptor labels.

The template nucleic acid molecule of this sequencing system can be attached to any suitable substrate or surface using any suitable method. in some embodiments, the template nucleic acid molecule can comprise one or more biotin moieties, the surface can comprise an avidin moiety, and the template nucleic acid is linked to the surface via one or more biotin-avidin bonds. In some embodiments, the template and surface can each comprise one or more biotin moieties, and be linked to each other through a linkage comprising an avidin moiety.

In some embodiments, the polymerase can be unlabeled. Alternatively, the polymerase can be linked to one or more label to form a labeled polymerase conjugate. In some embodiments, the label comprises at least one energy transfer moiety. The label can be an organic label (e.g., dye label) or an inorganic label (e.g., nanoparticle).

In some embodiments, the polymerase may be linked with at least one energy transfer donor moiety. One or more energy transfer donor moieties can be linked to the polymerase at the amino end or carboxyl end or may be inserted at any site therebetween. Optionally, the energy transfer donor moiety can be attached to the polymerase in a manner which does not significantly interfere with the nucleotide binding activity, or with the nucleotide incorporation activity of the polymerase. In such embodiments, the energy transfer moiety is attached to the polymerase in a manner that does not significantly interfere with polymerase activity.

In one embodiment, a single energy transfer donor moiety can be linked to more than one polymerase and the attachment can be at the amino end or carboxyl end or may be inserted within the polymerase.

In another embodiment, a single energy transfer donor moiety can be linked to one polymerase.

In one embodiment, the energy transfer donor moiety can be a nanoparticle (e.g., a fluorescent nanoparticle) or a fluorescent dye. The polymerase, which can be linked to the nanoparticle or fluorescent dye, typically retains one or more activities that are characteristic of the polymerase, e.g., polymerase activity, exonuclease activity, nucleotide binding, and the like.

In some embodiments, the polymerases of the present disclosure can include one or more mutations that improve the performance of the polymerase in the particular biological assay of interest. The mutations can include amino acid substitutions, insertions, or deletions.

Selecting a Polymerase

The selection of the polymerase for use in the disclosed methods can be based on the desired polymerase behavior in the particular biological assay of interest. For example, the polymerase can be selected to exhibit enhanced or reduced activity in a particular assay, or enhanced or reduced interaction with one or more particular substrates.

For example, in some embodiments the polymerase can be selected based on the polymerization kinetics of the polymerase either in unconjugated form or when linked to a label (labeled polymerase conjugate). Optionally, the label can be a nanoparticle or fluorescent dye; in some embodiments, the label can be energy transfer donor moiety. For example, the polymerase can be selected on the basis of kinetic behavior relating to nucleotide binding (e.g., association), nucleotide dissociation (intact nucleotide), nucleotide fidelity, nucleotide incorporation (e.g., catalysis), and/or release of the cleavage product. The selected polymerase can be wild-type or mutant.

In one embodiment, polymerases may be selected that retain the ability to selectively bind complementary nucleotides. In another embodiment, the polymerases may be selected which exhibit a modulated rate (faster or slower) of nucleotide association or dissociation. In another embodiment, the polymerases may be selected which exhibit a reduced rate of nucleotide incorporation activity (e.g., catalysis) and/or a reduced rate of dissociation of the cleavage product and/or a reduced rate of polymerase translocation (after nucleotide incorporation). Some modified polymerases which exhibit modified nucleotide binding and/or rates of nucleotide incorporation, as well as methods of identifying such polymerases, have been described. See, e.g., Rank, U.S. Published Patent Application No. 2008/0108082; Hanzel, U.S. Published Patent Application No. 2007/0196846; Clark, U.S. Published Patent Application No. 2009/0176233; Bjornsen, U.S. Published Patent Application No. 2009/0286245.

In polymerases from different classes (including DNA-dependent polymerases), an active-site lysine can interact with the phosphate groups of a nucleoside triphosphate molecule bound to the active site. The lysine residue has been shown to protonate the pyrophosphate leaving-group upon nucleotidyl transfer. Mutant polymerases having this lysine substituted with leucine, arginine, histidine or other amino acids, exhibit greatly reduced nucleotide incorporation rates (Castro, et al., 2009 Nature Structural and Molecular Biology 16:212-218). One skilled in the art can use amino acid alignment and/or comparison of crystal structures of polymerases as a guide to determine which lysine residue to replace with alternative amino acids. The sequences of Phi-29 polymerase (SEQ ID NO: 1), RB69 polymerase (SEQ ID NO: 15), an exemplary B103-like polymerase (SEQ ID NO: 7), and Klenow fragment can be used as the basis for selecting the amino acid residues to be modified (for B103 polymerase, see Hendricks, et al., U.S. Ser. No. 61/242,771, filed on Sep. 15, 2009, or U.S. Ser. No. 61/293,618, filed on Jan. 8, 2010). In one embodiment, a modified Phi-29 polymerase can include lysine at position 379 and/or 383 substituted with leucine, arginine or histidine.

In other embodiments, the polymerase can be selected based on the combination of the polymerase and nucleotides, and the reaction conditions, to be used for the nucleotide binding and/or nucleotide incorporation reactions. For example, certain polymerases in combination with nucleotides that comprise 3, 4, 5, 6, 7, 8, 9, 10 or more phosphate groups can be selected for performing the disclosed methods. In another example, certain polymerases in combination with nucleotides which are linked to an energy transfer moiety can be selected for performing the nucleotide incorporation methods.

In some embodiments, the modified polymerase can be attached to or associated with a substrate or surface. In some embodiments, the polymerase can be attached to or associated with a nucleic acid molecule (termed a template), and polymerize one or more nucleotides in a template-dependent fashion. In some embodiments, the template can be attached to or associated with a substrate or surface. In some embodiments, the polymerase, template, nucleotide, substrate or surface, or some combination thereof, can also be labeled.

In some embodiments, the methods of the present invention can be performed in multiplex and/or "high-throughput" format wherein multiple units of the modified polymerases of the present disclosure can each be visualized and monitored in parallel with each other. For example, in some embodiments, multiple modified polymerases may be positioned, associated with, or attached to different locations on a substrate, and a polymerase activity of one or more of these polymerases may be detected in isolation. In some embodiments, the polymerase or the template nucleic acid molecule are associated with or attached to a substrate or surface in array format. The array can be spatially addressable.

In some embodiments, the nucleic acid molecule, the, modified polymerase, or both, may be isolated within a suitable nanostructure. i.e., a structure having at least one dimension measuring 500 nm or less. The nanostructure can be useful in isolating a single nucleic acid molecule or polymerase. In some embodiments, the nanostructure can be useful in elongating the nucleic acid molecule to permit visualization of nucleotide synthesis along some or all of the length of the nucleic acid molecule. In some embodiments, the nanostructure is also useful in limiting the amount of background signal ("noise") in the system by reducing the excitation or detection volume, and/or by reducing the amount of labeled moieties present within the reaction chamber. In some embodiments, the nanostructure is designed to admit only a single polymeric molecule and elongate it as it flows through the nanostructure. Suitable devices comprising nanostructures that may be used to practice the inventions disclosed herein are described, for example, in U.S. Pat. No. 6,635,163; U.S. Pat. No. 7,217,562, U.S. Pub. No. 2004/0197843 and U.S. Pub. No. 2007/0020772. In some embodiments, the nanostructures of the nanofluidic device will satisfy three requirements: (1) they will have a sufficiently small dimension to elongate and isolate macromolecules; (2) they will be sufficient length to permit instantaneous observation of the entire elongated macromolecule; and (3) the nanochannels or other nanostructures will be sufficiently numerous to permit simultaneous and parallel observation of a large population of macromolecules. In one embodiment, the radius of the component nanostructures of the nanofluidic device will be roughly equal to or less than the persistence length of the target DNA. Suitable methods of detecting nucleotide incorporations using nanostructures are disclosed, for example, in U.S. Provisional Application Nos. 61/077,090, filed Jun. 30, 2008; 61/089,497, filed Aug. 15, 2008; and 61/090,346, filed Aug. 20, 2008; and International Application No. PCT/US09/049324, filed Jun. 30, 2009.

Typically, the polymerase reaction comprises a mixture including a modified polymerase, a nucleic acid molecule, at least one priming site for nucleotide polymerization, and one or more nucleotides for the modified polymerase. In some embodiments, the reaction can be initiated by preparing the mixture lacking one essential component for polymerization (for example, the polymerase or nucleotides) and then adding the withheld component to initiate the reaction. Suitable temperatures and the addition of other components such as divalent metal ions can be determined and optimized based on the particular polymerase and the target nucleic acid sequences.

In some embodiments, the polymerase reaction can be performed using buffer conditions comprising 50 mM Tris buffer pH 7.5, 50 mM NaCl, 10 mM $MgCl_2$, 0.5 mM $MnCl_2$. In some embodiments, 0.3% BSA and/or 0.05% Tween20 can be included in the reaction mix. In some embodiments, the reaction mix is further supplemented with 2 mM DTT and/or single stranded binding protein (SSBP) at a concentration of 100 µg/ml. Alternatively, the polymerase reaction can be performed using buffer conditions comprising 50 mM Tris pH 8.0, 50 mM NaCl and 10 mM $MgCl_2$. In some embodiments, divalent cations, such as calcium, can be added to the polymerase reaction in an amount sufficient to block further nucleotide incorporation. See, e.g., U.S. Provisional Application 61/242,762, filed Sep. 15, 2009.

In some embodiments, a suitable primer is included in the nucleic acid polymerase reaction. The primer length is typically determined by the specificity desired for binding the complementary template as well as the stringency of the annealing and reannealing conditions employed. The primer can be synthetic, or produced naturally by primases, RNA polymerases, or other oligonucleotide synthesizing enzymes. The primer can be any suitable length including at least 5 nucleotides, 5 to 10, 15, 20, 25, 50, 75, 100 nucleotides or longer in length. In some embodiments, the polymerase extends the primer by a plurality of nucleotides. In some embodiments, the primer is extended at least 50, 100, 250, 500, 1000, or at least 2000 nucleotide monomers. Alternatively, the initiation site for nucleotide polymerization can be created through any suitable means without requiring use of a primer. For example, the polymer to be sequenced can comprise, or be associated with, a polymerase priming site capable of extension via polymerization of monomers by the polymerase. The priming site can be generated, for example, by treatment of the polymer so as to produce nicks or cleavage sites. Yet another option is for the target polymer to undergo "hairpin" formation, either through annealing to a self-complementary region within the target sequence itself or through ligation to a self-complementary sequence, resulting in a structure that undergoes self-priming under suitable conditions. Alternatively, the priming can be facilitated through the use of various accessory proteins known to facilitate priming of DNA synthesis by a given polymerase, such as the terminal protein of Phi-29 DNA polymerase and/or B103 DNA polymerase. See, e.g., M. Salas, "Protein-priming of DNA replication", Ann. Rev. Biochem. 60:39-71 (1991).

In some embodiments, the labeled nucleotide is a nucleotide analog comprising a label linked to the base, sugar, phosphate or any other portion of the nucleotide analog. In some embodiments, the nucleotide can also comprise a blocking group that inhibits, slows down or blocks further incorporation of nucleotides onto the end of the nucleic acid molecule until the blocking group is removed from the nucleotide. In some embodiments, the blocking group can be removed from the nucleotide by exposure to chemical, enzymatic, or photocleaving agents. In some embodiments, the method further includes the step of adding one or more divalent cations to the polymerase reaction mixture in an amount sufficient for inhibiting further incorporation of nucleotides onto the end of the nucleic acid molecule by the modified polymerase. Such methods are described, for example, in U.S. Provisional Application No. 61/242,762, filed Sep. 15, 2009; and U.S. Provisional Application No. 61/184,774, filed on Jun. 5, 2009.

In some embodiments, the methods, compositions, systems and/or kits disclosed herein can involve the use of one or more moieties capable of undergoing energy transfer, for example resonance energy transfer (RET). Such energy transfer moieties can include resonance energy transfer donors and acceptors. The energy transfer moieties can be linked to the solid surfaces, nanoparticles, polymerases, nucleotides, target nucleic acid molecules, primers, and/or oligonucleotides.

In one aspect, the energy transfer moiety can be an energy transfer donor. For example, the energy transfer donor can be a nanoparticle or an energy transfer donor moiety (e.g., fluorescent dye). In another aspect, the energy transfer moiety can be an energy transfer acceptor. For example, the energy transfer acceptor can be an energy acceptor dye. In another aspect, the energy transfer moiety can be a quencher moiety.

In one aspect, the energy transfer pair can be linked to the same molecule. For example, the energy transfer donor and acceptor pair can be linked to a single polymerase, which can provide detection of conformational changes in the polymerase. In another aspect, the donor and acceptor can be linked to different molecules in any combination. For example, the donor can be linked to the polymerase, target molecule, or primer molecule, and/or the acceptor can be linked to the nucleotide, the target molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET) (L. Stryer 1978 Ann. Rev. Biochem. 47: 819-846; Schneider, U.S. Pat. No. 6,982,146, Hardin, U.S. Pat. No. 7,329,492; Hanzel U.S. published patent application No. 2007/0196846), scintillation proximity assays (SPA) (Hart and Greenwald 1979 Molecular Immunology 16:265-267; U.S. Pat. No. 4,658,649), luminescence resonance energy transfer (LRET) (G. Mathis 1995 Clin. Chem. 41:1391-1397), direct quenching (Tyagi et al, 1998 Nature Biotechnology 16:49-53), chemiluminescence energy transfer (CRET) (Campbell and Patel 1983 Biochem. Journal 216: 185-194), bioluminescence resonance energy transfer (BRET) (Y. Xu, et al 1999 Proc. Natl. Acad. Sci. 96:151456), and excimer formation (J. R. Lakowicz 1999 "Principles of Fluorescence Spectroscopy", Kluwer Academic/Plenum Press, New York).

In one exemplary embodiment, the energy transfer moieties can be a FRET donor/acceptor pair. FRET is a distance-dependent radiationless transmission of excitation energy from a first moiety, referred to as a donor moiety, to a second moiety, referred to as an acceptor moiety. Typically, the efficiency of FRET energy transmission is dependent on the inverse sixth-power of the separation distance between the donor and acceptor, r. For a typical donor-acceptor pair, r can vary between approximately 10-100 Angstroms. FRET is useful for investigating changes in proximity between and/or within biological molecules. In some embodiments, FRET efficiency may depend on donor-acceptor distance r as $1/r^6$ or $1/r^4$. The efficiency of FRET energy transfer can sometimes be dependent on energy transfer from a point to a plane which varies by the fourth power of distance separation (E. Jares•Erijman, et al., 2003 Nat. Biotechnol, 21:1387). The distance where FRET efficiency is at 50% is termed $R_0$, also know as the Forster distance. $R_0$ can be unique for each donor-acceptor combination and can range from between about 5 nm to about 10 nm. A change in fluorescence from a donor or acceptor during a FRET event (e.g., increase or decrease in the signal) can be an indication of proximity between the donor and acceptor.

FRET efficiency (E) can be defined as the quantum yield of the energy transfer transition, i.e. the fraction of energy transfer event occurring per donor excitation event. It is a direct measure of the fraction of photon energy absorbed by the donor which is transferred to an acceptor, as expressed in Equation 1: $E = k_{ET}/k_f + k_{ET} + \Sigma k_i$ where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r (nm) between the two fluorophores (i.e., donor and acceptor pair), as expressed in Equation 2: $E = 1/1 + (r/R_0)^6$.

Therefore, the FRET efficiency of a donor describes the maximum theoretical fraction of photon energy which is absorbed by the donor (i.e., nanoparticle) and which can then be transferred to a typical organic dye (e.g., fluoresceins, rhodamines, cyanines, etc.).

In biological applications, FRET can provide an on-off type signal indicating when the donor and acceptor moieties are proximal (e.g., within $R_0$) of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two (D. W. Piston and G. J. Kremers 2007 Trends Biochem. Sci. 32:407). Resonance energy transfer may be either an intermolecular or intramolecular event. Thus, the spectral properties of the energy transfer pair as a whole, change in some measurable way if the distance and/or orientation between the moieties are altered.

The production of signals from FRET donors and acceptors can be sensitive to the distance between donor and acceptor moieties, the orientation of the donor and acceptor moieties, and/or a change in the environment of one of the moieties (Deuschle et al. 2005 Protein Science 14: 2304-2314; Smith et al. 2005 Protein Science 14:64-73). For example, a nucleotide linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type ($NO_2$, $Ca^{+2}$, $Mg^{+2}$, $Zn^{+2}$, $Na^+$, $Cl^-$, $K^+$), oxygen saturation, and solvation polarity.

The FRET donor and/or acceptor may be a fluorophore, luminophore, chemiluminophore, bioluminophore, or quencher (P. Selvin 1995 Methods Enzymol 246:300-334; C. G. dos Remedios 1995 J. Struct. Biol. 115:175-185; P. Wu and L. Brand 1994 Anal Biochem 218:1-13).

In some embodiments, the energy transfer moieties may not undergo FRET, but may undergo other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

In one embodiment, the modified polymerases as provided herein can be linked to an energy transfer moiety, for example an energy transfer donor moiety. In another embodiment, the nucleotide can be linked to an energy transfer acceptor moiety. For example, in one embodiment the nucleotide comprises a polyphosphate chain and an energy transfer moiety linked to the terminal phosphate group of the polyphosphate chain. A change in a fluorescent signal can occur when the labeled nucleotide is proximal to the labeled polymerase.

In one embodiment, when an acceptor-labeled nucleotide is proximal to a donor-labeled modified polymerase as provided herein, the signal emitted by the donor moiety decreases. In another embodiment, when the acceptor-labeled nucleotide is proximal to the donor-labeled polymerase, the signal emitted by the acceptor moiety increases. In another embodiment, a decrease in donor signal and increase in acceptor signal correlates with nucleotide binding to the polymerase and/or correlates with polymerase-dependent nucleotide incorporation.

Quenchers

In some embodiments, the energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system, see I. L. Medintz, et al., 2003 Nature Materials 2:630. One exemplary method of primer extension using the modified polymerases of the present disclosure involves the use of quenchers in conjunction with reporters comprising fluorescent reporter moieties. In this strategy, certain nucleotides in the reaction mixture are labeled with a reporter comprising a fluorescent label, while the remaining nucleotides are labeled with one or more quenchers. Alternatively, each of the nucleotides in the reaction mixture is labeled with one or more quenchers. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates incorporation of a nucleotide labeled with a quencher. The degree of intensity reduction may be used to distinguish between different quenchers.

Examples of fluorescent donors and non-fluorescent acceptor (e.g., quencher) combinations have been developed for detection of proteolysis (Matayoshi 1990 Science 247: 954-958) and nucleic acid hybridization (L. Morrison, in: Nonisotopic DNA Probe Techniques, ed., L. Kricka, Academic Press, San Diego, (1992) pp. 311-352; S. Tyagi 1998 Nat. Biotechnol. 16:49-53; S. Tyagi 1996 Nat. Biotechnol. 14:947-8). FRET donors, acceptors and quenchers can be moieties which absorb electromagnetic energy (e.g., light) at about 300-900 nm, or about 350-800 nm, or about 390-800 nm.

Materials for Energy Transfer Moieties

Energy transfer donor and acceptor moieties can be made from materials which typically fall into four general categories (see the review in: K. E. Sapford, et al., 2006 Angew. Chem. Int. Ed. 45:4562-4588), including: (1) organic fluorescent dyes, dark quenchers and polymers (e.g., dendrimers): (2) inorganic material such as metals, metal chelates and semiconductors nanoparticles: (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers can include traditional dyes which emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9, 9-dimethylacridin-2-one)), resorufin, ALEXA FLUOR and BODIPY dyes (both Molecular Probes), HILYTE Fluors (AnaSpec), ATTO dyes (Atto-Tec), DY dyes (Dyonics GmbH), TAMRA (Perkin Elmer), tetramethylrhodamine (TMR), TEXAS RED, DYLIGHT (Thermo Fisher Scientific), FAM (AnaSpec), JOE and ROX (both Applied Biosystems), and Tokyo Green.

Additional fluorescent dyes which can be used as quenchers includes: DNP, DANSYL, QSY (Molecular Probes), ATTO (Atto-Tec), BHQ (Biosearch Technologies), QXL (AnaSpec), BBQ (Berry and Associates) and CY5Q/7Q (Amersham Biosciences).

The FRET donor and acceptor moieties which comprise inorganic materials include gold (e.g., quencher), silver, copper, silicon, semiconductor nanoparticles, and fluorescence-emitting metal such as a lanthanide complex, including those of Europium and Terbium.

Suitable FRET donor/acceptor pairs include: PAM as the donor and JOE, TAMRA, and ROX as the acceptor dyes. Other suitable pairs include: CYA as the donor and R6G, TAMRA, and ROX as the donor dyes. Other suitable donor/acceptor pairs include: a nanoparticle as the donor, and ALEXA FLUORS dyes (e.g., 610, 647, 660, 680, 700). DYOMICS dyes, such as 634 and 734 can be used as energy transfer acceptor dyes.

In some embodiments, the energy transfer moieties undergo RET, (for example, FRET) that is characterized by the generation of a signal, herein termed a RET or FRET signal, as the case may be. The RET or FRET signal can be an optically detectable signal, for example, an increase in acceptor fluorescence or a decrease in donor fluorescence.

In some embodiments, the modified polymerase as provided herein is linked to a FRET donor and contacted with one or more labeled nucleotide analogs, wherein the label of the one or more labeled nucleotides comprises a FRET acceptor. In some embodiments, interaction of the labeled nucleotide with the labeled polymerase (occurring, for example, in association with a productive incorporation, a non-productive incorporation or during association of a nucleotide with the polymerase active site) results in the emission of a FRET signal. The FRET signal can optionally be detected and analyzed to determine the occurrence of a polymerase-nucleotide interaction.

Typically, the one or more signals indicative of polymerase-nucleotide interaction are one or more FRET signals resulting from FRET between the label of the modified polymerase and the label of an incorporating nucleotide. The FRET can occur prior to, during or after productive incorporation of the nucleotide into a nucleic acid molecule. Alternatively, the FRET can occur prior to binding of the nucleotide to the polymerase active site, or while the nucleotide resides within the polymerase active site, during a non-productive incorporation.

In some embodiments, the modified polymerase comprises a FRET donor moiety and one or more nucleotides comprises a FRET acceptor moiety. The FRET acceptor moiety can in some embodiments be attached to, or comprise part of, the nucleotide sugar, the nucleobase, or analogs thereof.

In some embodiments, at least one nucleotide of the polymerase reaction is labeled with a nucleotide label. In some embodiments, the nucleotide label is linked to the nucleotide using a linker and/or spacer using suitable techniques. Any suitable methods for labeling nucleotides can be employed including but not limited to those described in U.S. Pat. Nos. 7,041,892, 7,052,839, 7,125,671 and 7,223,541; U.S. Pub. Nos. 2007/0072196 and 2008/0091005; Sood et al., 2005, *J. Am. Chem. Soc.* 127:2394-2395; Arzumanov et al., 1996, *J. Biol. Chem.* 271:24389-24394; and Kumar et al., 2005, *Nucleosides, Nucleotides & Nucleic Acids,* 24(5):401-408. Suitable labels that can be used in the disclosed methods and linked to the polymerase or the nucleotides include any molecule, nano-structure, or other chemical structure that capable of being detected by a detection system, including but not limited to fluorescent dyes.

In some embodiments, the nucleotide label is attached to a portion of the nucleotide that is released upon incorporation of the underlying nucleotide. For example, in some embodiments, the nucleotide label is attached to a portion of the nucleotide that is released upon incorporation of the underlying nucleotide, For example, in some embodiments, the nucleotide comprises a polyphosphate chain and the FRET acceptor is attached to a phosphate group of the nucleotide that is cleaved and released upon incorporation of the underlying nucleotide into the primer strand, for example the γ-phosphate, the β-phosphate or some other terminal phosphate of the incoming nucleotide. When this acceptor-labeled nucleotide polyphosphate is incorporated by the modified polymerase into a nucleic acid molecule, the polymerase cleaves the bond between the alpha and beta phosphate, thereby releasing a pyrophosphate moiety comprising the acceptor that diffuses away. Thus, in these embodiments, a signal indicative of nucleotide incorporation is generated through FRET between the nanoparticle and the acceptor bonded to the gamma, beta or other terminal phosphate as each incoming nucleotide is incorporated into the newly synthesized strand. By cleavage of the terminal phosphate(s) and release of the label upon incorporation of the incoming nucleotide, the FRET signal from the label ceases after the nucleotide is incorporated and the label diffuses away. By releasing the label upon incorporation, successive incorporation of labeled nucleotides can each be detected without interference from nucleotides previously incorporated into the complementary strand.

Alternatively, the nucleotide label can be linked to the alpha (α) phosphate, the beta (β) phosphate, another internal phosphate, base, sugar or any other portion of the nucleotide that typically becomes incorporated into the growing nucleic acid molecule. Although such labels typically are typically not cleaved and released during the incorporation process, and thus become incorporated into the growing nucleic acid molecule, they can optionally be removed and/or rendered inoperable via suitable treatments, e.g., chemical cleavage, enzymatic cleavage and/or photobleaching, later in the process. In some embodiments, the portion of the nucleotide that remains in the extending nucleic acid molecule after the label and/or blocking group is released or otherwise removed is structurally similar or identical to the portion incorporated from a natural nucleotide; alternatively, the incorporated portion may contain structural or chemical elements that are different from the incorporated portion of a natural nucleotide.

In some embodiments, a signal indicative of nucleotide incorporation is generated as each incoming nucleotide becomes incorporated by the polymerase of the conjugate. In embodiments where the nucleotide label is cleaved and released upon nucleotide incorporation, successive extensions can each be detected without interference from nucleotides previously incorporated into the complementary strand.

In some embodiments, the nucleotide and nucleotide label are linked using a linker. The linker can include multiple amino acid residues (e.g., arginine) that serve as an intervening linker between the nucleotide and the nucleotide label. For example, the linker can comprise four arginine residues that connect a dye label to a terminal phosphate group of the nucleotide.

In other embodiments, the label linked or attached to the nucleotide can be a quencher. Quenchers are useful as acceptors in FRET applications, because they produce a signal through the reduction or quenching of fluorescence from the donor fluorophore. For example, in a quencher-based system, illumination of the donor fluorophore excites the donor, and if an appropriate acceptor is not close enough to the donor, the donor fluoresces. This fluorescence is reduced or abolished when a quencher is in sufficient proximity to quench the donor, thereby reducing or abolishing donor fluorescence. Thus, interaction or proximity between a donor and quencher-acceptor can be detected by the reduction or absence of donor fluorescence. For an example of the use of a quencher as an acceptor with a nanoparticle donor, see, e.g., Medintz, I. L. et al. (2003) *Nat. Mater.* 2:630. Examples of quenchers include the QSY dyes available from Molecular Probes (Eugene, Oreg.).

One exemplary method of primer extension using the modified polymerases of the present disclosure involves the use of quenchers in conjunction with fluorescent labels. In some embodiments, certain nucleotides in the reaction mixture are labeled with a fluorescent label, while the remaining nucleotides are labeled with one or more quenchers. Alternatively, each of the nucleotides in the reaction mixture is labeled with one or more quenchers. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates incorporation of a nucleotide labeled with a quencher. The degree of intensity reduction can be used to distinguish between different quenchers.

Typically, the label of the modified polymerase and/or the label of the nucleotide will be selected and/or designed to minimize any adverse effect of such labels on the progress of the polymerization reaction as determined by speed, error rate, fidelity, processivity and average read length of the newly synthesized strand.

In some embodiments, the nucleotide can comprise a moiety that alters the functional properties of the nucleotide. For example, the moiety can interfere or impede the ability of the nucleotide to enter the polymerase active site, become released from the polymerase active site following incorporation of the nucleotide onto the end of an extending nucleic acid molecule, or become covalently linked to the end of the extending nucleic acid molecule. In some embodiments, the moiety can affect the kinetic properties of the nucleotide, such as, for example, modify the $K_m$, $V_{max}$, residence time or branching ratio of the nucleotide with one or more polymerases of the present disclosure.

In some embodiments, the nucleotide is a labeled analog of a naturally occurring nucleotide. The label can be an optically detectable label. For example, the label can be a photoluminescent, chemiluminescent, bioluminescent, fluorescent or fluorogenic moiety. The label can be a mass tag or molecular volume tag. In some embodiments, the label is a FRET moiety. In some embodiments, the identity of the label correlates with the base identity of the nucleotide. In some embodiments, the label is capable of emitting a signal that correlates with the base identity of the nucleotide. In some embodiments, the label of the labeled nucleotide is a chromophore, fluorophore or luminophore. In some embodiments, the label of the labeled nucleotide can be a fluorophore or fluorogen selected from the group consisting of: xanthine dye, fluorescein, cyanine, rhodamine, coumarin, acridine, Texas Red dye, BODIPY, ALEXA (Molecular Probes/Invitrogen, Life Technologies Corp.), GFP, and a derivative or modification of any of the foregoing. Some examples of suitable labels are described, for example, in International (PCT) Published Application No. WO/2008/030115; Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), all of which are incorporated herein by reference in their entireties.

In some embodiments, incorporation of the nucleotide into an extending nucleic acid molecule by a polymerase can generate a nucleic acid molecule comprising non-standard moieties, i.e., moieties that are not typically present in naturally occurring nucleic acid molecules. For example, the synthesized nucleic acid molecule may comprise one or more labels and/or include one or more atoms, for example sulfur or boron atoms, not typically present in naturally occurring nucleic acid molecules. In some embodiments, the label is linked to a base, sugar or phosphate moiety of the nucleotide via a linker.

The primer extension and/or single molecule sequencing methods using the modified polymerases of the present disclosure can be practiced using nucleotides. In some embodiments, the nucleotide can comprise a moiety that facilitates purification or detectability of the nucleotide. In some embodiments, the moiety is a label. The label can in some embodiments be linked to a base, sugar or phosphate moiety. In some embodiments, the nucleotide is a nucleotide polyphosphate and the label is linked to the terminal phosphate of the nucleotide polyphosphate.

In some embodiments the nucleotides can be linked with at least one energy transfer moiety. The energy transfer moiety can be an energy transfer acceptor moiety. The different types of nucleotides (e.g., adenosine, thymidine, cytidine, guanosine, and uridine) can be labeled with different energy transfer acceptor moieties so that the detectable signals from each of the different types of nucleotides can be distinguishable to permit base identity. The nucleotides can be labeled in a way that does not interfere with the events of polymerization. For example the attached energy transfer acceptor moiety does not interfere with nucleotide binding and/or does not interfere with nucleotide incorporation and/or does not interfere with cleavage of the phosphodiester bonds and/or does not interfere with release of the polyphosphate product. See for example, U.S. Ser. No. 61/164,091, Ronald Graham, filed Mar. 27, 2009. See for example U.S. Pat. Nos. 7,041,812, 7,052,839, 7,125,671, and 7,223,541; U.S. Pub. Nos. 2007/0072196 and 2008/0091005; Sood et al., 2005, J. Am. Chem. Soc. 127:2394-2395; Arzumanov et al., 1996, J. Biol. Chem. 271:24389-24394; and Kumar et al., 2005, Nucleosides, Nucleotides & Nucleic Acids, 24(5):401-408.

In one aspect, the energy transfer acceptor moiety may be linked to any position of the nucleotide.

For example, the energy transfer acceptor moiety can be linked to any phosphate group (or derivatized phosphate group), the sugar or the base. In another example, the energy transfer moiety can be linked to any phosphate group (or derivatized phosphate group) which is released as part of a phosphate cleavage product upon incorporation. In yet another example, the energy transfer acceptor moiety can be linked to the terminal phosphate group (or derivatized phosphate group). In another aspect, the nucleotide may be linked with an additional energy transfer acceptor moiety, so that the nucleotide is attached with two or more energy transfer acceptor moieties. The additional energy transfer acceptor moiety can be the same or different as the first energy transfer acceptor moiety. In one embodiment, the energy transfer acceptor moiety can be a FRET acceptor moiety.

In one aspect, the nucleotide may be linked with a reporter moiety which is not an energy transfer moiety. For example, the reporter moiety can be a fluorophore.

In one aspect, the energy transfer acceptor moieties and/or the reporter moiety can be attached to the nucleotide via a linear or branched linker moiety. An intervening linker moiety can connect the energy transfer acceptor moieties with each other and/or to the reporter moiety, any combination of linking arrangements.

In another aspect, the nucleotides comprise a sugar moiety, base moiety, and at least three, four, five, six, seven, eight, nine, ten, or more phosphate groups linked to the sugar moiety by an ester or phosphoramide linkage. The phosphates can be linked to the 3' or 5' C of the sugar moiety. The nucleotides can be incorporated and/or polymerized into a growing nucleic acid strand by a naturally occurring, modified, or engineered nucleic acid dependent polymerase.

In one aspect, different linkers can be used to operably link the different nucleotides (e.g., A, G, C, or T/U) to the energy transfer moieties or reporter moieties. For example, adenosine nucleotide can be attached to one type of energy transfer moiety using one type of linker, and guanosine nucleotide can be linked to a different type of energy transfer moiety using a different type of linker. In another example, adenosine nucleotide can be attached to one type of energy transfer moiety using one type of linker, and the other types of nucleotides can be attached to different types of energy transfer moieties using the same type of linker. One skilled in the art will appreciate that many different combinations of nucleotides, energy transfer moieties, and linkers are possible.

In one aspect, the distance between the nucleotide and the energy transfer moiety can be altered. For example, the linker length and/or number of phosphate groups can lengthen or shorten the distance from the sugar moiety to the energy transfer moiety. In another example, the distance between the nucleotide and the energy transfer moiety can differ for each type of nucleotide (e.g., A, G, C, or T/U).

In another aspect, the number of energy transfer moieties which are linked to the different types of nucleotides (e.g., A, G, C, or T/U) can be the same or different. For example: A can have one dye, and G, C, and T have two; A can have one dye, C has two, G has three, and T has four; A can have one dye, C and G have two, and T has four. One skilled in the art will recognize that many different combinations are possible.

In another aspect, the concentration of the labeled nucleotides used to conduct the nucleotide binding or nucleotide incorporation reactions can be about 0.0001 nM-1 µM, or about 0.0001 nM-0.001 nM, or about 0.001 nM-0.01 nM, or about 0.01 nM-0.1 nM, or about 0.1 nM-1.0 nM, or about 1 nM-25 nM, or about 25 nM-50 nM, or about 50 nM-75 nM, or about 75 nM-100 nM, or about 100 nM-200 nM, or about 200 nM-500 nM, or about 500 nM-750 nM, or about 750 nM-1000 nM, or about 0.1 µM-20 µM, or about 20 µM-50 µM, or about 50 µM-75 µM, or about 75 µM-100 µM, or about 100 µM-200 µM, or about 200 µM-500 µM, or about 500 µM-750 µM, or about 750 µM-1000 µM.

In another aspect, the concentration of the different types of labeled nucleotides, which are used to conduct the nucleotide binding or incorporation reaction, can be the same or different from each other.

Sugar Moieties

The nucleotides typically comprise suitable sugar moieties, such as carbocyclic moieties (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In one aspect, the 3'-position has a hydroxyl group, for strand/chain elongation.

Base Moieties

The nucleotides can include a hetero cyclic base which includes substituted or unsubstituted nitrogen-containing parent heteroaromatic ring which is commonly found in nucleic acids, including naturally-occurring, substituted, modified, or engineered variants. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7 mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in: *Practical Handbook of Biochemistry and Molecular Biology*, pp. 385-394, CRC Press, Boca Raton, Fla., and the references cited therein.

Examples of nucleotides include ribonucleotides, deoxyribonucleotides, modified ribonucleotides, modified deoxyribonucleotides, ribonucleotides, deoxyribonucleotides, modified ribonucleotides, modified deoxyribonucleotides, peptide nucleotides, modified peptide nucleotides, metallonucleosides, phosphonate nucleosides, and modified phosphate-sugar backbone nucleotides, and any variants of the foregoing.

Phosphate Groups

The nucleotides can optionally include phosphate groups which can be linked to the 2', 3' and/or 5' position of the sugar moiety. The phosphate groups include analogs, such as phosphoramidate, phosphorothioate, phosphorodithioate, and O-methylphosphoroamidite groups. In one embodiment, at least one of the phosphate groups can be substituted with a fluoro and/or chloro group. The phosphate groups can be linked to the sugar moiety by an ester or phosphoramide linkage. Typically, the nucleotide comprises three, four, five, six, seven, eight, nine, ten, or more phosphate groups linked to the 5' position of the sugar moiety.

In some embodiments, the primer extension and single molecule sequencing methods using the modified polymerases provided herein can be practiced using any nucleotide which can be incorporated by a polymerase, including naturally-occurring or recombinant polymerases. In one embodiment, the nucleotides can include a nucleoside linked to a chain of 1-10 phosphorus atoms. The nucleoside can include a base (or base analog) linked to a sugar (or sugar analog). The phosphorus chain can be linked to the sugar, for example linked to the 5' position of the sugar. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotides are described in Xu, U.S. Pat. No. 7,405,281.

In some embodiments, the nucleotide is a dye-labeled nucleotide that comprises a polyphosphate chain and a dye moiety linked to the terminal phosphate group. In some embodiments, the dye-labeled nucleotide comprises a dye moiety linked to the terminal phosphate through an alkyl linker. Optionally, the linker comprises a 6-carbon chain and has a reactive amine group, and the dye moiety is linked to the terminal phosphate bond though a covalent bond formed with the amine group of the linker. In some embodiments, the polyphosphate chain comprises 4, 5, 6, 7, 8, 9, 10 or more phosphates. One exemplary dye-labeled nucleotide that can be used in the disclosed methods and systems has the general structure shown in FIG. 11. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In some embodiments, the dye moiety can optionally comprise any one or more of the following dyes: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones;

eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1, 3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M. Kamiya, et al., 2005 Angew. Chem. Int. Ed. 44:5439-5441); and CF dyes including CF 647 and CF555 (Biotium).

In some embodiments, such dye-labeled nucleotides can be used to assay for the nucleotide incorporation kinetics of a particular polymerase according to the procedures described herein (see, e.g., Example 12).

Non-Hydrolyzable Nucleotides

The nucleotide binding and nucleotide incorporation methods can be practiced using incorporatable nucleotides and non-hydrolyzable nucleotides. In the presence of the incorporatable nucleotides (e.g., labeled), the non-hydrolyzable nucleotides (e.g., non-labeled) can compete for the polymerase binding site to permit distinction between the complementary and non-complementary nucleotides, or for distinguishing between productive and non-productive binding events. In the nucleotide incorporation reaction, the presence of the non-hydrolyzable nucleotides can alter the length of time, frequency, and/or duration of the binding of the labeled incorporatable nucleotides.

The non-hydrolyzable nucleotides can be non-labeled or can be linked to a reporter moiety (e.g., energy transfer moiety). The labeled non-hydrolyzable nucleotides can be linked to a reporter moiety at any position, such as the sugar, base, or any phosphate (or substituted phosphate group). For example, the non-hydrolyzable nucleotides can have the general structure:

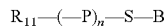

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-hydrolyzable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. Non-hydrolyzable nucleotide tetraphosphates having alpha-thio or alpha boreno substitutions having been described (Rank, U.S. published patent application No. 2008/0108082; and Gelfand, U.S. published patent application No. 2008/0293071).

The phosphate or phosphonate portion of the non-hydrolyzable nucleotide can have the general structure:

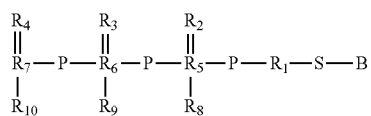

Where B can be a base moiety and S can be a sugar moiety. Where any one of the $R_1$-$R_7$ groups can render the nucleotide non-hydrolyzable by a polymerase. Where the sugar C5 position can be $CH_2$, $CH_2O$, $CH=$, CHR, or $CH_2CH_2$. Where the $R_1$ group can be O, S, $CH=$, CH(CN), or NH. Where the $R_2$, $R_3$, and $R_4$, groups can independently be O, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F, PhNH, PhO, or RS (where Ph can be a phenyl group or phenyl ring, and F can be a fluorine atom or group). The substituted groups can be in the S or R configuration.

The non-hydrolyzable nucleotides can be alpha-phosphate modified nucleotides, alpha-beta nucleotides, beta-phosphate modified nucleotides, beta-gamma nucleotides, gamma-phosphate modified nucleotides, caged nucleotides, or dinucleotides.

Many examples of non-hydrolyzable nucleotides are known (Rienitz 1985 Nucleic Acids Research 13:5685-5695), including commercially-available ones from Jena Bioscience (Jena, Germany).

In some embodiments, the nucleotide comprises a releasable label and/or a releasable blocking group that can be removed via suitable means prior to incorporation of the next nucleotide by the polymerase into the newly synthesized strand. The use of releasably labeled nucleotides wherein the label can be cleaved and removed via suitable means have been described, for example, in U.S. Pub. Nos. US2005/0244827 and US2004/0244827, as well as U.S. Pat. Nos. 7,345,159; 6,664,079; 7,345,159; and 7,223,568.

In some embodiments, the nucleotide is a nucleotide analog that is capable of acting as a reversible terminator of nucleic acid synthesis. Typically, reversible terminators can be incorporated by a polymerase onto the end of an extending nucleic acid molecule, but then "terminate" further synthesis by blocking further addition of nucleotides. In some embodiments, this "termination" capability can be manipulated by adjusting the reaction conditions and/or by suitable treatment. The ability to terminate can result from the presence of a moiety or group, typically named a "blocking" group, which is linked to the nucleotide. In some embodiments, the ability of the nucleotide analog to terminate nucleic acid synthesis can be eliminated through physical removal, cleavage, structural modification or disruption of the blocking group. The blocking group can be attached to any portion of the nucleotide analog including, for example, a base moiety, sugar moiety or phosphate moiety. The blocking group can be attached to the nucleotide analog via a linker. The linkage between the blocking group and the nucleotide analog can be a photocleavable, chemically cleavable, enzymatically cleavable, thermocleavable (i.e., cleavable upon adjustment of temperature) or pH-sensitive linkage. In some embodiments, the label (which is linked to the nucleotide) is the blocking group.

In some embodiments, the reversible terminator further comprises a label or tag that facilitates detection of nucleotide analog. The label can be a fluorescent label. In some embodiments, the label can also be removed via suitable treatment. In some embodiments, the label is released from the nucleotide analog during incorporation of the nucleotide analog into the extending nucleic acid molecule. Alternatively, the label becomes incorporated into the extending nucleic acid molecule and is then removed via suitable treatment. In some embodiments, the label is attached to the nucleotide analog via a cleavable linkage. The cleavable linkage can be a photocleavable, chemically cleavable, enzymatically cleavable, thermocleavable (i.e., cleavable upon adjustment of temperature) or pH-sensitive linkage.

The removal of the blocking group can be accomplished in a variety of ways. In some embodiments, the blocking group is attached to the nucleotide analog via a photocleavable linkage and can be removed from the nucleotide analog via exposure to photocleaving radiation. In some embodiments, the linkage is a chemically or enzymatically cleavable linkage. In some embodiments, the linkage can be disrupted by varying reaction conditions, e.g., pH, temperature, concentrations of divalent cations, etc.

Non-limiting examples of suitable reversible terminators include, inter alia, nucleotide base-labeled nucleotide analogs comprising one or more blocking groups attached to 3' hydroxyl group, the base moiety or a phosphate group. For example, the nucleotide analog can comprise an azidomethyl group linked to the 3' hydroxyl group and a fluorescent label linked to the base of the nucleotide analog. In some embodiments, the reversible terminator can comprise one or more blocking groups attached to the phosphate group. In some embodiments, the nucleotide analog can comprise a blocking group and a label. In some embodiments, both the blocking group and the label can be linked to the base moiety, while the 3' hydroxyl group is not modified. In some embodiments, the blocking group can be a photocleavable group linked to the base of the nucleotide analog. See, e.g., U.S. Publication No. 2008/0132692, published Jun. 5, 2008. Further examples of nucleotides comprising extension blocking groups and methods of their use in polymerase-based applications can be found, for example, in U.S. Pat. No. 7,078,499 issued Jul. 18, 2006; as well as in U.S. Published Application Nos. 2004/0048300 published Mar. 11, 2004; 2008/0132692 published Jun. 5, 2008; 2009/0081686, published Mar. 26, 2009; and 2008/0131952, published Jun. 5, 2008; Tsien, WO/1991/006678; Stemple, U.S. Pat. No. 7,270,951, Balasubramanian, U.S. Pat. No. 7,427,673; Milton, U.S. Pat. No. 7,541,444.

In some embodiments, the nucleotide analog comprises a cleavable label linked to the base. In some embodiments, the blocking group and the label can be removed via the same cleavage treatment. See, e.g., U.S. Pat. No. 7,553,949, issued Jun. 30, 2009. Alternatively, different treatments can be required to remove the blocking group and the label. In some embodiments, the label of the reversible terminator correlates with the base identity of the nucleotide analog. In some embodiments, each reversible terminator is added sequentially to the polymerase reaction; alternatively, different kinds of reversible terminators can be present simultaneously in the reaction mixture.

In some embodiments, the blocking group is linked to the 2' hydroxyl group of the sugar moiety. See, e.g., U.S. Pat. No. 7,553,949, issued Jun. 30, 2009.

In some embodiments, the reversible terminator can comprise more than one blocking group. In some embodiments, these multiple blocking groups may function cooperatively by enhancing the termination efficiency of the nucleotide analog. In one exemplary embodiment, the nucleotide analog comprises a blocking group linked to the base moiety, while another group linked to the terminal phosphate group further suppresses the incorporation of a nucleotide analog onto the free 3' hydroxyl group. See, e.g., U.S. patent application Ser. No. 12/355,487, filed Jan. 16, 2009.

Typically, the modified polymerases of the present disclosure can be used to sequence one or more nucleic acid molecules of interest using reversible terminators. In an exemplary method, the reversible terminator is incorporated in a template-dependent manner onto the 3' end of an extending nucleic acid molecule by a modified polymerase. The incorporated reversible terminator is detected and identified; and the blocking group of the reversible terminator is then removed. In some embodiments, the unincorporated reversible terminators can be washed away; in some embodiments, it is not necessary to wash or otherwise remove the unincorporated reversible terminators prior to detection, identification or subsequent extension of the extending nucleic acid molecule. In some embodiments, incorporation of the reversible terminator onto the end of a nucleic acid molecule can involve the formation of a covalent bond between the reversible terminator and the nucleotide moiety at the 3' end of the nucleic acid molecule. Alternatively, incorporation of reversible terminator onto the end of a nucleic acid molecule will not involve formation of any covalent bond between the reversible terminator and the nucleotide moiety at the 3' end of the nucleic acid molecule; instead, the reversible terminator is bound in a template-dependent fashion and positioned within the active site of the polymerase until the blocking group is cleaved or otherwise removed, following which the remaining portion of the reversible terminator can remain as a portion of the extending nucleic acid molecule or alternatively will also dissociate from the polymerase active site and diffuse away.

"Nanoparticle" may refer to any particle with at least one major dimension in the nanosize range. In general, nanoparticles can be made from any suitable metal (e.g., noble metals, semiconductors, etc.) and/or non-metal atoms. Nanoparticles can have different shapes, each of which can have distinctive properties including spatial distribution of the surface charge; orientation dependence of polarization of the incident light wave; and spatial extent of the electric field. The shapes include, but are not limited to: spheres, rods, discs, triangles, nanorings, nanoshells, tetrapods, nanowires, etc.

In one embodiment, the nanoparticle can be a core/shell nanoparticle which typically comprises a core nanoparticle surrounded by at least one shell. For example, the core/shell nanoparticle can be surrounded by an inner and outer shell. In another embodiment, the nanoparticle is a core nanoparticle which has a core but no surrounding shell. The outmost surface of the core or shell can be coated with tightly associated ligands which are not removed by ordinary solvation.

Examples of a nanoparticle include a nanocrystal, such as a core/shell nanocrystal, plus any associated organic ligands (which are not removed by ordinary solvation) or other materials which may coat the surface of the nanocrystal. In one embodiment, a nanoparticle has at least one major dimension ranging from about 1 to about 1000 nm. In other embodiments, a nanoparticle has at least one major dimension ranging from about 1 to about 20 nm, about 1 to about 15 nm, about 1 to about 10 nm or about 1 to 5 nm.

In some embodiments, a nanoparticle can have a layer of ligands on its surface which can further be cross-linked to each other. In some embodiments, a nanoparticle can have other or additional surface coatings which can modify the properties of the particle, for example, increasing or decreasing solubility in water or other solvents. Such layers on the surface are included in the term 'nanoparticle.'

In one embodiment, nanoparticle can refer to a nanocrystal having a crystalline core, or to a core/shell nanocrystal, and may be about 1 nm to about 100 nm in its largest dimension, about 1 nm to about 20 nm, about 1 nm to about 15 nm, about 1 nm to about 10 nm or preferably about 5 nm to about 10 nm in its largest dimension. Small nanoparticles are typically less than about 20 nm in their largest dimension.

"Nanocrystal" as used herein can refer to a nanoparticle made out of an inorganic substance that typically has an ordered crystalline structure. It can refer to a nanocrystal having a crystalline core (core nanocrystal) or to a core/shell nanocrystal.

A core nanocrystal is a nanocrystal to which no shell has been applied. Typically, it is a semiconductor nanocrystal that includes a single semiconductor material. It can have a homogeneous composition or its composition can vary with depth inside the nanocrystal.

A core/shell nanocrystal is a nanocrystal that includes a core nanocrystal and a shell disposed over the core nanocrystal. Typically, the shell is a semiconductor shell that includes a single semiconductor material. In some embodiments, the core and the shell of a core/shell nanocrystal are composed of different semiconductor materials, meaning that at least one atom type of a binary semiconductor material of the core of a core/shell is different from the atom types in the shell of the core/shell nanocrystal.

The semiconductor nanocrystal core can be composed of a semiconductor material (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb.

The semiconductor nanocrystal shell can be composed of materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb.

Many types of nanocrystals are known, and any suitable method for making a nanocrystal core and applying a shell to the core may be employed. Nanocrystals can have a surface layer of ligands to protect the nanocrystal from degradation in use or during storage.

"Quantum dot" as used herein refers to a crystalline nanoparticle made from a material which in the bulk is a semiconductor or insulating material, which has a tunable photophysical property in the near ultraviolet (UV) to far infrared (IR) range.

"Water-soluble" or "water-dispersible" is used herein to mean the item can be soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated (via hydrogen, electrostatic or other suitable physical/chemical bonding) and suspended in solvents which are compatible with their outer surface layer, thus a nanoparticle which is readily dispersed in water is considered water-soluble or water-dispersible. A water-soluble nanoparticle can also be considered hydrophilic, since its surface is compatible with water and with water solubility.

"Hydrophobic nanoparticle" as used herein refers to a nanoparticle which is readily dispersed in or dissolved in a water-immiscible solvent like hexanes, toluene, and the like. Such nanoparticles are generally not readily dispersed in water.

"Hydrophilic" as used herein refers to a surface property of a solid, or a bulk property of a liquid, where the solid or liquid exhibits greater miscibility or solubility in a high-dielectric medium than it does in a lower dielectric medium. By way of example, a material which is more soluble in methanol than in a hydrocarbon solvent such as decane would be considered hydrophilic.

"Coordinating solvents" as used herein refers to a solvent such as TDPA, OP, TOP, TOPO, carboxylic acids, and amines, which are effective to coordinate to the surface of a nanocrystal. 'Coordinating solvents' also include phosphines, phosphine oxides, phosphonic acids, phosphinic acids, amines, and carboxylic acids, which are often used in growth media for nanocrystals, and which form a coating or layer on the nanocrystal surface. Coordinating solvents can exclude hydrocarbon solvents such as hexanes, toluene, hexadecane, octadecene and the like, which do not have heteroatoms that provide bonding pairs of electrons to coordinate with the nanocrystal surface. Hydrocarbon solvents which do not contain heteroatoms such as O, S, N or P to coordinate to a nanocrystal surface are referred to herein as non-coordinating solvents. Note that the term 'solvent' is used in its ordinary way in these terms: it refers to a medium which supports, dissolves or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

As used herein, the term "population" refers to a plurality of nanoparticles having similar physical and/or optical properties. 'Population' can refer to a solution or structure with more than one nanoparticle at a concentration suitable for single molecule analysis. In some embodiments, the population can be monodisperse and can exhibit less than at least 15% rms deviation in diameter of the nanoparticles, and spectral emissions in a narrow range of no greater than about 75 nm full width at half max (FWHM). In the context of a solution, suspension, gel, plastic, or colloidal dispersion of nanoparticles, the nature of the population can be further characterized by the number of nanoparticles present, on average, within a particular volume of the liquid or solid, or the concentration. In a two-dimensional format such as an array of nanoparticles adhered to a solid substrate, the concept of concentration is less convenient than the related measure of particle density, or the number of individual particles per two-dimensional area. In this case, the maximum density would typically be that obtained by packing particles "shoulder-to-shoulder" in an array. The actual number of particles in this case would vary due to the size of the particles—a given array could contain a large number of small particles or a small number of larger particles.

As used herein, the terms "moderate to high excitation" refers to monochromatic illumination or excitation (e.g., laser illumination) having a high power intensity sufficiently high such that the absorbed photons per second for a given sample is between about 200,000 and about 1,600,000.

In one aspect, the nanoparticle is a semiconductor nanoparticle having size-dependent optical and electronic properties. For example, the nanoparticle can emit a fluorescent signal in response to excitation energy. The spectral emission of the nanoparticle can be tunable to a desired energy by selecting the particle size, size distribution, and/or composition of the semiconductor nanoparticle. For example, depending on the dimensions, the semiconductor nanoparticle can be a fluorescent nanoparticle which emits light in the UV-visible-IR spectrum. The shell material can have a bandgap greater than the bandgap of the core material.

In one aspect, the nanoparticle is an energy transfer donor. The nanoparticle can be excited by an electromagnetic source such as a laser beam, multi-photon excitation, or electrical excitation. The excitation wavelength can range between about 190 to about 800 nm including all values and ranges there in between. In some embodiments, the nanoparticle can be excited by an energy source having a wavelength of about 405 nm. In other embodiments, in response to excitation, the nanoparticle can emit a fluorescent signal at about 400-800 nm, or about 605 nm.

In one aspect, the nanoparticle can undergo Raman scattering when subjected to an electromagnetic source (incident photon source) such as a laser beam. The scattered photons have a frequency that is different from the frequency of the incident photons. As a result, the wavelength of the scattered photons is different than the incident photon source. In one embodiment, the nanoparticle can be attached to a suitable tag or label to enhance the detectability of the nanoparticle via Raman spectroscopy. The associated tag can be fluorescent or nonfluorescent. Such approaches can be advantageous in avoiding problems that can arise in the context of fluorescent nanoparticles, such as photobleaching and blinking. See, e.g., Sun et al., "Surface-Enhanced Raman Scattering Based Non-fluorescent Probe for Multiplex DNA Detection", Anal. Chem. 79(11):3981-3988 (2007).

In one aspect, the nanoparticle is comprised of a multi-shell layered core which is achieved by a sequential shell material deposition process, where one shell material is added at a time, to provide a nanoparticle having a substantially uniform shell of desired thickness which is substantially free of defects. The nanoparticle can be prepared by sequential, controlled addition of materials to build and/or applying layers of shell material to the core. See e.g., U.S. PCT Application Serial No. PCT/US09/61951 which is incorporated herein by reference as if set forth in full.

In another aspect, a method is provided for making a nanoparticle comprising a core and a layered shell, where the shell comprises at least one inner shell layer and at least one outer shell layer. The method comprises the steps: (a) providing a mixture comprising a core, at least one coordinating solvent; (b) heating the mixture to a temperature suitable for formation of an inner shell layer; (c) adding a first inner shell precursor alternately with a second inner shell precursor in layer additions, to form an inner shell layer which is a desired number of layers thick; (d) heating the mixture to a temperature suitable for formation of an outer shell layer; and (e) adding a first outer shell precursor alternately with a second outer shell precursor in layer additions, to form an outer shell layer which is a desired number of layers thick. In one embodiment, if the coordinating solvent of (a) is not amine, the method further comprises an amine in (a).

In one aspect, at least one coordinating solvent comprises a trialkylphosphine, a trialkylphosphine oxide, phosphonic acid, or a mixture of these. In another aspect, at least one coordinating solvent comprises trioctylphosphine (TOP), trioctylphosphine oxide (TOPO), tetradecylphosphonic acid (TDPA), or a mixture of these. In yet another aspect, the coordinating solvent comprises a primary or secondary amine, for example, decylamine, hexadecylamine, or dioctylamine.

In one aspect, the nanoparticle comprises a core comprising CdSe. In another aspect, the nanoparticle shell can comprise YZ wherein Y is Cd or Zn, and Z is S, or Se. In one embodiment, at least one inner shell layer comprises CdS, and the at least one outer shell layer comprises ZnS.

In one aspect, the first inner shell precursor is $Cd(OAc)_2$ and the second inner shell precursor is bis(trimethylsilyl) sulfide ($TMS_2S$). In other aspects, the first and second inner shell precursors are added as a solution in trioctylphosphine (TOP). In other aspects, the first outer shell precursor is diethylzinc ($Et_2Zn$) and the second inner shell precursor is dimethyl zinc ($TMS_2S$). Sometimes, the first and second outer shell precursors are added as a solution in trioctylphosphine (TOP).

In one aspect, the nanoparticle can have ligands which coat the surface. The ligand coating can comprise any suitable compound(s) which provide surface functionality (e.g., changing physicochemical properties, permitting binding and/or other interaction with a biomolecule, etc.). In some embodiments, the disclosed nanoparticle has a surface ligand coating (in direct contact with the external shell layer) that adds various functionalities which facilitate it being water-dispersible or soluble in aqueous solutions. There are a number of suitable surface coatings which can be employed to permit aqueous dispersibility of the described nanoparticle. For example, the nanoparticle(s) disclosed herein can comprise a core/shell nanocrystal which is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of ligand coatings can include, but are not limited to, amphiphilic polymer (AMP), bidentate thiols (i.e., DHLA), tridentate thiols, dipeptides, functionalized organophosphorous compounds (e.g., phosphonic acids, phosphinic acids), etc.

Non-Blinking Nanoparticles

Provided herein are nanoparticles which exhibit modulated, reduced, or no intermittent (e.g., continuous, non-blinking) fluorescence.

In one aspect, the nanoparticle or populations thereof exhibit modulated, reduced or non-detectable intermittent (e.g., continuous, etc.) fluorescence properties. The nanoparticles can have a stochastic blinking profile in a timescale which is shifted to very rapid blinking or very slow or infrequent blinking relative to a nanoparticle previously described in the art (conventional nanoparticles are described in the art as having on-time fractions of <0.2 in the best of conditions examined). For example, the nanoparticles may blink on and off on a timescale which is too rapid to be detected under the methods employed to study this behavior.

In one aspect the nanoparticle or populations thereof are photostable. The nanoparticles can exhibit a reduced or no photobleaching with long exposure to moderate to high intensity excitation source while maintaining a consistent spectral emission pattern.

In one aspect, the nanoparticle or populations thereof have a consistently high quantum yield. For example, the nanoparticles can have a quantum yield greater than: about 10%, or about 20%, or about 30%, or about 40%, or about 50%, or about 60%, or about 70% or about 80%.

As used herein, fluorescence (or Forster) resonance energy transfer (FRET) is a process by which a fluorophore (the donor) in an excited state transfers its energy to a proximal molecule (the acceptor) by nonradiative dipole-dipole interaction (Forster, T. "Intermolecular Energy Migration and Fluorescence", *Ann. Phys.*, 2:55-75, 1948; Lakowicz, J. R., *Principles of Fluorescence Spectroscopy*, 2nd ed. Plenum, New York. 367-394, 1999).

FRET efficiency (E) can be defined as the quantum yield of the energy transfer transition, i.e. the fraction of energy transfer event occurring per donor excitation event. It is a direct measure of the fraction of photon energy absorbed by the donor which is transferred to an acceptor, as expressed in Equation 1: $E = k_{ET}/k_f + k_{ET} + \Sigma k_i$ where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r (nm) between the two fluorophores (i.e., donor and acceptor pair), as expressed in Equation 2: $E = 1/1 + (r/R_0)^6$.

The distance where FRET efficiency is at 50% is termed $R_0$, also know as the Forster distance. $R_0$ can be unique for each donor-acceptor combination and can range from between about 5 nm to about 10 nm. Therefore, the FRET efficiency of a donor (i.e., nanoparticle) describes the maximum theoretical fraction of photon energy which is absorbed by the donor (i.e., nanoparticle) and which can then be transferred to a typical organic dye (e.g., fluoresceins, rhodamines, cyanines, etc.).

In some embodiments, the disclosed nanoparticles are relatively small (i.e., <15 nm) and thus may be particularly well suited to be used as a donor or an acceptor in a FRET reaction. That is, some embodiments of the disclosed nanoparticles exhibit higher FRET efficiency than conventional nanoparticles and thus are excellent partners (e.g., donors or acceptors) in a FRET reaction.

"Quantum yield" as used herein refers to the emission efficiency of a given fluorophore assessed by the number of times which a defined event, e.g., light emission, occurs per photon absorbed by the system. In other words, a higher quantum yield indicates greater efficiency and thus greater brightness of the described nanoparticle or populations thereof.

Any suitable method can be used to measure quantum yield. In one example, quantum yield can be obtained using standard methods such as those described in Casper et al (Casper, J. V.; Meyer, T. J. *J. Am. Chem. Soc.* 1983, 105, 5583) and can be analyzed relative to known fluorophores chosen as appropriate for maximal overlap between standard emission and sample emission (e.g., fluorescein, Rhodamine 6G, Rhodamine 101). Dilute solutions of the standard and sample can be matched or nearly matched in optical density prior to acquisition of absorbance and emission spectra for both. The emission quantum yield ($\phi_{em}$) then can be determined according to Equation 3:

$$\phi_{em} = \phi'_{em}\left(\frac{I}{I'}\right)\left(\frac{A'}{A}\right)$$

where A and A' are the absorbances at the excitation wavelength for the sample and the standard respectively and I and I' are the integrated emission intensities for the sample and standard respectively. In this case $\phi'_{em}$ can be the agreed upon quantum yield for the standard.

Disclosed herein are fluorescent nanoparticles with superior and robust properties which significantly expand the applications in which nanoparticles are useful. These nanoparticles are superior and surprisingly robust in that they are simultaneously stable, bright, and sensitive to environmental stimuli. Moreover, the disclosed nanoparticles have limited or no detectable blinking (i.e., where the nanoparticle emits light non-intermittently when subject to excitation), are highly photostable, have a consistently high quantum yield, are small (e.g., ≤20 nm) and can act as a donor which undergoes FRET with a suitable acceptor moiety (e.g., fluorescent dyes, etc.). The photostability of these nanoparticles is reflected in their exhibiting reduced or no photobleaching (i.e., fading) behavior when subjected to moderate to high intensity excitation for at least about 20 minutes. Additionally, the particles can remain substantially free from photo-induced color shifting.

Put another way, the nanoparticles can maintain a consistent spectral emission pattern (i.e., maintain the ability to fluoresce) even when exposed to a large quantity of photons (i.e., moderate to high intensity excitation) for a long period of time. This unique combination of characteristics makes these types of nanoparticles sensitive tools for single molecule analysis and other sensitive high throughput applications. Moreover, these properties make the nanoparticles particularly well suited for use as highly efficient donor fluorophores in energy transfer reactions such as FRET reactions (i.e., high FRET efficiency) or other reactions as well as applications which require or are enhanced by greater response to the environment.

Without being bound to a particular theory, blinking or fluorescence intermittency may arise during the nanoparticle charging process when an electron is temporarily lost to the surrounding matrix (Auger ejection or charge tunneling) or captured to surface-related trap states. The nanoparticle is "on" or fluorescing when all of the electrons are intact and the particle is "neutral" and the particle is "off" or dark when the electron is lost and the particle is temporarily (or in some cases permanently) charged. It is important to note that the complete suppression of blinking may not necessarily be required and in some instances may not be desirable. Blinking which occurs on a timescale much shorter or much longer than the interrogation period for a particular assay has relatively little impact on the performance of the system. Thus, nanoparticles and nanoparticle populations having modulated blinking properties, where blinking occurs on a very short or very fast timescale relative to the assay interrogation periods are also useful and fall within the scope of the present disclosure. Localization of timescale or simply pushing timescale to one side (e.g., to where the blinking is undetectable within the assay system) can provide substantial benefit in application development.

The blinking behavior of the nanoparticles described herein can be analyzed and characterized by any suitable number of parameters using suitable methodologies. The probability distribution function of the "on" and "off" blinking time durations (i.e., blinking behavior) can be determined using the form of an inverse power law. A value, alpha (α) can be calculated, wherein α □ represents an exponent in the power law. As the percentage of the population which is non-blinking increases, the value of $\alpha_{on}$ theoretically approaches zero. In conventional nanoparticle populations previously described, $\alpha_{on}$ typically ranges from about 1.5 to about 2.5, under moderate to high excitation energy.

Most alpha calculations can use a predetermined threshold to determine the "on" and "off" values of alpha-on and alpha-off (i.e., $\alpha_{on}$ and $\alpha_{off}$). Typically, an alpha estimator which calculates the on/off threshold for each dot individually can be employed. The data can be represented by a plot of signal versus frequency, and typically appears as a series of Gaussian distributions around the "off state" and one or more "on states." A log-log plot of frequency versus time for each period of time that the dot is "on" provides a straight line having a slope of $\alpha_{on}$. The value of alpha-off ($\alpha_{off}$) can be similarly determined.

In a specific example (the "TIRF example"), the fluorescent intermittency measurements can be made using a Total Internal Reflection Fluorescence (TIRF) microscope fitted with a 60× oil immersion objective lens, using a dual view with a longpass filter on the acceptor side and a bandpass filter on the donor side. Using the TIRF setup, the nanoparticles were imaged at 30 Hz (33 ms), typically for 5 minutes, to produce a movie showing the time and intensity of the emitted light for each individual spot (corresponding to a single particle) within a binned frame which was 33 ms long; the intensity for each binned frame can be integrated. Each data set can be manually analyzed dot-by-dot, and aggregates and other artifacts were excluded. From the edited results, the following parameters can be calculated: alpha-on ("$\alpha_{on}$"); alpha-off ("$\alpha_{off}$"); the percent on; longest on/longest off; overlap scores; and the median values for each of these parameters.

In some aspects, provided herein is a nanoparticle or population thereof which has an $\alpha_{on}$ of less than about 1.5, $\alpha_{on}$ of less than about 1.4, $\alpha_{on}$ of less than about 1.3, $\alpha_{on}$ of less than about 1.2, or an $\alpha_{on}$ of less than about 1.1, under moderate to high excitation energy. In some embodiments, at least about 50%, at least about 60%, at least about 70%, at least about 80%, at least about 90%, at least about 95%, at least about 98%, at least about 99% or more of the population has an $\alpha_{on}$ of less than about 1.5, $\alpha_{on}$ of less than about 1.4, $\alpha_{on}$ of less than about 1.3, $\alpha_{on}$ of less than about 1.2, or $\alpha_{on}$ of less than about 1.1 for the time observed, under moderate to high excitation energy. The observation time can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy. Compositions comprising such a nanoparticle and populations thereof also are contemplated.

In some aspects, provided herein is a nanoparticle or a population thereof having a stochastic blinking profile which is either undetectable or rare (e.g., no more than 1-2 events during the interrogation period) over an observed timescale. In this case, "undetectable" encompasses the situation in which evidence might exist for ultra-fast blinking on a timescale which is faster than the binning timescale (e.g., dimming and brightening from bin to bin) but there are no "off" events persisting for longer than the bin time. Therefore, in some embodiments, a nanoparticle or population thereof has a stochastic blinking profile which is undetectable for at least about 50%, at least about 60%, at least about 70%, at least about 80%, at least about 85%, at least about 90%, at least about 95%, at least about 98%, at least about 99% or more of the time observed, under moderate to high excitation energy. In other embodiments, at least about 50%, at least about 60%, at least about 70%, at least about 80%, at least about 90%, at least about 95%, at least about 98%, at least about 99% or more of the individual nanoparticles in a population have a stochastic blinking on a timescale which is undetectable for the time observed, under moderate to high excitation energy. The timescale can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

In some aspects, the longest on and longest off values can relate to the longest period of time a nanoparticle is observed to be in either the "on" or the "off" state. In particular, the longest on value can be important to determining the length of time and amount of data which may be measured in a particular assay.

Thus, the blinking characteristics of the nanoparticles herein can also be characterized by their on-time fraction, which represents the (total on-time)/(total experiment time). Under the TIRF example disclosed herein, the total on time can be determined by the total number of frames "on" multiplied by 33 ms, and the total experiment time is 5 minutes. For example, the blinking properties of the disclosed nanoparticles or populations thereof can be determined under continuous irradiation conditions using a 405 nm laser with an intensity of about 1 watt per $cm^2$ during an experimental window of at least 5 minutes.

On-time fractions can be used to characterize the blinking behavior of a single nanoparticle or of a population of nanoparticles. It is important to note that the on-time fraction for a particular nanoparticle or population of nanoparticles is a function of the specific conditions under which the percent of blinking or "non-blinking" nanoparticles is determined.

In some aspects, provided herein is a nanoparticle or population thereof having an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. In some embodiments, a nanoparticle or populations thereof having a percent on-time of about 98%, about 99% (i.e., on-time fraction of about 0.99) can be considered to be "non-blinking," under moderate to high excitation energy. In some embodiments, at least about 50%, at least about 60%, at least about 70%, at least about 80%, at least about 90%, at least about 95%, at least about 98%, at least about 99%, or more of the individual nanoparticles in a population of nanoparticles can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. The on-times of the nanoparticles are typically for at least about 5 minutes, at least about 10 minutes, at least about 15 minutes, at least about 20 minutes, at least about 30 minutes, at least about 45 minutes, at least about 60 minutes, at least about 70 minutes, at least about 80 minutes, at least about 90 minutes, at least about 120 minutes under moderate to high intensity excitation of the nanoparticle or nanoparticle population. Under one set of conditions, continuous irradiation with 405 nm laser with an approximate intensity of 1 watt per $cm^2$ was used to determine the stochastic blinking profile.

In some embodiments, nanoparticles which have a stochastic (i.e., random) blinking profile in a timescale which shifts from very rapid blinking or very slow/infrequent blinking (relative to a nanoparticle previously described in the art) can be considered to have modulated blinking properties. In some embodiments, these nanoparticles may blink on and off on a timescale which is too rapid to be detected under the methods employed to study this behavior. Thus, certain nanoparticles can effectively appear to be "always on" or to have on-time fractions of about 0.99, when in fact they flicker on and off at a rate too fast or too slow to be detected. Such flickering has relatively little impact on the performance of a system, and for practical purposes such nanoparticles can be considered to be non-blinking.

In some instances, the disclosed nanoparticles and populations thereof are not observed to blink off under the analysis conditions, and such particles can be assessed as "always on" (e.g., non-blinking). The percent of usable dots which are "always on" can be a useful way to compare nanoparticles or populations of nanoparticles. However, a determination of "always on" may mean that the "off" time was insufficient to provide enough a signal gap for accurate determination and thus the value in the regime of particles is insufficient to calculate. Even these "non-blinking" nanoparticles may flicker on and off on a timescale which is not detected under the conditions used to assess blinking. For example, certain particles may blink on a timescale which is too fast to be detected, or they may blink very rarely, and, in some embodiments, such particles may also be considered to be "always-on" or non-blinking, as the terms are used herein.

In one aspect, provided herein is a nanoparticle or population thereof which demonstrate some fluctuation in fluorescence intensity. In some embodiments, the change in fluorescence intensity for the nanoparticle is less than about 5%, less than about 10%, less than about 20%, or less than about 25% of the nanoparticle or populations thereof at its greatest intensity, under moderate to high excitation energy. In some embodiments, such changes in fluorescence intensity of less than about 5%, less than about 10%, less than about 20%, or less than about 25% of the highest intensity can occur in at least about 50%, at least about 60%, at least about 70%, at least about 80%, at least about 85%, at least about 90%, at least about 95%, at least about 98%, at least about 99% of the nanoparticles in the population, under moderate to high excitation energy.

In some aspects, the nanoparticles with modulated, reduced or no intermittent (e.g., continuous, non-blinking) fluorescence provided herein can comprise of a core and a layered gradient shell. In some embodiments, the nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed nanoparticle(s) is less than about 15 nm See for example, PCT Application Serial No. PCT US/09/61951. See also PCT/US09/061951 and PCT/US09/061953 both filed on Oct. 23, 2009.

As discussed previously, the disclosed nanoparticles may be particularly well suited for use as a donor or acceptor which undergoes FRET with a suitable complementary partner (donor or acceptor). A "FRET capable" nanoparticle refers to a nanoparticle which can undergo a measurable FRET energy transfer event with a donor or an acceptor moiety. In some embodiments, a FRET capable nanoparticle is one which has at least about 25% efficiency in a FRET reaction.

Thus, in one aspect, a FRET capable fluorescent nanoparticle or population thereof with modulated, reduced or non intermittent (e.g., continuous, etc.) fluorescence is provided. In some embodiments, the nanoparticle is the donor in a FRET reaction. In some embodiments, the nanoparticle is the acceptor in the FRET reaction.

In some embodiments, the FRET capable non-blinking fluorescent nanoparticle(s) disclosed herein can comprise a core and a layered gradient shell. In some embodiments, the FRET capable non-blinking nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed FRET capable nanoparticle(s) is less than about 15 nm.

In some embodiments, the nanoparticle or population thereof has a FRET efficiency of at least about 20%, at least about 40%, at least about 50%, at least about 60%, at least about 70%, at least about 80%, at least about 90%, at least about 95%, at least about 98%, at least about 99%, or greater.

In some embodiments, at least about 30%, at least about 40%, at least about 50%, at least about 60% at least about 70%, at least about 80%, at least about 90%, at least about 95%, at least about 98%, at least about 99% or more of the individual nanoparticles in the population have a FRET efficiency of at least about 20%, at least about 40%, at least about 50%, at least about 60%, at least about 70%, at least about 80%, at least about 90%, at least about 95%, at least about 98%, at least about 99% or more.

In some embodiments, the FRET efficiency of the disclosed nanoparticle or population thereof can be maintained for at least about the first 10%, at least about the first 20%, at least about the first 30%, at least about the first 40%, at least about the first 50%, at least about the first 60%, at least about the first 70%, at least about the first 80%, at least about the first 90% or more of the total emitted photons under conditions of moderate to high excitation.

As discussed above, the nanoparticle(s) provided herein can be considered to be surprisingly photostable. In particular, the nanoparticle and populations described herein can be photostable over an extended period of time while maintaining the ability to effectively participate in energy transfer (i.e., FRET) reactions. The disclosed nanoparticles can be stable under high intensity conditions involving prolonged or continuous irradiation over an extended period of time from a moderate to high excitation source.

Thus, in one aspect, provided herein is a non-blinking fluorescent nanoparticle and population thereof which is photostable.

In some embodiments, the disclosed photostable nanoparticle and population thereof can have an emitted light or energy intensity sustained for at least about 10 minutes and does not decrease by more than about 20% of maximal intensity achieved during that time. Further, these nanoparticles and populations thereof can have a wavelength spectrum of emitted light which does not change more than about 10% upon prolonged or continuous exposure to an appropriate energy source (e.g. irradiation).

In one embodiment, the photostable nanoparticles disclosed herein can remain photostable under moderate to high intensity excitation from at least about 10 minutes to about 2 hours. In another embodiment, the photostable nanoparticles disclosed herein can remain photostable under moderate to high intensity excitation from at least about 10 minutes to about 10 hours. In still another embodiment, the photostable nanoparticles disclosed herein can remain photostable under moderate to high from about 10 minutes to about 48 hours. However, it should be appreciated, that these are just example photostable times for the disclosed nanoparticles, in practice the nanoparticles can remain photostable for longer periods of time depending on the particular application.

It should be appreciated that nanoparticles which are photostable over longer timescales in combination with moderate to high excitation energy sources are well suited for more sensitive and broad-ranging applications such as the real-time monitoring of single molecules involving FRET. That is, the nanoparticle and population thereof described herein can be photostable over an extended period of time while maintaining the ability to effectively participate in energy transfer (i.e., FRET) reactions, which makes the subject nanoparticles particularly useful for many applications involving the real-time monitoring of single molecules. As such, in some embodiments the photostable nanoparticles disclosed herein have FRET efficiencies of at least about 20%.

In some embodiments, the disclosed nanoparticles are stable upon prolonged or continuous irradiation (under moderate to high excitation rate) in which they do not exhibit significant photo-bleaching on the timescales indicated. Photobleaching can result from the photochemical destruction of a fluorophore (and can be characterized by the nanoparticles losing the ability to produce a fluorescent signal) by the light exposure or excitation source used to stimulate the fluorescence. Photobleaching can complicate the observation of fluorescent molecules in microscopy and the interpretation of energy transfer reactions because the signals can be destroyed or diminished increasingly as timescales for the experiment increase or the energy intensity increases.

Photobleaching can be assessed by measuring the intensity of the emitted light or energy for a nanoparticle or nanoparticle population using any suitable method. In some embodiments, the intensity of emitted light or energy from the disclosed nanoparticle or population thereof does not decrease by more than about 20% (and in some embodiments, not more than about 10%) upon prolonged or continuous irradiation (under moderate to high excitation rate). In some embodiments, the intensity of emitted light from the disclosed nanoparticle or population thereof does not decrease by more than about 20%, about 15%, about 10%, about 5% or less upon irradiation from about 10 minutes, about 20 minutes, about 30 minutes, about 45 minutes, about 60 minutes, about 90 minutes, about 2 hours, about 3 hours to about 4 hours, under moderate to high excitation energy.

In some embodiments, the photostable nanoparticles provided herein further demonstrate enhanced stability in which they exhibit a reduction in or absence of spectral shifting during prolonged excitation. In the conventional nanoparticles previously described in the art, increased exposure to an excitation source—whether via increase time or power—results in a spectral shift of the wavelength emission wavelength profile of a nanoparticle and populations thereof from a longer wavelength to an increasingly shorter wavelength. Such spectral shifting of emission wavelength represents a significant limitation as precise resolution of emission spectra is required for applications which require rapid detection, multi-color analysis, and the like. Shifting of any significance then requires that the wavelength emissions used in an assay be sufficiently separated to permit resolution, thus reducing the number of colors available as well as increasing signal to noise ratio to an unacceptable level as the initial spectral profile cannot be relied upon once spectral shifting begins. Such shifting may require shortened observation times or use of fluorophores with widely separated emission spectra. The nanoparticles provided herein have little to no spectral shift, particularly over extended periods of excitation.

Wavelength emission spectra can be assessed by any suitable method. For example, spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Thus, in some embodiments, the photostable nanoparticle and population thereof has a wavelength spectrum of emitted light which does not change more than about 10% upon prolonged or continuous exposure to an appropriate energy source (e.g. irradiation) over about 4 minutes to about 10 minutes, under moderate to high excitation energy. In some embodiments, the wavelength emission spectra does not change more than about 5%, more than about 10%, more than about 20% over 10 minutes, about 20 minutes, about 30 minutes, about 45 minutes, about 60 minutes, about 90 minutes, about 2 hours, about 3 hours to about 4 hours.

It should be appreciated that there can be various other objective indicia of nanoparticle photostability. For example, a nanoparticle can be classified as photostable when the nanoparticle, under moderate to high excitation, emits about 1,000,000 to about 100,000,000 photons or more preferably about 100,000,001 to about 100,000,000,000 photons or even more preferably more than about 100,000,000,000 photons before becoming non-emissive (i.e., bleached).

A nanoparticle with modulated, reduced or no fluorescent intermittency (e.g., continuous, non-blinking, etc.); reduced or absent spectral shifting; low to no photobleaching; high quantum yield; and sufficient FRET efficiency can be of any suitable size. Typically, it is sized to provide fluorescence in the UV-visible portion of the electromagnetic spectrum as this range is convenient for use in monitoring biological and biochemical events in relevant media. The disclosed nanoparticle and population thereof can have any combination of the properties described herein.

Thus, in some embodiments the nanoparticle or population thereof has modulated or no blinking, are photostable (e g, limited or no photobleaching, limited or no spectral shift), has high quantum yield, have high FRET efficiency, has a diameter of less than about 15 nm, is spherical or substantially spherical shape, or any combination of all these properties as described herein.

Likewise, in some embodiments, at least about 50%, at least about 60%, at least about 70%, at least about 80%, at least about 90%, at least about 95%, at least about 98%, at least about 99%, or more of the individual nanoparticles in a population of nanoparticles have modulated or no blinking, are photostable (e.g., limited or no photobleaching, limited or no spectral shift), have high quantum yield, have high FRET efficiency, have diameters of less than about 15 nm, are spherical or substantially spherical shape, or any combination of or all of these properties as described herein.

In one aspect, the FRET capable, non-blinking and/or photostable nanoparticle or population thereof provided herein has a maximum diameter of less than about 20 nm. In some embodiments, the nanoparticle(s) can be less than about 15 nm, less than about 10 nm, less than about 8 nm, less than about 6 nm, less than about 5 nm, less than about 4 nm, less than about 3 nm or less in its largest diameter when measuring the core/shell structure. Any suitable method may be used to determine the diameter of the nanoparticle(s). The nanoparticle(s) provided herein can be grown to the desired size using any of the methods disclosed herein. In some embodiments, at least about 50%, at least about 60%, at least about 70%, at least about 80%, at least about 90%, at least about 95%, at least about 98%, at least about 99%, or more of the individual members of a population of nanoparticles have maximum diameters (when measuring the core, core/shell or core/shell/ligand structure) which are less than about 20 nm, less than about 15 nm, less than about 10 nm, less than about 8 nm, less than about 6 nm, less than about 5 nm, less than about 4 nm, less than about 3 nm or less.

The FRET capable, non-blinking and/or photostable nanoparticle(s) provided herein and populations thereof can be spherical or substantially spherical. In some embodiments, a substantially spherical nanoparticle can be one where any two radius measurements do not differ by more than about 10%, about 8%, about 5%, about 3% or less. In some embodiments, at least about 50%, at least about 60%, at least about 70%, at least about 80%, at least about 90%, at least about 95%, at least about 98%, at least about 99%, or more of the individual members of a population of nanoparticles are spherical or substantially spherical.

Nanoparticles can be synthesized in shapes of different complexity such as spheres, rods, discs, triangles, nanorings, nanoshells, tetrapods, nanowires and so on. Each of these geometries can have distinctive properties: spatial distribution of the surface charge, orientation dependence of polarization of the incident light wave, and spatial extent of the electric field. In some embodiments, the nanoparticles are substantially spherical or spheroidal.

For embodiments where the nanoparticle is not spherical or spheroidal, e.g. rod-shaped, it may be from about 1 to about 15 nm, from about 1 nm to about 10 nm, or 1 nm to about 5 nm in its smallest dimension. In some such embodiments, the nanoparticles may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm and ranges between any two of these values.

The single-color preparation of the nanoparticles disclosed herein can have individual nanoparticles which are of substantially identical size and shape. Thus, in some embodiments, the size and shape between the individual nanoparticles in a population of nanoparticles vary by no more than about 20%, no more than about 15%, no more than about 10%, no more than about 8%, no more than about 6%, no more than about 5%, no more than about 4%, no more than about 3% or less in at least one measured dimension. In some embodiments, disclosed herein is a population of nanoparticles, where at least about 60%, at least about 70%, at least about 80%, at least about 90%, at least about 95%, and ideally about 100% of the particles are of the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values. Such a collection of particles is sometimes referred to as being a "monodisperse" population.

The color (emitted light) of a nanoparticle can be "tuned" by varying the size and composition of the particle. Nanoparticles as disclosed herein can absorb a wide spectrum of wavelengths, and emit a relatively narrow wavelength of light. The excitation and emission wavelengths are typically different, and non-overlapping. The nanoparticles of a monodisperse population may be characterized in that they produce a fluorescence emission having a relatively narrow wavelength band. Examples of emission widths include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. In some embodiments, the width of emission is less than about 60 nm full width at half maximum (FWHM), or less than about 50 nm FWHM, and sometimes less than about 40 nm FWHM, less than about 30 nm FWHM or less than about 20 nm FWHM. In some embodiments, the emitted light preferably has a symmetrical emission of wavelengths.

The emission maxima of the disclosed nanoparticle and population thereof can generally be at any wavelength from about 200 nm to about 2,000 nm Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

As discussed previously, the disclosed nanoparticle or populations thereof can comprise a core and a layered shell, wherein the shell includes at least one inner (intermediate) shell layer comprising a first shell material and at least one outer (external) shell layer comprising a second shell material, and wherein the layered shell is substantially uniform in coverage around the core and is substantially free of defects.

Thus, in one aspect, the nanoparticle or population thereof comprises a core ($M^1Y$) and a layered shell, wherein the shell comprises m inner shell monolayers comprising a first shell material $(M^1X)_m$ and n outer shell monolayers comprising a second shell material $(M^2X)_n$, wherein M can be a metal atom and X can be a non-metal atom, each of m and n is independently an integer from 1 to 10, and the layered shell is substantially uniform in coverage around the core and is substantially free of defects. In specific embodiments, the sum of m+n is 3-20, or 5-14, or 6-12, or 7-10.

In certain embodiments, the disclosed nanoparticles can further comprise one or more additional shell layers between the at least one inner shell layer and the at least one outer shell layer.

In some embodiments, the nanoparticle core and population thereof can have a first bandgap energy and the first shell material can have a second bandgap energy, wherein the second bandgap energy can be greater than the first bandgap energy.

In a further aspect, provided herein is a nanoparticle or population thereof comprising a core and a layered shell, wherein the shell comprises sequential monolayers comprising an alloyed multi-component shell material of the form $M^1_xM^2_yX$, where $M^1$ and $M^2$ can be metal atoms and X can be a non metal atom, where the composition becomes successively enriched in $M^2$ as the monolayers of shell material are deposited, where x and y represent the ratio of $M^1$ and $M^2$ in the shell material, and wherein the monolayered shell is substantially uniform in coverage around the core and is substantially free of defects. In some embodiments, the layered shell sometimes has about 3-20 monolayers of shell material, sometimes about 5-14 monolayers of shell material, sometimes about 6-12 monolayers of shell material, or sometimes about 7-10 monolayers of shell material.

In one aspect, provided herein is a nanoparticle or population thereof comprising a core and a layered shell having a gradient potential, wherein the shell comprises at least one inner shell layer and at least one outer shell layer, and wherein the layered shell is substantially uniform in coverage around the core and is substantially free of defects.

The layered shell may be engineered such that the sequential monolayers are selected to provide a gradient potential from the nanoparticle core to the outer surface of the nanoparticle shell. The steepness of the potential gradient may vary depending on the nature of the shell materials selected for each monolayer or group of monolayers. For example, a nanoparticle comprising several sequential monolayers of the same shell material may reduce the potential through a series of steps, while a more continuous gradient may be achievable through the use of sequential monolayers of a multi-component alloyed shell material. In some embodiments, both single component and multi-component shell materials may be applied as different monolayers of a multi-layer shell on a nanoparticle.

The nanoparticles can be synthesized as disclosed to the desired size by sequential, controlled addition of materials to build and/or apply monolayers of shell material to the core. This is in contrast to conventional methods of adding shells where materials (e.g., diethylzinc and bis(trimethylsilyl)sulfide) are added together. Sequential addition permits the formation of thick (e.g., >2 nm) relatively uniform individual shells (e.g., uniform size and depth) on a core. The layer additions generally require the addition of an appropriate amount of the shell precursors to form a single monolayer, based on the starting size of the underlying core. This means that as each monolayer of shell material is added, a new "core" size must be determined by taking the previous "core" size and adding to it the thickness of just-added shell monolayer. This leads to a slightly larger volume of the following shell material needing to be added for each subsequent monolayer of shell material being added.

Each monolayer of shell material can be independently selected, and may be made up of a single component, or may comprise a multi-component (e.g., alloyed, etc.) shell material. In some embodiments, it is suitable to apply one or more sequential monolayers of a first shell material, followed by one or more sequential monolayers of a second shell material. This approach allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited.

In some embodiments, the layered shell can be about 3-20 monolayers of shell material thick, sometimes about 5-14 monolayers of shell material thick, sometimes about 6-12 monolayers of shell material thick or sometimes about 7-10 monolayers of shell material thick. In some embodiments, at least one inner shell layer can be comprised of about 3-5 monolayers, sometimes about 3-7 monolayers, of the first shell material. In other embodiments, at least one outer shell layer can be comprised of about 3-5 monolayers, sometimes about 3-7 monolayers, of the second shell material. In some embodiments, the inner shell layer can be at least 3 monolayers thick; in other embodiments, the outer shell layer can be at least 3 monolayers thick. The individual monolayers can be formed by the controlled, sequential addition of the layer materials methods described herein. The monolayers may not always be completely distinct as they may, in some embodiments, be a latticing between the surfaces of contacting monolayers.

In certain embodiments, provided herein are nanoparticles having a thick, uniform, layered shell, as described herein, wherein the core comprises CdSe, the at least one inner shell layer comprises CdS, and the at least one outer shell layer comprises ZnS. In a particular embodiment, provided herein is a nanoparticle or population thereof having a CdSe core and a layered shell comprising 4CdS+3.5ZnS layers. In some embodiments, provided herein is a nanoparticle which consists essentially of CdSe/4CdS–3.5ZnS.

Also disclosed herein are methods of making a nanoparticle and population thereof with modulated, reduced or no fluorescence intermittency or "blinking". These nanoparticles can be small, photostable, bright, highly FRET efficient or some combination thereof. These nanoparticles can have a multi-shell layered core achieved by a sequential shell material deposition process, whereby one shell material is added at a time, to provide a nanoparticle having a substantially uniform shell of desired thickness which is substantially free of defects.

In one aspect, provided herein is a method for making a nanoparticle or population thereof with modulated, reduced or no fluorescence intermittency, comprising: providing a mixture comprising a core and at least one coordinating solvent; adding a first inner shell precursor alternately with a second inner shell precursor in layer additions, to form an inner shell layer which is a desired number of layers thick; and adding a first outer shell precursor alternately with a second outer shell precursor in layer additions, to form an outer shell layer which is a desired number of layers thick. If the coordinating solvent of is not amine, the method further comprises an amine in.

In some embodiments, the mixture can be heated to a temperature which is suitable for shell formation before and/or after every sequential addition of a shell precursor. In some embodiments, the shell is substantially uniform in coverage around the core and is substantially free of defects. In some embodiments, the resulting nanoparticles have a diameter of less than about 15 nm. In other embodiments, the nanoparticles have a diameter of between about 6 nm to about 10 nm. The nanoparticles made by this method can have quantum yields greater than about 80%. The nanoparticle made by this method can have on-time fractions (i.e., ratio of the time which nanoparticle emission is turned "on" when the nanoparticle is excited) of greater than about 0.80 (under moderate to high excitation energy).

In another aspect, provided herein is a method for making a FRET capable nanoparticle and populations thereof with modulated, reduced or no fluorescence intermittency, comprising: (a) providing a mixture comprising a plurality of nanocrystal cores and at least one coordinating solvent; (b) adding a first intermediate shell precursor alternately with a second intermediate shell precursor in layer additions to form an intermediate shell layer on each of the plurality of nanocrystal cores, wherein the intermediate shell layer is comprised of more than one monolayer; (c) adding a first external shell precursor alternately with a second external shell precursor in layer additions to form an external shell layer on each of the plurality of nanocrystal cores, wherein the external shell layer is disposed on top of the intermediate shell layer and is comprised of more than one monolayer; (d) adding an aqueous solution comprising a hydrophilic ligand; and (e) maintaining the mixture under conditions which cause the plurality of nanocrystals to migrate into an aqueous phase. If the coordinating solvent is not an amine, at least one amine can be included in step (a). In some embodiments, the resulting population of FRET capable non-blinking nanoparticles has a $\alpha_{on}$ value which is less than about 1.4. In other embodiments, the resulting population of FRET capable non-blinking nanoparticles has an on-time fraction of least about 0.8 (under moderate to high excitation energy). In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the methods disclosed above utilize a one step or a two step ligand exchange process to replace the hydrophobic ligands on the nanoparticles with hydrophilic ligands to cause the plurality of nanocrystals to migrate into the aqueous phase. See PCT Application Serial No. PCT/US09/53018 and PCT/US09/59456 which are expressly incorporated herein by reference as if set forth in full.

In another aspect, provided herein is a method for making a FRET capable nanoparticle and populations thereof with modulated, reduced or no fluorescence intermittency, comprising: providing a mixture comprising a plurality of nanocrystal cores, functionalized organophosphorous-based hydrophilic ligands and at least one coordinating solvent; adding a first intermediate shell precursor alternately with a second intermediate shell precursor in layer additions to form an intermediate shell layer on each of the plurality of nanocrystal cores; and adding a first external shell precursor alternately with a second external shell precursor in layer additions to form an external shell layer on each of the plurality of nanocrystal cores. In some embodiments, the resulting population of FRET capable non-blinking nanoparticles has an $\alpha_{on}$ value which is less than about 1.4. In other embodiments, the resulting population of FRET capable non-blinking nanoparticles has an on-time fraction of least about 0.8. In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the functionalized organophosphorous-based hydrophilic ligands are multi-functional surface ligands which include a phosphonate/phosphinate nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the FRET capable and non-blinking nanoparticles produced by the disclosed methods may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See PCT Application Serial No. PCT/US09/59117 which is expressly incorporated herein by reference as if set forth in full.

In another aspect, provided herein is a method of making a nanoparticle or population thereof comprising a core and a layered gradient shell, wherein the shell comprises an multi-component (e.g., alloy, etc.) shell material of the form $M^1_x M^2_y X$, where x and y represent the ratio of $M^1$ and $M^2$ in the shell material. The method comprising: (a) providing a mixture comprising a core, at least one coordinating solvent; (b) heating said mixture to a temperature suitable for formation of the shell layer; and (c) adding a first inner shell precursor comprising $M^1_x$ and $M^2_y$ alternately with a second inner shell precursor comprising X in layer additions, wherein the ratio of y to x gradually increases in sequential layer additions, such that the shell layers becomes successively enriched in $M^2$, to form a layered gradient shell which is a desired number of monolayers thick. If the coordinating solvent is not an amine, at least one amine can be included in step (a).

In one embodiment, the method described above provides a nanoparticle having a layered gradient shell, wherein the core comprises CdSe and the shell comprises sequential layers of $Cd_xZn_yS$, where the ratio of y to x increases gradually from the innermost shell layer to the outermost shell layer, to provide a layered gradient shell with a finely graded potential. In some such embodiments, the outermost shell layer is essentially pure ZnS. In some embodiments, the percent of Zn in the gradient shell varies from less than about 10% at the innermost shell layer to greater than about 80% at the outermost shell layer.

Typically, the heating steps in the disclosed methods are conducted at a temperature within the range of about 150-350° C., more preferably within the range of about 200-300° C. In some embodiments, the temperature suitable for formation of at least one inner shell layer is about 215° C. In some embodiments, the temperature suitable for formation of at least one outer shell layer is about 245° C. It is understood that the above ranges are merely exemplary and are not intended to be limiting in any manner as the actual temperature ranges may vary, dependent upon the relative stability of the precursors, ligands, and solvents. Higher or lower temperatures may be appropriate for a particular reaction. The determination of suitable time and temperature conditions for providing nanoparticles is within the level of skill in the art using routine experimentation.

It can be advantageous to conduct the nanoparticle-forming reactions described herein with the exclusion of oxygen and moisture. In some embodiments the reactions are conducted in an inert atmosphere, such as in a dry box. The solvents and reagents are also typically rigorously purified to remove moisture and oxygen and other impurities, and are generally handled and transferred using methods and apparatus designed to minimize exposure to moisture and/or oxygen. In addition, the mixing and heating steps can be conducted in a vessel which is evacuated and filled and/or flushed with an inert gas such as nitrogen. The filling can be periodic or the filling can occur, followed by continuous flushing for a set period of time.

In some embodiments, the at least one coordinating solvent comprises a trialkylphosphine, a trialkylphosphine oxide, a phosphonic acid, or a mixture of these. Sometimes, the at least one coordinating solvent comprises TOP, TOPO, TDPA, OPA or a mixture of these. The solvent for these reactions often comprises a primary or secondary amine, for example, decylamine, hexadecylamine, or dioctylamine. In some embodiments, the amine is decylamine. In some embodiments, the first inner shell precursor is $Cd(OAc)_2$ and the second inner shell precursor is bis(trimethylsilyl)sulfide ($TMS_2S$). Sometimes, the first and second inner shell precursors are added as a solution in TOP. In some embodiments, the first outer shell precursor is $Et_2Zn$ and the second inner shell precursor is $TMS_2S$. Sometimes, the first and second outer shell precursors are added as a solution in TOP.

In certain embodiments, the disclosed nanoparticles may be prepared using the method described herein to build a layered CdS—ZnS shell on a CdSe quantum size core. The shells for these materials can have varying numbers of layers of CdS and ZnS. Prototypical materials containing a CdSe core and approximately 4 monolayers CdS and 3.5 monolayers of ZnS (the final 0.5 monolayer is essentially pure Zn), or a CdSe core and 9 monolayers CdS and 3.5 monolayers of ZnS were prepared as described in the examples.

In some embodiments, for either the inner or outer layer, or both, less than a full layer of the appropriate first shell precursor can be added alternately with less than a full layer of the appropriate second shell precursor, so the total amount of the first and second shell precursor required is added in two or more portions. Sometimes, the portion is about 0.25 monolayers of shell material, so that the 4 portions of 0.25 monolayer of first shell precursor are added alternately with 4 portions of 0.25 monolayer of second shell precursor; sometimes the portion is about 0.5 monolayers of shell material, and sometimes about 0.75 monolayers of shell material.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethylzinc ($Et_2Zn$) or dimethyl cadmium are typically considered to be a source of neutral zinc atoms ($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn$ (oleate)$_2$), zinc chloro(oleate), zinc undecylenate, zinc salicylate, and other zinc salts. In some embodiments, the first precursor is salt of Cd or Zn. In some embodiments, it is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a C4-C24 alkyl group which is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

When the first precursor comprises a metal cation, the second precursor can provide an uncharged (i.e., neutral) non-metal atom in solution. In frequent embodiments, when the first precursor comprises a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and tri-alkylphosphine adducts of S, Se and Te. Such trialkylphosphine adducts are sometimes described herein as $R_3P=X$, wherein X is S, Se or Te, and each R is independently H, or a C1-C24 hydrocarbon group which can be straight-chain, branched, cyclic, or a combination of these, and which can be unsaturated. Exemplary second precursors of this type include tri-n-(butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors which provide anionic species under the reaction conditions are typically used with a first precursor which provides a neutral metal atom, such as alkylmetal compounds and others described above or known in the art.

In some embodiments, the second precursor provides a negatively charged non-metal ion in solution (e.g., S-2, Se-2 or Te-2). Examples of suitable second precursors providing an ionic species include silyl compounds such as bis(trimethylsilyl)selenide (($TMS)_2Se$), bis(trimethylsilyl)sulfide (($TMS)_2S$) and bis(trimethylsilyl)telluride (($TMS)_2Te$). Also included are hydrogenated compounds such as H2Se, H2S, H2Te; and metal salts such as NaHSe, NaSH or NaHTe. In this situation, an oxidant can be used to oxidize a neutral metal species to a cationic species which can react with the anionic precursor in a 'matched' reaction, or an oxidant can be used increase the oxidation state of the anionic precursor to provide a neutral species which can undergo a 'matched' reaction with a neutral metal species.

Other exemplary organic precursors are described in U.S. Pat. Nos. 6,207,229 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

Both the first and the second precursors can be combined with an appropriate solvent to form a solution for use in the disclosed methods. The solvent or solvent mixture used to form a first precursor solution may be the same or different from that used to form a second precursor solution. Typical coordinating solvents include alkyl phosphines, alkyl phosphine oxides, alkyl phosphonic acids, alkyl phosphinic acids, or carboxylic acid containing solvents, or mixtures of these.

Suitable reaction solvents include, by way of illustration and not limitation, hydrocarbons, amines, alkyl phosphines, alkyl phosphine oxides, carboxylic acids, ethers, furans, phosphoacids, pyridines and mixtures thereof. The solvent may actually comprise a mixture of solvents, often referred to in the art as a "solvent system". In some embodiments, the solvent comprises at least one coordinating solvent. In some embodiments, the solvent system comprises a secondary amine and a trialkyl phosphine (e.g., TBP or TOP) or a trialkylphosphine oxide (e.g., TOPO). If the coordinating solvent is not an amine, an amine can be included.

A coordinating solvent might be a mixture of an essentially non-coordinating solvent such as an alkane and a ligand as defined below.

Suitable hydrocarbons include alkanes, alkenes and aromatic hydrocarbons from 10 to about 30 carbon atoms; examples include octadecene and squalane. The hydrocarbon may comprise a mixture of alkane, alkene and aromatic moieties, such as alkylbenzenes (e.g., mesitylene).

Suitable amines include, but are not limited to, monoalkylamines, dialkylamines, and trialkylamines, for example dioctylamine, oleylamine, decylamine, dodecylamine, hexyldecylamine, and so forth. Alkyl groups for these amines typically contain about 6-24 carbon atoms per alkyl, and can include an unsaturated carbon-carbon bond, and each amine typically has a total number of carbon atoms in all of its alkyl groups combined of about 10-30 carbon atoms.

Exemplary alkyl phosphines include, but are not limited to, the trialkyl phosphines, tri-n-butylphosphine (TBP), tri-n-octylphosphine (TOP), and so forth. Alkyl groups for these phosphines contain about 6-24 carbon atoms per alkyl, and can contain an unsaturated carbon-carbon bond, and each phosphine has a total number of carbon atoms in all of its alkyl groups combined of about 10-30 carbon atoms.

Suitable alkyl phosphine oxides include, but are not limited to, the trialkyl phosphine oxide, tri-n-octylphosphine oxide (TOPO), and so forth. Alkyl groups for these phosphine oxides contain about 6-24 carbon atoms per alkyl, and can contain an unsaturated carbon-carbon bond, and each phosphine oxide has a total number of carbon atoms in all of its alkyl groups combined of about 10-30 carbon atoms.

Exemplary fatty acids include, but are not limited to, stearic, oleic, palmitic, myristic and lauric acids, as well as other carboxylic acids of the formula R—COOH, wherein R is a C6-C24 hydrocarbon group and can contain an unsaturated carbon-carbon bond. It will be appreciated that the rate of nanocrystal growth generally increases as the length of the fatty acid chain decreases.

Exemplary ethers and furans include, but are not limited to, tetrahydrofuran and its methylated forms, glymes, and so forth.

Suitable phosphonic and phosphinic acids include, but are not limited to hexylphosphonic acid (HPA), tetradecylphosphonic acid (TDPA), and octylphosphinic acid (OPA), and are frequently used in combination with an alkyl phosphine oxide such as TOPO. Suitable phosphonic and phosphinic acids are of the formula $RPO_3H_2$ or $R_2PO2H$, wherein each R is independently a C6-C24 hydrocarbon group and can contain an unsaturated carbon-carbon bond.

Exemplary pyridines include, but are not limited to, pyridine, alkylated pyridines, nicotinic acid, and so forth.

Suitable alkenes include, e.g., octadecene and other C4-C24 hydrocarbons which are unsaturated.

Nanoparticle core or shell precursors can be represented as a M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo)(oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a C8-C20 alkyl amine). The X donor can include, for example, a phosphine chalcogenide, a bis(trialkylsilyl)chalcogenide, a dioxygen species, an ammonium salt, or a tris(trialkylsilyl)phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a $C_6$-$C_{20}$ alkyl diol or a $C_6$-$C_{20}$ aldehyde.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or C1-C8 alkyl or lower alkenyl.

The X donor is a compound capable of reacting with the M-containing salt to form a material with the general formula MX. The X donor is generally a chalcogenide donor or a phosphine donor, such as a phosphine chalcogenide, a bis(silyl)chalcogenide, dioxygen, an ammonium salt, or a tris(trialkylsilyl)phosphine. Suitable X donors include dioxygen, elemental sulfur, bis(trimethylsilyl)selenide ((TMS)$_2$Se), trialkyl phosphine selenides such as (tri-n-octylphosphine)selenide (TOPSe) or (tri-n-butylphosphine)selenide (TBPSe), trialkyl phosphine tellurides such as (tri-n-octylphosphine)telluride (TOPTe) or hexapropylphosphorustriamide telluride (HPPTTe), bis(trimethylsilyl)telluride ((TMS)$_2$Te), sulfur, bis(trimethylsilyl)

sulfide ((TMS)$_2$S), a trialkyl phosphine sulfide such as (tri-n-octylphosphine)sulfide (TOPS), tris(dimethylamino) arsine, an ammonium salt such as an ammonium halide (e.g., NH$_4$Cl), tris(trimethylsilyl)phosphide ((TMS)$_3$P), tris(trimethylsilyl)arsenide ((TMS)$_3$As), or tris(trimethylsilyl)antimonide ((TMS)$_3$Sb). In certain embodiments, the M donor and the X donor can be moieties within the same molecule.

Ligand Exchange Processes for Coating Nanoparticles

Provided herein are ligand exchange processes that permit efficient conversion of a conventional hydrophobic nanoparticle or population thereof into a water-dispersible and functionalized nanoparticle or population of nanoparticles. It also permits preparation of small nanoparticles which are highly stable and bright enough to be useful in biochemical and biological assays. The resulting nanoparticles can also be linked to a target molecule or cell or enzyme (e.g., polymerase) of interest.

Typically, the nanoparticle used for this process is a core/shell nanocrystal which is coated with a hydrophobic ligand such as tetradecylphosphonic acid (TDPA), trioctylphosphine oxide (TOPO), trioctyl phosphine (TOP), octylphosphonic acid (OPA), and the like, or a mixture of such ligands; these hydrophobic ligands typically have at least one long-chain alkyl group, i.e. an alkyl group having at least 8 carbons, or for the phosphine/phosphine oxide ligands, this hydrophobic character may be provided by two or three alkyl chains on a single ligand molecule having a total of at least 10 carbon atoms. Therefore, in some embodiments, the surface of the core/shell nanocrystal or population thereof can be coated with varying quantities of TDPA hydrophobic ligands prior to replacement with hydrophilic ligand(s). For example, TDPA can represent at least about 10%, at least about 20%, at least about 30%, at least about 40%, at least about 50%, at least about 80%, at least about 95%, at least about 98%, at least about 99% or more of the total surface ligands coating the core/shell nanoparticles. Moreover, certain hydrophobic ligands show an unexpected and apparent ease of replacement with the hydrophilic ligand. For example, nanoparticles with OPA on the surface have been observed to transfer into aqueous buffer more readily and more completely than the same type of core-shell with TDPA on the surface. Therefore, in some embodiments, the surface of the core/shell nanocrystal or populations thereof can be coated with varying quantities of OPA hydrophobic ligands prior to replacement with hydrophilic ligand(s). For example, OPA can represent at least about 10%, at least about 20%, at least about 30%, at least about 40%, at least about 50%, at least about 80%, at least about 95%, at least about 98%, at least about 99% or more of the total surface ligands coating the core/shell nanocrystal.

In one aspect, provided herein is a "one-step" ligand exchange process to apply various types of ligands to the surface of a nanoparticle, by substituting a desired hydrophilic ligand for a conventional hydrophobic ligand like TOPO, TOP, TDPA, OPA, and the like. The process steps, comprising: providing a nanocrystal coated with a surface layer comprising a hydrophobic ligand, and dissolved or dispersed in a non-aqueous solvent, contacting the nanocrystal dispersion with a phase transfer agent and an aqueous solution comprising a hydrophilic ligand, to form a biphasic mixture having an aqueous phase and a non-aqueous phase and maintaining the mixture under conditions that cause the nanocrystal to migrate from the non-aqueous solvent into the aqueous phase. See PCT Application Serial No. PCT/US09/53018 which is expressly incorporated herein by reference as if set forth in full.

The 'one-step' ligand exchange process described herein utilizes phase transfer catalysts which are particularly effective, and provide faster exchange reactions. Butanol has been utilized as a phase transfer catalyst for this type of exchange reaction; however, the reaction takes several days typically, and requires heating to about 70° C. The time for this reaction exposes the nanoparticles to these reaction conditions for a long period of time, which may contribute to some reduction in its ultimate stability. The embodiments disclosed herein provide more efficient conditions which achieve ligand exchange more rapidly, thus better protecting the nanoparticles. As a result of accelerating the exchange reaction and allowing use of milder conditions, these phase transfer catalysts produce higher quality nanoparticles.

The phase transfer agent for this process can be a crown ether, a PEG, a trialkylsulfonium, a tetralkylphosphonium, and an alkylammonium salt, or a mixture of these. In some embodiments, the phase transfer agent is 18-crown-6, 15-crown-5, or 12-crown-4. In some embodiments, the phase transfer agent is a PEG, which can have a molecular weight from about 500 to about 5000. In some embodiments, the phase transfer agent is a trialkylsulfonium, tetralkylphosphonium, or alkylammonium (including monoalkylammonium, dialkylammonium, trialkylammonium and tetralkylammonium) salt.

Tetralkylammonium salts are sometimes preferred as phase transfer agents. Examples of suitable tetralkylammonium salts include triethylbenzyl ammonium, tetrabutylammonium, tetraoctylammonium, and other such quaternary salts. Other tetralkylammonium salts, where each alkyl group is a C1-C12 alkyl or arylalkyl group, can also be used. Typically, counting all of the carbons on the alkyl groups of a trialkylsulfonium, tetralkylphosphonium, and alkylammonium salt, the phase transfer agent will contain a total of at least 2 carbons, at least 10 carbons and preferably at least 12 carbon atoms. Each of the trialkylsulfonium, tetralkylphosphonium, and alkylammonium salts has a counterion associated with it; suitable counterions include halides, preferably chloride or fluoride; sulfate, nitrate, perchlorate, and sulfonates such as mesylate, tosylate, or triflate; mixtures of such counterions can also be used. The counterion can also be a buffer or base, such as borate, hydroxide or carbonate; thus, for example, tetrabutylammonium hydroxide can be used to provide the phase transfer catalyst and a base. Specific phase transfer salts for use in these methods include tetrabutylammonium chloride (or bromide) and tetraoctylammonium bromide (or chloride).

Suitable hydrophilic ligands are organic molecules which provide at least one binding group to associate tightly with the surface of a nanocrystal. The hydrophilic ligand typically is an organic moiety having a molecular weight between about 100 and 1500, and contains enough polar functional groups to be water soluble. Some examples of suitable hydrophilic ligands include small peptide having 2-10 amino acid residues (preferably including at least one histidine or cysteine residue), mono- or polydentate thiol containing compounds.

Following ligand exchange, the surface layer can optionally be crosslinked.

In another aspect, provided herein is a "two-step" ligand exchange process to apply various types of ligands to the surface of a nanoparticle, by substituting a desired hydrophilic ligand for a conventional hydrophobic ligand like TOPO, TOP, TDPA, OPA, and the like. The process involves the removal of phosphonate or phosphinate ligands from the surface of a nanoparticle or nanocrystal by treatment with sulfonate reagents, particularly silylsulfonate derivatives of weak bases or other poorly coordinating groups.

The process steps, comprising: providing a nanocrystal whose surface comprises a phosphonate ligand, contacting the nanocrystal with a sulfonate reagent in an organic solvent, contacting the sulfonate ligand coated nanocrystal with a functionalized organic molecule (i.e., hydrophilic ligand)

comprising at least one nanocrystal surface attachment group, contacting the nanocrystal dispersion with an aqueous solution to form a biphasic mixture having an aqueous phase and a non-aqueous phase, and maintaining the biphasic mixture under conditions which cause the nanocrystal to migrate from the non-aqueous phase into the aqueous phase. See PCT Application Serial No. PCT/US09/59456 which is expressly incorporated herein by reference as if set forth in full.

The result of this removal of phosphonate ligands is replacement of the phosphonates with the weakly coordinating groups. One example is the use of silyl sulfonates, such as trimethylsilyl triflate, to form a sulfonate-coated nanoparticle. Triflate is a conventional/common name for a trifluoromethanesulfonyloxy group, $CF_3SO_2O$—.

The same type of replacement process can also occur on nanoparticles having phosphinic acid ligands of the formula $R_2P(=O)$—OH or on nanoparticles having carboxylic acid ligands of the formula $RC(=O)$—OH, which could be incorporated on the surface of a nanocrystal by known methods; R can be a $C_1$-$C_{24}$ hydrocarbon group in these phosphinates, and the two R groups can be the same or different. Thus, it is understood that when phosphonate-containing nanocrystals are described herein, phosphinate-containing nanocrystals can be used instead, with similar results.

This process provides a mild and selective method for removing phosphonate, phosphinate, and carboxylate ligands from the surface of a nanocrystal. As a result, it provides a way for a user to remove these groups and replace them, without removing other ligands which are not displaced or affected by the silylsulfonate.

The sulfonate ligands can comprise an alkyl or aryl moiety linked to —$SO_3X$, where X can represent whatever the sulfonate group is attached to. For example, where the sulfonate ligand is a sulfonate anion (i.e., triflate), X would represent a nanocrystal, or the surface of a nanocrystal. Some of the sulfonate embodiments disclosed herein can also be described with reference to feature 'A' of Formula I, as set forth below.

Examples of silylsulfonate ligands can include, but are not limited to: (trimethylsilyl)triflate, (triethylsilyl)triflate, (t-butyldimethylsilyl)triflate, (phenyldimethylsily)triflate, trimethylsilyl fluoromethanesulfonate, trimethylsilyl methanesulfonate, trimethylsilyl nitrophenylsulfonate, trimethylsilyl trifluoroethylsulfonate, trimethylsilyl phenylsulfonate, trimethylsilyl toluenesulfonate, diisopropylsilyl bis(trifluoromethanesulfonate), tertbutyldimethylsilyl trifluoromethanesulfonate, triisopropylsilyl trifluoromethanesulfonate and trimethylsilyl chlorosulfonate.

Examples of other sulfonate ligands can include, but are not limited to: trifluoromethanesulfonate (triflate), fluoromethanesulfonate, methanesulfonate (mesylate), nitrophenylsulfonate (nosylate), trifluorethylsulfonate, phenylsulfonate (besylate) and toluenesulfonate (tosylate).

Some suitable examples of the hydrophilic ligand are disclosed, for example, in Naasani, U.S. Pat. Nos. 6,955,855; 7,198,847; 7,205,048; 7,214,428; and 7,368,086. Suitable hydrophilic ligands also include imidazole containing compounds such as peptides, particularly dipeptides, having at least one histidine residue, and peptides, particularly dipeptides, having at least one cysteine residue. Specific ligands of interest for this purpose can include carnosine (which contains beta-alanine and histidine); His-Leu; Gly-His; His-Lys; His-Glu; His-Ala; His-His; His-Cys; Cys-His; His-Ile; His-Val; and other dipeptides where His or Cys is paired with any of the common alpha-amino acids; and tripeptides, such as Gly-His-Gly, His-Gly-His, and the like. The chiral centers in these amino acids can be the natural L-configuration, or they can be of the D-configuration or a mixture of L and D. Thus a dipeptide having two chiral centers such as His-Leu can be of the L,L-configuration, or it can be L,D- or D,L; or it can be a mixture of diastereomers.

Furthermore, suitable hydrophilic ligands can also include mono- or polydentate thiol containing compounds, for example: monodentate thiols such as mercaptoacetic acid, bidentate thiols such as dihydrolipoic acid (DHLA), tridentate thiols such as compounds of Formula II-VII as shown below, and the like.

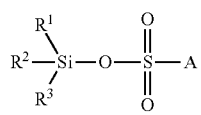

I wherein $R^1$, $R^2$, $R^3$ and A are each, independently, C1-C10 alkyl or C5-C10 aryl; and each alkyl and aryl is optionally substituted.

The alkyl groups for Formula I compounds are independently selected, and can be straight chain, branched, cyclic, or combinations of these, and optionally can include a C1-C4 alkoxy group as a substituent. Typically, the alkyl groups are lower alkyls, e.g., C1-C4 alkyl groups which are linear or branched. Methyl is one suitable example.

The aryl group for the compounds of Formula I can be phenyl, naphthyl or a heteroaryl having up to 10 ring members, and can be monocyclic or bicyclic, and optionally contain up to two heteroatoms selected from N, O and S as ring members in each ring. (It will be understood by those skilled in the art that the 5-membered aryl is a heteroaryl ring.) Phenyl is a preferred aryl group; and an aryl group is typically only present if the other organic groups on the silicon other than the sulfonate are lower alkyls, and preferably they are each Me.

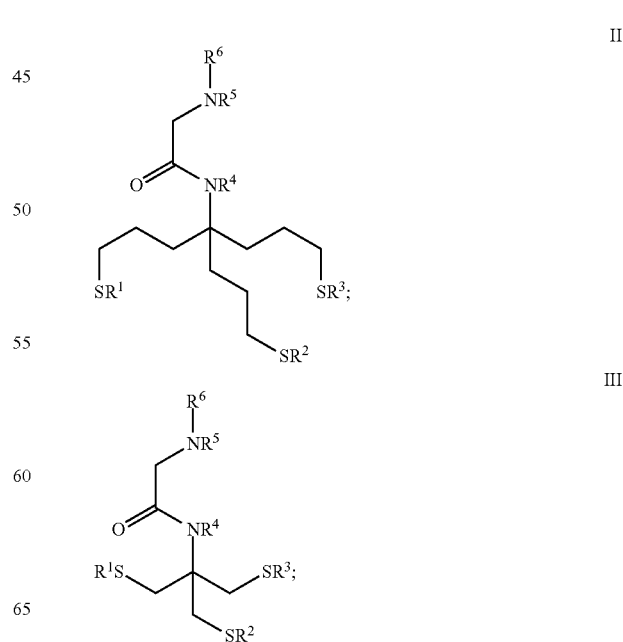

IV

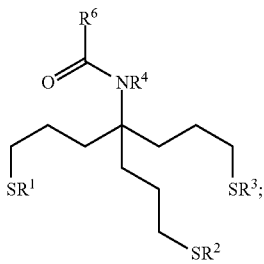

V

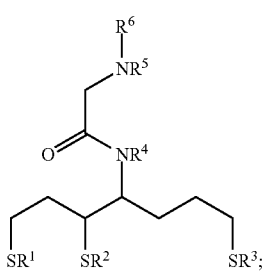

VI

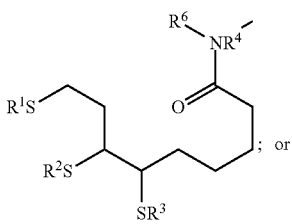

VII

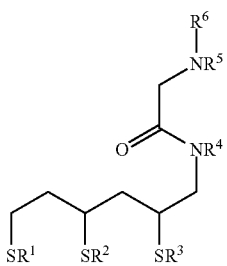

In compounds of Formula II-VII, $R^1$, $R^2$, $R^3$ can independently be H, halo, hydroxyl, $-(C=O)-C_1-C_{22}$, $-(C=O)CF_3$,) alkanoyl, $C_1-C_{22}$ alkyl, $C_1-C_{22}$ heteroalkyl, $((CO)OC_1-C_{22})$alkylcarbonato, alkylthio $(C_1-C_{22})$ or $-(CO)NH(C_1-C_{20})$ or $-(CO)N(C_1-C_{20})_2$)alkylcarbamoyl. In some embodiments, $R^1$, $R^2$, and $R^3$ are different. In other embodiments, $R^1$, $R^2$, and $R^3$ are the same.

In compounds of Formula II-VII, $R^4$, and $R^5$ can independently be H, $C_1-C_{20}$ alkyl, $C_6-C_{18}$ aryl, $C_1-C_{22}$ heteroalkyl or $C_1-C_{22}$ heteroaryl. In some embodiments, $R^4$ and $R^5$ are different. In other embodiments, $R^4$ and $R^5$ are the same.

In compounds of Formula II-VII, $R^6$ can be H or a polyethylene glycol based moiety of Formula VIII:

VIII

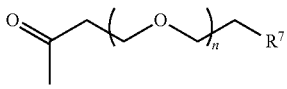

In certain embodiments of Formula VIII, $R^7$ can be $-NH_2$, $-N_3$, $-NHBoc$, $-NHFmoc$, $-NHCbz$, $-COOH$, $-COOt-Bu$, $-COOMe$, iodoaryl, hydroxyl, alkyne, boronic acid, allylic alcohol carbonate, $-NHBiotin$, $-(CO)NHNH-Boc$, $(CO)NHNHFmoc$ or $-OMe$. In some embodiments, n can be an integer from 1 to 100.

In still further embodiments, the tridentate thiol ligands can be a compound of Formula IX, X, XI, XII, XIII, XIV, XV, XVI, XVII, XVIII, XIX, XX, XXI, XXII, XXIII or XXIV:

IX

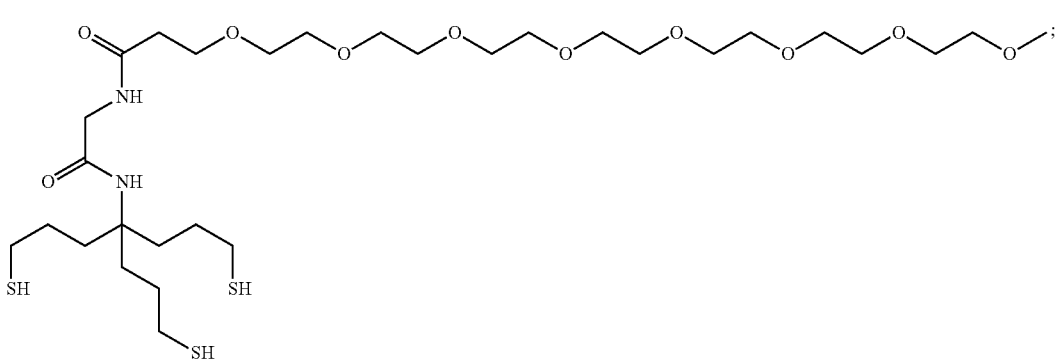

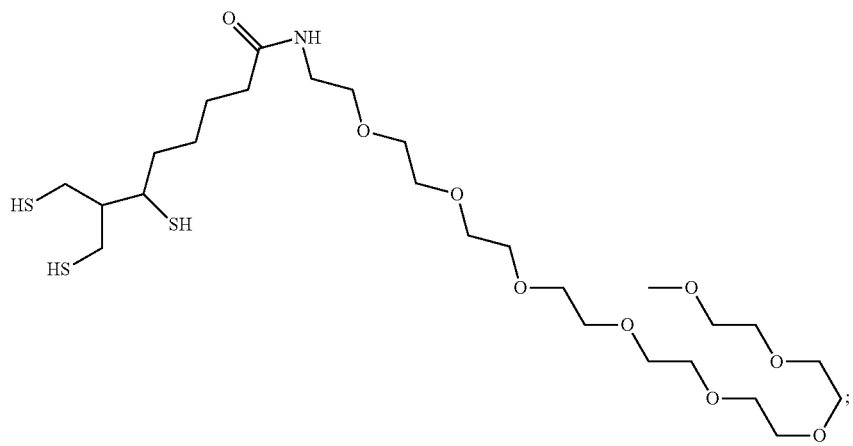
X
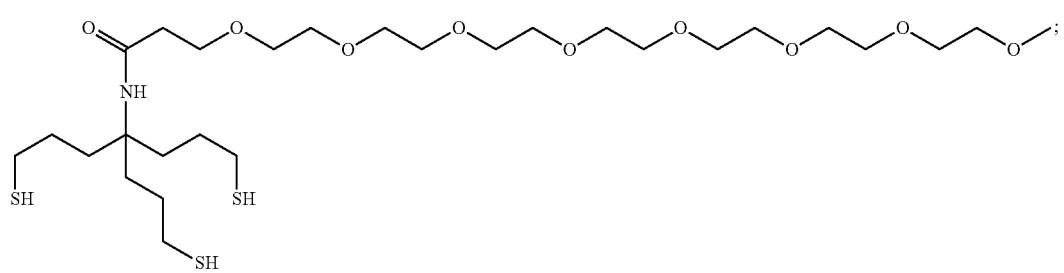
XI
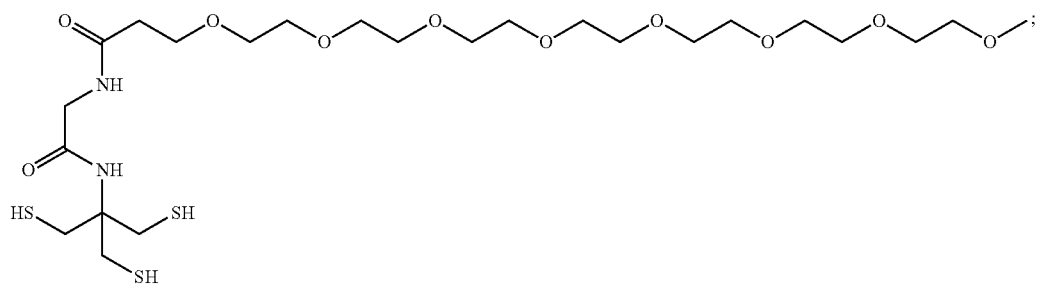
XII
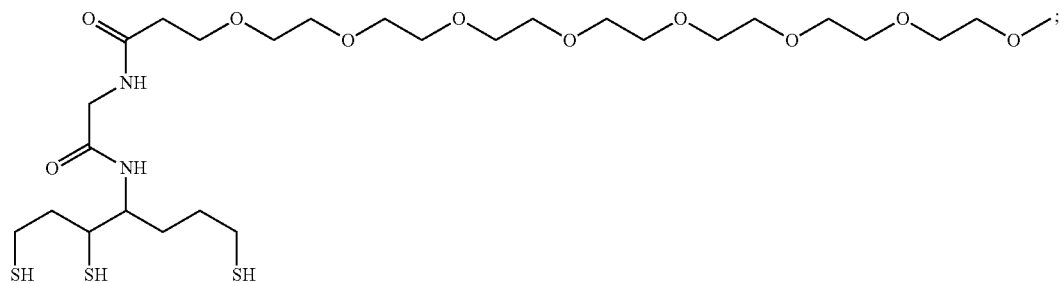
XIII
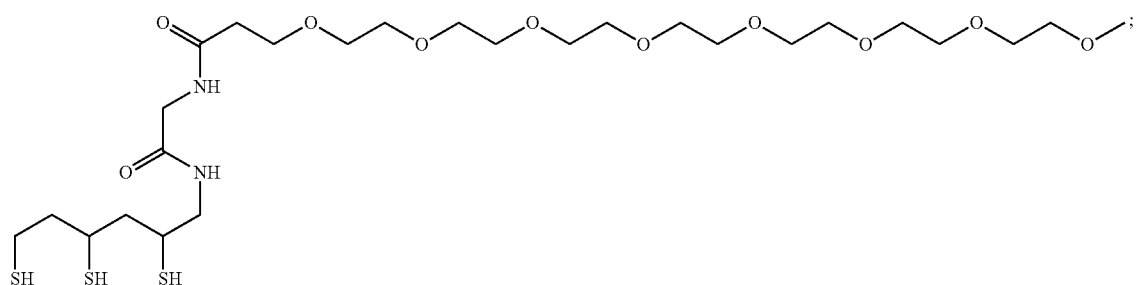
XIV

-continued
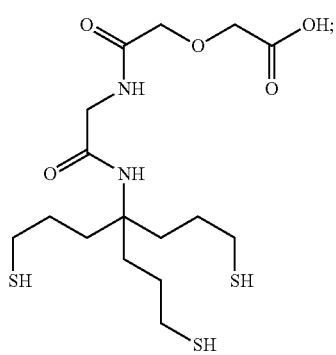 XV
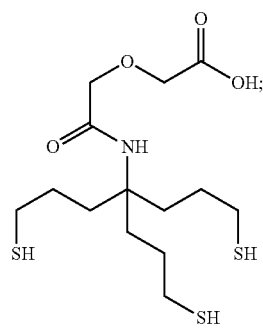 XVI
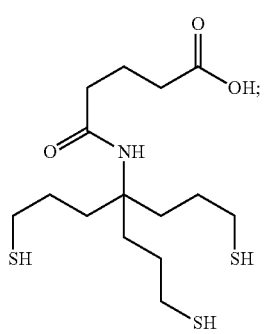 XVII
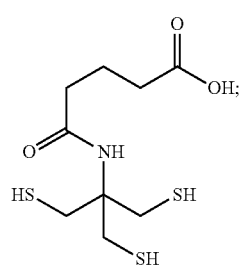 XVIII
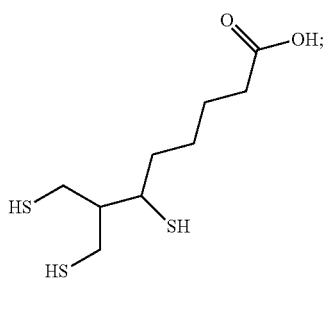 XIX
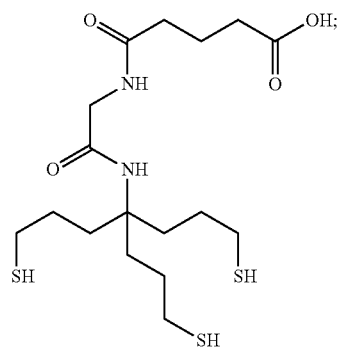 XX
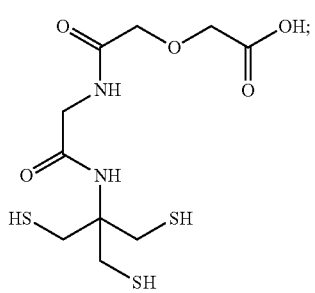 XXI
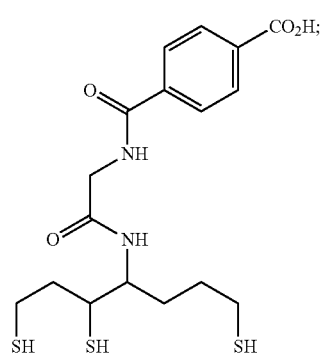 XXII -continued

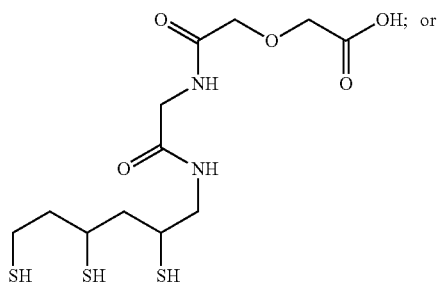

XXIII

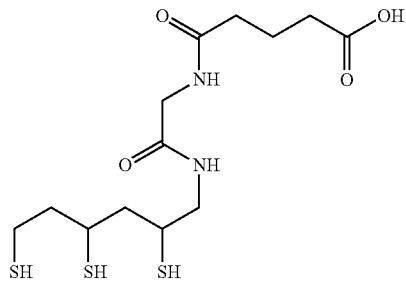

XXIV

Functionalized TDPA Ligands on Nanoparticles

Provided herein are methods for preparing water-soluble semi-conducting, insulating, or metallic nanoparticles including the steps of admixing one or more nanocrystal precursors and one or more multi-functional surface ligands with a solvent to form a solution and heating the solution to a suitable temperature, and in certain embodiments, methods may include the steps of admixing nanocrystal cores, one or more nanocrystal precursors, and one or more multi-functional surface ligands with a solvent to form a solution and heating the solution to a suitable temperature. In such embodiments, the one or more multi-functional surface ligands may at least include a nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the nanoparticles produced by the methods of such embodiments may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See for example PCT Application Serial No. PCT/US09/59117 filed Sep. 30, 2009 which are expressly incorporated herein by reference as if set forth in full.

In some embodiments, the one or more signals indicative of nucleotide incorporation can be detected to permit visualization of polymerase activity. In some embodiments, such visualization happens in real time or near real time. In some embodiments, the signal can be an optically detectable signal. In some embodiments, the optically detectable signal can be a fluorescent signal or a nonfluorescent signal.

In some embodiments, one or more labels must be excited before they can be visualized. In some embodiments, illumination of the reaction site permits observation of the signals, e.g., FRET signals, which indicate the nucleotide incorporation event. In some embodiments, the optical system comprises at least two elements, namely an excitation source and a detector. The excitation source generates and transmits incident radiation used to excite the reactants contained in the array. Depending on the intended application, the source of the incident light can be a laser, laser diode, a light-emitting diode (LED), a ultra-violet light bulb, and/or a white light source. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously.

The one or more signals indicative of nucleotide incorporation can be detected and analyzed using any suitable methods and related devices. Typically, the optical system will achieve these functions by generating and transmitting an incident wavelength to the polynucleotides isolated within nanostructures, and collecting and analyzing the emissions from the reactants.

In some embodiments, detection is simplified by placing one or few polymerase and nucleic acid molecules in a sufficiently small volume such that background signal from non-incorporated nucleotides is minimized. This can be done, for example, by isolating, confining or immobilizing a single polymerase, or a single template nucleic acid molecule, in an optical confinement such as a zero-mode waveguide. In some embodiments, the polymerase and/or template nucleic acid molecule can be placed within a nanochannel. In some embodiments, the nanochannel can be structured to permit isolation and/or elongation of individual nucleic acid molecules.

Exemplary labeling and detection strategies for use with one or more of the modified polymerases disclosed herein include, but are not limited to, those disclosed in U.S. Pat. Nos. 6,423,551 and 6,864,626; U.S. Published Application Nos. 2005/0003464, 2006/0176479, 2006/0177495, 2007/0109536, 2007/0111350, 2007/0116868, 2007/0250274 and 2008/08825. A wide variety of detectors are available in the art. Representative detectors include but are not limited to optical readers, high-efficiency photon detection systems, photodiodes (e.g. avalanche photo diodes (APD); APD arrays, etc.), cameras, charge couple devices (CCD), electron-multiplying charge-coupled device (EMCCD), intensified charge coupled device (ICCD), photomultiplier tubes (PMT), a multi-anode PMT, and a confocal microscope equipped with any of the foregoing detectors. Where desired, the subject arrays can contain various alignment aides or keys to facilitate a proper spatial placement of each spatially addressable array location and the excitation sources, the photon detectors, or the optical transmission element as described below.

In some embodiments, the detection system comprises: excitation illumination, optical transmission elements, detectors, and/or computers. In some embodiments, the detection system can comprise excitation illumination which can excite the energy transfer or reporter moieties which produce a signal. The excitation illumination can be electromagnetic energy, such as radio waves, infrared, visible light, ultraviolet light, X-rays or gamma rays. The source of the electromagnetic radiation can be a laser, which possesses properties of mono-chromaticity, directionality, coherence, polarization, and/or intensity. The laser can produce a continuous output beam (e.g., continuous wave laser) or produce pulses of light (e.g., Q-switching or mode-locking). The laser can be used in a one-photon or multi-photon excitation mode. The laser can produce a focused laser beam. The wavelength of the electromagnetic radiation can be between about 325-840 nm, or between about 325-752 nm, or between about 330-752 nm, or between about 405-752 nm.

In some embodiments, the detection system comprises suitable optical transmission elements that are capable of transmitting light from one location to another with the desired refractive indices and geometries. The optical transmission elements transmit the excitation illumination and/or the emitted energy in an unaltered or altered form. The optical transmission elements include: lens, optical fibers, polarization filters (e.g., dichroic filters), diffraction gratings (e.g., etched diffraction grating), arrayed waveguide gratings (AWG), optical switches, mirrors, dichroic mirrors, dichroic beam splitter, lenses (e.g., microlens and nanolens), collimators, filters, prisms, optical attenuators, wavelength filters (low-pass, band-pass, or high-pass), wave-plates, and delay lines, or any combination thereof.

In some embodiments, spectral detection can also be combined and/or replaced by other detection methods capable of discriminating between chemically similar or different labels in parallel, including, but not limited to, polarization, lifetime, Raman, intensity, ratiometric, time-resolved anisotropy, fluorescence recovery after photobleaching (FRAP) and parallel multi-color imaging. See, for example, Lakowitz, supra. In the latter technique, use of an image splitter (such as, for example, a dichroic mirror, filter, grating, prism, etc.) to separate the spectral components characteristic of each label allows the same detector, typically a CCD, to collect the images in parallel.

In some embodiments, multiple cameras or detectors can be used to view the sample through optical elements (such as, for example, dichroic mirrors, filters, gratings, prisms, etc.) of different wavelength specificity. Other suitable methods to distinguish emission events include, but are not limited to, correlation/anti-correlation analysis, fluorescent lifetime measurements, anisotropy, time-resolved methods and polarization detection.

Suitable imaging methodologies that can be implemented for detection of emissions include, but are not limited to, confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, multi-foci multi-photon, and/or other forms of microscopy.

In some embodiments, the detection system can include one or more optical transmission elements that serve to collect and/or direct the incident wavelength to the reactant array; to transmit and/or direct the signals emitted from the reactants to the photon detector; and/or to select and modify the optical properties of the incident wavelengths or the emitted wavelengths from the reactants. Illustrative examples of suitable optical transmission elements and optical detection systems include but are not limited to diffraction gratings, arrayed wave guide gratings (AWG), optic fibers, optical switches, mirrors, lenses (including microlens and nanolens), collimators. Other examples include optical attenuators, polarization filters (e.g., dichroic filters), wavelength filters (low-pass, band-pass, or high-pass), wave-plates, and delay lines. Examples of a suitable sequencing and detection systems that may be used according to the present disclosure include, for example, U.S. Provisional Application Nos. 61/077,090, filed Jun. 30, 2008; 61/089,497, filed Aug. 15, 2008; 61/090,346, filed Aug. 20, 2008; and 61/164,324, filed Mar. 27, 2009.

All of the compositions and methods disclosed and claimed herein can be made and executed without undue experimentation in light of the present disclosure. While the compositions and methods of this invention may have been described in terms of specific examples or preferred embodiments, these examples and embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLES

Example 1

Production of a Polynucleotide Encoding an Exemplary Modified Polymerase

Figure 2:
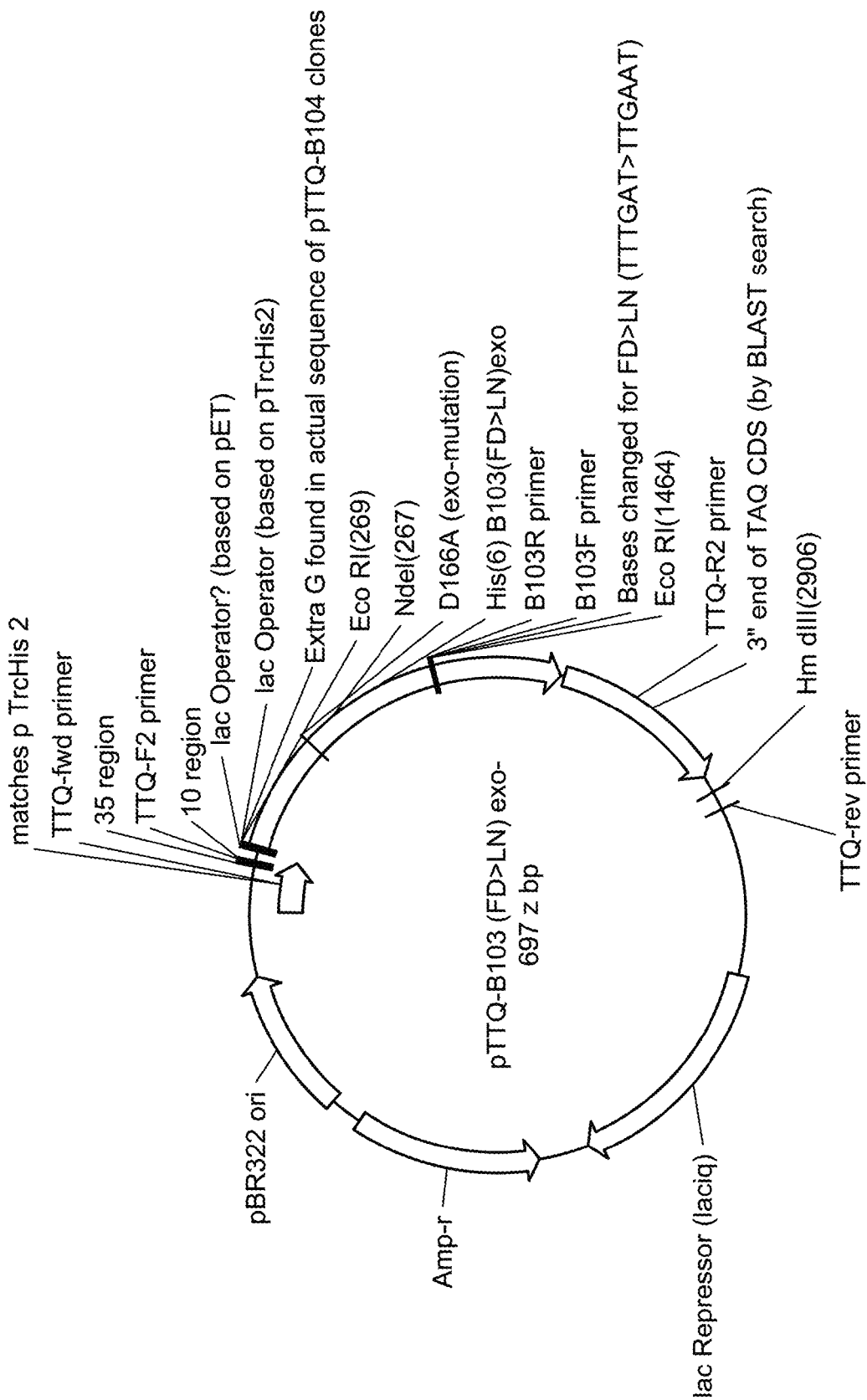
FIG. 2 depicts an expression vector, pTTQ-B104-exo minus, comprising the amino acid sequence of SEQ ID NO: 8 fused downstream of an isopropyl β-D-1-thiogalactopyranoside (IPTG) promoter in the expression vector pTTQ.

This example illustrates the production of a polynucleotide encoding an exemplary modified polymerase comprising the amino acid sequence of SEQ ID NO: 7. A nucleotide sequence encoding a B103 polymerase having the amino acid sequence of SEQ ID NO: 6 was synthesized and cloned into a suitable expression vector. The recombinant expression construct was transformed into a suitable bacterial strain, and transformants were picked and screened for expression of the recombinant protein. The mutations F383L and D384N were introduced via site-directed mutagenesis according to standard methods, thereby generating a nucleotide sequence encoding a modified polymerase comprising the amino acid sequence of SEQ ID NO: 7 cloned into the expression vector pTTQ. FIG. 2 provides an exemplary depiction of this expression vector comprising an open reading frame comprising the amino acid sequence of SEQ ID NO: 7 (referred to in FIG. 2 as "B104").

Example 2

Purification of an Exemplary Modified Polymerase

To obtain a purified preparation of the modified polymerase protein, a highly expressing clone was selected and cultured to a cell density of 0.5 OD at 37° C. The culture was shifted to 18° C. At OD 0.6, expression of the recombinant protein was induced by the addition of IPTG to a final concentration of 0.5 or 1 mM, and the culture was grown for an additional 18 hours. Cells were harvested by differential centrifugation. The yield was approximately 5 g cells/liter. The cell pellets were frozen at −80° C. until processed. Unless otherwise indicated, all subsequent steps were performed on ice or at 4° C. To purify the modified polymerase, cell pellets were resuspended in 5-10 ml lysis buffer (50 mM Tris pH 7.5, 50 mM glucose, 0.1 mM EDTA pH 8.0, 0.05% Tween-20, 1 mM DTT) per gram of cell paste. The cells were lysed under high pressure using a Microfluidizer, M110 (Microfluidics Corp, Boston, Mass.). Streptomycin sulfate (50% solution in 50 mM Tris pH 7.5) was added to the lysate to a final concentration of 2% while stirring on ice. The lysate was stirred for 30 minutes. The cell debris was pelleted by centrifugation at 10,000 rpm in a SLC1500 rotor for 30 minutes. The pellets were discarded. A 10% solution of polyethyleneimine (pH 7.5) was added to the lysate, drop wise, to a final concentration of 0.2% while stiffing on ice. The lysate continued stirring for 30 minutes and then centrifuged as described previously. The supernatant was returned to the ice bath. Solid ammonium sulfate was added to the stirring supernatant to a final concentration of 65% ammonium sulfate saturation (43 grams/100 mls lysate). The sample was stirred for an additional one hour. The precipitated proteins were collected by centrifugation in an SS34 rotor for 30 minutes at 15,000 rpm. The supernatant was discarded. The precipitated protein pellets were stored at −20° C.

The pellets were also subjected to affinity purification using a His-TRAP FF (GE Healthcare). One 5 ml His-TRAP FF column was equilibrated in HIS Buffer A (25 mM Hepes pH 7.5, 500 mM NaCl, 1 mM DTT) and 5% His Buffer B (25 mM Hepes pH 7.5, 500 mM NaCl, 1 mM DTT, 500 mM imidazole pH 7.5) on an AKTA 10S (GE Healthcare). The ammonium sulfate pellets were resuspended in resuspension buffer (25 mM Hepes pH 7.5, 500 mM NaCl, 1 mM DTT, 25 mM imidazole). Each sample was filtered with a 1 µM filter (Acrodisc) and then applied to the His-TRAP column with a P960 pump. The sample was eluted from the column with a 12-70 column volume gradient of His Buffer B ranging from 5% to 100%. 1.8 ml fractions were collected. An aliquot of each fraction was subjected to SDS PAGE to determine which fractions contained the purest expressed protein (SDS PAGE: 10% NuPage, MES).

The protein-containing fractions were pooled and diluted using HIS Buffer A to a conductivity of 17 millisiemens/cm. The diluted solution was then subjected to affinity purification using a Heparin column. A Poros HE50 column (10 mm×100 mm; 7.8 mls, Applied Biosystems) was equilibrated in HE Buffer A (25 mM Hepes pH 7.5, 1 mM DTT, 0.05% Tween 20) containing 10% HE Buffer B (25 mM Hepes pH 7.5, 1M NaCl, 1 mM DTT, 0.05% Tween 20) on the AKTA10S. Fractions from the His-trap column containing the purest protein as judged by SDS PAGE, were pooled and diluted with HE Buffer A to ~12-20 mS/cm. The sample (~250 ml) was loaded onto the HE column at 10 mls a minute with the P960 pump. The proteins were eluted from the column with a 20 column volume gradient from 10% to 100% HE Buffer B at flow rate of 8 ml/min (156 ml) and 4 ml fractions were collected. An aliquot of each fraction was subjected to SDS PAGE to determine the fractions that contained the purest fraction of the expressed protein (SDS PAGE: 10% NuPage, MES).

The purest protein samples (as determined by SDS PAGE) were pooled and dialyzed overnight against Storage Buffer (10 mM Tris pH 7.5, 100 mM NaCl, 0.1 mM EDTA, 1 mM DTT, 50% glycerol). The concentration of the dialysates was then determined by UV spectroscopy. The dialyzed protein was diluted 1:10 or 1:20 in buffer containing 10 mM Tris pH 7.5, 0.1 mM EDTA, 100 mM NaCl; 25% glycerol. A UV wavelength scan from 220 nm to 320 nm was performed using a DU780 spectrometer (Beckman). The protein concentration was determined from the average of three readings at 280 nM. The molar extinction coefficient as determined by the Vector NTI package (Invitrogen, Life Technologies) is 98,130 $M^{-1}$ $cm^{-1}$ and the predicted molecular weight was 67,717.

Example 3

Characterization of Extension Activity and Nucleotide Incorporation Activity of Exemplary Reference and Modified Polymerases The fractional extension activity of an exemplary modified polymerase having the amino acid of SEQ ID NO: 8 (referred to as "B104(exo-)" in FIG. 3) was measured and compared to the fractional extension activities of two different exemplary reference polymerases, including an RB69 reference polymerase comprising the amino acid sequence SEQ ID NO: 15 and a His-tagged Phi-29 reference polymerase comprising the amino acid sequence of SEQ ID NO: 20 (referred to herein as "HP1 polymerase"). All polymerases were prepared according to the method of Example 1. Both modified and reference polymerases were evaluated and compared in an assay to measure the fractional extension activity of each polymerase, i.e., the fraction of nucleic acid templates that are extended by at least one nucleotide in a polymerase reaction. In this assay, the fractional extension activity of a polymerase is defined as the fraction (measured as a percentage fraction) of nucleic acid templates that are extended by at least one nucleotide by the test or reference polymerase under the following reaction conditions: 50 mM Tris, pH 7.0, 50 mM NaCl, 1 mM $MnCl_2$, 1 µM dNTP, 330 nM enzyme, 100 nM primer-template duplex and 0.5% BSA, wherein the extension is performed at room temperature for 10 seconds.

The primer-template duplex was formed by annealing the following polynucleotides:

```
                                   (SEQ ID NO: 21)
        5'-GGTACTAAGCGGCCGCATG-3'  ("TOP")
```

This primer comprises a fluorescein moiety linked to the 5' terminal nucleotide.

```
                                       (SEQ ID NO: 22)
    3'-CCATGATTCGCCGGCGTACTTTTTTT-5' ("BOT T6T")

(SEQ ID NO: 23)
    3'-CCATGATTCGCCGGCGTACAAAAAAA-5' ("BOT A6A")
```

```
                                           (SEQ ID NO: 24)
3'-CCATGATTCGCCGGCGTACCCCCCCC-5' ("BOT C6C")

(SEQ ID NO: 25)
3'-CCATGATTCGCCGGCGTACGGGGGGG-5' ("BOT G6G")
```

Annealing of the primer of SEQ ID NO: 21 with any of the templates of SEQ ID NOS: 22-25 results in formation of a non-extendible duplex comprising a 7-nucleotide overhang.

The polymerase reaction products were resolved using PAGE electrophoresis. The extended products were visualized by scanning the gel with a Bio-Rad Imager for fluorescence emissions at 488 nm. The results are depicted in FIG. 3. As shown in FIG. 3, the fractional extension activity (as measured by both intensity and length of products, as well as by reduced intensity of starting material) of a modified polymerase comprising the amino acid sequence of SEQ ID NO: 8 was observed to be higher than the fractional extension activity of the reference RB69 polymerase comprising the amino acid sequence of SEQ ID NO: 15 and of the reference His-tagged Phi-29 polymerase comprising the amino acid sequence of SEQ ID NO: 20.

Example 4

Characterization of Exonuclease Activity of Exemplary Reference and Modified Polymerases An assay comparing the endogenous exonuclease activity of a reference polymerase, T7 DNA polymerase, with the exonuclease activity of a polymerase comprising the amino acid of SEQ ID NO: 7, was performed. Exonuclease activity was measured by incubating 2, 4 or 10 µg of each enzyme sample with 7.5 µL Invitrogen Low Mass ladder, (10068-013) in a 50 µL reaction containing 10 mM Tris, pH 7.5, 50 mM NaCl and 10 mM MgCl$_2$ for 16 hours at 37° C. in an ABI 9700 PCR machine. The samples were resolved via electrophoresis on a 1.2% E-Gel (Life Technologies). The extent of exonuclease activity was estimated by visually assessing the disappearance of the bands of the Low Mass ladder, as compared to negative control reactions, to which water ("W") or enzyme storage buffer ("SB") was added instead of purified polymerase). T7 DNA polymerase served as the reference polymerase (positive control, indicated as "+ control" in FIG. 4. The amount of protein added to each reaction is indicated at the top of each well. (2, 4, 10 µg protein, or water ("W") or storage buffer ("SB") for negative control lanes) As shown in FIG. 4, both the reference and modified polymerases exhibited comparable levels of exonuclease activity.

To determine if the product contained single-strand DNase (ssDNase) activity that could result from contaminating polypeptides, the enzyme was tested with AMBION DNase Alert according to manufacturer's instructions (AM1970, Applied Biosystems). The fluorescently labeled DNase Alert substrate (suspended in TE) (10 µL), the supplied 10× buffer, and increasing concentrations of the test enzyme were combined in a final volume of 100 µL. The samples were read in a Molecular Devices Plate reader at 485/590 excitation/emission for 60 min at 37° C. No detectable fluorescence was recorded. DNase I served as a positive control. No ssDNase activity was observed in either control or sample reactions (results not shown). Exemplary results are depicted in FIG. 4.

Example 5

Characterization of Nanoparticle Tolerance of Exemplary Reference and Modified Polymerases The nanoparticle tolerance of exemplary modified and reference polymerases was measured and compared. The nucleotide incorporation activity of an exemplary modified polymerase comprising the amino acid sequence of SEQ ID NO: 19 and further comprising the amino acid substitution D175A was measured both in the absence and presence of equimolar amounts of a test nanoparticle. The results were compared to those of an exemplary reference Phi-29 polymerase comprising the amino acid sequence of SEQ ID NO: 20.

Primer extension activity was measured using an assay wherein free pyrophosphate released as a result of extension of a primer:template duplex is detected as a fluorescent product. Reaction conditions included 50 mM Tris, pH 7.5, 50 mM NaCl, 5 mM DTT, 100 nM polymerase, 100 nM hairpin-template, and 2 mM MnCl$_2$ at 23° C., either with or without 100 nM of nanoparticle added to the mixture. Individual reactions were set up in microtiter plate wells and initiated by the addition of 2 µl of 100 µM terminally-labeled nucleotide. The resulting fluorescence emissions were monitored as a function of time using a plate reader (Molecular Devices, SpectraMax M5). Reactions without nucleotides were also monitored as negative controls. Reactions were monitored for 20 minutes or until the samples reached saturation.

Exemplary results are depicted in FIG. 5, which provides a graph of relative fluorescence observed in each sample (RFU, arbitrary units, Y axis) against time (seconds, X axis). The various fluorescence traces depicted in FIG. 5 are as follows: solid circles and solid squares (two curves along X axis): fluorescence traces of negative control reactions lacking polymerase and including or not including nanoparticles; open diamonds: reaction including a reference Phi-29 polymerase comprising the amino acid sequence of SEQ ID NO: 1 and further comprising the amino acid substitution N62D (Φ29(exo-)) and including nanoparticles; open squares and open circles: modified polymerase comprising the amino acid sequence of SEQ ID NO: 19, including and not including nanoparticles, respectively. Primer extension activity was measured as the average slope of the curve obtained by plotting fluorescence (RFU) vs. time (seconds, X axis) between the zero time point and at 5 minutes. The primer extension activity in the presence and absence of dots was computed. Nanoparticle tolerance is determined as the percentage of primer extension activity, measured in the presence of test nanoparticle, relative to the amount of primer extension activity observed in the absence of the test nanoparticle. These slope values for each fluorescence trace are depicted below the graph in FIG. 5.

According to the results of FIG. 5, the modified polymerase of SEQ ID NO: 19 exhibits approximately 10% loss in primer extension activity in the presence of equimolar amounts of the test nanoparticle (i.e., 90% nanoparticle tolerance under these defined reaction conditions), as compared to a 50% loss in primer extension activity exhibited by the reference Phi-29 polymerase under identical test conditions (i.e., 50% nanoparticle tolerance exhibited by the Phi-29 polymerase under these defined reaction conditions).

Example 6

Characterization of Photostability of Exemplary Reference and Modified Polymerases The photostability of an exemplary reference polymerase comprising a His-tagged version of Phi-29 polymerase ("HP1; see, e.g., U.S. Provisional Application No. 61/184,770, filed Jun. 5, 2009 for disclosure of HP1 sequence and purification) comprising the amino acid sequence of SEQ ID NO: 20, and an exemplary modified polymerase comprising the amino acid sequence of SEQ ID NO: 19 and further comprising the amino acid substitution D175A were characterized by measuring the amount of primer extension observed in each sample prior to and following exposure to excitation radiation at 405 nm Reactions (100 μL) containing 50 mM Tris, pH 7.5, 50 mM NaCl, 1 mM DTT, 2 mM MnCl$_2$, 0.3% BSA, 10-200 nM polymerase and 100 nM nanoparticles (or premade polymerase-nanoparticle conjugates; see, e.g., U.S. Provisional Application No. 61/184,770 filed Jun. 5, 2009), and 100 nM 5'-[$^{32}$P]-labeled templates or 5'-TAMRA-labeled templates were prepared with and without the Oxygen Scavenging System (OSS). The OSS consists of 0.1 mg/ml Glucose Oxidase (Sigma, Catalog #G3660-1CAP), 2 units/μl Katalase (Fluka, Catalog #02071), 2 mM Trolox, and 0.5% glucose (added just prior to illuminations with 405 laser). Aliquots (4 μL) were added to a quartz cuvette having a path length of 1.5 mm and a height of 15 mm (Hellma, 105.252-QS) and illuminated with a 405 nm laser for a specified time and at specified power levels. After illumination, samples were removed and placed on ice until extensions were performed at 23° C. The extensions were performed by addition of 5 μM nucleotide hexaphosphates comprising a hexaphosphate moiety linked to the 3' carbon of the sugar moiety, and further comprising a 6-carbon linker attached to the terminal phosphate but without any fluorescent label. Extensions were performed for 30 seconds followed by termination with loading buffer (90% formamide, 10 mM EDTA). Samples were resolved on denaturing polyacrylamide gels (8M urea, 20% polyacrylamide) and exposed to phosphorimager screen. Representative results are provided in FIG. 6A. Polymerase activity was quantified as the % of extended primer (as compared to the total starting amount of primer), as measured by densitometric analysis. Phototoxicity is quantified by measuring the percent decrease in polymerase activity that occurs when samples are illuminated compared to non-illuminated samples. The photostability is quantified by subtracting the observed photosensitivity from 100.

FIG. 6B shows the % activity retained (Y axis) after 30 seconds of exposure to radiation of various intensities (X axis, W/cm$^2$). As shown in FIG. 6B, the modified polymerase comprising the amino acid sequence of SEQ ID NO: 19 and the amino acid substitution D175A (solid diamonds) retained 80-90% activity following exposure at 50 W/cm2, whereas the reference Phi-29 polymerase comprising the amino acid sequence of HP1 (solid squares) retained less than 40% activity.

Example 7

Characterization of $t_{-1}$ Values of Exemplary Reference and Modified Polymerases In this example, the $t_{-1}$ values of an exemplary modified polymerase comprising the amino acid of SEQ ID NO: 8 and an exemplary reference polymerase comprising the amino acid sequence of SEQ ID NO: 20 were measured and compared. These kinetic parameters were evaluated using an assay system wherein mixtures comprising a test polymerase and a primer:template duplex were mixed in a stopped-flow assay with nucleotides. To measure $t_{-1}$, the primer used to form the primer:template duplex was a non-extendible primer including a dideoxynucleotide at its 3' end, and the template was a synthetic DNA template comprising a donor Alexa Fluor 546 moiety at its 5' end. This primer-template duplex was preincubated with a test polymerase and a terminally-labeled nucleoside hexaphosphate or tetraphosphate ("ωdN4P" or "ωdN6P", respectively) to form an E•DNA•ωdN4P or E•DNA•ωdN6P ternary complex. These terminally-labeled nucleotides comprise terminal-phosphate-labeled nucleotides having an alkyl linker with a functional amine group attached to the dye. The ternary complex was mixed with unlabeled nucleotides in a stopped-flow experiment, and the resulting fluorescence was monitored as described below. Unless noted otherwise, all concentrations refer to the initial concentrations prior to mixing. All experiments were carried out in 50 mM Tris pH 7.5, 50 mM NaCl, 4 mM DTT, 2 mM MnCl$_2$ and 0.2% BSA ("extension buffer") using an Applied Photophysics SX20 stopped-flow spectrometer (Applied Photophysics, London, U.K.).

To prepare the primer:template duplex, 20 μM of primer and 20 μM of template were mixed in solution. The solution was heated to 90° C. for 5 minutes and then cooled stepwise in a thermocycler to 4° C. at a rate of 1° C. every 18 seconds. Five different primer:template duplexes were prepared, each comprising a different template sequence as described below.

The nucleotide sequence of the primer was as follows:

(SEQ ID NO: 26)
5'-GCC TCG CAG CCG TCC AAC CAA CTC$^{dd}$C-3' where $^{dd}$C indicates a dideoxycytosine triphosphate moiety. This sequence is referred to as "dd-Top-25-mer".

Four different templates were tested in separate assays. The nucleotide sequence of the first template was as follows:

(SEQ ID NO: 27)
AF546-5'-CAG TAA CGG AGT TGG TTG GAC GGC TGC GAG GC-3' where AF546 indicates an Alexa Fluor 546 moiety. This sequence is referred to as "dd-Template C-32-mer".

The nucleotide sequence of the second template was as follows:

(SEQ ID NO: 28)
AF546-5'-CAG TAA GGG AGT TGG TTG GAC GGC TGC GAG GC-3' where AF546 indicates an Alexa Fluor 546 moiety. This sequence is referred to as "dd-Template G-32-mer".

The nucleotide sequence of the third template was as follows:

(SEQ ID NO: 29)
AF546-5'-CAG TAA AGG AGT TGG TTG GAC GGC TGC GAG GC-3' where AF546 indicates an Alexa Fluor 546 moiety. This sequence is referred to as "dd-Template A-32-mer".

The nucleotide sequence of the fourth template was as follows:

(SEQ ID NO: 30)
AF546-5'-CAG TAA TGG AGT TGG TTG GAC GGC TGC GAG GC-3' where AF546 indicates an Alexa Fluor 546 moiety. This sequence is referred to as "dd-Template T-32-mer".

Annealing of the primer of SEQ ID NO: 25 with any of the templates of SEQ ID NOS: 26-30 results in formation of a non-extendible duplex comprising a 7-nucleotide overhang.

Preincubated mixtures comprising 200 nM of a primer:templex duplex, 660 nM of test polymerase, and 14 µM of ωdN4P were prepared and then mixed with a solution comprising the unlabeled cognate nucleotide (50 µM) in a stopped-flow apparatus. The fluorescence at both 546 nm and 647 nm was monitored following mixing. The averaged stopped-flow fluorescence traces were fitted with a single exponential function having the form of Equation (1) to extrapolate the $t_{-1}$ value of the test polymerase. Using the above procedure, the estimated $t_{-1}$ values of an exemplary modified polymerase comprising the amino acid sequence of SEQ ID NO: 8 and an exemplary reference polymerase comprising the amino acid sequence of SEQ ID NO: 1 were determined to be comparable (data not shown).

Example 8

Characterization of $t_{pol}$ Values of Exemplary Reference and Modified Polymerases In this example, the $t_{pol}$ values of an exemplary modified polymerase comprising the amino acid of SEQ ID NO: 8 and was measured and compared to the $t_{pol}$ value of an exemplary reference polymerase comprising the amino acid sequence of SEQ ID NO: 20. These kinetic parameters were evaluated using a stopped-flow assay wherein a mixture comprising an extendible dye-labeled primer:template duplex and test polymerase was mixed with a solution comprising terminally-labeled nucleotide tetraphosphates or terminally-labeled nucleotide hexaphosphates. These terminally-labeled nucleotides comprise terminal-phosphate-labeled nucleotides having an alkyl linker with a functional amine group attached to the dye. The fluorescence of the resulting mixture was monitored over time. Unless noted otherwise, all concentrations refer to the initial concentrations prior to mixing. All experiments were carried out in 50 mM Tris pH 7.5, 50 mM NaCl, 4 mM DTT, 2 mM MnCl$_2$ and 0.2% BSA ("extension buffer") using an Applied Photophysics SX20 stopped-flow spectrometer (Applied Photophysics, London, U.K.).

The primer-template duplex comprised an extendible primer annealed to a synthetic DNA template comprising a donor Alexa Fluor 546 moiety at its 5' end. To prepare the primer:template duplex, 20 µM of primer and 20 µM of template were mixed in solution. The solution was heated to 90° C. for 5 minutes and then cooled stepwise in a thermocycler to 4° C. at a rate of 1° C. every 18 seconds.

The nucleotide sequence of the primer was as follows:

```
                                      (SEQ ID NO: 31)
5'-GTT GCA AAG GAG CGG GCG-3'
```

Four different templates were prepared and tested in separate assays. The nucleotide sequence of the first template was as follows:

```
                                      (SEQ ID NO: 32)
AF546-5'-CGT TCC CCG CCC GCT CCT TTG CAA C-3'
``` where AF546 indicates an Alexa Fluor 546 moiety.
The nucleotide sequence of the second template was as follows:

```
                                      (SEQ ID NO: 33)
AF546-5'-CGT TCC GCG CCC GCT CCT TTG CAA C-3'
``` where AF546 indicates an Alexa Fluor 546 moiety.

The nucleotide sequence of the third template was as follows:

```
                                      (SEQ ID NO: 34)
AF546-5'-CGT TCC ACG CCC GCT CCT TTG CAA C-3'
``` where AF546 indicates an Alexa Fluor 546 moiety.
The nucleotide sequence of the fourth template was as follows:

```
                                      (SEQ ID NO: 35)
AF546-5'-CGT TCC TCG CCC GCT CCT TTG CAA C-3'
``` where AF546 indicates an Alexa Fluor 546 moiety.
Annealing of the primer of SEQ ID NO: 25 with any of the templates of SEQ ID NOS: 26-29 results in formation of an extendible duplex comprising a 7-nucleotide overhang.

Each primer-template duplex (200 nM) was preincubated with test polymerase (660 nM) and to form an E•DNA binary complex. This binary complex was mixed with the cognate omega-labeled nucleoside tetraphosphate (ωdN4P; 14 µM) in a stopped-flow experiment, and the fluorescence at both 546 nm and 647 nm was monitored following mixing. The averaged stopped-flow fluorescence traces were fitted with the double exponential function of Equation (2) to extrapolate the $t_{pol}$ value of the test polymerase:

Using the above procedure, the estimated $t_{pol}$ values of an exemplary modified polymerase comprising the amino acid sequence of SEQ ID NO: 8 and an exemplary reference polymerase comprising the amino acid sequence of SEQ ID NO: 1 were determined to be comparable (data not shown).

Example 9

Kinetics of Nucleotide Incorporation by Reference and Modified Polymerases with Different Nucleotide Compounds In this example, the kinetics of nucleotide incorporation by exemplary reference and modified polymerases were analyzed and compared in a stopped-flow nucleotide incorporation reaction comprising the test polymerase of interest, labeled nucleotide polyphosphates and an extendible primer:template duplex labeled with ALEXA FLUOR 546 ("AF546"). The AF546-labeled primer-template duplex was preincubated with the test polymerase, and then mixed in a stopped-flow assay with terminally-labeled nucleotides comprising a dye label attached to the terminal phosphate group using identical reaction conditions as used for $t_{pol}$ measurements in the preceding Example (Example 8, above).

In one study, the primer:template duplex was formed using a primer having SEQ ID NO: 31 and a template having SEQ ID NO: 32. Three separate assays were conducted, each using a mutant Phi-29 polymerase and any single one of the following three different terminally labeled nucleotides: AF647dG3P, AF647dG4P, AF647dG6P. These nucleotides comprise an ALEXA FLUOR dye ("AF647") on the terminal phosphate, but differ from each other in the number of phosphates included in the polyphosphate chain. The resulting fluorescence time traces are depicted in FIG. 7A, reaction comprising AF647dG3P; FIG. 7B, reaction comprising AF647dG4P; FIG. 7C, reaction comprising AF647dG6P.

In another study, the fluorescence time traces observed using two different Phi-29 mutant polymerases were obtained and compared. The results are depicted in FIGS. 8A and B.

As illustrated by FIGS. 7A, B and C, and FIGS. 8A and B, different polymerase-nucleotide combinations result in different time traces of fluorescence emission. By testing various polymerase-nucleotide combinations, it is possible to select combinations that exhibit optimal nucleotide binding affinities and binding speeds, as well as optimal amplitudes of fluorescence change during the nucleotide incorporation reaction so as to optimize the detectability of the reaction progress.

Example 10

Real-Time Single Molecule Sequencing Reaction Using an Exemplary Modified Polymerase and Labeled Nucleotides A exemplary modified polymerase comprising the amino acid sequence of SEQ ID NO: 8 was used in a nucleotide incorporation reaction comprising donor-labeled template and acceptor-labeled nucleotides. A graphical depiction of this nucleotide incorporation reaction system, showing the immobilized donor-labeled template, test polymerase and acceptor-labeled nucleotides, is provided in FIG. 9.

Preparing PEG-Biotin Surfaces:

Glass coverslips surfaces were plasma cleaned and treated with a mixture of poly-ethyleneglycol (PEG) and biotin-PEG to produce a low density biotin surface with a PEG coating to prevent non-specific background of proteins and macromolecules.

Fluidic Chamber Assembly:

Fluidic cassettes were assembled with glass coverslips to create fluidic chambers capable of containing approximately 2 µl of fluid.

Attaching Biotinylated DNA to Low Density PEG-Biotin Surfaces:

Streptavidin protein was diluted to 200 pM in Incubation Buffer (50 mM NaCl; 50 mM Tris-Cl pH=7.5; 0.5% BSA was optionally added in some experiments). Diluted streptavidin was flowed into fluidic chamber and streptavidin was incubated for 10-15 minutes. Chambers were washed 1× with 1 ml Incubation Buffer. Biotinylated-DNA templates were diluted to 10 pM in Incubation Buffer and allowed to bind for 10-15 minutes. Surfaces were washed 1× with 1 ml Incubation Buffer.

The primer sequence was as follows:

(SEQ ID NO: 36)
5'-GCCTCGCAGCCGTCCAACCAA CTCC-3'

The template sequence was as follows:

(SEQ ID NO: 37)
Cy3-5'-TGCCACC<u>GGAGTTGGT TGGACGGCTGCGAGG C</u>-3'-Biotin

The extension sequence for a duplex formed between this primer and template in the presence of guanine- and thymine-comprising nucleotides is GGTGG.

A reaction mix of 100 uL was prepared comprising 200 nM dye-labeled guanine nucleotide hexaphosphates, which included the dye AF647 attached to the omega-phosphate group (AF647-ω-dG6P); 200 nM unlabeled thymine nucleotide tetraphosphates (dT4P); and 200 nM of test polymerase in extension buffer (50 mM ACES, pH 6.5; 50 mM NaCl) supplemented with 0.4% Glucose, 0.1 mg/mL Glucose Oxidase, 2000 unit/mL Katalase, 2 mM Trolox and 2 mM $MnCl_2$ This reaction mixture was injected into the fluidic chamber comprising immobilized biotinylated duplex and the surface was imaged by exciting the fluorescence donor at a power density of about 100 W/cm$^2$ at 532 nm. Images were recorded using an Olympus microscope outfitted with a TIRF objective lens (100×; 1.45 NA). Emissions were imaged on a CCD camera. Images were collected at a frame rate of approximately 30 ms/frame.

To convert the observed fluorescence emissions detected during the nucleotide incorporation reaction into nucleotide sequence information, the raw data comprising a movie of observed emissions was first processed by using a Hidden Markov Model (HMM)-based algorithm to detect and identify FRET events. The subsequent detected FRET events were filtered and filtered sequences were aligned. Each of these two steps, FRET event detection and sequence analysis, are described in more detail below. The HMM-based algorithm was used to analyze the data.

1) Detection of FRET Events

The analysis underlying FRET event detection is designed to process spatially correlated movie(s) comprising real time sequence fluorescence emission data, and extract time-series of interest from those data. A movie typically contains one or more channels where each channel represents the same spatial location at different wavelengths. The analysis chain begins with the submission of one or more movies to the analysis machine via a comprehensive user interface. The user interface requires the user to input various parameters which describe the movie(s) (e.g. channel regions, dye emission properties). Once this data is submitted the movie(s) are then processed by the image analysis software where a sliding window of N frames propagates through the movie calculating a temporal local average of the frames within the window. At each position of the window in the movie, the local average image is then further processed and enhanced using well known image processing algorithms and a record of the maximum projection of all the local average images is recorded to produce a global image of the movie. This global image is the input into a spot identification algorithm which produces a set of spots identified by a unique spot identification, its x and y location and its corresponding channel. Each set of spots for a given channel is then registered to the set of spots in every other channel. In this way a set of spot tuples is constructed. If a detected spot in one channel does not have a corresponding detected spot in another channel, then the position of the undetected spot using the transformation between the two channels and the location of the detected spot is inferred. Once a complete set of spot tuples is constructed the movie is iterated over and at each frame the amplitude of each spot is calculated and appended to the appropriate time-series.

The collection of time-series from a spot tuple consists of time-series from donor and corresponding acceptor channels. This collection is called a Vector Time-Series (VTS). The FRET detection process starts with a data segmentation step using a Markov Chain Monte-Carlo (MCMC) algorithm. Each segment of VTS is modeled by a multivariate Gaussian model, with each of the channel modeled by a mean and a standard deviation. This model establishes a baseline for each channel, from which quantities such as "Donor Down" and "Acceptor Up" can be calculated. A Hidden Markov Model (HMM) was used to model the observed data. The underlying states consist of a null state, a blink state and a number of FRET states (one for each acceptor channel). Each state has its emission probability, which reflects the state's corresponding physical concept. FRET states are characterized by significant "donor down" and "acceptor up" signals. Blink state is characterized by significant "donor down" with no "acceptor up". Null state is characterized by no "donor down" and no "acceptor up". Given the observed VTS signal, the emission matrix, and a state transition probability matrix, the most probable state path can be computed using the Viterbi algorithm. This state path assigns each of the frames to a state. Temporally neighboring FRET frames are grouped into FRET events. For each of the detected FRET events, a list of event features are calculated, including event duration, signal average, signal to noise ratio, FRET efficiency, probability of event, color calling and other features. This list of events and corresponding features are stored in a file.

The final stage of the automated analysis generates a report summarizing the results in the form of a web page containing summary image, statistics of the spots and FRET detection, together with line intensity plots and base call plots. See for example, Watkins et al., "Detection of Intensity Change Points in Time-Resolved Single-Molecule Measurements" J. Phys. Chem. B., 109(1):617-628 (2005).

Using the above process, the movie data obtained from the sequencing reactions was analyzed to detect and identify FRET events according to the process described above. The FRET events were then processed to identify sequences as described below.

Sequence Analysis

Beginning with the set of detected Førster resonance energy transfer (FRET) events, a data overview was constructed in the form of a color image interpreted as a sequencing plot. To generate the plot, the original FRET event data was pre-processed using a set of filters constructed by a priori knowledge of the sequence. For each reaction site (each molecule) an ordered sequence of FRET events was constructed. The base call letters for each FRET event (e.g. "A", "C", "G" or "T") were concatenated to form a sequence ASCII string. The order of letters in the string reflects the temporal relationship of the events. Given that the expected sequence was known a priori, a regular expression was then constructed which represented the full or partial expected sequence or sequence pattern. Matching against the regular expression (expected sequence) was then computed for each sequence in the set and the start and stop indices of the match were recorded. A color plot image was then constructed where each row corresponds to a sequence in the set. The plot image was padded to accommodate sequences of different lengths. A color map of 2*N+1 colors was constructed, where N denotes the number of possible base calls in each sequence (N=2 for the plot of this Example). N colors were assigned to the base characters which fell within the pattern, N colors were assigned to the base characters which did not fall within the pattern (muted color), and finally a color was assigned to the padding (background) of the image. The rows of the image were then sorted according to the number of base calls in the first part of the sequence pattern. The rows of the image were also aligned such that the start of the expected sequence is in the same column for all rows of the plot.

One representative output using the reaction conditions described above is depicted in FIG. 10.

Example 11

Detecting Nucleotide Incorporation with Labeled Biomolecule Conjugates Comprising a Modified B103 Polymerase Linked to a Fluorescent Dye Label In this Example, a modified B103 polymerase comprising the amino acid sequence of SEQ ID NO: 42, below, was prepared, biotinylated and labeled as outlined below. This modified B103 polymerase comprises the amino acid sequence of SEQ ID NO: 8 and further includes the mutation H370R as well as a biotinylation site and His tag fused to the N-terminus of the protein. The dye-labeled polymerase conjugate was then used to study nucleotide incorporations in single molecule format.

Preparation of Biotinylated Polymerase

The construct HB B104 (H370R) _pAN6 was transformed and expressed in CVB101 (for in vivo biotinylation) cells. The cells were grown at 30° C. to OD 0.6 and induced with 0.5 mM IPTG. Upon induction 200 uM D-Biotin was added and cultures were moved to 18° C. shaker and grown 0/N and harvested the following morning. Cell pellets were resuspended in Buffer B and sonicated to lyse. PEI (0.3%) was added to cell resuspension and incubated on ice for 30 min. Cell resuspension was centrifuged to remove cell debris and DNA Ammonium sulfate was added to cell lysate at final concentration of 55%. Lysate was centrifuged and pellets containing HB B104 (H370R) were resuspended in Buffer, loaded onto EMD-sulfate column and eluted with linear gradient 10-100% BufferB. Fractions containing HB B104 (H370R) were pooled and loaded onto a His Trap column, eluted with linear gradient from 5-100% Buffer C. Peak fractions were pooled and loaded onto a Heparin column, eluted with a linear gradient from 10-100% B. Fractions were then quantitated and analyzed for polymerase activity.

Buffer compositions were as follows:

Buffer A: 30 mM Tris pH 7.5, 100 mM NaCl, 2 mM DTT, 0.1 mM EDTA, 8% glycerol

Buffer B: 30 mM Tris pH 7.5, 1 M NaCl, 2 mM DTT, 0.1 mM EDTA, 8% glycerol

Buffer C: 30 mM Tris pH 7.5, 100 mM NaCl, 2 mM DTT, 0.5M Imidazole, 8% glycerol

Preparing NHS-Ester Surfaces:

Glass coverslips surfaces were plasma cleaned and treated with a mixture of poly-ethyleneglycol (PEG) and NHS-ester to produce a low density NHS-ester surface with a PEG coating to prevent non-specific background of proteins and macromolecules.

Fluidic Chamber Assembly:

Fluidic cassettes were assembled with glass coverslips to create fluidic chambers capable of carrying approximately 2 µl of fluid.

Attaching Amine Terminated Hairpin DNA to Low Density NHS-Ester Surfaces:

Target DNA Hairpin Sequence:

5'-TTTTTTTTACCCCCGGGTGACAGGTTXTTCCTGTCACCC-3'

(SEQ ID NOS 38 and 49, respectively, in order of appearance) where "X" is an amine group.

The target DNA was diluted to 500 nM in 1 M NaHCO$_3$. The diluted target molecules were flowed into the fluidic chamber and incubated for 1 hour. Chambers were washed 1× with 1 ml deactivating buffer (ethanolamine). Surfaces were washed 1× with 1 ml incubation buffer (50 mM Tris-Cl, pH=7.5; 50 mM NaCl; 0.3% BSA).

SA-Polymerase Conjugate Preparation:

Streptavidin was labeled with Cy3. Streptavidin-Cy3 was mixed with biotinylated mutant B103 polymerase (b-B103-exo minus) comprising the amino acid sequence of SEQ ID NO: 42 at a 1:1 ratio of SA-protein:b-B103-exo minus in 1× PBS to produce conjugates comprising biotinylated mutant B103 polymerase linked to dye.

Briefly, 500 µl of a 3.4 µM solution of Cy3 streptavidin (Invitrogen, SA1010) was mixed with 25 µl of 200 µM biotin-B104 H370R. Twenty five microliters of 5M NaCl were added to the mixture and it was left at 4 deg C. for 1 hour. To remove any free, unconjugated labeled streptavidin, the mixture was diluted with an equal volume of phosphate buffer saline buffer (PBS) and loaded onto a 1 ml HisTrap cartridge (GE Healthcare). Following the loading, the cartridge was washed with PBS until the initially colored eluate from the cartridge became completely colorless. Finally, the bound Cy3 streptavidin—biotin B104 H370R conjugate was eluted off the cartridge with a solution of 500 mM imidazole in PBS buffer containing 200 mM additional NaCl. To the eluted material was added 50 mM biocytin to a final concentration of 5 mM, and the mixture was dialyzed overnight against a solution containing 50% glycerol, 50 mM Tris-HCl pH 7.5, 200 mM NaCl, 5 mM DTT.

SA-Cy3-b-B103 Binding to Templates:

The conjugates were diluted to 1 nM in binding buffer (50 mM Tris-Cl; pH=7.5; 0.3% BSA; 100 mM NaCl). The conjugates were flowed into the fluidic chamber which were previously loaded with DNA templates on the surface. Surfaces were incubated for 5 minutes with conjugates. Surfaces were washed with 1×1 ml incubation buffer.

Fluorescence Imaging:

The microscope body was purchased from Olympus and was outfitted with a TIRF objective lens (100×; 1.45 NA). The excitation light passes through an excitation filter (EX FT-543/22), and dichroic mirror (DM-532) and the sample was epi-illuminated (Coherent) using TIR at typically 100 W/cm². Upon excitation, the resulting epifluorescence emission passed through an emission filter (EM FT-540LP) and the resulting emission was split into three paths (tri-view) using 2 dichroic mirrors and the appropriate bandpass filters for the dye sets of choice. Using this filter combination, we were able to spectrally resolve 1 donor dye and 3 acceptor dyes in 3 detection channels.

In separate experiments, 1 donor dye and 4 different acceptor dyes could be resolved in 4 detection channels. The optical detection scheme was as follows: DC1=635, F1 640LP; DC2=675, F2=688/31; DC3=705, F3=700 LP. The donor dye used in this case was CY3 and the 4 acceptor dyes are as follows DY634, AF647, AF676, AF700

The emissions resulting in each experiment were imaged on a CCD camera. Images were collected at a frame rate of approximately 20 ms.

Three-Color Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM MnCl$_2$; 300 nM procatuate dioxygenase; 4 mM 3,4 dihydroxyl benzoic acid; 1 mM 2-nitrobenzoic acid; 400 µM 1,2 phenylenediamine; 100 µM ferrocene monocarboxylic acid; 0.02% cyclooctratetraene; 6 mM TROLOX). Nucleotide mix was flowed into channel with conjugate bound to DNA template and images are recorded for approximately 2 minutes at approximately 20 ms frame rates. In this example, the synthesized strand is expected to have the following sequence: $(G)_5T(A)_8$ (SEQ ID NO: 50). Terminal phosphate-labeled nucleotides and 125 nM cold dC6P were used for the nucleotide incorporation reaction. The labeled nucleotides included 125 nM 647-dT6P, 125 nM 676-dG6P, 125 nM 700-dA6P. The spectral signatures for the ALEXA FLUOR-676 G signal, AF-647 T signal, and AF-700 A signal were identified that resulted from fluorescence resonance energy transfer (FRET) from the Cy3 donor molecule, and corresponded to the correct insertion sequence pattern.

Analysis of Three-Color Sequencing Results

Resulting pattern sequencing data was processed using an alignment algorithm. The alignment algorithm found 100 molecules in the field of view, which demonstrated completion of the full 14-nucleotide sequence $((G)_5T(A)_8$, which represented approximately 20% of the total single molecule donor population. The consensus sequence was determined using an HMM alignment algorithm (e.g., see Example 14). By plotting the accuracy definition (measured as a percentage value) against the HMM score (X axis), a linear relationship was detected (data not shown). Various measurements of accuracy can be devised that can be suitable for such analysis. In one exemplary experiment, the accuracy was estimated according to the following equation:

$$\alpha(T, A) = \frac{\beta - \delta - \eta + \lambda}{2\lambda}$$

The measurement of accuracy in the above equation is intended to provide some measure of similarity between some given template, T, and some alignment, A, of an observed sequence O. It should be noted that alphabet of T, A, and O are identical. The length of T is denoted by $\lambda$, the number of deletions in the alignment A by $\delta$, the number of insertions in the alignment by $\eta$, and the number of matches in the alignment by $\beta$. Equation (1) is normalized by $\lambda$ such that a an accuracy of 1 indicates a total agreement, and an accuracy of 0 indicates no agreement between T and A. The above definition of accuracy is provided as an example only and is in no way intended to limit the disclosure to any particular theory or definition of accuracy; alternative definitions of accuracy are also possible and it may be suitable to use such alternative definitions in some contexts.

The accuracy in this system using an HMM alignment threshold of 0 was estimated to be approximately 80% (data not shown).

Four-Color Nucleotide Incorporation Reaction:

Oligonucleotides

401 Template Molecule:

```
                                        (SEQ ID NO: 39)
TTTTTCCCCGACGATGCCTCCCC g ACA Cgg Agg TTC TAT CAT

CgT CAT CgT CAT CgT CAT Cg-Biotin TEG-T-3
```

Primer for 401 Template:

```
                                        (SEQ ID NO: 40)
           5' TGA TAG AAC CTC CGT GTC 3'
```

In this example, the synthesized strand is expected to have the following sequence:

```
                                        (SEQ ID NO: 41)
           GGGGAGGCATCGTCGGGAAAA
```

Nucleotide Incorporation Reaction:

Hexa-phosphate dye-labeled nucleotides were diluted to 200 nM in extension buffer (50 mM MOPS pH=7.1; 75 mM potassium acetate (pH=7.0); 0.3% BSA; 1 mM MnCl$_2$; 300 nM procatuate dioxygenase; 4 mM 3,4 dihydroxyl benzoic acid; 1 mM 2-nitrobenzoic acid; 400 µM 1,2 phenylenediamine; 100 µM ferrocene monocarboxylic acid; 0.02% cyclooctratetraene; 6 mM TROLOX). Nucleotide mix was flowed into channel with SA-Cy3-b-B103 bound to DNA template and images are recorded for approximately 2 minutes at approximately 20 ms frame rates.

The terminal phosphate-labeled nucleotides used for the nucleotide incorporation reaction included 125 nM DY634-dA6P, 125 nM 647-dT6P, 125 nM 676-dG6P, 125 nM 700-dC6P. The spectral signatures for the DY-634 A signal, and the ALEXA FLUOR G, T and C signals (AF-676 G signal, AF-647 T signal, and AF-700 C signal) were identified that resulted from fluorescence resonance energy transfer (FRET) from the Cy3 donor molecule, and corresponded to the correct insertion sequence pattern. 4-color sequence alignment was obtained by visual inspection.

The observed FRET event durations for various SA-Cy3-b-B103 conjugates, the event count distributions, and the observed extension speeds of various SA-Cy3-b-B103 conjugates were calculated.

The amino acid sequence of the modified B103 polymerase comprising the mutation H370R and a biotinylation site and His tag fused to its N-terminus was as follows:

(SEQ ID NO: 42)

```
         10         20         30         40
MSHHHHHHSM SGLNDIFEAQ KIEWHEGAPG ARGSKHMPRK 50         60         70         80
MFSCDFETTT KLDDCRVWAY GYMEIGNLDN YKIGNSLDEF 90        100        110        120
MQWVMEIQAD LYFHNLKFDG AFIVNWLEHH GFKWSNEGLP 130        140        150        160
NTYNTIISKM GQWYMIDICF GYKGKRKLHT VIYDSLKKLP 170        180        190        200
FPVKKIAKDF QLPLLKGDID YHAERPVGHE ITPEEYEYIK 210        220        230        240
NAIEIIARAL DIQFKQGLDR MTAGSDSLKG FKDILSTKKF 250        260        270        280
NKVFPKLSLP MDKEIRRAYR GGFTWLNDKY KEKEIGEGMV 290        300        310        320
FDVNSLYPSQ MYSRPLPYGA PIVFQGKYEK DEQYPLYIQR 330        340        350        360
IRFEFELKEG YIPTIQIKKN PFFKGNEYLK NSGAEPVELY 370        380        390        400
LTNVDLELIQ EHYEMYNVEY IDGFKFREKT GLFKEFIDKW 410        420        430        440
TYVKTREKGA KKQLAKLMLN SLYGKFASNP DVTGKVPYLK 450        460        470        480
EDGSLGFRVG DEEYKDPVYT PMGVFITAWA RFTTITAAQA 490        500        510        520
CYDRIIYCDT DSIHLTGTEV PEIIKDIVDP KKLGYWAHES 530        540        550        560
TFKRAKYLRQ KTYIQDIYAK EVDGKLIECS PDEATTTKFS 570        580        590        600
VKCAGMTDTI KKKVTFDNFR VGFSSTGKPK PVQVNGGVVL

VDSVFTIK
```

Example 12

Measurement of $t_{-1}$ and $t_{pol}$ Values of Modified Phi-29 and B103 Polymerases In this example, the $t_{-1}$ and $t_{pol}$ values of a Phi-29 polymerase comprising the amino acid sequence of SEQ ID NO: 1 and a modified B103 polymerase comprising the amino acid sequence of SEQ ID NO: 8 (referred to as "mB103 in the table below) and further including amino acid substitutions at various positions were measured using a stopped-flow procedure. The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320).

Stopped-Flow Measurements of $t_{pol}$

Template C Sequence:

(SEQ ID NO: 44)
5'-CGTTAA<u>CC</u>GCCCGCTCCTTTGCAAC-3'

Primer Sequence:

(SEQ ID NO: 45)
5'-GTTGCAAAGGAGCGGGCG-3'

The template sequence (SEQ ID NO: 44) further included an Alexa Fluor 546 dye moiety bonded to the 5' position of the template.

The kinetics of nucleotide incorporation by each polymerase was measured in an Applied Photophysics SX20 stopped-flow spectrometer by monitoring changes in fluorescence from the dye-labeled primer-template duplex complexed to enzyme, following the mixing of the enzyme-DNA complex with dye-labeled nucleotides. These dye-labeled nucleotides comprise terminal-phosphate-labeled nucleotides having an alkyl linker with a functional amine group attached to the dye, and have the general structure shown in FIG. 11. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In this example, the particular dye-labeled nucleotide added was a labeled nucleotide hexaphosphate comprising a guanine base at the N (base) position and an Alexa Fluor 647 (AF647) at the dye position, and is referred to herein as "AF647-C6-dG6P".

The primer and template were annealed to form a dye-labeled primer-template duplex using standard methods. This duplex was preincubated with polymerase. The mixture included 330 nM recombinant DNA polymerase, 100 nM template/primer duplex in buffer ("reaction buffer") comprising 50 mM Tris-HCl, pH 7.5, 50 mM NaCl, 4 mM DTT, 0.2% BSA, and 2 mM $MnCl_2$. The dye-labeled nucleotide AF647-C6-dG6P was then added to a final concentration of 7 μM, and the resulting fluorescence was monitored over time.

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \quad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively.

Stopped-Flow Measurements of $t_{-1}$

The stopped-flow techniques for measuring $t_{-1}$ ($1/k_{-1}$) followed the techniques described by M. Bakhtina (2009 Biochemistry 48:3197-3208).

Template C Sequence:

(SEQ ID NO: 46)
5'-CAGTAACGG AGT TGG TTG GAC GGC TGC GAG GC-3'

Dideoxy-Primer Sequence:

(SEQ ID NO: 47)
5'-GCC TCG CAG CCG TCC AAC CAA CTC ddC-3'

The rate of the nucleotide dissociation ($k_1$) from the ternary complex of [enzyme•DNA•nucleotide] was measured in an Applied Photophysics SX20 stopped-flow spectrometer by monitoring changes in fluorescence from in fluorescence from a duplex Alexa fluor 546 dye-labeled-DNA template following the mixing of the [enzyme•DNA•labeled nucleotide] ternary complex with 50 µM cognate non-labeled deoxynucleoside triphosphate in a buffer containing 50 mM Tris-HCl (pH 7.5), 50 mM NaCl, 4 mM DTT, 0.2% BSA, and 2 mM $MnCl_2$.

The ternary complexes were prepared using: 330 nM polymerase, 100 nM template/primer duplex, and 7 µM terminal phosphate-labeled nucleotides (AF647-C6-dG6P).

The averaged stopped-flow fluorescence traces (>1.5 msec) were fitted with a single exponential equation (2) to extrapolate the rate of the nucleotide dissociation ($k_{-1}$) from the [enzyme•DNA•nucleotide] ternary complex.

$$\text{Fluorescence} = A_1 * e^{-k-1*t} + C \quad \text{(equation 2)}$$

where $A_t$ represents the corresponding fluorescence amplitude, C is an offset constant, and $k_{-1}$ and the observed rate constants for the fluorescence transition.

Some representative results of the stopped flow data are shown in the table below.

TABLE

Summary of $t_{pol}$ and $t_{-1}$ measurements for various exemplary modified Phi-29 and B103 polymerases

| Protein | $t_{pol}$ | $t_{-1}$ |
|---|---|---|
| mB103 (SEQ ID: 8) | 14 | 16 |
| mB103 + H370R | 17 | 43 |
| mB103 + H370Y | 15 | 12 |
| mB103 + E371R | 11 | 17 |
| mB103 + E371Y | 11 | 7 |
| K372R | 14 | 12 |
| K380R | 783 | 17 |
| mB103 + D507G | 11 | 13 |
| mB103 + D507H | 7 | 16 |
| mB103 + K509Y | 10 | 20 |
| Phi-29 (exo−) | 11 | 27 |
| Phi-29 (exo−) + T373R | 15 | 81 |
| Phi-29 (exo−) + T373Y | 14 | 45 |

Example 13

Measurement of Primer Extension Activity of a Sample Polymerase Using a Fluorescein-Labeled Oligonucleotide This example provides an exemplary assay for primer extension activity in a sample. Primer extension activity is quantified by monitoring the fluorescence intensity change over time during extension of a fluorescein-labeled hairpin oligonucleotide, comprising the following nucleotide sequence, known as "oligo 221" (SEQ ID NO: 43). The fluorescence intensity correlates with the level of primer extension activity in the sample.

(SEQ ID NO: 43)
(5'-TTTTTTTGCAGGTGACAGGTTTTTCCTGTCA-
CC(fluorescein-T)GC-3').

The extension reactions are performed in 1× extension buffer (50 mM Tris buffer pH 7.5, 50 mM NaCl, 10 mM $MgCl_2$ and 0.5 mM $MnCl_2$). To reaction wells that contain 100 µL of 150 nM of a fluorescein-labeled hairpin oligonucleotide, oligo221 (SEQ ID NO: 43, above) and 10 nM of polymerase (or conjugated polymerase) in extension buffer, 2 µL of 1 mM dATP (final concentration: 20 µM) is added to initiate the enzymatic reaction and the fluorescence intensity in each well is recorded at 525 nm fluorescence with 490 nm excitation for every 20 seconds for the next 10 minutes. Control reaction wells include the same components without any addition of dATP. The fluorescence intensity at 525 nm (as measured in arbitrary fluorescence units, RFU, y axis) is plotted against time (seconds, X axis) for each sample, as well as the control wells (no nucleotide). The fluorescence time course data from each well is used to calculate the primer extension activity of each sample using the following equations:

$$\text{Activity(base/sec/}enz) = \frac{\Delta RFU_{sample}\_\text{per\_sec}}{\Delta RFU_{max}\_\text{per\_nMsubs}} \times \frac{1}{50nM} \times 7(\text{base})$$

and $$\Delta RFU_{max}\_\text{per\_nMsubs} = \frac{RFU_{max} - RFU_{min}}{\text{substr\_conc.}(nM)}$$

Where: $RFU_{max}$ is the average maximal RFU in the reference polymerase reaction wells; $RFU_{min}$ is the average minimal RFU in the reference polymerase control wells; Substr_conc. (nM) is the oligo 221 concentration in assay, which is 150 nM; and:

$$\Delta RFU_{sample}\_\text{per\_sec} = \frac{RFU_t - RFU_0}{t(\text{sec})}$$

Where: t (sec) is the time period where the fluorescence intensity increases in the reference enzyme reaction well linearly from the start; $RFU_t$ is the average RFU of the reference enzyme extension wells at t second point; and $RFU_0$ is the average RFU of the reference enzyme extension wells at the start point.

Example 14

Preparation of Core-Shell Nanoparticle CdSe/4CdS-3.5ZnS

Core Synthesis

Cores are prepared using standard methods, such as those described in U.S. Pat. No. 6,815,064, the only change being that the growth is halted at 535 nm emission. These cores were precipitated and cleaned in the standard methods and resuspended into hexane for use in the shell reaction.

Shell Synthesis:

A 1:1 (w:v) mixture of tri-n-octylphosphine oxide (TOPO) and tri-n-octylphosphine (TOP) was introduced into a flask.

Tetradecylphosphonic acid (TDPA) was added to the flask in an amount suitable to fully passivate the final material, as can be calculated from the reaction scale and the expected final nanoparticle size. The contents of the flask were heated to 125° C. under vacuum and then the flask was refilled with $N_2$ and cooled.

Inside the glovebox, a solution of a suitable cadmium precursor (such as dimethylcadmium or cadmium acetate) in TOP was prepared in a quantity sufficient to produce a desired thickness of shell, as can be calculated by one of ordinary skill in the art. When a zinc shell was also desired, a solution of a suitable zinc precursor (such as diethylzinc or zinc stearate) was prepared in TOP in a quantity sufficient to produce the desired shell thickness. Separately, a solution of trimethylsilylsulfide [$(TMS)_2S$] in TOP was prepared in a quantity sufficient to produce the desired shell thickness. Each of these solutions was taken up in separate syringes and removed from the glove box.

Of the previously prepared core/hexane solution, 17 mL (at an optical density of 21.5 at the band edge) was added to the reaction flask and the hexane was removed by vacuum; the flask was then refilled with $N_2$. The flask was heated to the desired synthesis temperature, typically about 200 to about 250° C. During this heat-up, 17 mL of decylamine was added. The cadmium and sulfur precursor solutions were then added alternately in layer additions, which were based upon the starting size of the underlying cores. So this means that as each layer of shell material was added, a new "core" size was determined by taking the previous "core" size and adding to it the thickness of just-added shell material. This leads to a slightly larger volume of the following shell material needing to be added for each subsequent layer of shell material.

After a desired thickness of CdS shell material was added, the cadmium precursor solution was replaced with the zinc precursor solution. Zinc and sulfur solutions were then added alternately in layer additions until a desired thickness of ZnS was added. A final layer of the zinc solution was added at the end, the reaction flask was cooled, and the product was isolated by conventional precipitation methods.

Example 15

Exchange Process Using Dipeptide Ligands and Butanol as a Cosolvent

Core/shell nanocrystals (quantum dots) were prepared by standard methods, and were washed with acetic acid/toluene several times, and suspended in hexanes. 10 nmol of core/shell nanocrystals were suspended in 40 mL hexane. This was mixed with 10 mL of a 300 mM solution of carnosine and 10 mL of 1 M sodium carbonate solution. n-Butanol (14 mL) was added, and the vessel was flushed with argon. The mixture was mixed vigorously overnight at room temperature. The mixture was then heated and allowed to cool to room temperature. The aqueous phase was then removed and filtered through a 0.2/0.8 micron syringe filter.

Excess carnosine was removed by dialyzing against 3.5 L of 25 mM NaCl for one hour. The solution was concentrated to 1 mL using a 10K MWCO (10,000 molecular weight cut-off) Amicon centricon. A solution was then prepared with 568 mg of His-Leu dipeptide plus 212 mg of Gly-His dipeptide in 9 mL sodium carbonate solution, and this solution was combined with the aqueous solution of quantum dots. This mixture was stirred overnight at room temperature. The mixture of water-soluble quantum dots was then dialyzed against 3.5 L of 25 mM NaCl for one hour.

To crosslink the peptide ligands (clarify) A solution of 0.5 mM 4-aminobenzophenone in ethanol was then added to the aqueous quantum dots mixture, and the mixture was irradiated at 365 nm for 4 hours to effect reaction of the aminobenzophenone with the surface molecules on the quantum dots. To this, 5 mmol of THP (tris(hydroxymethyl)phosphine) was added, and the mixture was stirred at RT overnight, to induce crosslinking. Another 5 mmol of THP was added, and again the mixture was stirred overnight at RT. Another 5 mmol of THP was added the next day, along with 300 micromoles of PEG1000-COOH. This was mixed overnight at room temperature, then another 5 mmol of THP was added along with 30 mmol of glycine, and the mixture was stirred overnight at RT.

The material was purified by dialysis using the 10K MWCO Amicon centricon, and was washed with 50 mM borate buffer (pH 9). The final material was dispersed into 50 mM borate buffer to a final concentration of 2.5 micromolar for storage.

Example 16

Exchange Process Using Trithiol Ligands

A solution of hydrophobic phosphonate-coated quantum dots in organic solvent (e.g. toluene, chloroform, etc) with a concentration of between about 0.1 and 10 micromolar quantum dots was prepared. Approximately 1000 to 1000000 equivalents of a suitable trithiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 17

Two-Step Ligand Exchange: Process for Exchanging Phosphonate Ligands with Sulfonate (Triflate) Ligands A nanoparticle comprising a core/shell nanocrystal having TDPA ligands on its surface is dissolved in dichloromethane, and excess TMS triflate is added to it. After 1-2 hours at room temperature, analysis indicates that the TDPA ligands have been removed, and the nanoparticle remains dispersed in the solvent. It is dialyzed against dichloromethane using a 10K MWCO (10,000 molecular-weight cut-off) dialysis membrane to remove excess TMS triflate and the TMS-TDPA produced by the reaction of TMS triflate with the TDPA ligands. This produces a solution/suspension of nanoparticles comprising triflate ligands on the surface of nanocrystals. These triflate-containing nanoparticles are soluble in many organic solvents, but may not be readily soluble in hexanes, depending upon the complement of ligands present.

Two-Step Process for Exchanging Sulfonate (Triflate) Ligands with PEG Conjugated Dithiol (DHLA) Ligands Using n-Butanol as an Intermediate Ligand and DMF as a Co-Solvent The triflate-containing nanoparticle solution, described above, can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. This intermediate nanoparticle is contacted with an excess of a dihydrolipoic acid-PEG conjugate of this formula:

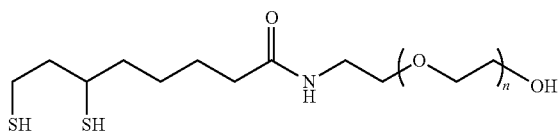

where n is 1-100.

The product is a water-soluble, stable nanoparticle. It can be collected by extraction into a pH 9 buffer, and isolated by conventional methods, including dialysis with a 10K MWCO dialysis filter, or by size exclusion (gel filtration) chromatography.

Two-Step Process for Exchanging Sulfonate (Triflate) Ligands with Nucleophilic Reactant Group Containing Ligands Using n-Butanol as an Intermediate Ligand and DMF as a Co-Solvent The triflate-containing nanoparticle solution from can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. To further modify it, it is treated with a new ligand containing at least one nucleophilic reactant group: suitable ligands include HS—$CH_2$—$CH_2$—PEG; aminomethyl phophonic acid; dihydrolipoic acid; omega-thio-alkanoic acids, and carboxymethylphosphonic acid. The mixture is then treated with TMEDA (tetramethylethylene diamine), and monitored until triflate is displaced, then the nanocrystal product is extracted into pH 9 buffer and purified by conventional methods.

Process for Exchanging Sulfonate (Triflate) Ligands with Carboxylate Functionalized Dithiol (DHLA) Ligands The triflate-containing nanoparticle is contacted with neat dihydrolipoic acid (DHLA) for an hour at room temperature, and is then dispersed into pH 9 buffer and isolated by conventional methods. This provides a nanoparticle having carboxylate groups to provide water solubility, and having two thiol groups binding the carboxylate to the nanocrystal surface. The product is water soluble and stable in aqueous buffer. It provides good colloidal stability, and a moderate quantum yield. This composition containing DHLA as a ligand contains free carboxyl groups which can be used to attach other groups such as a PEG moiety, optionally linked to a functional group or a biomolecule. The same reaction can be performed to replace triflate groups on a nanoparticle with thioglycolic acid (HS—$CH_2$—COOH) ligands. This provides a highly stabilized nanoparticle which produces a high quantum yield, but has lower colloidal stability than the product having DHLA on its surface.

Process for Exchanging Sulfonate (Triflate) Ligands with Amine Ligands

The triflate-containing nanoparticle is dispersed in dichloromethane plus hexanes, and an alkylamine is added. Suitable alkylamines are preferably primary amines, and include, e.g., $H_2N$—$(CH_2)_r$-PEG (r=2-10), p-aminomethylbenzoic acid, and lysine ethyl ester. After an hour at room temperature, the exchange process is completed, and the nanoparticle product can be isolated by conventional methods.

Process for Pre-Treating Phosphonate Coated Nanocrystals with Toluene Acetic Acid to Remove Impurities Prior to Exchanging with Sulfonate (Triflate) Ligands TDPA-covered nanocrystals were synthesized which emitted light at 605 nm and had shells of CdS and of ZnS. These when treated with 200,000 equivalents of TMS triflate in hexanes did not produce a precipitate. This was attributed to excess TDPA-derived impurities in the nanocrystals. This was alleviated by dissolving the nanocrystals in toluene-acetic acid and precipitating them with methanol, to remove TDPA salts or related by-products. The resultant TDPA nanocrystals behaved as described above, demonstrating that impurities were causing the nanocrystals to behave differently when made with excess TDPA present, and that those impurities can be removed by precipitation under conditions better suited to dissolving TDPA-related impurities.

Process for Exchanging Activated (Sulfonate Coated) Nanocrystals with Dithiol (DHLA) Ligands Using Butanol, DMF or Isopropyl Alcohol as Dispersants Three different methods of depositing the DHLA ligands were employed, each of which was considerably more rapid than the classic approach using non-activated dots. In the first approach, the activated dot powder was dispersed in butanol and stirred with DHLA, then precipitated with hexane and collected in aqueous buffer. In the second approach, the activated dot powder was dispersed in dimethylformamide (DMF) and stirred with DHLA, then precipitated with toluene and collected in aqueous buffer. In the third approach, the activated dot powder was stirred as a slurry in neat DHLA, then dispersed in isopropyl alcohol, precipitated with hexane, and collected in aqueous buffer and purified with a filtration membrane.

These three samples, plus a sample derived from non-activated dots were diluted to 60 nM for a colloidal stability challenge, wherein the absorbance is monitored over the course of days to watch for precipitation. Samples 1 (butanol-mediated), 2 (DMF-mediated), and 4 (classic) all precipitated on day 3 or 4 of the stability challenge, but sample 3 (neat DHLA) lasted twice as long, coming out of solution on day 7. HPLC measurements indicated that the DHLA-coated particles produced from activated dots showed even less aggregation than the classic DHLA particles made by the displacement of TOPO or pyridine ligands from nanocrystals. Thus the invention provided rapid reactions leading to improved colloidal stability and comparable or lower aggregation levels than conventional ligand replacement methods of putting DHLA on a nanocrystal. Similar treatment with other thiol ligands like mercaptoundecanoic acid (MUA) or the PEGylated thiol also provided water-dispersible nanocrystals. Reacting triflate-coated nanoparticles with MUA or PEG-thiol gave particles which were readily dispersible in water, indicating that ligand exchange had occurred. The observed quantum yield was over 70% in each case.

Process for Exchanging Activated (Sulfonate Coated) Nanocrystals with Hydrophilic Phosphonate Ligands Triflate-coated dots were dispersed in butanol and then stirred with phosphonoacetic acid. Triethylamine was added to form the triethylammonium salt of both the phosphonate and carboxylate functionalities, and then pH 9 aqueous borate buffer was added to extract the hydrophilic particles. The result was a bright orange aqueous dispersion of quantum dots, with no remaining color observed in the butanol layer. The particles were purified by centrifugal filtration and the quantum yield was measured to be 72%. Multiple batches of particles were prepared and remained in solution through room temperature storage for at least eight weeks. The same method can be successfully employed with DHLA, MUA, and PEGylated thiol ligands.

Process for Exchanging Activated (Sulfonate Coated) Nanocrystals with a Variety of Hydrophilic Phosphonate Ligands Via Biphasic Exchange Using a biphasic exchange method, dispersing the quantum dots in organic solvents such as chloroform and the exchangeable ligands in aqueous solution, quantum dots were made water soluble and stable after ligand exchange with N,N-Bis(phosphonomethyl)glycine (1) or phosphonoacetic acid (2). In a typical biphasic ligand exchange experiment, 1 nmol of quantum dots were dispersed in 1 mL of chloroform and placed in a vial with 2 mL of 300 mM phosphonic acid in basic buffer and the mixture was rapidly stirred at room temperature for 2 days. Quantum yields as high as 53% were achieved; however the quantum yields achieved were dependent on core-shell batch employed, probably as a result of variable amounts of long-chain alkyl phosphonates remaining on the nanocrystal surface post-ligand exchange. This demonstrated that complete removal of TDPA from nanocrystals is important for successful modification of the surface. Though the dots were rendered water stable by the above phosphonate-containing ligands, they were not successfully modified with PEG2000-diamine using standard EDC condensation chemistry.

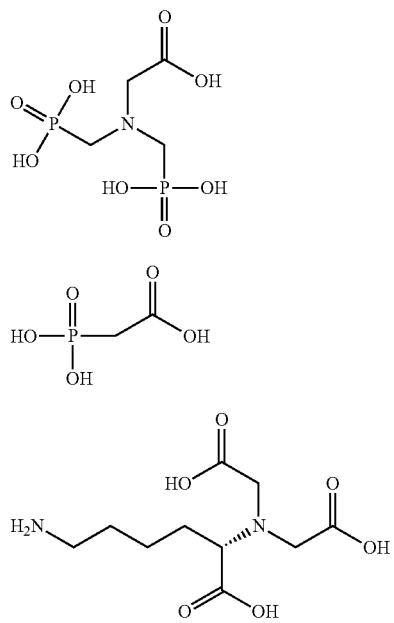

Nanocrystals coated with compounds 1, 2, or 3 were readily prepared by this method, as well as nanocrystals having a mixture of compounds 1 and 2, or 1 and 3, or 2 and 3. In each case, the nanocrystals were stable, bright and water-soluble. Using mixed ligands, it was found that PEGylation (with PEG2000-diamine using standard EDC condensation chemistry) could be achieved with these phosphonate-containing ligands to produce highly stable, bright, water soluble nanoparticles. These nanoparticles can be further stabilized by at least partially crosslinking the ligands using a diamine such as putrescine, cadaverine, 1,2-diaminoethane, bis(hexamethylene)triamine, PAMAM dendrimer, and cystamine.

Two-Step Ligand Exchange Process with Tridentate Thiol Ligands

Triflate exchange step was performed following the procedure described above. Next, the triflate nanoparticles were dispersed in organic solvent (e.g. toluene, chloroform, etc) with a concentration of between about 0.1 and 10 micromolar quantum dots. Approximately 1000 to 1000000 equivalents of a suitable tridentate thiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 18

Functionalized Ligands on Nanoparticles

General Core Reaction Procedure

Into a 25 mL 3 neck flask with 14/20 joints, 1.575 g of >99% tri-n-octylphosphine oxide (TOPO) was weighed. To this, 1-1000 micromoles of a bi-functional phosphonate ligand was added. A stir bar was added to this flask. The flask was connected to an inert atmosphere manifold and evacuated thoroughly, then refilled with nitrogen. A solution of a suitable cadmium salt in tri-n-octylphosphine (TOP) was prepared with a concentration of 0.5 mol Cd per kg solution. A desired amount of cadmium as required for growth of nanoparticles of a desired size was extracted from this solution, diluted with 0.9 mL of additional TOP, and added to the flask. The flask was stirred and heated to ~200-350° C. under nitrogen flow. A 1 molar solution of selenium in TOP was prepared and a desired amount as required for growth of nanoparticles of a desired size was added to the solution, optionally with addition of a reaction promoter to achieve desired levels of particle nucleation. One minute after the reaction was initiated by adding these final reagents, a 20 microliter sample was removed from the reaction, mixed with 5 mL of hexane, and an emission spectrum was collected. This aliquot removal and measurement process was repeated after 2, 3, 4, 5, 6, 7, 8, 10, 12, and 14 minutes. After 14 minutes, the reaction was rapidly cooled and the products were isolated by methods understood in the art.

Control Core Reaction with Tetradecylphosphonic Acid [TDPA]

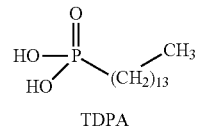
TDPA

The core reaction using TDPA as the phosphonate ligand was demonstrated as a control reaction. This reaction proceeded with an initial emission reading at 1 minute of ~490 nm and progressing to a final emission reading of ~544 nm at 14 minutes. The full width at half maximum intensity (FWHM) never got above 28 nm. The final "growth solution" of the cores was yellow/light orange in appearance by eye. The aliquoted samples of this reaction remained dispersed and clear solutions in hexane.

Core Reaction with 11-methoxy-11-oxo-undecylphosphonic acid

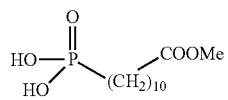

The reaction using 11-methoxy-11-oxo-undecylphosphonic acid as the phosphonate ligand proceeded with an initial emission reading at 1 minute was ~560 nm; this was redder than the final emission of the control reaction. The final emission of this reaction was ~610 nm. The FWHM of this reaction started at ~35 nm and steadily got more broad throughout the reaction for a final FWHM of ~50 nm.

The aliquoted samples were not soluble in hexane, and became almost instantly flocculated and settled to the bottom of the vials within minutes.

Core Reaction with 6-Ethoxy-6-Oxohexylphosphonic Acid

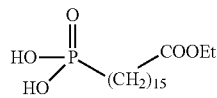

The core reaction using 6-ethoxy-6-oxohexylphosphonic acid as the phosphonate ligand had an initial emission reading at 1 minute of ~560 nm and a final emission reading of ~606 nm. The FWHM of this reaction started out at 1 minute at ~43 nm and narrowed to a final FWHM of ~40.5 nm.

The solubility of the aliquoted samples was observed. The hexane samples were immediately cloudy, however the flocculation did not settle to the bottom of the vials. Six of the aliquoted samples were centrifuged and the resulting clear, colorless supernatants were discarded. The pellets were soluble in toluene, dichloromethane ($CH_2Cl_2$), dimethylformamide (DMF), and methanol (MeOH). The pellets were not soluble in water, 50 mM borate buffer at pH=8.3 or hexane.

Particles synthesized in the presence of TDPA are soluble in hexane, toluene, $CH_2Cl_2$, DMF and hexane. The 6-ethoxy-6-oxohexylphosphonic acid itself is not soluble in hexane, and neither were the resulting particles from this reaction, suggesting that the ligand was indeed coating the nanoparticles—a suggestion which was confirmed with infrared and NMR spectroscopy indicating the expected ester functionality. Using a solvent system of toluene as the solubilizing solvent and hexane as a precipitating solvent, a pellet can be formed along with a clear, colorless supernatant. The resulting pellet can be re-solubilized in toluene. This resulting toluene solution allowed an absorbance spectrum of these cores to be obtained.

These data suggest that quantum confined nanoparticles have been formed with 6-ethoxy-6-oxohexylphosphonic acid on the particle surface. The resulting core particles were taken further into a shell reaction.

Shell Reaction Procedure using 6-ethoxy-6-oxohexylphosphonic acid

Core Precipitation

Three (3) mL of growth solution cores using 6-ethoxy-6-oxohexylphosphonic acid ligand (prepared according to the procedure of Example 17) was solubilized into 3 mL toluene in a 250 mL conical bottom centrifuge tube. A total of 135 mL of hexane was added to precipitate the cores. The tube was centrifuged at 3000 RPM for 5 min. The resulting clear, colorless supernatant was discarded and the pellet was dispersed into 3 mL of toluene.

Shell Reaction

Into a 25 mL 3 neck flask with 14/20 joints, 1.4 g of TOPO was weighed. To this, 1-1000 mg of 6-ethoxy-6-oxohexylphosphonic acid was added. A stir bar and 1.4 mL of TOP were added to the flask. The flask was connected to an inert atmosphere manifold and evacuated thoroughly, then refilled with nitrogen. 2.6 mL of the toluene solution of cores was added to the flask and the flask was warmed and evacuated to remove the toluene, then refilled with nitrogen. Approximately 1 mL of a suitably high-boiling amine was added to the flask and the flask was heated to 200-350° C. Solutions of suitable cadmium and zinc precursors in TOP were prepared with a concentration of 0.5 mol metal ion per kg of solution. A solution of 10% trimethylsilylsulfide in TOP by weight was prepared as well. The metal and sulfur precursor solutions were added slowly over the course of several hours to minimize additional nanoparticle nucleation. Sufficient shell precursors were added to grow a shell of a desired thickness, as can be calculated by one of ordinary skill in the art. When the desired shell thickness was reached, the reaction was cooled and the core/shell nanoparticles were isolated by conventional means. Aliquots taken during the reaction permitted monitoring of the progress of the shell reaction. It was observed that the emission maximum after heating but before addition of shell precursors was very similar to that of the initial cores (~600 nm), suggesting that the bi-functional phosphonate was sufficiently strongly coordinated to the nanoparticle surface to minimize Ostwald ripening. A red-shift during shell precursor addition of ~50 nm was typical of a shell as deposited in a reaction employing TDPA, suggesting that the shell formed as expected. In addition, the nanoparticle solution became much more intensely emissive, as would be expected of successful deposition of an insulating shell. Infrared and NMR spectroscopy confirmed that the functionalized phosphonates were present on the nanoparticles.

What is claimed:

1. A mutant DNA polymerase comprising the amino acid sequence of SEQ ID NO:7.

2. The mutant DNA polymerase of claim 1, which exhibits reduced 3' to 5' exonuclease activity compared to a wild type DNA polymerase which comprises the amino acid sequence of SEQ ID NO:6.

3. The mutant DNA polymerase of claim 1, further comprising a peptide tag which includes 2-8 consecutive histidine residues, wherein the peptide tag is linked to the N-terminal or C-terminal end of the mutant DNA polymerase.

4. The mutant DNA polymerase of claim 3, wherein the peptide tag further comprises zinc, nickel, cobalt or copper ions.

5. The mutant DNA polymerase of claim 1, further comprising a peptide tag which includes the amino acid sequence MNHLVHHHHHHIEGRHMELGTLEGS (SEQ ID NO:51), wherein the peptide tag is linked to the N-terminal or C-terminal end of the mutant DNA polymerase.

6. The mutant DNA polymerase of claim 1, further comprising a peptide tag which includes the amino acid sequence MHHHHHHKH (SEQ ID NO:52), wherein the peptide tag is linked to the N-terminal or C-terminal end of the mutant DNA polymerase.

7. The mutant DNA polymerase of claim 1, further comprising a peptide tag which includes the amino acid sequence LLGAAAKGAAAKGSAA (SEQ ID NO:16), wherein the peptide tag is linked to the N-terminal or C-terminal end of the mutant DNA polymerase.

8. The mutant DNA polymerase of claim 1, further comprising a peptide tag which includes the amino acid sequence LLGGGGSGGGGSAAAGSAA (SEQ ID NO:17), wherein the peptide tag is linked to the N-terminal or C-terminal end of the mutant DNA polymerase.

9. The mutant DNA polymerase of claim 1, further comprising a peptide tag which includes the amino acid sequence GLNDIFEAQKIEWHE (SEQ ID NO:53), wherein the peptide tag is linked to the N-terminal or C-terminal end of the mutant DNA polymerase.

* * * * *